US012492420B2

(12) United States Patent
Nye et al.

(10) Patent No.: US 12,492,420 B2
(45) Date of Patent: Dec. 9, 2025

(54) COMPOSITIONS, KITS, AND METHODS FOR IN VITRO TRANSCRIPTION

(71) Applicant: New England Biolabs, Inc., Ipswich, MA (US)

(72) Inventors: Dillon B. Nye, Somerville, MA (US); Jennifer L. Curcuru, Gloucester, MA (US); Tien-Hao Chen, Wakefield, MA (US); Lili Mitchell, Ipswich, MA (US); Ivan R. Correa, Jr., Hamilton, MA (US)

( * ) Notice: Subject to any disclaimer, the term of this patent is extended or adjusted under 35 U.S.C. 154(b) by 0 days.

(21) Appl. No.: 19/095,861

(22) Filed: Mar. 31, 2025

(65) Prior Publication Data

US 2025/0305019 A1 Oct. 2, 2025

Related U.S. Application Data

(60) Provisional application No. 63/571,752, filed on Mar. 29, 2024.

(51) Int. Cl.

| | |
|---|---|
| ***C12P 21/00*** | (2006.01) |
| ***C12N 9/10*** | (2006.01) |
| ***C12N 9/12*** | (2006.01) |
| ***C12N 15/52*** | (2006.01) |

(52) U.S. Cl.

CPC ............ *C12P 21/00* (2013.01); *C12N 9/1007* (2013.01); *C12N 9/1247* (2013.01); *C12N 15/52* (2013.01); *C12Y 207/07006* (2013.01)

(58) Field of Classification Search

CPC ........ C12P 21/00; C12P 19/34; C12N 9/1007; C12N 9/1247; C12N 15/52; C12Y 207/07006; C12Y 207/0705; C12Y 301/03033; C07K 2319/00

See application file for complete search history.

(56) References Cited

U.S. PATENT DOCUMENTS

| | | | |
|---|---|---|---|
| 6,107,037 | A | 8/2000 | Sousa et al. |
| 7,074,596 | B2 | 7/2006 | Darznkiewicz et al. |
| 7,335,471 | B2 | 2/2008 | Guillerez et al. |
| 8,383,340 | B2 | 2/2013 | Ketterer et al. |
| 8,551,752 | B2 | 10/2013 | Oe et al. |
| 9,193,959 | B2 | 11/2015 | Sobek et al. |
| 9,428,535 | B2 | 8/2016 | de Fougerolles et al. |
| 9,629,804 | B2 | 4/2017 | Heartlein et al. |
| 9,745,588 | B2 | 8/2017 | Striedner et al. |
| 9,790,531 | B2 | 10/2017 | Wang et al. |
| 10,034,951 | B1 | 7/2018 | Roy et al. |
| 10,465,190 | B1 | 11/2019 | Chen et al. |
| 10,519,431 | B2 | 12/2019 | Ong et al. |
| 10,793,831 | B2 | 10/2020 | Chin et al. |
| 10,793,841 | B2 | 10/2020 | Miller et al. |
| 10,975,369 | B2 | 4/2021 | DeRosa et al. |
| 11,028,379 | B1 | 6/2021 | Ganatra et al. |
| 11,066,655 | B2 | 7/2021 | Richardson et al. |
| 11,066,686 | B2 | 7/2021 | Rabideau et al. |
| 11,259,184 | B1 | 2/2022 | Pickering et al. |
| 11,268,157 | B2 | 3/2022 | Von Der Mülbe et al. |
| 11,359,184 | B2 | 6/2022 | Ong et al. |
| 11,485,960 | B2 | 11/2022 | Dousis et al. |
| 2012/0251618 | A1 | 10/2012 | Schrum et al. |
| 2015/0024435 | A1 | 1/2015 | Boulain et al. |
| 2015/0376581 | A1 | 12/2015 | Brakmann et al. |
| 2016/0032316 | A1 | 2/2016 | Weissman et al. |
| 2016/0038432 | A1 | 2/2016 | DeRosa et al. |
| 2017/0119740 | A1 | 5/2017 | Beachy et al. |
| 2018/0237817 | A1 | 8/2018 | Roos et al. |
| 2019/0083602 | A1 | 3/2019 | Roos et al. |
| 2019/0256842 | A1 | 8/2019 | Liu et al. |
| 2020/0040370 | A1 | 2/2020 | Eber et al. |
| 2020/0332371 | A1 | 10/2020 | Dickinson et al. |
| 2021/0040526 | A1 | 2/2021 | Wochner et al. |
| 2021/0054016 | A1 | 2/2021 | Robb et al. |
| 2022/0064688 | A1 | 3/2022 | Blake et al. |
| 2022/0145381 | A1 | 5/2022 | Elich et al. |
| 2022/0222059 | A1 | 7/2022 | Yamaguchi |
| 2022/0288240 | A1 | 9/2022 | Roy et al. |
| 2022/0289786 | A1 | 9/2022 | Hogrefe et al. |
| 2023/0287376 | A1 | 9/2023 | Xu et al. |

FOREIGN PATENT DOCUMENTS

| | | | |
|---|---|---|---|
| WO | 2013151666 | A3 | 1/2014 |
| WO | 2014152211 | A1 | 9/2014 |
| WO | 2015085142 | A1 | 6/2015 |
| WO | 2017123748 | A1 | 7/2017 |
| WO | 2019199807 | A1 | 10/2019 |

(Continued)

OTHER PUBLICATIONS

Li, et al., RNA Polymerase (endogenous virus)[Vibrio phage Vc1], GenBank: AHN84679, 2014.
Kore, Nucleosides, Nucleotides, and Nucleic Acids, 2006, 25: 15 307-14.
Kore, Nucleosides, Nucleotides, and Nucleic Acids, 2006, 25: 337-40.
Ramanathan, Nucleic Acids Res. 2016 44: 7511-7526.
O'Leary, Nucleic Acids Research, 44, D733-D745, 2016.
Rabiey, Microbial Biotechnology (2020) 13, 5, 1428-1445.
Huerta-Cepas, Mol. Biol. Evol. 2016, 33(6): 1635-1638.
Altschul, J. Mol. Biol. (1990) 215, 403-410.
Ambrosini, Bioinformatics (2018) 34, 2483-2484.

(Continued)

*Primary Examiner* — Iqbal H Chowdhury
(74) *Attorney, Agent, or Firm* — New England Biolabs, Inc

(57) ABSTRACT

The present disclosure relates, according to some embodiments, to cold-active RNA polymerases, variants thereof, compositions and kits comprising cold-active RNA polymerases, and methods of using cold-active RNA polymerases. Cold-active polymerases may have, for example, an amino acid sequence ≥90%, ≥91%, ≥92%, ≥93%, ≥94%, ≥95%, ≥96%, ≥97%, ≥98%, ≥99% identical (e.g., ≥95% or ≥98% identical) to any of SEQ ID NOS: 1-19 and optionally may have at least one substitution relative to SEQ ID NO:1.

16 Claims, 14 Drawing Sheets

Specification includes a Sequence Listing.

(56) References Cited

FOREIGN PATENT DOCUMENTS

| | | | |
|---|---|---|---|
| WO | 2020243026 | A1 | 12/2020 |
| WO | 2024026287 | A2 | 2/2024 |

OTHER PUBLICATIONS

Chen, Sci. Rep. (2022) 12, 13017.
Wolf, Acs Pharmacol. Transl. Sci. (2023) 6, 1692-1702.
Potapov, Nucleic Acids Res. (2018) 46, 5753-5763.
Fleming, Nucleic Acids Res. (2023) 51, 1914-1926.
Fujita, Anal. Biochem. (2019) 566, 46-49.

T7 TAATACGACTCACTATAGG
SP6 ATTTAGGTGACACTATAGA
Njord ATTTAAGTTGCATTATAGG

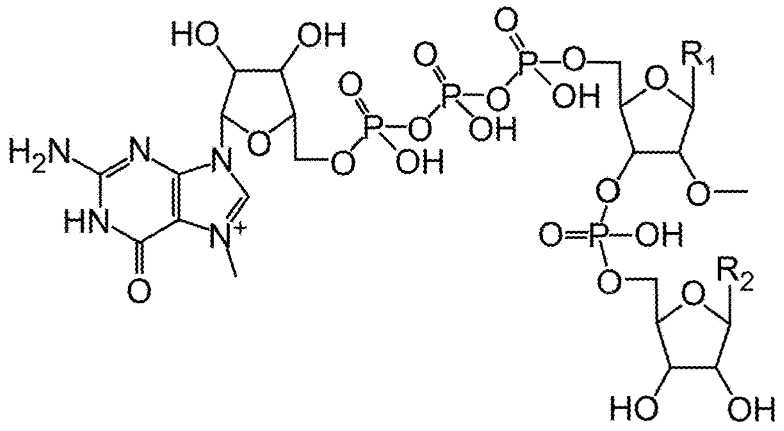

Cap GG: $R_1$ = Guanine, $R_2$ = Guanine
Cap GU: $R_1$ = Guanine, $R_2$ = Uracil
Cap AG: $R_1$ = Adenine, $R_2$ = Guanine
Cap AU: $R_1$ = Adenine, $R_2$ = Uracil

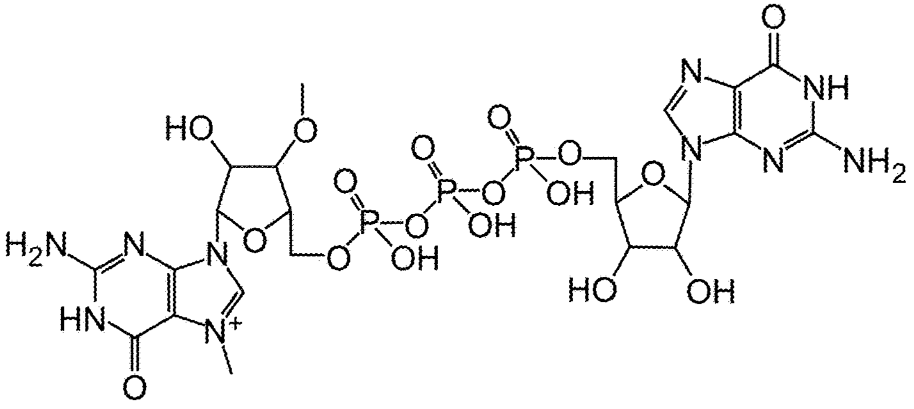

Anti-reverse cap analog (ARCA)

T7 GG: TAATACGACTCACTATAGG
T7 GU: TAATACGACTCACTATAGT
T7 AG: TAATACGACTCACTATAAG
T7 AU: TAATACGACTCACTATAAT

CA-RNAP GG: TTTTAAGTTGCATTATAGG
CA-RNAP GU: TTTTAAGTTGCATTATAGT
CA-RNAP AG: TTTTAAGTTGCATTATAAG
CA-RNAP AU: TTTTAAGTTGCATTATAAT

Template promoter sequences

FIG. 4A

COMPOSITIONS, KITS, AND METHODS FOR IN VITRO TRANSCRIPTION

CROSS-REFERENCE TO RELATED APPLICATIONS

This application also claims priority to U.S. Provisional Application No. 63/571,752 filed Mar. 29, 2024, the entire contents of which are hereby incorporated in their entirety by reference.

SEQUENCE LISTING STATEMENT

This disclosure includes a Sequence Listing submitted electronically in .xml format under the file name "NEB-487-US.xml" created on Mar. 31, 2025, and having a size of 219,978 bytes. This Sequence Listing is incorporated herein in its entirety by this reference.

BACKGROUND mRNA therapeutics can be tailored to induce cellular expression of any encoded protein, representing a customizable and adaptable drug modality that is rapidly maturing. Therapeutic mRNAs have applications as cancer immunotherapies, infectious disease vaccines, protein replacement treatments and gene editing tools. The synthetic mRNA drug substance is required to mimic eukaryotic transcripts and typically contains an N7-methylguanosine cap, 5' and 3' untranslated regions, and a 3' polyadenosine tail. These structural elements are desirable for reducing or preventing RNA degradation and/or promoting RNA translation. Typically, the mRNA is synthesized by in vitro transcription (IVT) using T7 RNA polymerase or one of its variants. The designed mRNA sequence is encoded on a linearized plasmid which contains the T7 promoter and is used as an IVT template to produce large amounts of RNA. Covalent modifications at the 5' terminus can be installed co-transcriptionally by supplying the IVT reaction with cap analogs, or added in subsequent enzymatic reactions, or eschewed altogether by circularizing the RNA and including an internal ribosome entry site. The mRNA can be designed to include the replication machinery and subgenomic promoter of an alphavirus, yielding a large self-amplifying RNA (saRNA) molecule. Modified nucleotides such as pseudouridine (ψ) can be incorporated into the mRNA to attenuate unwanted immunostimulatory properties of the drug substance. Whatever forms the mRNA therapy takes, its design and production are beholden to the capabilities of T7 RNA polymerase.

SUMMARY

Accordingly, needs have arisen for improved RNA polymerases, for example, cold-active RNA polymerases and/or RNA polymerases that produce transcripts with desirable properties (e.g., transcripts having reduced immunogenicity when administered to humans or other mammals). The present disclosure relates, in some embodiments, to cold-active RNA polymerases and variants thereof. For example, cold-active polymerases may have an amino acid sequence ≥90%, ≥91%, ≥92%, ≥93%, ≥94%, ≥95%, ≥96%, ≥97%, ≥98%, ≥99% identical (e.g., ≥95% or ≥98% identical) to any of SEQ ID NOS: 1-29 (e.g., any of SEQ ID NOS: 1-19; any of SEQ ID NOS: 1-15) and may have at least one substitution relative to SEQ ID NO:1. In some embodiments, a variant cold-active RNA polymerase may have (a) an amino acid sequence ≥90%, ≥91%, ≥92%, ≥93%, ≥94%, ≥95%, ≥96%, ≥97%, ≥98%, ≥99% identical (e.g., ≥95% or ≥98% identical) to any of SEQ ID NOS: 1-29 (e.g., any of SEQ ID NOS: 1-19; any of SEQ ID NOS: 1-15), and (b) optionally at least one conservative substitution relative to SEQ ID NO: 1. A variant cold-active RNA polymerase may have (a) an amino acid sequence ≥90%, ≥91%, ≥92%, ≥93%, ≥94%, ≥95%, ≥96%, ≥97%, ≥98%, ≥99% identical (e.g., ≥95% or ≥98% identical) to any of SEQ ID NOS: 1-29 (e.g., any of SEQ ID NOS: 1-19; any of SEQ ID NOS: 1-15), and (b) at least one conservative substitution relative to SEQ ID NO:1 or at least two conservative substitutions relative to SEQ ID NO:1. Optionally, a variant cold-active RNA polymerase may have a third substitution relative to SEQ ID NO:1. In some embodiments, a variant cold-active RNA polymerase may be fused to another polypeptide or protein. According to some embodiments, a fusion may comprise, in an N-terminal to C-terminal direction, (I) a purification tag or a sorting signal peptide, and (II) any of the cold-active RNA polymerases set forth in this paragraph (or otherwise disclosed herein) operably linked to (I) or a fusion may comprise, in an N-terminal to C-terminal direction, (III) any of the cold-active RNA polymerases set forth in this paragraph (or otherwise disclosed herein) and (IV) a purification tag or a sorting signal peptide operably linked to (III).

The present disclosure also relates, in some embodiments, to compositions comprising any of the cold-active RNA polymerases, variants thereof or fusions thereof set forth in the preceding paragraph (or otherwise disclosed herein). For example, a composition may comprise a cold-active RNA polymerase (or a variant thereof or a fusion thereof) and a template comprising a sequence encoding an RNA of interest. A template may comprise (e.g., may further comprise) a cold-active RNA polymerase promoter. Example cold-active RNA polymerase promoters include promoters having any of the nucleotide sequences of SEQ ID NOS: 31-46. Compositions, according to some embodiments, may comprise at least one of a buffering agent and a polyamine or may comprise both a buffering agent and a polyamine. Example buffering agents include HEPES, MES, MOPS, TAPS, tricine, Tris, ACES, ADA, BES, Bicine, CAPS, carbonic acid/bicarbonic acid, CHES, citric acid, DIPSO, EPPS, histidine, MOPSO, phosphoric acid, PIPES, POPSO, TAPS, TAPSO, and triethanolamine. Example polyamines include spermidine, spermine, putrescine, polyethylenimine, 1,4,7-triazacyclononane, cyclen, ethylenediamine, and 1, 3, 5,-triazinane.

The present disclosure further relates to methods of making an RNA of interest. Methods may comprise, according to some embodiments, contacting a cold-active RNA polymerase having an amino acid sequence ≥90%, ≥91%, ≥92%, ≥93%, ≥94%, ≥95%, ≥96%, ≥97%, ≥98%, ≥99% identical (e.g., ≥95% or ≥98% identical) to any of SEQ ID NOS: 1-29; a template comprising a nucleotide (e.g., DNA) sequence encoding the RNA of interest; optionally, one or more NTPs; optionally, one or more modified NTPs; and optionally, a buffer, to produce the RNA of interest, wherein the contacting is at a temperature in a range of 18° C.-32° C. and/or for a time in the range of seconds to hours and/or the RNA of interest is a therapeutic RNA. A template, in some embodiments, may comprise (e.g., may further comprise) a cold-active RNA polymerase promoter. Example cold-active RNA polymerase promoters include promoters having any of the nucleotide sequences of SEQ ID NOS: 31-46. In some embodiments, an RNA of interest may be capped (e.g., comprise a capped RNA). For example, contacting may further comprise contacting the polymerase, the template, the optional components, if present, and a capping enzyme to produce the capped RNA. A method may comprise, in some embodiments, contacting the RNA of interest with one or more pharmaceutically acceptable additives.

The present disclosure also relates to cold-active RNA polymerase kits, according to some embodiments. A kit may comprise, for example, any cold-active RNA polymerase disclosed herein (optionally in a storage buffer) and one or more NTPs. A kit may comprise one or more modified NTPs (e.g., wTP) and/or a capping enzyme (e.g., VCE or FCE). A kit, in some embodiments, may comprise a reaction buffer (e.g., a reaction buffer comprising a buffering agent and a polyamine). Example buffering agents include HEPES, MES, MOPS, TAPS, tricine, Tris, ACES, ADA, BES, Bicine, CAPS, carbonic acid/bicarbonic acid, CHES, citric acid, DIPSO, EPPS, histidine, MOPSO, phosphoric acid, PIPES, POPSO, TAPS, TAPSO, and triethanolamine. Example polyamines include spermidine, spermine, putrescine, polyethylenimine, 1,4,7-triazacyclononane, cyclen, ethylenediamine, and 1, 3, 5,-triazinane.

The present disclosure, in some embodiments, relates to compositions comprising a cold-active RNA polymerase (a cold-active RNA polymerase having an amino acid sequence ≥90, ≥95, ≥98% identical to any of SEQ ID NOS: 1-19) and a capping enzyme. A cold-active RNA polymerase may be a non-naturally occurring cold-active RNA polymerase or a cold-active RNA polymerase of *Pseudomonas* phage Njord, *Pseudomonas* phage Nerthus, *Pseudomonas* phage Alpheus, *Pseudomonas* phage Achelous, *Pseudomonas* phage uligo, *Vibrio* phage φA318, *Vibrio* phage φAS51, *Vibrio* phage Vp670, *Vibrio* phage Vc1, *Vibrio* phage VEN, *Marinomonas* phage CPP1m, *Marinomonas* phage CB5A, *Pseudomonas* phage Ulina01, *Pseudomonas* phage Ulitu01, or *Pseudomonas* phage BUCT553. A capping enzyme may be a non-naturally occurring capping enzyme or a single chain capping enzyme (e.g., a capping enzyme of Faustovirus, mimivirus, or moumouvirus). In some embodiments, a cold-active RNA polymerase may have an amino acid sequence that is (a) at least 95% identical to any of SEQ ID NOS: 1-19, (b) 100% identical to SEQ ID NO:17, and/or (C) <100% identical to each of SEQ ID NOS: 1-15. A cold-active RNA polymerase may have, according to some embodiments, ≥1, ≥2, ≥3, ≥4, ≥5, ≥6, ≥8, ≥10, ≥12, ≥15, ≥18, ≥20 conservative substitutions relative to SEQ ID NO:1. A capping enzyme may have an amino acid sequence ≥90, ≥95, ≥98% identical to any of SEQ ID NOS: 75-80, according to some embodiments. In some embodiments, a cold-active RNA polymerase may be immobilized to a support or a capping enzyme may be immobilized to a support or the polymerase and the capping enzyme each may be immobilized to a separate support or the polymerase and the capping enzyme each may be immobilized to a common support (e.g., with each attached separately to the support or with the polymerase and the capping enzyme fused and the fusion attached to the support). A composition, in some embodiments, may comprise a fusion protein, wherein the fusion protein comprises the cold-active RNA polymerase and the capping enzyme (e.g., in an N-terminal to C-terminal direction, (a) the polymerase and the capping enzyme or (b) the capping enzyme and the polymerase), optionally with or without a linker disposed between the polymerase and the capping enzyme. A composition may comprise one or more components suitable for capping reactions including, for example, guanosine triphosphate (GTP) or modified GTP, a methyl group donor (e.g., S-adenosyl methionine), a 2' O-methyltransferase, and a buffering agent. A composition may comprise one or more components suitable for a transcription reaction including, for example, a polynucleotide template (e.g., comprising, in a 5' to 3' direction, a promoter corresponding to the polymerase and a sequence of interest), NTPs, a cap analog, and a buffering agent. A promoter may have a nucleotide sequence according to one of SEQ ID NOS: 31-46 (or a sequence ≥85%, ≥90%, or ≥95% identical thereto) and/or wherein the sequence of interest comprises a coding sequence. Example coding sequences include therapeutic protein coding sequences, vaccine protein coding sequence (e.g., proteins that trigger a desirable immune response, for example, conferring resistance to a microbial infection), replacement protein coding sequence (e.g., a protein or enzyme that is defective or missing in a host cell of interest), supplemental protein coding sequences (e.g., a protein or enzyme that is present in a host cell of interest, but in insufficient quanitites). In some embodiments, a composition may comprise a polyribonucleotide product of the polymerase (e.g., a transcription product). A polyribonucleotide product of the polymerase, in some embodiments, may have fewer double-stranded RNA molecules (e.g., fewer polyribonucleotide product molecules comprising a double-stranded region, fewer double-stranded regions per molecule, and/or shorter double-stranded regions) than a polyribonucleotide product of T7 RNA polymerase having the same nucleotide sequence. In some embodiments, a composition may comprise at least one of a buffering agent and/or a polyamine. Examples buffering agents include or comprise HEPES, MES, MOPS, TAPS, tricine, Tris, ACES, ADA, BES, Bicine, CAPS, carbonic acid/bicarbonic acid, CHES, citric acid, DIPSO, EPPS, histidine, MOPSO, phosphoric acid, PIPES, POPSO, TAPS, TAPSO, or triethanolamine. Examples polyamines include or comprise spermidine, spermine, putrescine, polyethylenimine, 1,4,7-triazacyclononane, cyclen, ethylenediamine, or 1, 3, 5,-triazinane.

The present disclosure relates, in some embodiments, to fusions comprising a polymerase (e.g., a naturally or non-naturally occurring cold-active RNA polymerase) and a capping enzyme. A fusion may comprise, for example, an N-terminal polymerase and a C-terminal capping enzyme or an N-terminal capping enzyme and a C-terminal polymerase.

In some embodiments, a fusion may comprise (a) in an N-terminal to C-terminal direction, (i) a polymerase, wherein the polymerase (1) is a non-naturally occurring cold-active RNA polymerase or a cold-active RNA polymerase of *Pseudomonas* phage Njord, *Pseudomonas* phage Nerthus, *Pseudomonas* phage Alpheus, *Pseudomonas* phage Achelous, *Pseudomonas* phage uligo, *Vibrio* phage φA318, *Vibrio* phage φAS51, *Vibrio* phage Vp670, *Vibrio* phage Vc1, *Vibrio* phage VEN, *Marinomonas* phage CPPIm, *Marinomonas* phage CB5A, *Pseudomonas* phage Ulina01, *Pseudomonas* phage Ulitu01, or *Pseudomonas* phage BUCT553; and (2) has an amino acid sequence at least 90%, at least 95%, or at least 98% identical to any of SEQ ID NOS: 1-19; and (ii) a capping enzyme, wherein the capping enzyme is a non-naturally occurring capping enzyme or a capping enzyme of Faustovirus, mimivirus, or moumouvirus (e.g., having n amino acid sequence at least 90%, at least 95%, or at least 98% identical to any of SEQ ID NOS: 75-78); or (b) in an N-terminal to C-terminal direction, the capping enzyme and the polymerase. For example, a fusion may comprise (e.g., in an N-terminal to C-terminal direction) a cold active RNA polymerase and a capping enzyme, wherein the polymerase has an amino acid sequence at least 98% identity to SEQ ID NO:1 and/or the capping enzyme has at least 98% identity to SEQ ID NO:75. In some embodiments, a fusion may be immobilized to a support (e.g., a magnetic bead, a surface of a container) with or without a linker (e.g., a linker disposed between the fusion and the support). A fusion may include, according to some embodiments, a purification tag or a sorting signal peptide. For example, a fusion may comprise in an N-terminal to C-terminal direction, the purification tag or the sorting signal, the polymerase, and the capping enzyme, or in an N-terminal to C-terminal direction, the purification tag or the sorting signal, the capping enzyme and the polymerase.

The present disclosure further provides kits including a cold-active RNA polymerase and one or more other materials (e.g., materials for a cold-active RNA polymerase reaction). A kit may include, for example, any of the disclosed cold-active RNA polymerases including disclosed fusions and (optionally) one or more of guanosine triphosphate (GTP) or modified GTP; a methyl group donor; a 2' O-methyltransferase; and a buffering agent. A kit may include a support to which a cold-active RNA polymerase and/or a cold-active RNA polymerase fusion may be immobilized or a kit may include an immobilized cold-active RNA polymerase and/or a cold-active RNA polymerase fusion.

The present disclosure further provides methods of using a cold-active RNA polymerase and/or a cold-active RNA polymerase fusion. A method may include, for example, contacting an RNA polymerase (e.g., a cold-active RNA polymerase having an amino acid sequence at least 90%, at least 95%, or at least 98% identical to any of SEQ ID NOS: 1-19) and a polynucleotide template comprising an expression control sequence of the RNA polymerase (e.g., operable, together with the polymerase, to initiate transcription) and a coding sequence operably linked to the expression control sequence to produce a transcript (e.g., an elicitor transcript that is heterologous to and/or translatable by a mammalian cell and/or operable to elicit desired reaction or have a desired effect on such cell). A method may further comprise contacting the transcript (e.g., elicitor transcript) with the mammalian cell to form a translation product of the elicitor transcript. In some embodiments, a mammalian cell contacted with a transcript (e.g., elicitor transcript) that arises from a cold-active RNA polymerase and/or a cold-active RNA polymerase fusion may produce smaller quantities of at least one cytokine than a reference mammalian cell (e.g., a reference mammalian cell comprising a reference transcript, wherein the reference transcript is produced by contacting the same polynucleotide template under the same conditions except with T7 RNA polymerase instead of the cold-active RNA polymerase). In some embodiments, the transcript (e.g., elicitor transcript) may be produced in vitro by cold-active RNA polymerase and/or a cold-active RNA polymerase fusion at a first temperature (e.g., 25° C.) and the reference transcript may be produced by T7 RNA polymerase at a second temperature (e.g., 37° C.). In some embodiments, a translation product of a transcript (e.g., an elicitor transcript) expressible in a mammalian cell may have a desired (e.g., therapeutic, cytotoxic) effect on the cell in which is formed. A method may include contacting the transcript (e.g., elicitor transcript) with a mammalian cell that is contiguous with and/or in communication (e.g., in fluid communication) with other mammalian cells in a mammal. For example, a method may include contacting the transcript (e.g., elicitor transcript) in situ with a mammalian cell of the respiratory system, circulatory system, immune system, digestive system, nervous system, integumentary system, musculoskeletal system, excretory system, cardiovascular system, heart, the nervous system, and/or the endocrine system. In some embodiments, a coding sequence may be operable to give rise to and/or a transcript (e.g., elicitor transcript) may comprise a therapeutic RNA and/or a vaccine RNA. In some embodiments, a coding sequence may be operable to give rise to and/or a transcript (e.g., elicitor transcript) may be an artificial transcript.

A method may include, according to some embodiments, contacting (i) an RNA polymerase at least 90%, at least 95%, or at least 98% identical to any of SEQ ID NOS: 1-19; (ii) a polynucleotide template comprising an expression control sequence of the RNA polymerase and a coding sequence encoding an artificial transcript, the coding sequence operably linked to the expression control sequence; and (iii) ribonucleotide triphosphates, to produce the artificial transcript. A method may further comprise (b) contacting the artificial transcript with a capping enzyme and one or more of (i) guanosine triphosphate (GTP) or modified GTP, (ii) a methyl group donor, (iii) a 2' O-methyltransferase, and (iv) a buffering agent, to produce a capped artificial transcript.

BRIEF DESCRIPTION OF THE FIGURES

FIG. 3A shows total combined error rates with uridine and the indicated analogs. FIG. 3B shows a base substitution profile for each polymerase with specific substitutions as indicated in the legend. Results reflect 4 independent experiments, including two IVT reactions using template Fidelity 1 (T7 SEQ ID NO:54; CA-RNAP SEQ ID NO:53) to produce RNA SEQ ID NO:55 and two IVT reactions using template Fidelity 2 (T7 SEQ ID NO:57; CA-RNAP SEQ ID NO:56) to produce RNA SEQ ID NO:58. "CA" refers to cold-active RNA polymerase.

FIG. 4A, FIG. 4B, and FIG. 4C show aspects of cap analog incorporation by T7 and cold-active RNA polymerases. FIG. 4A shows structures of cap analogs and template sequences (SEQ ID NOS: 43-46 and 71-74) used for an example demonstration of co-transcriptional capping. "CA-RNAP" refers to cold-active RNA polymerase. FIG. 4B shows the mass of RNA (μg) produced by in vitro transcription reactions with T7 (left) and cold-active RNA polymerase (right) RNA polymerases using the indicated templates in the presence or absence of trinucleotide cap analogs. Below, the proportions of 5' capped mRNA observed in reactions including the trinucleotide cap analogs is shown as determined by mass spectrometry. The trinucleotide cap analogs and the template sequences used are indicated by the dinucleotide sequence. FIG. 4C shows the proportions of 5' capped mRNA observed in reactions with varying concentrations of ARCA using a self-amplifying RNA template (T7 SEQ ID NO:57; CA-RNAP SEQ ID NO:56) to produce RNA SEQ ID NO: 58.

FIG. 5A shows native polyacrylamide gel electrophoresis analysis of unstructured RNA (SEQ ID NO:67) produced by T7 and cold-active RNA polymerases using a template (T7 SEQ ID NO:65; CA-RNAP SEQ ID NO:66). Acridine orange was used to stain the gel and fluorescence emission was collected at two wavelengths to visualize single-stranded RNA (670 nm) and double-stranded RNA (525 nm). Digestion of the reactions by either RNase $I_f$ or RNase III confirmed production of dsRNA by T7 RNAP and not cold-active RNA polymerase. "CA-RNAP" refers to cold-active RNA polymerase. FIG. 5B shows homogeneous time-resolved fluorescence measurement of double-stranded RNA reactions produced by T7 and cold-active RNA polymerases. The ratio of fluorescence emission at 665 nm and 620 nm is proportional to the amount of double-stranded RNA present in the IVT reaction. IVT reactions were performed using C. luciferase templates (T7 SEQ ID NO:63; CA-RNAP SEQ ID NO:62) to produce RNA SEQ ID NO:64 and self-amplifying RNA templates (T7 SEQ ID NO:60; CA-RNAP SEQ ID NO:59) to produce RNA SEQ ID NO:61. Abbreviations: IVT–CTC=IVT with co-transcriptional capping; IVT–PTEC=IVT with post-transcriptional enzymatic capping; and CA–RNAP=Cold active RNA polymerase.

FIG. 6A shows expression of the delivered mRNA measured by detecting activity in cell lysates of the firefly luciferase enzyme encoded by the mRNA. The expression levels are reported relative to a control *Renilla* luciferase mRNA which was co-transfected with the test mRNA. Regardless of polymerase used or nucleotide modification, the expression levels are not significantly different. Data point icons represent independent mRNA preparations. FIG. 6B shows secreted cytokine interferon beta (IFN-B) measured in the culture supernatant using an enzyme-linked immunosorbent assay. Data points lying on the y-axis represent levels below the detection limit of the assay.

FIG. 7A shows the luciferase expression levels obtained by treating the mice with luciferin and assessing signal intensity of collected images. In parallel, interferon alpha (IFN-A) concentration was measured in serum collected from mice that received a higher dose of the mRNA nanoparticles. FIG. 7B shows the results of quantifying IFN-A concentration with an enzyme-linked immunosorbent assay.

BRIEF DESCRIPTION OF THE SEQUENCES

Figure 1A:
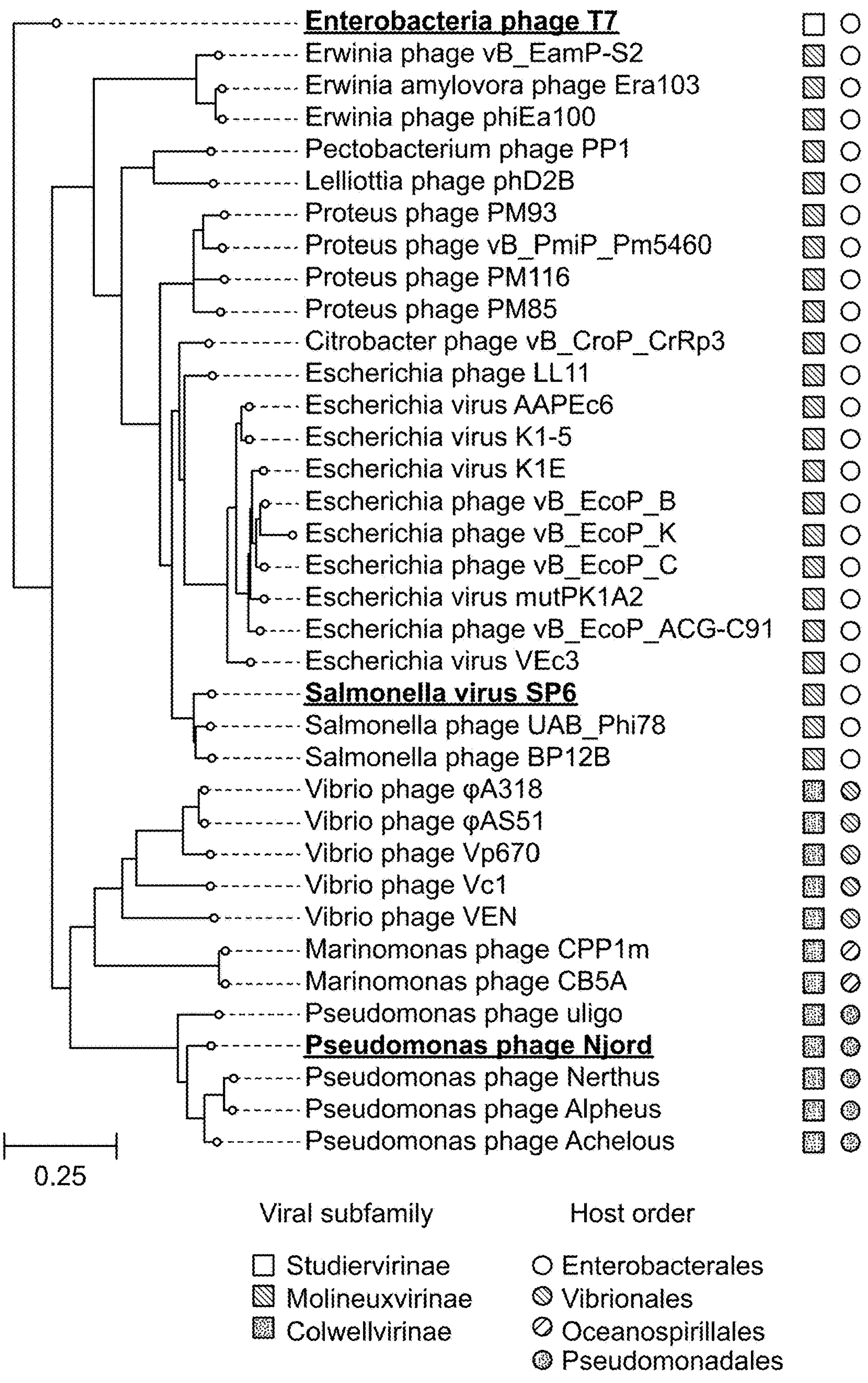
FIG. 1A shows an example phylogenetic tree of Molineuxvirinae and Colwellvirinae bacteriophages. Phage T7 was included and used to root the tree. The scale bar of 0.25 represents the phylogenomic distance (Bioinformatics 33, 3396-3404 (2017)).

Some embodiments of this disclosure relate to the following provided sequences of example polynucleotides and/or example polypeptides.

SEQ ID NO:1 is an example cold-active RNA polymerase of *Pseudomonas* phage Njord.

SEQ ID NO:2 is an example cold-active RNA polymerase of *Pseudomonas* phage Nerthus.

SEQ ID NO:3 is an example cold-active RNA polymerase of *Pseudomonas* phage Alpheus.

SEQ ID NO:4 is an example cold-active RNA polymerase of *Pseudomonas* phage Achelous.

SEQ ID NO:5 is an example cold-active RNA polymerase of *Pseudomonas* phage uligo.

SEQ ID NO:6 is an example cold-active RNA polymerase of *Vibrio* phage φA318.

SEQ ID NO:7 is an example cold-active RNA polymerase of *Vibrio* phage φAS51.

SEQ ID NO:8 is an example cold-active RNA polymerase of *Vibrio* phage Vp670.

SEQ ID NO:9 is an example cold-active RNA polymerase of *Vibrio* phage Vc1.

SEQ ID NO:10 is an example cold-active RNA polymerase of *Vibrio* phage VEN.

SEQ ID NO:11 is an example cold-active RNA polymerase of *Marinomonas* phage CPP1m.

SEQ ID NO:12 is an example cold-active RNA polymerase of *Marinomonas* phage CB5A.

SEQ ID NO:13 is an example cold-active RNA polymerase of *Pseudomonas* phage Ulina01.

SEQ ID NO:14 is an example cold-active RNA polymerase of *Pseudomonas* phage Ulitu01.

SEQ ID NO:15 is an example cold-active RNA polymerase of *Pseudomonas* phage BUCT553.

SEQ ID NO:16 is an example variant cold-active RNA polymerase with a his tag.

SEQ ID NO:17 is an example variant cold-active RNA polymerase consensus sequence, wherein B=D or N, J=I or L, Z=Q or E, X=any residue.

SEQ ID NO:18 is an example variant cold-active RNA polymerase consensus sequence.

SEQ ID NO:19 is an example variant cold-active RNA polymerase consensus sequence.

SEQ ID NO:20 is an example cold-active RNA polymerase and Faustovirus capping enzyme fusion.

SEQ ID NO:21 is an example fusion protein comprising a cold-active RNA polymerase, a linker, and a capping enzyme.

SEQ ID NO:22 is an example fusion protein comprising a cold-active RNA polymerase, a linker, and a capping enzyme.

SEQ ID NO:23 is an example fusion protein comprising a cold-active RNA polymerase, a linker, and a capping enzyme.

SEQ ID NO:24 is an example fusion protein comprising a cold-active RNA polymerase, a linker, and a capping enzyme.

SEQ ID NO:25 is an example fusion protein comprising a cold-active RNA polymerase, a linker, and a capping enzyme.

SEQ ID NO:26 is an example fusion protein comprising a cold-active RNA polymerase, a linker, and a capping enzyme.

SEQ ID NO:27 is an example fusion protein comprising a cold-active RNA polymerase, a linker, and a capping enzyme.

SEQ ID NO:28 is an example fusion protein comprising a cold-active RNA polymerase, a linker, and a capping enzyme.

SEQ ID NO:29 is an example fusion protein comprising a cold-active RNA polymerase, a linker, and a capping enzyme.

SEQ ID NO:30 is an example cold-active RNA polymerase expression plasmid.

SEQ ID NO:31 is an example cold-active RNA polymerase promoter sequence (1).

SEQ ID NO:32 is an example cold-active RNA polymerase promoter sequence (2).

SEQ ID NO:33 is an example cold-active RNA polymerase promoter sequence (3).

SEQ ID NO:34 is an example cold-active RNA polymerase promoter sequence (4).

SEQ ID NO:35 is an example cold-active RNA polymerase promoter sequence (5).

SEQ ID NO:36 is an example cold-active RNA polymerase promoter sequence (6).

SEQ ID NO:37 is an example cold-active RNA polymerase promoter sequence (7).

SEQ ID NO:38 is an example cold-active RNA polymerase promoter sequence (8).

SEQ ID NO:39 is an example cold-active RNA polymerase promoter sequence (Core 1).

SEQ ID NO:40 is an example cold-active RNA polymerase promoter sequence (Core 2).

SEQ ID NO:41 is an example cold-active RNA polymerase promoter sequence (Core 3).

SEQ ID NO:42 is an example cold-active RNA polymerase promoter sequence.

SEQ ID NO:43 is an example cold-active RNA polymerase template promoter sequence (GG).

SEQ ID NO:44 is an example cold-active RNA polymerase template promoter sequence (GU).

SEQ ID NO:45 is an example cold-active RNA polymerase template promoter sequence (AG).

SEQ ID NO:46 is an example cold-active RNA polymerase template promoter sequence (AU).

SEQ ID NO:47 is an example cold-active RNA polymerase transcription template (Firefly luciferase).

SEQ ID NO:48 is an example T7 RNA polymerase transcription template (Firefly luciferase).

SEQ ID NO:49 is an example transcription product of Firefly luciferase SEQ ID NO:50 is an example firefly luciferase suitable for transfection of mammalian cells.

SEQ ID NO:51 is an example cold-active RNA polymerase transcription template (Promoter optimization template).

SEQ ID NO:52 is an example transcription product of promoter optimization template SEQ ID NO:53 is an example cold-active RNA polymerase transcription template (Fidelity 1).

SEQ ID NO:54 is an example T7 RNA polymerase transcription template (Fidelity 1).

SEQ ID NO:55 is an example transcription product of Fidelity 1

SEQ ID NO:56 is an example cold-active RNA polymerase transcription template (Fidelity 2).

SEQ ID NO:57 is an example T7 RNA polymerase transcription template (Fidelity 2).

SEQ ID NO:58 is an example transcription product of Fidelity 2

SEQ ID NO:59 is an example cold active RNA polymerase transcription template, self-amplifying RNA.

SEQ ID NO:60 is an example T7 transcription template, self-amplifying RNA.

SEQ ID NO:61 is an example cold-active RNA polymerase and T7 transcription product, self-amplifying RNA.

SEQ ID NO:62 is an example cold-active RNA polymerase transcription template (C. luciferase).

SEQ ID NO:63 is an example T7 RNA polymerase transcription template (C. luciferase).

SEQ ID NO:64 is an example transcription product of C. luciferase.

SEQ ID NO:65 is an example T7 RNA polymerase transcription template (unstructured)

SEQ ID NO:66 is an example cold-active RNA polymerase transcription template (unstructured)

SEQ ID NO:67 is an example transcription product of unstructured RNA SEQ ID NO:68 is an example oligonucleotide used for measurement of 5' capping efficiency.

SEQ ID NO:69 is an example T7 RNA polymerase promoter sequence (initiating guanosine underlined).

SEQ ID NO:70 is an example SP6 RNA polymerase promoter sequence (initiating guanosine underlined).

SEQ ID NO:71 is an example T7 RNA polymerase template promoter sequence (GG).

SEQ ID NO:72 is an example T7 RNA polymerase template promoter sequence (GU).

SEQ ID NO:73 is an example T7 RNA polymerase template promoter sequence (AG).

SEQ ID NO:74 is an example T7 RNA polymerase template promoter sequence (AU).

SEQ ID NO:75 is an example Faustovirus D5b capping enzyme.

SEQ ID NO:76 is an example Faustovirus E12 capping enzyme.

SEQ ID NO:77 is an example Faustovirus ST1 capping enzyme.

SEQ ID NO:78 is an example Faustovirus LC9 capping enzyme.

SEQ ID NO:79 is an example mimivirus capping enzyme.

SEQ ID NO:80 is an example moumouvirus capping enzyme.

SEQ ID NO:81 is an example linker usable in fusion proteins (GAATAGT).

SEQ ID NO:82 is an example linker usable in fusion proteins (GAATAG).

SEQ ID NO:83 is an example linker usable in fusion proteins.

SEQ ID NO:84 is an example linker usable in fusion proteins.

SEQ ID NO:85 is an example linker usable in fusion proteins.

SEQ ID NO:86 is an example linker usable in fusion proteins.

SEQ ID NO:87 is an example linker usable in fusion proteins.

SEQ ID NO:88 is an example linker usable in fusion proteins.

SEQ ID NO:89 is an example linker usable in fusion proteins.

SEQ ID NO:90 is an example linker usable in fusion proteins.

SEQ ID NO:91 is an example cold active RNA polymerase transcription template, firefly luciferase suitable for transfection of mammalian cells.

SEQ ID NO:92 is an example T7 RNA polymerase transcription template, firefly luciferase suitable for transfection of mammalian cells.

DETAILED DESCRIPTION

Since its discovery over fifty years ago, the RNA polymerase from *Escherichia* phage T7 (T7 RNA polymerase) has played an outsized role in molecular biology. Owing to its high transcriptional activity, stringent promoter specificity, and ease of use as a single subunit enzyme, T7 RNA polymerase has enabled technologies which include recombinant protein expression, in vitro transcription and translation, genetic circuitry, molecular diagnostics, and single-cell whole-genome sequencing methods, among others. T7 RNA polymerase is also the principal enzymatic tool used in the manufacturing of mRNA drugs.

A key limitation to the efficacy of mRNA therapeutics is off-target immune stimulation caused by recognition of the delivered nucleic acid as foreign. Despite the benefits of nucleotide modification, unwanted immunostimulatory species formed in the IVT reaction remain a barrier to the development of mRNA drugs beyond immunotherapies. The problematic reaction byproducts may include degraded or uncapped RNA molecules, or double-stranded RNA (dsRNA) species. dsRNA activates cellular sensors which recognize viral genomes and may be the principle immunostimulatory species present in mRNA therapeutic formulations. Two mechanisms by which T7 RNA polymerase produces dsRNA have been elucidated. In one mechanism, the run-off transcript folds back on itself to prime the 3' end and is extended by the weak RNA-dependent RNA polymerase activity of T7 RNA polymerase. In another mechanism, T7 RNA polymerase initiates transcription at the terminus of the linear DNA template lacking a T7 promoter to produce a fully complementary anti-sense RNA molecule. Production of dsRNA species during IVT can be minimized by conducting IVT at elevated temperatures or in the presence of chaotropes to disfavor RNA self-annealing, or the desired single-stranded RNA (ssRNA) can be purified from byproducts by gel electrophoresis or chromatography. These methods are imperfect and may be difficult to scale up. New RNA polymerases which produce a higher quality drug substance with less required purification steps are desirable to help realize the full potential of this drug modality.

T7 RNA polymerase has been extensively investigated and engineered; mutations to T7 RNA polymerase that confer thermotolerance, reduce abortive transcription, alter promoter specificity, or result in lower levels of dsRNA in IVT have been identified. The residue Ser43 was implicated as a determinant of dsRNA production by two independent groups who took distinct approaches, a result that highlights the limited sequence space which can be explored by mutating T7 RNA polymerase. Moreover, T7 RNA polymerase activity depends on the initially transcribed sequence and directing evolution on a single DNA template may produce enzymes which are specifically adapted for that sequence. An alternative approach to the discovery of improved RNA polymerases is exploring natural homologs of T7 RNA polymerase found in the Autographiviridae (self-transcribing) family of bacteriophages. *Salmonella* phage SP6 RNA polymerase has served for decades as a comparison to T7 RNA polymerase and synthesizes RNA with similarly high yield, but also produces high levels of immunostimulatory contaminants. Polymerases from Synechococcus phage Syn5, *Klebsiella* phage KP34 and *Pseudomonas* phage VSW-3 have some advantages compared to T7 RNA polymerase including higher processivity, lower temperature optima, and reduced byproduct synthesis, but all suffer from low RNA yield.

The present disclosure relates, in some embodiments, compositions, kits, methods, workflows, and systems for the synthesis of RNA molecules. For example, RNA molecules (e.g., therapeutic mRNA molecules) may be synthesized using the RNA polymerase derived from bacteriophage T7. Rapid growth in the field of mRNA therapies motivates engineering and discovery of novel RNA polymerases which have specific advantages for mRNA manufacturing. The present disclosure provides, in some embodiments, cold-active RNA polymerases including, for example, an RNA polymerase from *Pseudomonas* phage Njord. Cold-active RNA polymerases may be derived from a viral subfamily adapted for lytic infection of marine bacteria (e.g., Colwellvirinae). These polymerases may synthesize RNA at yields comparable to SP6 and T7 RNA polymerases but with peak activity at a temperature that is ≥5° C., ≥10° C., ≥12° C., ≥15° C., ≥18° C., or ≥20° C. lower than the peak activity of wildtype SP6 or T7.

According to some embodiments, a cold-active RNA polymerase may synthesize RNA with high fidelity (e.g., higher fidelity than wild type T7 RNA polymerase). A cold-active RNA polymerase may have the capacity to initiate RNA synthesis from a 5' cap analog oligonucleotide, in some embodiments. A cold-active RNA polymerase may synthesize RNA molecules, in some embodiments, comprising fewer immunostimulatory double-stranded RNA molecules than a reference RNA polymerase (e.g., T7 RNA polymerase). For example, RNA synthesis (e.g., IVT) with a cold-active RNA polymerase may result in formation of fewer long double-stranded byproducts than a reference RNA polymerase (e.g., T7 RNA polymerase) as reflected by reduced interferon induction in cell culture. RNA synthesis (e.g., IVT) with a cold-active RNA polymerase may constitute a useful alternative to T7 RNA polymerase when reduced temperature during transcription is desired, for example in the synthesis of self-amplifying mRNA vaccines. Liquid RNA synthesis reactions comprising an RNA polymerase from *Pseudomonas* phage Njord (and/or other cold-active RNA polymerases) may yield high-quality mRNAs at yields comparable to T7 polymerase, but at temperatures ≤35° C., ≤30° C., ≤25° C., ≤20° C., ≤15° C., ≤10° C., and/or ≤5° C. Activity at lower temperatures may be desirable, for example, in reactions for synthesizing saRNA vaccines.

Synthetic RNA for use as a therapeutic drug substance may be capped at its 5' terminus with a N7-methylguanosine residue via a triphosphate linkage. This 'mRNA cap' is conserved in the biology of higher eukaryotes. RNA produced by a bacteriophage RNA polymerase bears a 5' triphosphate moiety and cannot be translated by eukaryotic ribosomes. Thus, additional measures must be taken to convert the RNA 5' triphosphate group to the N7-methylguanosine cap, and additional methylation events may further improve its quality as a drug substance. A method of producing capped RNA with bacteriophage RNA polymerases may include using synthetic oligonucleotides to initiate transcription. In some embodiments, a method of producing capped RNA may include using capping enzymes derived from viruses of eukaryotes to post-transcriptionally cap the RNA. A challenge in manufacturing mRNA therapies is the inability of T7 RNA polymerase to perform co-transcriptional capping with vaccinia capping enzyme. An RNA polymerase that can function in concert with a capping enzyme and/or which performs well when fused to a capping enzyme may facilitate the synthesis of capped mRNA therapies. Thus, a desirable RNA polymerase for mRNA synthesis would both produce low levels of dsRNA and facilitate co-transcriptional mRNA capping.

General Considerations

Aspects of the present disclosure can be understood in light of the provided descriptions, figures, sequences, embodiments, section headings, and examples, none of which should be construed as limiting the entire scope of the present disclosure in any way. Accordingly, the innovations set forth herein should be construed in view of the full breadth and spirit of the disclosure.

Each of the individual embodiments described and illustrated herein has discrete components and features which can be readily separated from or combined with the components and/or features of any of the other several embodiments without departing from the scope or spirit of the present teachings. Lists of example species within a particular genus may vary in length at different places throughout the disclosure. Species lists shortened for convenience shall not be construed to exclude example species listed elsewhere in the specification. Any recited method can be carried out in the order of events recited or in any other order which is logically possible. Unless otherwise expressly stated to be required herein, each component, feature, and method step disclosed herein is optional and the disclosure contemplates embodiments in which each optional element may be expressly excluded. As such, this statement is intended to serve as antecedent basis for use of such exclusive terminology as "solely," "only" and the like in connection with the recitation of claim elements or use of a "negative" limitation. It is further intended to serve as antecedent basis for use of such elective terminology as "optionally" and the like in connection with the recitation of one or more claim elements.

Unless otherwise defined, all technical and scientific terms used herein have the same meaning as commonly understood by one of ordinary skill in the art to which this disclosure belongs. Still, certain terms are defined herein with respect to embodiments of the disclosure and for the sake of clarity and ease of reference.

Sources of commonly understood terms and symbols may include: standard treatises and texts such as Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Singleton, et al., Dictionary of Microbiology and Molecular biology, 2d ed., John Wiley and Sons, New York (1994), and Hale & Markham, the Harper Collins Dictionary of Biology, Harper Perennial, N.Y. (1991) and the like.

As used herein and in the appended claims, the singular forms "a" and "an" include plural referents unless the context clearly dictates otherwise. For example, the term "a protein" refers to one or more proteins, i.e., a single protein and multiple proteins.

Numeric ranges are inclusive of the numbers defining the range. All numbers should be understood to encompass the midpoint of the integer above and below the integer i.e., the number 2 encompasses 1.5-2.5. The number 2.5 encompasses 2.45-2.55 etc. When sample numerical values are provided, each alone may represent an intermediate value in a range of values and together may represent the extremes of a range unless specified. Percent ranges with only one end point (e.g., ≥90% or ≤10%) optionally include a second endpoint at the maximum or minimum percentage (e.g., ≥90% includes a range of 90%-100% and ≤10% includes a range of 0%-10%). Ranges (including percent ranges) with only one end point (e.g., ≥90 or ≤10) optionally include a second endpoint 10% higher or 10% lower than the provided endpoint (e.g., ≥90 includes a range of 90-99 and ≤10 includes a range of 1-10). Concentration percentages are w/v percentages unless otherwise indicated.

In the context of the present disclosure, "artificial transcript" refers to a non-naturally occurring transcript that is translatable in a mammalian cell (e.g., to form a translation product) and/or heterologous to such mammalian cell. In some embodiments, a translation product may also be heterologous to mammalian cells. In some embodiments, the mammalian cell is a human cell. Example artificial transcripts include therapeutic RNAs and vaccines. An artificial transcript may be encoded by an artificial coding sequence. An artificial RNA transcript may differ from naturally-occurring RNA transcripts, for example, in that it comprises one or more modified nucleotides, it comprises a non-naturally occurring nucleotide sequence (e.g., designed by a computer algorithm or artificial intelligence), and/or it is bound (e.g., covalently) to a support (e.g., immobilized), a dye, fluorophore or other label, a protein (e.g., enzyme), an additional RNA molecule to form a branched structure, and/or or a carbohydrate.

In the context of the present disclosure, "buffer" and "buffering agent" refer to a chemical entity or composition that itself resists and, when present in a solution, allows such solution to resist changes in pH when such solution is contacted with a chemical entity or composition having a higher or lower pH (e.g., an acid or alkali). Examples of suitable non-naturally occurring buffering agents that may be used in disclosed compositions, kits, and methods include HEPES, MES, MOPS, TAPS, tricine, and Tris. Additional examples of suitable buffering agents that may be used in disclosed compositions, kits, and methods include ACES, ADA, BES, Bicine, CAPS, carbonic acid/bicarbonic acid, CHES, citric acid, DIPSO, EPPS, histidine, MOPSO, phosphoric acid, PIPES, POPSO, TAPS, TAPSO, and triethanolamine.

In the context of the present disclosure, "cap" refers to a natural polyribonucleotide cap (e.g., $^7$mG) and to a compound of the general formula R3p$_3$N1-[p-N](x), where R3 is a guanine, adenine, cytosine, uridine or analogs thereof (e.g., N$^7$-methylguanosine; m$^7$G), p$_3$ is a triphosphate linkage, N1 and Nx are ribonucleosides, x is 0-8 and p is, independently for each position, a phosphate group, a phosphorothioate, a phosphorodithioate, an alkylphosphonate, an arylphosphonate, or a N-phosphoramidate linkage. R3 may have an added label at the 2' or 3' position of the ribose, and, in some embodiments, the label may be an oligonucleotide, a detectable label such as a fluorophore, or a capture moiety such as biotin or desthiobiotin, where the label may be optionally linked to the ribose of the nucleotide by a linker, for example. See, e.g., WO 2015/085142. A cap may have a cap 0 structure, a cap 1 structure or a cap 2 structure (e.g., as reviewed in Ramanathan, Nucleic Acids Res. 2016 44:7511-7526), depending on which enzymes and/or whether SAM is present in the capping reaction.

Caps include dinucleotide cap analogs, e.g., of formula m$^7$G(5')p$_3$(5')G, in which a guanine nucleotide (G) is linked via its 5'OH to the triphosphate bridge. In some dinucleotide caps the 3'-OH group is replaced with hydrogen or OCH$_3$ (U.S. Pat. No. 7,074,596; Kore, Nucleosides, Nucleotides, and Nucleic Acids, 2006, 25:15 307-14; and Kore, Nucleosides, Nucleotides, and Nucleic Acids, 2006, 25:337-40). Dinucleotide caps include m$^7$G(5')p$_3$G, 3'-OMe-m$^7$G(5')p$_3$G (ARCA). Caps also include trinucleotide cap analogs (defined below) as well as other, longer, molecules (e.g., cap that have four, five or six or more nucleotides joined to the triphosphate bridge). In a cap analog, the 2' and 3' groups on the ribose of the m$^7$G may be independently selected O-alkyl (e.g., O-methyl), halogen, a linker, hydrogen or a hydroxyl and the sugars 20 in N1 and NX may be independently selected from ribose, deoxyribose, 2'-O-alkyl, 2'-O-methoxyethyl, 2'-O-allyl, 2'-O-alkylamine, 2'-fluororibose, and 2'-deoxyribose. N1 and NX may independently (for each position) comprise a base selected from adenine, uridine, guanine, or cytidine or analogs of adenine, uridine, guanine, or cytidine, and nucleotide modifications can be selected from N$^6$-methyladenine, N$^1$-methyladenine, N$^6$-2'-Odimethyladenosine, pseudouridine, N$^1$-methylpseudouridine, 5-iodouridine, 4-thiouridine, 2-thiouridine, 5-methyluridine, pseudoisocytosine, 5-methoxycytosine, 2-thiocytosine, 5-hydroxycytosine, N$^4$-methylcytosine, 5-hydroxymethylcytosine, hypoxanthine, N1-methylguanine, O$^6$-methylguanine, 1-methyl-guanosine, N$^2$-methyl-guanosine, N$^2$,N$^2$-dimethyl-guanosine, 2-methyl-2'-O-methyl-guanosine, N$^2$,N$^2$-dimethyl-2'-O-methyl-guanosine, 1-methyl-2'-O-methyl-guanosine, N$^2$,N$^7$-dimethyl-2'-O-methyl-guanosine, and isoguanineadenine.

In the context of the present disclosure, "capping" refers to the enzymatic addition of a Nppp-moiety onto the 5' end of an RNA, where N a nucleotide such as G or a modified G. A modified G may have a methyl group at the N7 position of the guanine ring, or an added label at the 2 or 3 position of the ribose, and, in some embodiments, the label may be an oligonucleotide, a detectable label such as a fluorophore, or a capture moiety such as biotin or desthiobiotin, where the label may be optionally linked to the ribose of the nucleotide by a linker, for example. See, e.g., WO 2015/085142. A cap may have a Cap-0 structure, a Cap-1 structure or a cap 2 structure (as reviewed in Ramanathan, Nucleic Acids Res. 2016 44:7511-7526), depending on which enzymes are included (e.g., a 2' O-methyl transferase) and/or whether SAM is present in the capping reaction.

In the context of the present disclosure, "capping enzyme" refers to an enzyme operable to cap RNA. A capping enzyme may be referred to as a single-chain capping enzyme if it consists of a single polypeptide chain that alone has detectable RNA triphosphatase (TPase), guanylyltransferase (GTase), and guanine-N7 methyltransferase (N7 MTase) activities (e.g., without the necessity of forming a dimer with another polypeptide chain). Faustovirus, mimivirus and moumouvirus capping enzymes are examples of single-chain RNA capping enzymes. Naturally occurring vaccinia capping enzyme (VCE) is a heterodimer and, as such, is not a single-chain RNA capping enzyme. Examples of capping enzymes may be found in US20210054016, U.S. Pat. No. 11,028,379, and US20230287376. Faustovirus capping enzymes include, for example, RNA capping enzymes of Faustovirus D5b, Faustovirus E12, Faustovirus ST1, and Faustovirus LC9. A single-chain capping enzyme, according to some embodiments, may have ≥75%, ≥80%, ≥85%, ≥90%, ≥92%, ≥94%, ≥95%, ≥98%, or ≥99% identity to any of SEQ ID NOS: 75-80.

In the context of the present disclosure, "cold-active RNA polymerase" refers to an enzyme that catalyzes template-dependent, 5' to 3' synthesis of RNA with peak catalytic activity at temperatures in ranges X to Y, where X is any of 18° C., 19° C., 20° C., 21° C., 22° C., 23° C., 24° C., 25° C., Y is any of 21° C., 22° C., 23° C., 24° C., 25° C., 26° C., 27° C., 28° C., 29° C., 30° C., 31° C., 32° C., and X<Y. For example, a cold-active RNA polymerase may have its peak catalytic activity at temperatures in ranges 18° C.-32° C., 20° C.-30° C., 22° C.-28° C. or 24° C.-28° C. Example cold-active RNA polymerases include *Pseudomonas* phage Njord (SEQ ID NO:1), *Pseudomonas* phage Nerthus (SEQ ID NO:2), *Pseudomonas* phage Alpheus (SEQ ID NO:3), *Pseudomonas* phage Achelous (SEQ ID NO:4), *Pseudomonas* phage uligo (SEQ ID NO:5), *Vibrio* phage φA318 (SEQ ID NO:6), *Vibrio* phage φAS51 (SEQ ID NO:7), *Vibrio* phage Vp670 (SEQ ID NO:8), *Vibrio* phage Vc1 (SEQ ID NO:9), *Vibrio* phage VEN (SEQ ID NO: 10), *Marinomonas* phage CPP1m (SEQ ID NO:11), *Marinomonas* phage CB5A (SEQ ID NO: 12), *Pseudomonas* phage Ulina01 (SEQ ID NO:13), *Pseudomonas* phage Ulitu01 (SEQ ID NO: 14), and *Pseudomonas* phage BUCT553 (SEQ ID NO:15). A cold-active RNA polymerase may have catalytic activity at temperatures in ranges X to Y, where X is any of 1° C., 2° C., 3° C., 4° C., 5° C., 6° C., 7° C., 8° C., 10° C., 15° C., 20° C., 24° C., 25° C., 28° C. and Y is any of 5° C., 10° C., 15° C., 20° C., 24° C., 25° C., 28° C., 30° C., 32° C., 35° C. and X<Y. For example, a cold-active RNA polymerase may have catalytic activity at temperatures in ranges 4° C.-35° C., 8° C.-32° C., 10° C.-37° C., 15° C.-35° C., 12° C.-32° C., 16° C.-32° C., 20° C.-32° C., 18° C.-30° C., or 20° C.-30° C.

Activity of a cold-active RNA polymerase may be expressed in terms of units where a unit of a cold-active RNA polymerase is the amount of enzyme needed to catalyze synthesis of over 10 micrograms of RNA from 1 microgram on DNA template (having a promoter matched to the polymerase) in the presence of 5 millimolar of each nucleoside triphosphate at 25° C. (e.g., in a volume of 20 μL). Specific activity of a cold-active RNA polymerase may be expressed in terms of units per milligram of cold-active RNA polymerase protein. Substrate specificity of a cold-active RNA polymerase may be expressed in terms of the probability of achieving a unit of activity on a random sequence of 1000 nucleotides of DNA and this probability may be less than 1 in 107.

A cold-active RNA polymerase may have an amino acid sequence having ≥75%, ≥80%, ≥85%, ≥90%, ≥92%, ≥94%, ≥95%, ≥98%, or ≥99% identity to any of SEQ ID NOS: 1-19, optionally wherein ≤25, ≤20, ≤15, ≤10, ≤9, ≤8, ≤7, ≤6, ≤5, ≤4, ≤3, or ≤2 of the amino acids differ from SEQ ID NOS: 1-15. In some embodiments, a cold-active RNA polymerase may have an amino acid sequence that is at least 90% identical to one or more of SEQ ID NOS: 1-16 with any/all variations from the reference sequence (e.g., SEQ ID NO:1-16) at non-conserved positions. For example, conserved positions of a cold-active RNA polymerase may include all positions (other than those represented as "Xaa" of SEQ ID NO:17. In this light, a cold-active RNA polymerase may have an amino acid sequence that is ≥90%, ≥92%, ≥95%, ≥97%, or ≥98% identical to one (or more) of SEQ ID NOS: 1-16 and 100% identical to SEQ ID NO: 17. A non-naturally occurring cold-active RNA polymerase may have an amino acid sequence having less than 100% identity with all of SEQ ID NOS: 1-15 (but having ≥90%, ≥92%, ≥95%, ≥97%, or ≥98% identity to one (or more) of SEQ ID NOS: 1-16) and 100% identity with SEQ ID NO: 17.

A cold-active RNA polymerase may comprise one or more amino acids in addition to a corresponding wild type enzyme. For example, a cold-active RNA polymerase (e.g., SEQ ID NOS: 1-19) may comprise (e.g., at its amino terminal end or carboxy terminal end) 1-25 additional amino acids. Such additional amino acids may enable, facilitate and/or enhance translation, expression, cellular sorting, inactivation (e.g., by including a protease recognition and/or cleavage site), and/or purification. Such additional amino acids may constitute a linker, for example, to a support (e.g., a magnetic bead) or another protein.

A cold-active RNA polymerase may catalyze template-dependent, 5' to 3' synthesis of RNA, which RNA (a) may be less immunostimulatory than an RNA having the same sequence but synthesized by T7 RNA polymerase (e.g., at 37° C.) or another RNA polymerase (e.g., at its optimal temperature) and/or (b) may comprise less dsRNA than an RNA having the same sequence but synthesized by T7 RNA polymerase (e.g., at 37° C.) or another RNA polymerase (e.g., at its optimal temperature).

In the context of the present disclosure, "container" refers to a human-made container. A container may comprise one or more walls (e.g., defining an interior volume) and optionally one or more openings. Containers comprising one or more openings may further comprise one or more closures (e.g., a removable closures) for some or all such openings. A closure optionally may comprise an aperture or a septum, for example, to provide fluid communication with a volume of the container and a connected or inserted tube or syringe. Examples of containers include boxes, cartons, bottles, tubes (e.g., test tubes, microcentrifuge tubes), plates (e.g., 96-well, 384-well plates), vials, pipette tips, and ampules. Containers and/or closures may comprise any desired material including paper, plastics, glass, silicone, composites, metals, alloys, or combinations thereof. Containers and/or closures may comprise materials that are compostable, recyclable, and/or sustainable.

In the context of the present disclosure and with respect to an amino acid residue or a nucleotide base position, "corresponding to" refers to positions that lie across from one another when sequences are aligned, e.g., by the BLAST algorithm. An amino acid position in a functional or structural motif in one polymerase may correspond to a position within a functionally equivalent functional or structural motif in another polymerase.

In the context of the present disclosure, "elicitor transcript" refers to an RNA transcript operable to impact a cell, tissue, organ or organism in which is introduced or made. For example, an elicitor transcript may directly or through a translation product have a therapeutic effect on a cell, tissue, organ or organism. A therapeutic effect may be direct (e.g., where the translation product is a functional version of a protein that is defective or missing from the cell, tissue, organ or organism) or indirect (e.g., where the translation product is cytotoxic or catalyzes formation of a product that is cytotoxic to a malignant cell or otherwise undesirable cell in which it is produced, but remaining cells, tissues, organs, and/or the organism benefits from targeted removal of the unwanted cells).

In the context of the present disclosure, "expression system" refers to systems for producing a protein from a polynucleotide template comprising components to produce the protein according to an RNA template (e.g., enzymes, amino acids, an energy source), (optionally) components to produce the RNA template according to another RNA template or a DNA template (e.g., enzymes, nucleotides, an energy source). An expression system may comprise a bacterial (e.g., *Escherichia coli*) or yeast (e.g., *Kluyveromyces lactis* or *Pichia pastoris*) expression system in which the protein is encoded by an RNA or DNA template within an expression cassette, a plasmid or other expression vector. An expression system may comprise a viral expression system in which the protein is encoded by an RNA or DNA template (e.g., in an expression cassette) within a viral genome or viral expression vector. Examples of cell-free expression systems may include or comprise cell extracts of *Escherichia coli* S30, rabbit reticulocytes or wheat germ, PURE-EXPRESS® (New England Biolabs, Ipswich, MA), an insect cell extract system (e.g., Promega #L1101), or HeLa cell lysate-based protein expression systems (e.g., Thermo Fisher Scientific #88882). An expression cassette may comprise, in some embodiments, an expression control sequence (e.g., promoter), a coding sequence encoding the gene product (e.g., protein) of interest (e.g., a vaccinia capping enzyme fusion), and/or one or more termination sequences (e.g., terminators). An expression control sequence (e.g., promoter) may comprise any promoter operative in a desired expression system, including, for example, a GAP promoter, an AOX1 promoter, a LAC4 promoter, a P350 hybrid promoter, a T7 promoter, a T5 promoter, a Ptac promoter, a Ptrc promoter, ParaBAD promoter, a PrhaBAD promoter, a Tet promoter or a PhoA phosphate-starvation promoter.

In the context of the present disclosure, "fusion" refers to two or more polypeptides, subunits, or proteins covalently joined to one another (e.g., by a peptide bond). For example, a protein fusion may refer to a non-naturally occurring polypeptide comprising a protein of interest covalently joined to a second polypeptide. Examples of a second polypeptide include a reporter protein (e.g., a green fluorescent protein), a purification tag, and expression tag, a polynucleotide binding protein, an enzyme (e.g., a capping enzyme), a conjugation tag (e.g., a SNAP® tag), and a peptide linker (e.g., a flexible linker, an inflexible linker, a cleavable linker). Unless otherwise disclosed, the protein of interest may be nearer to the N-terminal end or nearer to the C-terminal end than the second polypeptide to which it is joined. For example, a fusion may comprise a cold-active RNA polymerase fused at its N-terminal or C-terminal end to a capping enzyme. A fusion may comprise a non-naturally occurring combined polypeptide chain comprising two proteins or two protein domains joined directly to each other by a peptide bond or joined through a peptide linker. In some embodiments, a fusion may comprise a cold-active RNA polymerase (e.g., a wt or variant cold-active RNA polymerase) covalently joined to a second polypeptide. In some embodiments, a variant cold-active RNA polymerase may include a fusion to an exogenous DNA binding domain. Examples are provided in Table 1 of U.S. Pat. No. 11,259,184. In some embodiments, a fusion may comprise a cold-active RNA polymerase covalently joined to a second polypeptide (e.g., a capping enzyme). A fusion, in some embodiments, may comprise a cold-active RNA polymerase operably linked to a capping enzyme wherein both enzymes are catalytically active. For example, a cold-active RNA polymerase and a capping enzyme may be directly joined or may be joined by a peptide linker. For clarity, the temperature of peak activity and the peak activity itself may differ for a given polymerase and/or capping enzyme in the context of a fusion protein relative to the temperature and peak activity of the enzymes outside the context of the fusion (e.g., as a standalone enzyme).

In the context of the present disclosure, "immobilized" refers to covalent attachment of an enzyme (e.g., a cold-active RNA polymerase, a capping enzyme) to a solid support with or without a linker. Examples of solid supports include beads (e.g., magnetic, agarose, polystyrene, polyacrylamide, chitin). Beads may include one or more surface modifications (e.g., $O^6$-benzyleguanine, polyethylene glycol) that facilitate covalent attachment and/or activity of an enzyme of interest. For example, a support may comprise a ligand and an enzyme may have a receptor for such ligand or an enzyme may comprise a ligand and a support may comprise a receptor for such ligand. Receptor-ligand binding may be covalent or non-covalent. Non-covalent attachment (e.g., avidin:biotin, chitin:CBP) may be useful in some embodiments, for example, where the level of dissociation of the binding partner is deemed tolerable. A linker may be disposed between a support and an enzyme. For example, linker disposed between a support and an enzyme may have a first covalent bond to the support and a second covalent bond to the enzyme. An immobilized enzyme comprising a ligand-receptor attachment may have a linker disposed between the support and the ligand-receptor attachment, a linker disposed between the enzyme and the ligand-receptor attachment, or both. An immobilized enzyme comprising a linker may also comprise an optional covalent bond directly between the enzyme and the support. A linker may be of any desired length and have any desired range of motion. A peptide linker may comprise one or more repeats (e.g., 1-10 repeats) of glycine-serine.

In the context of the present disclosure, "in vitro transcription" (IVT) refers to a cell-free reaction in which a DNA template is copied by a DNA-directed RNA polymerase (e.g., a cold-active RNA polymerase) to produce a product that comprises one or more RNA molecules having a sequence copied from the template. For clarity, IVT optionally may include co-transcriptional capping.

In the context of the present disclosure, "IVT fusion" refers to an enzyme comprising a polymerase (e.g., a cold-active RNA polymerase) and a capping enzyme (e.g., a Faustovirus capping enzyme).

In the context of the present disclosure, "modified nucleotide" refers to nucleotides having a modification on the sugars (e.g., 2'-fluororibose, ribose, 2'-deoxyribose, arabinose, and hexose); and/or in the phosphate groups (e.g., phosphorothioates and 5'-N-phosphoramidite linkages); and/or in the nucleotide base (e.g., as described in U.S. Pat. No. 8,383,340; WO 2013/151666; U.S. Pat. No. 9,428,535 B2; US 2016/0032316). Examples of modified nucleotides include pseudouridine and N1-methyl-pseudouridine.

In the context of the present disclosure, "non-naturally occurring" refers to a molecule (e.g., a polynucleotide, polypeptide, carbohydrate, or lipid) or composition that does not exist in nature. Such a molecule or composition may differ from naturally occurring molecules or compositions in one or more respects. For example, a polymer (e.g., a polynucleotide, polypeptide, or carbohydrate) may differ in the kind and arrangement of the component parts (e.g., nucleotide sequence, amino acid sequence, or sugar molecules). A polymer may differ from a naturally occurring polymer with respect to the molecule(s) to which it is linked. For example, a "non-naturally occurring" polypeptide (e.g., protein) may differ from naturally occurring polypeptides in its secondary, tertiary, or quaternary structure, by having (or lacking) a chemical bond (e.g., a covalent bond including a peptide bond, a phosphate bond, a disulfide bond, an ester bond, and ether bond, and others) to a lipid, a carbohydrate, a second polypeptide (e.g., a fusion protein), or any other molecule. Similarly, a "non-naturally occurring" polynucleotide or nucleic acid may comprise (or lack) one or more other modifications (e.g., an added label or other moiety) to the 5'-end, the 3' end, and/or between the 5'- and 3'-ends (e.g., methylation) of the nucleic acid. A "non-naturally occurring" molecule or composition may differ from naturally occurring compositions in one or more of the following respects: (a) having components that are not combined in nature, (b) having components in ratios and/or concentrations not found in nature, (c) lacking one or more components otherwise found in naturally occurring molecules or compositions (e.g., a cell-free composition, a chromosome-free composition, a histone-free composition, a polymerase-free composition, a cell membrane-free composition), (d) having a form not found in nature (e.g., dried, freeze dried, lyophilized, crystalline, aqueous, immobilized), and (e) having one or more additional components beyond those found in nature (e.g., a buffering agent, a detergent, a dye, a solvent or a preservative).

In the context of the present disclosure, "polymerase" refers to an enzyme that synthesizes a polyribonucleotide from NTPs with or without a template. Examples of polymerases include T3 RNA polymerase, T7 RNA polymerase, SP6 polymerase, cold-active RNA polymerases, among others and variants thereof including psychrophilic, mesophilic, and/or thermostable variants (e.g., International PCT Publication No. WO2017123748 and U.S. Pat. Nos. 10,519,431 and 11,259,184).

With reference to an amino acid, "position" refers to the place such amino acid occupies in the primary sequence of a peptide or polypeptide numbered from its amino terminus to its carboxy terminus.

In the context of the present disclosure, "substitution" refers to an amino acid residue at a position in a comparator amino acid sequence that differs with respect to a corresponding position of a reference amino acid sequence, where the comparator and reference sequences are at least 60% identical to each other or at least 70% identical to each other or at least 80% identical to each other. A reference sequence and comparator sequence may have the same length or similar lengths (e.g., differing by ≤12%, ≤5%, ≤1%). A substitute amino acid residue at a position, in addition to differing from the corresponding position of a reference amino acid sequence, may differ from the amino acid at the corresponding position of all naturally-occurring sequences that are at least 60% identical to each other or at least 70% identical to each other or at least 80% identical to the reference sequence. Optionally, a substitute amino acid may have different properties than the amino acid in the corresponding position of the reference sequence. Optionally, a substitute amino acid may have similar properties to the amino acid in the corresponding position of the reference sequence (a "conservative" substitution). For example, a non-polar amino acid (e.g., A, V, L, I, M, W, and F (and optionally C, G, and P) may substitute for another non-polar amino acid, a polar amino acid (e.g., N, Q, S, T, and Y) may substitute for another polar amino acid (e.g., C, D, E, H, K, N, P. Q, R, S, and T), a positively charged amino acid (H, K, and R) may substitute for another positively charged amino acid, and a negatively charged amino acid (e.g., D and E) may substitute for another negatively charged amino acid. A substitute amino acid may be a natural amino acid (e.g., replacing another natural amino acid or a non-natural amino acid). A substitute amino acid may be a non-natural amino acid (e.g., replacing a natural amino acid or another non-natural amino acid).

In the context of the present disclosure, "transcript" refers to a polyribonucleotide template encoding a polypeptide. A transcript may comprise RNA (e.g., ssRNA), a cap or cap analog, and/or a polyA tail. A transcript may be capable of translation in a cell (e.g., a bacterial cell and/or a yeast cell). For example, a transcript may be or comprise mRNA. A fusion transcript may comprise polynucleotide templates for two or more polypeptides in a single polynucleotide. A transcript may comprise or consist of a single strand polynucleotide (e.g., having few or no hairpins, internal loops, bulge loops, or other double-stranded portions). For example, a transcript formed by a cold-active RNA polymerase may have fewer and/or shorter double-stranded portions than a transcript having the same sequence formed by T7 RNA polymerase.

In the context of the present disclosure, "uncapped" refers to an RNA (a) that does not have a cap and (b) that can be used as a substrate for a capping enzyme. Uncapped RNA typically has a tri- or di-phosphorylated 5' end. RNAs transcribed in vitro have a triphosphate group at the 5' end.

All publications, patents, and patent applications mentioned in this specification are herein incorporated by reference to the same extent as if each individual publication, patent, or patent application was specifically and individually indicated to be incorporated by reference. Reagents referenced in this disclosure may be made using available materials and techniques, obtained from the indicated source, and/or obtained from New England Biolabs, Inc. (Ipswich, MA).

Enzymes and Compositions

The present disclosure relates, in some embodiments, to cold-active RNA polymerases (including variant cold-active RNA polymerases) having one or more desirable properties including, for example, efficient and cold synthesis of RNA relative to, for example, wildtype T7 RNA protease.

According to some embodiments, a cold-active RNA polymerase composition may comprise a cold-active RNA polymerase (e.g., a wildtype or variant cold-active RNA polymerase) and, optionally, any of (including one or more of) a buffering agent (e.g., a storage buffer, a reaction buffer), an excipient, a salt (e.g., NaCl, $MgCl_2$, $CaCl_2$)), a protein (e.g., a capping enzyme, a 2' O-methyl transferase, another enzyme or protein), a stabilizer, a detergent (for example, ionic, non-ionic, and/or zwitterionic detergents (e.g., octoxinol, polysorbate 20)), a polyanion (e.g., spermidine, spermine, putrescine), a polynucleotide (e.g., a template comprising a sequence encoding an RNA of interest and optionally a cold-active RNA polymerase promoter), a cell (e.g., intact, digested, or any cell-free extract), a biological fluid or secretion (e.g., mucus, pus, blood, urine, saliva), an aptamer, a pH indicator (e.g., azolitimin, bromocresol purple, bromothymol blue, methylene blue, cresol red, neutral red, naphtholphthalein, phenol red), a crowding agent, a sugar (e.g., a mono, di, tri, tetra, or higher saccharide), a starch, cellulose, a glass-forming agent (e.g., glycerol, raffinose, stachyose, or trehalose for lyophilization), a lipid, an oil, aqueous media, a support (e.g., a bead) and/or (non-naturally occurring) combinations thereof. Combinations may include for example, two or more of the listed components (e.g., a salt and a buffer) or a plurality of species of a single listed component (e.g., two different salts or two different sugars). In some embodiments, a composition may comprise 0.5-25 mM $MgCl_2$, e.g., 2 mM $MgCl_2$. Compositions may comprise one or more polyanions at any desired concentration (e.g., individually or total concentrations of 0.1-10 mM, 0.5-5 mM, 1 mM, 1.5 mM, 2 mM, 2.5 mM, 3 mM, 3.5 mM, 4 mM, 4.5 mM or 5 mM) and may be included to bind negatively charged molecules. Example polyanions include spermidine, spermine, putrescine, polyethylenimine, 1,4,7-triazacyclononane, cyclen, ethylenediamine, or 1, 3, 5,-triazinane. According to some embodiments, cold-active RNA polymerase compositions may comprise (a) a cold-active RNA polymerase (e.g., a wt or variant cold-active RNA polymerase), (b) a buffer, and optionally (c) a polynucleotide (e.g., a template DNA) or a cellular extract or a cell-free preparation comprising a polynucleotide.

Cold-active RNA polymerases and variant cold-active RNA polymerases described herein have RNA polymerase activity and, as such, have the capacity to catalyze the formation of RNA in the 5'→3' direction using a DNA template. A DNA template may comprise a suitable promoter (e.g., a sequence having ≥85%, ≥90% or 100% identity to any of SEQ ID NOS: 31-46).

A cold-active RNA polymerase composition may comprise, for example, a variant cold-active RNA polymerase (e.g., having an amino acid sequence at least 85% identical to SEQ ID NO:1) and having at least one substitution, deletion, or insertion relative to wildtype cold-active RNA polymerase. A cold-active RNA polymerase composition may be free of one or more other catalytic activities. For example, a cold-active RNA polymerase (e.g., a wt or variant cold-active RNA polymerase) may be free of proteases (e.g., non-specific proteases or proteases having other cleavage recognition sites), free of nucleases (e.g., RNases and/or DNases), free of other polymerase activity, free of RNA and/or DNA modification activity, free of kinase activity, and/or free of phosphorylation and/or glycosylation activities, in each case, under desired test conditions (e.g., conditions of time, temperature, pH, salinity, model or intended substrate and/or others), for example, conditions intended to replicate conditions of a specific use of the cold-active RNA polymerase composition or intended to represent conditions for a range of uses.

The present disclosure relates, in some embodiments, to an immobilized enzyme comprising a support and an enzyme immobilized thereto. For example, an immobilized cold-active RNA polymerase may comprise a cold-active RNA polymerase (e.g., a wt or variant cold-active RNA polymerase), a glycine-serine linker attached to the variant cold-active RNA polymerase by a peptide bond, a protein tag (e.g., a SNAP-tag) attached to the linker by a peptide bond, $O^6$-benzyleguanine bound to the protein tag (e.g., SNAP-tag®); and beads (e.g., magnetic beads) having a surface modification comprising the $O^6$-benzyleguanine. In some embodiments, a support of an immobilized cold-active RNA polymerase (e.g., an immobilized variant cold-active RNA polymerase) may comprise a magnetic bead. A magnetic bead may comprise, for example, one or more surface modifications. Surface modifications may include, for example, $O^6$-benzyleguanine and/or $PEG_{750}$. In some embodiments, an immobilized enzyme may comprise a ligand (e.g., $O^6$-benzyleguanine) and a receptor or tag (e.g., a SNAP-tag®) capable of binding the ligand. For example, ligands may be disposed on a support and corresponding receptors may be disposed on (e.g., covalently attached to) an enzyme to be immobilized on the support. An immobilized enzyme may comprise, in some embodiments, an enzyme (e.g., variant cold-active RNA polymerase), optionally, a first linker (e.g., a peptide linker) attached to the enzyme, a polypeptide tag (e.g., a SNAP-tag®) attached to the first linker, if present, or the enzyme, a ligand corresponding to the polypeptide tag (e.g., $O^6$-benzyleguanine) attached (e.g., covalently attached) to the tag, optionally, a second linker (e.g., polyethylene glycol) attached to the ligand, and a support (e.g., a magnetic bead) attached to the second linker if present or the ligand, the structure of which may be illustrated, in an N-≥C direction, as:

ENZYME-[LINKER-]TAG-LIGAND-[LINKER-]SUPPORT or

SUPPORT-[LINKER-]LIGAND-[LINKER-]ENZYME (collectively "iA"), wherein dashes represent bonds (covalent or non-covalent) and brackets represent optional elements.

In some embodiments, cold-active RNA polymerases (e.g., variant cold-active RNA polymerases) and compositions comprising one or more cold-active RNA polymerases (e.g., one or more variant cold-active RNA polymerases) may have any desirable form including, for example, a liquid, a gel, a film, a powder, a cake, and/or any dried or lyophilized form. A cold-active RNA polymerase composition may comprise a cold-active RNA polymerase (e.g., a wt or variant cold-active RNA polymerase) and a support or matrix, for example, a film, gel, fabric, column or bead comprising, for example, a magnetic material, agarose, polystyrene, polyacrylamide, and/or chitin. A cold-active RNA polymerase (e.g., a wt or variant cold-active RNA polymerase) and compositions comprising a cold-active RNA polymerase (e.g., a wt or variant cold-active RNA polymerase) may be active at lower temperatures. For example, a cold-active RNA polymerase (e.g., a wt or variant cold-active RNA polymerase) or a cold-active RNA polymerase composition (e.g., comprising a cold-active RNA polymerase or a variant cold-active RNA polymerase) may display RNA synthesis activity at 4° C.-35° C., 8° C.-32° C., 10° C.-37° C., 15° C.-35° C., 12° C.-32° C., 16° C.-32° C., 20° C.-32° C., 18° C.-30° C., or 20° C.-30° C. that exceeds the activity of T7 RNA polymerase (wild type) with the same template under the same conditions. Aqueous compositions (e.g., comprising a cold-active RNA polymerase or a variant cold-active RNA polymerase) may include, for example, one or more elements that reduce the composition's melting temperature including, for example, DMSO, methanol, glycerol, ethylene glycol, propylene glycol, sugars, amino acids, and proteins among others.

In some embodiments, a cold-active RNA polymerase (e.g., a wt or variant cold-active RNA polymerase) may be encoded by a nucleic acid sequence that, when transcribed, translated, and/or processed, results in an amino acid sequence having at least 75%, at least 80%, at least 85%, at least 88%, at least 90%, at least 91%, at least 93%, at least 95%, at least 96%, at least 97%, at least 98% or at least 99% identity to one or more of SEQ ID NOS: 1-29 (e.g., one of more of SEQ ID NOS: 1-19; one of more of SEQ ID NOS: 1-15). A nucleic acid encoding a variant cold-active RNA polymerase may be included in an expression cassette, expression vector, or other expressible form suitable for in vitro or in vivo expression (e.g., in *E. coli* or other bacteria or *P. pastoris* or other yeast). A nucleic acid encoding a cold-active RNA polymerase (e.g., a wt or variant cold-active RNA polymerase) may be modified or optimized (e.g., codon optimized) for expression in a desired organism or cell-free expression system.

Methods and Workflows

The present disclosure further relates to methods and workflows that include a cold-active RNA polymerase (e.g., a wt or variant cold-active RNA polymerase). A method of producing a cold-active RNA polymerase may comprise, for example, contacting (a) a cold-active RNA polymerase transcript comprising an RNA encoding an amino acid sequence having (i) at least 75%, at least 80%, at least 85%, at least 88%, at least 90%, at least 91%, at least 93%, at least 95%, at least 96%, at least 97%, at least 98% or at least 99% identity to one or more of SEQ ID NOS: 1-29 (e.g., one of more of SEQ ID NOS: 1-19; one of more of SEQ ID NOS: 1-15), and (ii) optionally at least one conservative substitution relative to SEQ ID NO: 1 with (b) an expression system (e.g., a cell-based or cell-free expression system). A cold-active RNA polymerase transcript may be capped or uncapped, according to some embodiments. Uncapped RNA may be synthesized using solid-phase oligonucleotide synthesis chemistry or by transcribing a DNA (or RNA) template using a polymerase (e.g., a cold-active RNA polymerase) in an in vitro transcription reaction, for example. Capped RNA may be synthesized co-transcriptionally by contacting a template DNA encoding an RNA of interest with a cold-active RNA polymerase and a cap. In some embodiments, a composition may comprise a capping enzyme, S-adenosyl methionine (SAM), and/or a cap 2' methyltransferase enzyme (2'OMTase).

In some embodiments, a cold-active RNA polymerase (e.g., a wt or variant cold-active RNA polymerase) may be produced by contacting a cold-active RNA polymerase protein expression DNA construct operably linked to an expression control sequence (e.g., an appropriate promoter)

to an in vitro transcription/translation system such as PURExpress In vitro Protein Synthesis Kit (New England Biolabs, Inc.) or TnT Quick Coupled Transcription/Translation System (Promega). In addition, a cold-active RNA polymerase (e.g., a wt or variant cold-active RNA polymerase) can be produced by contacting a cold-active RNA polymerase expression DNA construct under the control of an appropriate promoter to a cell-free protein synthesis system derived from organisms such as *E. coli* (e.g., NEBExpress Cell-free *E. coli* Protein Synthesis System (New England Biolabs, Inc.), rabbit, wheat germ, insect, or human. Reaction conditions (e.g., time, temperature, reaction composition) may be maintained or adjusted as needed to express the cold-active protein. Expressed cold-active protein may be purified by appropriate methods (e.g., chromatographic methods).

The present disclosure relates, in some embodiments, to methods for making an RNA of interest. An RNA of interest may be any RNA molecule including, for example, non-naturally occurring RNA, viral RNA, prokaryotic RNA, eukaryotic RNA, and/or archaeal RNA. An RNA of interest may be a messenger RNA (mRNA), ribosomal RNA (rRNA), transfer RNA (tRNA), small RNA (sRNA), microRNA (miRNA), long noncoding RNA (lncRNA), circular RNA (circRNA), aptamer RNA, antisense RNA, silencing RNA (siRNA), guide RNA (gRNA), or any combination thereof. An RNA of interest may be itself a therapeutic RNA or may be included in a therapeutic RNA composition. A method may comprise, for example, contacting a template DNA (or RNA) encoding the RNA of interest with a cold-active RNA polymerase (e.g., a wild type or a variant according to Table 1) to produce the RNA of interest. A template may comprise a cold-active promoter (e.g., a sequence having ≥70%, ≥75%, ≥80%, ≥85%, or ≥90% identity to SEQ ID NO:1) operably linked to the coding sequence for the RNA of interest. Contacting may include contacting at temperatures in ranges X to Y, where X is any of 1° C., 2° C., 3° C., 4° C., 5° C., 6° C., 7° C., 8° C., 10° C., 15° C., 20° C., 24° C., 25° C., 28° C. and Y is any of 5° C., 10° C., 15° C., 20° C., 24° C., 25° C., 28° C., 30° C., 32° C., 35° C. and X<Y. For example, contacting the polymerase and template may comprise contacting the two at a temperature in a range of 4° C.-35° C., 8° C.-32° C., 10° C.-37° C., 15° C.-35° C., 12° C.-32° C., 16° C.-32° C., 20° C.-32° C., 18° C.-30° C., or 20° C.-30° C. Contacting may further comprise suitable conditions for RNA synthesis including, for example, contacting the temple, polymerase, NTPs and optionally one or more modified NTPs. Contacting may further comprise contacting one or more of the foregoing in a composition comprising a buffer and/or having a pH in a range from $X^{\dagger}$ to $Y^{\dagger}$, where $X^{\dagger}$ is any of pH 4, 4.5, 5, 5.5, 6, 6.5, 7, and $Y^{\dagger}$ is any of pH 6.5, 7, 7.5, 8, 8.5, 9, 9.5, 10, 10.5, 11 and $X^{\dagger}<Y^{\dagger}$. For example, a composition may have a pH from 6-9, 6.5-8.5 or 7-8. In some embodiments, a method may comprise contacting a cold-active RNA polymerase (e.g., a wt or variant cold-active RNA polymerase), a polynucleotide template (e.g., DNA or RNA) comprising a sequence encoding an RNA of interest (e.g., a therapeutic RNA), one or more NTPs, one or more modified NTPs, a buffer, and a salt (e.g., $MgCl_2$) at a temperature in a range of 4° C.-35° C., 8° C.-32° C., 10° C.-37° C., 15° C.-35° C., 12° C.-32° C., 16° C.-32° C., 20° C.-32° C., 18° C.-30° C., or 20° C.-30° C. and a pH in a range of 6-9, 6.5-8.5 or 7-8.

According to some embodiments, a method may further include capping the transcript, for example, by contacting the transcript and a capping enzyme (e.g., a Vaccinia capping enzyme, a Faustovirus capping enzyme). RNA transcript produced by a cold-active RNA polymerase (e.g., a wt or variant cold-active RNA polymerase) may comprise a smaller fraction of double-stranded RNA than similar RNA transcript produced by, for example, T7 RNA polymerase. For example, a cold-active RNA polymerase may produce RNA transcript having less than ½, less than ⅓, less than ¼, or less than ⅒ the double stranded RNA found in the same total quantity of RNA transcript produced by T7 RNA polymerase as measured, for example, by the CE and LC-MS methods of Examples 4 and 5 or by antibodies specific for dsRNA. Example methods may be found in U.S. Pat. No. 10,034,951. In some embodiments, RNA transcript produced by a cold-active RNA polymerase (e.g., a wt or variant cold-active RNA polymerase) may be less immunostimulatory than a like amount of a similar RNA transcript produced by, for example, T7 RNA polymerase. For example, a cold-active RNA polymerase may produce RNA transcript having less than ½, less than ⅓, less than ¼, or less than ⅒ the immunostimulatory activity of a like amount of a the same RNA transcript produced by T7 RNA polymerase as measured by, for example, interferon and/or cytokine expression by mammalian cells following exposure to such transcripts. RNA transcript produced by a cold-active RNA polymerase (e.g., a wt or variant cold-active RNA polymerase) may have increased homogeneity at the 3' end of the transcript. For example, a cold-active RNA polymerase may produce an RNA transcript for which the majority of the RNA species have the same nucleotides at the 3' end, and this proportion of RNA species with the same 3' end may be ≥2×, ≥5×, ≥8×, ≥10×, ≥12×, ≥15×, ≥18×, ≥20× higher than a similar RNA transcript produced by, for example, T7 RNA polymerase. Example methods may be found in U.S. Pat. No. 10,034,951.

The present disclosure provides, in some embodiments, nucleic acid sequence based amplification ("NASBA") methods using a cold-active RNA polymerase described herein. NASBA methods may be used as a rapid diagnostic test for pathogenic (among other) RNA viruses (e.g., influenza A, foot-and-mouth disease virus, severe acute respiratory syndrome (SARS)-associated coronavirus, HIV-1, human bocavirus (HBOV)) and also parasites like *Trypanosoma brucei*. NASBA methods are isothermal, often run at a constant temperature of at least 41° C. Use of a cold-active RNA polymerase (e.g., wildtype or a variant thereof) permits decreasing the reaction temperature (e.g., to 18° C.-32° C.). In some embodiments, an NASBA method comprises contacting a cold-active RNA polymerase, an RNA template, and a primer containing a promoter sequence wherein the primer hybridizes to a complementary site at the 3' end of the template, and reverse transcriptase synthesizes the opposite, complementary DNA strand. RNAse H destroys the RNA template from the DNA-RNA hybrid, and a second primer hybridizes to the 5' end of the cDNA strand. The second primer is extended using the cDNA as a template, resulting in double stranded DNA. An cold-active RNA polymerase may continuously produce complementary RNA strands of this template, which results in amplification. The amplicons are antisense to the original RNA template. A higher incubation temperature results in less non-specific binding of DNA primers to the RNA. In some embodiments, the reaction may include a temperature-sensitive inhibitor of the polymerase, thereby allowing the polymerase to remain inactive until the temperature rises.

The present disclosure provides, in some embodiments, transcription-mediated amplification ("TMA") methods using a cold-active RNA polymerase described herein. TMA methods may be performed as isothermal, single-tube nucleic acid amplifications using two enzymes, a cold-active RNA polymerase and reverse transcriptase, to rapidly amplify a target RNA/DNA. TMA may be configured to provide simultaneous detection of multiple pathogenic organisms in a single tube, allowing, for example, clinical laboratories to perform nucleic acid test (NAT) assays for blood screening with fewer steps, less processing time, and faster results. It may be used in molecular biology, forensics, and medicine for the rapid identification and diagnosis of pathogenic organisms. In contrast to similar techniques such as polymerase chain reaction and ligase chain reaction, this method involves RNA transcription (via an RNA polymerase) and DNA synthesis (via reverse transcriptase) to produce an RNA amplicon (the source or product of amplification) from a target nucleic acid. This technique can be used for both target RNA and DNA.

A method of making an RNA of interest may further comprise contacting the produced RNA with a one or more pharmaceutically acceptable additives (e.g., excipients, diluents, and/or carriers), including, for example, fluids, solvents, dispersion media, wetting agents, crowding agents, micelles, lipidoids, liposomes, polymers, lipoplexes, peptides, proteins, salts, surface active agents, isotonic agents, thickeners, emulsifiers, preservatives, stabilizers, solubilizers, buffers, sugars, starches, cellulose, waxes, glycols, polyols, polyesters, polycarbonates, polyanhydrides, hyaluronidase, nanoparticles (e.g., lipid nanoparticles, core-shell nanoparticles, and/or nanoparticle mimics), and combinations thereof. In some embodiments, pharmaceutically acceptable additives protect, preserve, and/or stabilize an RNA of interest during manufacture, storage, use, and/or administration to a subject. Examples of pharmaceutical acceptable additives include those described in U.S. Patent Publication No. 2017/0119740. A method of making an RNA of interest may further comprise contacting the RNA with one or more additives selected from lipidoids, liposomes, polymers, lipoplexes, peptides, proteins, cells transfected with HCMV RNA vaccines (e.g., for transplantation into a subject), hyaluronidase, nanoparticles (e.g., lipid nanoparticles, core-shell nanoparticles, and/or nanoparticle mimics).

Manufactured RNAs may be formulated for delivery and/or delivered to a eukaryotic organism. Examples of subjects that may receive a manufactured RNA include humans and non-human animals (e.g., mouse, rat, rabbit, dog, cat, cattle, swine, sheep, horse or primate). Manufactured RNAs may be delivered to plants or plant cells, according to some embodiments, to confer or augment resistance to or tolerance of an environmental condition (e.g., drought, salt) and/or to prevent, mitigate or treat herbivory, pathogen infection, or the effects thereof. Manufactured RNA also may be delivered to one or more yeast cells.

In some embodiments, the present disclosure provides methods for preparing an RNA dosage form comprising, contacting a cold-active RNA polymerase and a transcript encoding the RNA of interest to produce a transcribed RNA, optionally capping the transcribed RNA with a capping enzyme to form a capped RNA, and contacting produced RNA or the capped RNA with one or more pharmaceutically acceptable additives, binders, buffers, coatings, colors, controlled release agents, delivery agents (e.g., liposomes, propellants), diluents, disintegrants, dyes, excipients, fillers, lipids, lubricants, salts, sorbants, stabilizers, and/or other agents to produce an RNA dosage form. An RNA of interest may be combined with (e.g., in a single dosage form) or delivered concurrently or in sequence with one or more other active pharmaceutical agents. An RNA and/or its encoded translation product(s) may function in a subject as an active pharmaceutical agent, according to some embodiments. An RNA (e.g., a capped RNA dosage form) may be administered by any suitable route of administration, including transdermal, oral, enteral, parenteral, ocular, ottic, transmucosal, sublingual, and pulmonary (e.g., by nebulization and/or inhalation) routes, and combinations thereof.

An RNA of interest can either be naked or formulated in a suitable form for delivery to a subject, e.g., a human. Formulations can include liquid formulations (solutions, suspensions, dispersions), topical formulations (gels, ointments, drops, creams), liposomal formulations (such as those described in: U.S. Pat. No. 9,629,804 B2; US 2012/0251618 A1; WO 2014/152211; US 2016/0038432 A1). The cells into which the RNA product is introduced may be in vitro (i.e., cells that have been cultured in vitro on a synthetic medium). Accordingly, the RNA product may be transfected into the cells. The cells into which the RNA product is introduced may be in vivo (cells that are part of a mammal). The cells into which the RNA product is introduced may be present ex vivo (cells that are part of a tissue, e.g., a soft tissue that has been removed from a mammal or isolated from the blood of a mammal).

Kits

The present disclosure further relates to kits including a cold-active RNA polymerase (e.g., a wt or variant cold-active RNA polymerase). For example, a kit may include a cold-active RNA polymerase (e.g., a wt or variant cold-active RNA polymerase) and NTPs, other enzymes (e.g., other polymerases, capping enzymes, others), buffering agents, or combinations thereof. Enzymes may be included in a storage buffer. Any suitable storage buffer may be used, for example, buffers comprising one or more of a cryoprotectant (e.g., a polyol such as glycerol, an antifreeze protein), a salt, a detergent, a reducing agent, a sugar, a chelator, and an antimicrobial agent and having a pH tolerated by the enzyme to be stored, for example, between pH 6 and 9. A composition or kit may include a reaction buffer which may be in concentrated form, and the buffer may contain additives (e.g. glycerol), salt (e.g. NaCl, KCl), reducing agent, EDTA or detergents, among others. Detergents include non-ionic detergents (e.g., t-octylphenoxypolyethoxyethanol), anionic detergents (e.g., alkylbenzene sulfonates), cationic detergents (e.g., alkylbenzene quaternary ammonium), and zwitterionic detergents. A composition or kit comprising rNTPs may include one, two, three of all four of rATP, rUTP, rGTP and rCTP. A kit may further comprise one or more modified nucleotides. A kit may optionally comprise one or more primers (random primers, bump primers, exonuclease-resistant primers, chemically-modified primers, custom sequence primers, or combinations thereof).

A kit may be a non-natural collection of components configured, for example, for convenient storage, shipping, delivery, and/or use. One or more components of a kit may be included in one container for a single step reaction, or one or more components may be contained in one container, but separated from other components for sequential use or parallel use. The contents of a kit may be formulated for use in a desired method or process.

A kit is provided that contains: (i) a cold-active RNA polymerase (e.g., a wt or variant cold-active RNA polymerase); and (ii) a buffer. A cold-active RNA polymerase (e.g., a wt or variant cold-active RNA polymerase) may have a lyophilized form or may be included in a buffer (e.g., a storage buffer or a reaction buffer in concentrated form). A kit may contain a cold-active RNA polymerase (e.g., a wt or variant cold-active RNA polymerase) in a mastermix suitable for receiving and amplifying a template nucleic acid. A cold-active RNA polymerase (e.g., a wt or variant cold-active RNA polymerase) may be a purified enzyme so as to contain substantially no DNA or RNA and no nucleases. The reaction buffer in (ii) and/or storage buffers containing the RNA polymerase in (i) may include a non-ionic surfactant, an ionic surfactant (e.g. an anionic or zwitterionic surfactant) and/or a crowding agent. A kit may include a cold-active RNA polymerase (e.g., a wt or variant cold-active RNA polymerase) and the reaction buffer in a single tube or in different tubes.

A subject kit may further include instructions for using the components of the kit to practice a desired method. The instructions may be recorded on a suitable recording medium. For example, instructions may be printed on a substrate, such as paper or plastic, etc. As such, the instructions may be present in the kits as a package insert, in the labeling of the container of the kit or components thereof (i.e., associated with the packaging or subpackaging) etc. Instructions may be present as an electronic storage data file residing on a suitable computer readable storage medium (e.g. a CD-ROM, a flash drive). Instructions may be provided remotely using, for example, cloud or internet resources with a link or other access instructions provided in or with a kit.

EXAMPLES

Some specific example embodiments may be illustrated by one or more of the examples provided herein.

Example 1: Materials

Plasmids for cold-active RNA polymerase overexpression and for use as templates in IVT reactions were ordered from GenScript (Piscataway, NJ, USA) or prepared by site-directed mutagenesis and are represented by SEQ ID NOS: 47, 48, 51, 53, 54, 56, 57, 59, 60, 62, 63, 65, 66, 91, 92. All plasmid sequences were verified by Oxford Nanopore Sequencing using the Rapid Barcoding Kit (SQK-RBK114.96, ONT, Oxford, UK) and the clone validation assembly workflow. Linearized plasmids were prepared by digestion with BspQI (NEB) and assessed by agarose gel electrophoresis. Oligonucleotides were purchased from IDT (Coralville, IA, USA). Trinucleotide cap analogs were purchased from Northern RNA (Calgary, CN) and modified nucleotides were purchased from Trilink (San Diego, CA, USA). Unless otherwise noted, all enzymes and reagents were provided by New England Biolabs (NEB).

Example 2: Cold-Active RNA Polymerase Promoter Identification

Genomes of bacteriophages given the taxonomic assignment of Colwellvirinae and Molineauxvirinae were collected from the RefSeq database using the webserver search function (Nucleic Acids Res. 44, D733-D745 (2016); Microb Biotechnol 13, 1428-1445 (2019)). A phylogenetic tree was built from whole genomes with VICTOR using the do formula and visualized with the ETE 3 toolkit (Bioinformatics 33, 3396-3404 (2017); Mol. Biol. Evol. 33, 1635-1638 (2016)). To identify transcriptional promoters a BLAST alignment was performed using the cold-active RNA polymerase genomes as both the query and subject sequence with a cutoff E-value of 0.1 and high scoring pairs were inspected (J. Mol. Biol. 215, 403-410 (1990)). Promoters identified by BLAST analysis were used to construct a position-specific weight matrix and search the genome for additional instances of the motif with PWMScan (Bioinformatics 34, 2483-2484 (2018)).

Example 3: Recombinant Purification of Cold-Active RNA Polymerase

An expression vector for cold-active RNA polymerase with an N-terminal hexahistidine tag was designed using the pET28 vector. Competent *E. coli* cells (C3013, NEB) were transformed with the expression plasmid and grown at 37 C with 220 RPM shaking to an optical density of 0.6 absorbance units. The temperature was reduced to 16° C., IPTG was added to a final concentration of 0.5 mM and protein overexpression occurred during overnight incubation of the culture. Cultures were centrifuged (5000 rcf, 4 C, 30 min) and cell pellets were resuspended in Buffer A (50 mM Tris-HCl pH 8.0, 300 mM NaCl, 20 mM imidazole, 10% v/v glycerol) and lysed by sonication. Cellular debris was pelleted by centrifugation (15000 rcf, 4 C, 45 min) and the clarified lysate was applied to a HisTrap FF column (Cytiva, Marlborough, MA, USA). Bound protein was eluted with a step gradient to Buffer B (50 mM Tris-HCl pH 8.0, 0.1 M NaCl, 0.3 M imidazole, 10% v/v glycerol) and fractions were analyzed by SDS-PAGE (ThermoFisher, Waltham, MA, USA). Fractions containing cold-active RNA polymerase were pooled, diluted in Buffer B and applied to a HiTrap Heparin HP column (Cytiva). Protein was eluted with a linear gradient to Buffer C (50 mM Tris-HCl pH 8.0, 1.0 M NaCl, 1 mM DTT, 1 mM EDTA, 10% v/v glycerol), then diluted in Buffer D (50 mM Tris-HCl pH 8.0, 0.05 M NaCl, 1 mM DTT, 1 mM EDTA, 10% v/v glycerol), applied to a HiTrap Q FF column (Cytiva), and finally eluted with a linear gradient to Buffer C. Fractions containing cold-active RNA polymerase were pooled and dialyzed against storage buffer (50 mM Tris-HCl pH 8.0, 100 mM NaCl, 0.5 mM TCEP, 0.1 mM EDTA, 50% v/v glycerol). Final purity of cold-active RNA polymerase was judged to be ≥95% by SDS-PAGE and the concentration was measured with a Bradford assay. Purified protein was stored at −20 C until use.

Example 4: In Vitro Transcription Reactions

Transcription reactions (25 μL) were performed in IVT buffer (40 mM Tris-HCl pH 7.9, 20 mM MgCl2, 1 mM DTT, 2 mM spermidine) containing 5 mM of each NTP or modified nucleotide ($m^6A$, 5moU, 5hmU, 5mC, Ψ, or $m^1Ψ$), 20 U murine RNAse inhibitor (NEB), 0.05 U *E. coli* inorganic pyrophosphatase (NEB), and 1 μg of linear DNA template. Reactions were pre-incubated at the appropriate temperature for 10 minutes, and transcription was initiated by addition of either T7 or cold-active RNA polymerase. Unless otherwise indicated, IVT was performed with cold-active RNA polymerase at 25 C and with T7 at 37 C. After incubation for 1 hour, reactions were treated with TURBO DNase (ThermoFisher) at 37 C for 30 minutes and the RNA was purified using a Monarch RNA Cleanup Kit (T2050, NEB), or the reaction was quenched with 2× buffer (20 mM Tris-HCl pH 8.0, 100 mM EDTA, 0.2% Triton X-100) and analyzed immediately. For determination of RNA yield, 5 μL of serially diluted quenched IVT reaction was combined with 95 μL Qubit RNA BR buffer (ThermoFisher) and fluorescence (Ex: 625 nm; Em: 655 nm) was measured using a SpectraMax ID5 (Molecular Devices, San Jose, CA, USA)

plate reader. Agarose gel electrophoresis was performed with RNA samples denatured by heating to 70 C for 5 minutes in RNA Loading Dye (NEB) and gels were stained with SYBR Gold (ThermoFisher) and visualized on a Typhoon scanner (Cytiva).

Example 5: Cold-Active RNA Polymerase Promoter Optimization

Polymerase chain reaction (PCR) primers were designed to include the 19 nt Njord transcriptional promoter (SEQ ID NO:33) or all 57 possible single-nucleotide substitutions. For example, the thymidine nucleotide at position-17 in the promoter was replaced by each of the other three nucleotides. Saturation mutagenesis in this way for 19 positions in the promoter sequence yield 57 total sequences under investigation. PCR was carried out using Q5 High Fidelity 2× Master Mix (M0492, NEB) using a pUC-derived plasmid as template to produce SEQ ID NO:51 with all 57 possible single-nucleotide substitutions. PCR amplicons were purified using magnetic beads (NEB) and a KingFisher Flex (ThermoFisher), assessed with the TapeStation High Sensitivity D5000 kit (Agilent) and quantified with a Nanodrop 8000 (Nanodrop). IVT reactions were performed in triplicate using 250 ng of template at 25 C for 60 minutes followed by quenching of the reaction, serial dilution and RNA quantification.

Example 6: Cold-Active RNA Polymerase Transcriptional Fidelity

An assay developed for polymerase fidelity measurement with a Pacific Biosciences sequencing platform was applied to Njord and T7 RNA polymerase at 25 C. Standard in vitro transcription reactions were performed with 300 ng of a linearized plasmid template designed to include all trinucleotide sequences (SEQ ID NOS: 53, 54, 56, 57), except that T7 RNA polymerase reactions were performed with 10 mM NTPs and incubated for 2 hours. Synthesis of cDNA, Pacific Biosciences SMRTBell library preparation, sequencing on a Sequel system, and data analysis were performed as described previously (Sci. Rep. 12, 13017 (2022)).

Example 7: Analysis of Cap Analog Incorporation

Co-transcriptional capping IVT reactions (20 μL) were performed in IVT buffer with 5 mM each NTP, 5 mM trinucleotide cap analog, and 1 μg linearized plasmid (SEQ ID NOS: 59, 60) with promoters and initiating nucleotides corresponding to the cap analog (SEQ ID NOS: 43-46 and 71-74). Concentrations of NTPs were varied when anti-reverse cap analog (ARCA, NEB) was used. RNA was purified using a Monarch RNA Cleanup Kit and the concentration was measured with a Nanodrop 8000 (Nanodrop). Incorporation of cap analogs was measured as previously described (ACS Pharmacol. Transl. Sci. 6, 1692-1702 (2023)). Purified RNA (15 fmole) was combined with a complementary biotinylated DNA oligo (30 fmole), heated to 80° C. for 2 minutes then gradually cooled to 20 C. NEBuffer r1.1 was added to a final 1× concentration (10 mM Bis-Tris-Propane-HCl pH 7, 10 mM $MgCl_2$, 100 μg/mL recombinant BSA) and human RNase IV (0.1 ng, NEB) was used to digest the RNA at 37 C for 1 hour and then inactivated by addition of 50 U murine RNase inhibitor (NEB). The RNA/DNA heteroduplex was purified with streptavidin beads (NEB) and eluted by heating the beads in water to 80° C. for 5 minutes.

Example 8: Assays for dsRNA Formation

To assay DNA-terminus initiated transcription, IVT templates designed to produce unstructured RNA were generated by PCR (SEQ ID NOS: 65, 66). Purified PCR amplicons (1 μg) were used as input for IVT at 30 C, DNA was digested and the RNA was purified. RNA was subjected to digestion by either RNAse III in the presence of manganese (M0245, NEB) or by RNAse $I_f$ (M0243, NEB) and run on a 6% polyacrylamide TBE Gel (EC6265BOX, ThermoFisher). Gels were stained with either SYBR Gold or 4.3 μM acridine orange (A1301, ThermoFisher) and visualized on a Typhoon scanner.

A homogeneous time resolved fluorescence (HTRF) dsRNA-detection kit (64RNA PEG, Revvity, Waltham, MA, USA) was used to measure dsRNA content in IVT RNA (Anal. Biochem. 566, 46-49 (2019)). Quenched IVT reactions were serially diluted into 1× quench buffer in a 96-well plate alongside the Qubit ssRNA standard and the HTRF dsRNA standard. For measurement of total RNA, samples were diluted 20-fold in Qubit BR RNA detection buffer and fluorescence was measured using a SpectraMax ID5 plate reader. For measurement of dsRNA, samples were diluted 10-fold into the kit lysis buffer, and then 10 μL was combined with 10 μL of a 1:1 donor: acceptor antibody mix. HTRF was measured using a SpectraMax ID5 plate reader equipped with a TRF Enhancement Module according to the manufacturer's instructions.

Example 9: Identification and Initial Characterization of Cold-Active RNA Polymerase

*Salmonella* phage SP6 belongs to the Molineuxvirinae, a viral subfamily in the taxonomy established by the International Committee on Taxonomy of Viruses. Bacteriophages in this subfamily infect different species of Enterobacteriacae, while those in the related subfamily Colwellvirinae target hosts in the genera *Vibrio, Pseudomonas* and *Marinomonas* (FIG. 1A). Isolates of Colwellvirinae have been obtained from wastewater, aquaculture tanks and the Mediterranean Sea. The *Vibrio* phage strains φA318 and φAS51 were isolated from aquaculture waterways and efficiently form plaques when grown at 25° C. (BMC Genomics 15, 505 (2014)). Colwellvirinae may then be expected to thrive, e.g. carry out rapid lytic infection of the host, in cooler environments than the Molineuxvirinae. Given the central role of RNA polymerase in the bacteriophage lytic cycle, we reasoned that Colwellvirinae RNA polymerases may be adapted for efficient transcription at low temperatures. One cold-active RNA polymerase was chosen as a representative Colwellvirinae RNA polymerase and tested for its temperature dependence and utility for in vitro mRNA synthesis.

IVT templates may comprise a coding sequence of interest and a promoter operably linked to the coding sequence. Each RNA polymerase may recognize a different promoter or set of promoters than other RNA polymerases and IVT reactions with mismatched RNA polymerases and promoters may result in little or no transcription product. The following steps were taken to identify cognate promoter sequence(s) for cold-active RNA polymerase and may be adapted to identify cognate promoter sequences for other cold-active RNA polymerases.

Figure 1B:
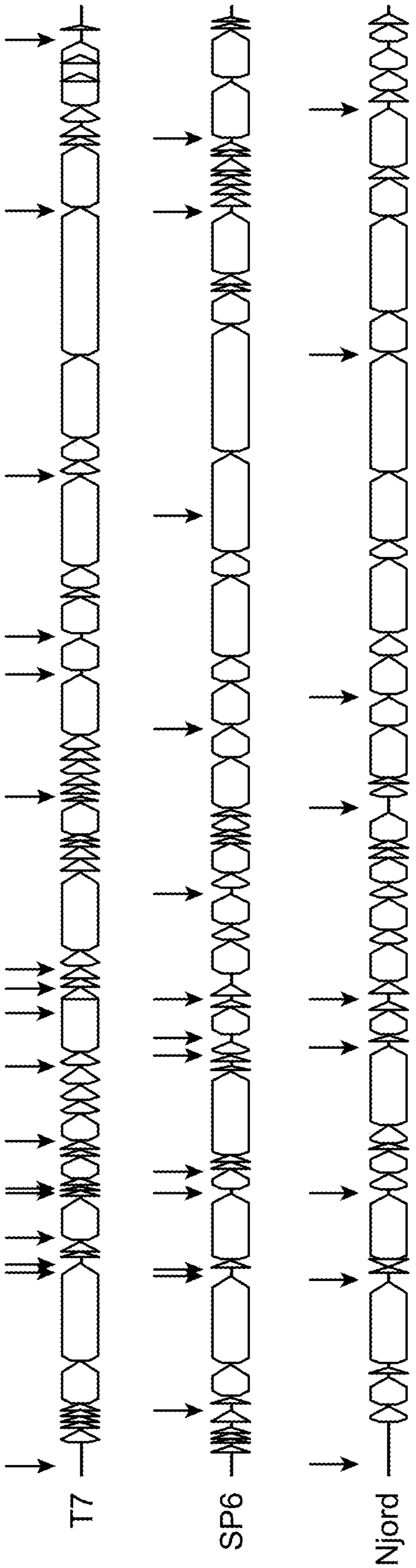
FIG. 1B shows example results of an assessment of the locations of transcriptional promoters in the genomes of phages T7, SP6 and Njord. Open reading frames are denoted with blocks and promoters are indicated with arrows. Representative promoter sequences are shown with the initiating guanosine underlined (T7 SEQ ID NO:69; SP6 SEQ ID NO: 70; Njord SEQ ID NO:38). "CA-RNAP" refers to cold-active RNA polymerase.

Searching the Njord phage genome for repeated sequences revealed a motif dispersed throughout intergenic regions, which has homology to the transcriptional promoter of *Salmonella* phage SP6. These repeated sequences were assigned as promoters and used to build a position-specific weight matrix and rescan the genome, resulting in identification of nine candidate transcriptional promoters in *Pseudomonas* phage Njord (FIG. 1B and SEQ ID NOS: 31-41). T7, SP6 and cold-active RNA promoters share common elements that include an AT-rich 5' sequence, a 3' TATA sequence, and a guanosine residue incorporated as the first nucleotide in the transcript.

Figure 1C:
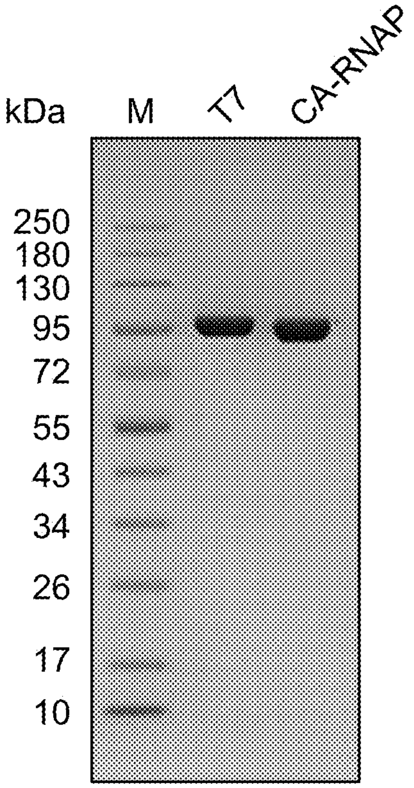
FIG. 1C shows an example SDS-PAGE analysis of T7 RNAP and cold-active RNA polymerase preparations.
Figure 1D:
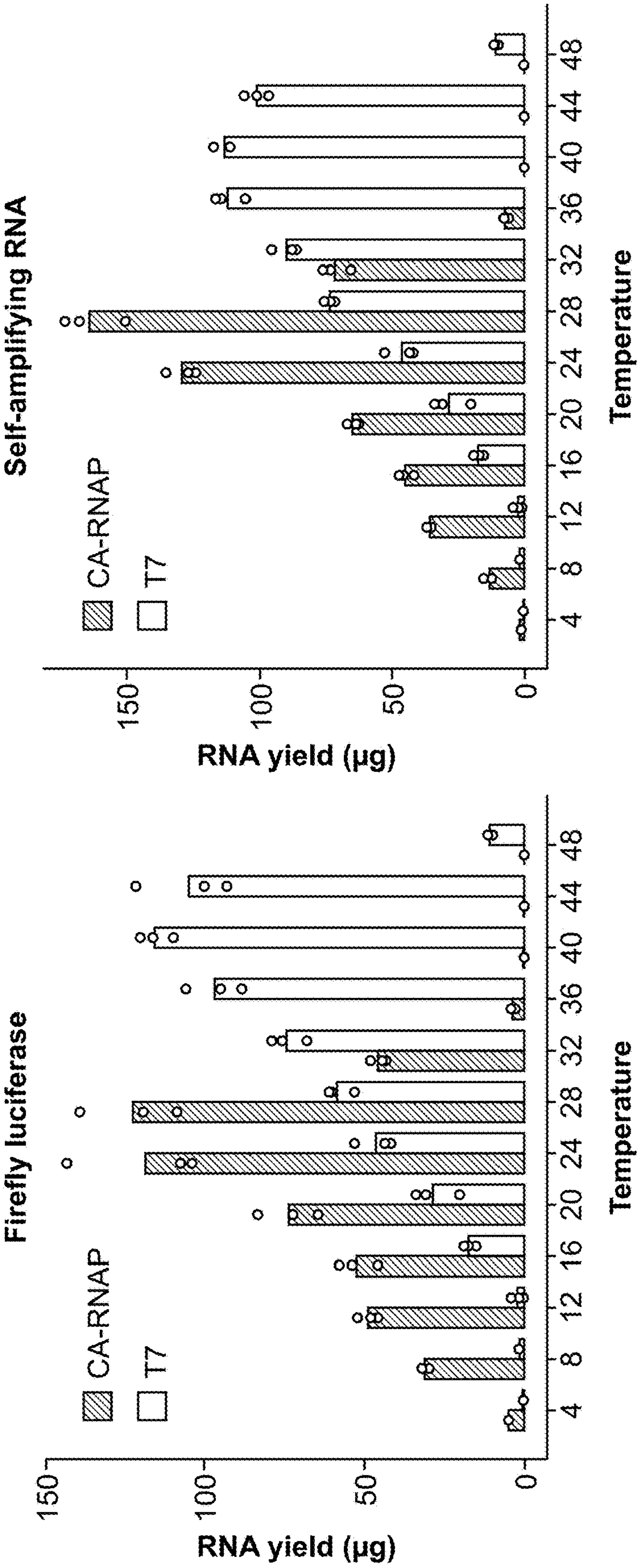
FIG. 1D shows results of example IVT reactions performed with T7 and cold-active RNA polymerases at various temperatures but otherwise identical conditions. IVT reactions were performed in triplicate and RNA yield was measured using a dye-based assay. IVT was performed using a Firefly luciferase template (T7 SEQ ID NO:48; CA-RNAP SEQ ID NO:47) to produce RNA SEQ ID NO:49, or using a self-amplifying RNA template (T7 SEQ ID NO:57; CA-RNAP SEQ ID NO:56) to produce RNA SEQ ID NO: 58.

Two linearized plasmids containing the appropriate promoter sequences were used as templates for IVT reactions (SEQ ID NOS: 47, 48, 59, 60). The encoded transcripts represent a standard mRNA and a self-amplifying mRNA and are 2.1 and 9.7 kb in length, respectively. Each has a different 5' untranslated region, but both start with guanosine and terminate in a polyA sequence. In vitro transcription was performed with these templates and T7 or cold-active RNA polymerase (FIG. 1C) at different temperatures. Apparent RNA yields of cold-active RNA and T7 RNA polymerases show similar temperature profiles with both enzymes retaining activity below their optima and showing a precipitous drop in RNA yield at elevated temperatures (FIG. 1D). The temperature optimum for transcription by cold-active RNA polymerase is 10 to 15° C. lower than that of T7 RNA polymerase, but both enzymes have comparable RNA yields at their respective optima. Using the saRNA template, cold-active RNA polymerase approaches the theoretical limit of RNA synthesized in a 25 μL reaction using 20 mM total NTPs at 28° C., and at 12° C. produces tens of micrograms of RNA. The high yields of cold-active RNA polymerase at reduced temperature and the lack of activity above 30° C. indicate that this enzyme is adapted to cooler environments than T7 and SP6 polymerases.

Figure 1E:
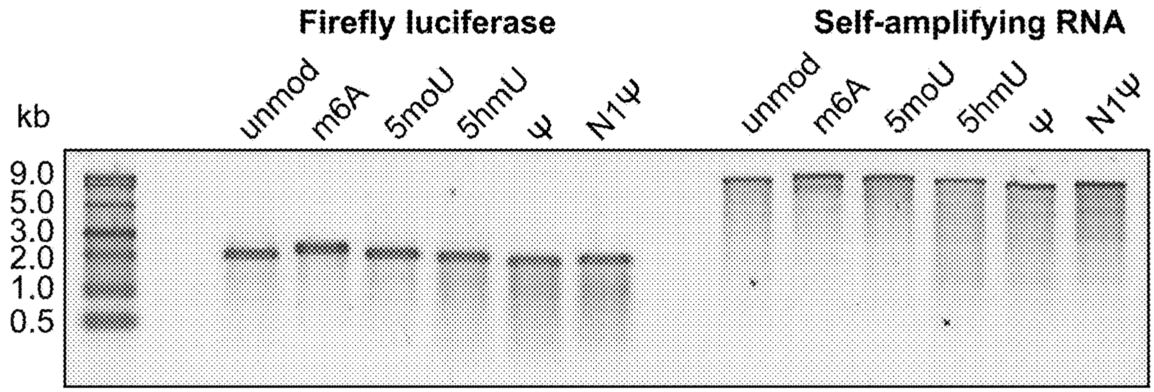
FIG. 1E shows an example agarose gel electrophoresis analysis of transcripts produced using cold-active RNA polymerase with unmodified or modified nucleotides. IVT was performed as indicated for FIG. 1D.

Example 10: Synthesis of RNA with Modified Nucleotides Using Cold-Active RNA Polymerase Therapeutic mRNAs may be synthesized with modified nucleotides to mitigate undesirable immune stimulation following administration of the therapeutic mRNA. The ability of a cold-active RNA polymerase to incorporate the modified nucleotides N6-methyladenosine ($m^6A$), 5-hydroxymethyluridine (5hmU), 5-methoxyuridine (5moU), pseudouridine (Y'), and N1-methylpseudouridine (N1m'P') into RNA was tested. Production of full-length 2.1 kb and 9.7 kb transcripts indicate complete incorporation of these modified nucleotides (FIG. 1E). Incomplete transcripts are apparent under the conditions used, and their formation appears to be dependent on the nucleotides supplied in the IVT reaction. Nevertheless, cold-active RNA polymerase is clearly capable of producing full-length transcripts up to about 10 kb in length with a variety of nucleotide modifications.

Figure 2:
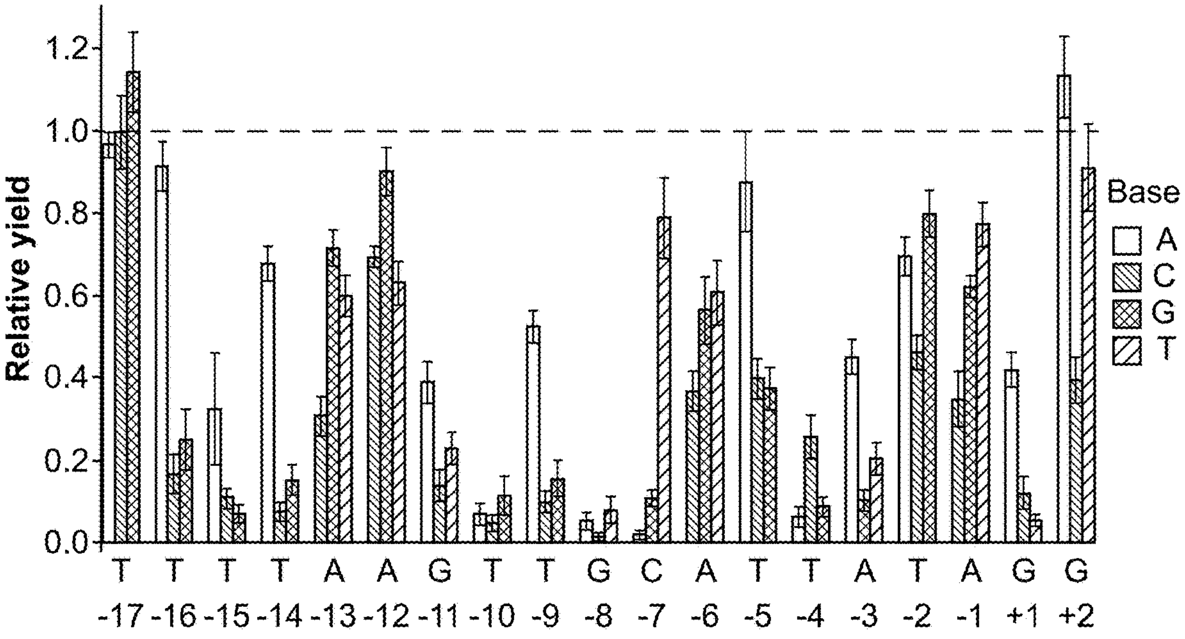
FIG. 2 shows example results of experiments examining the RNA yield from IVT reactions performed with variations of a Njord promoter. The sequence of the reference Njord promoter (SEQ ID NO:33) appears on the bottom with positions numbered according to the T7 promoter convention. IVT was performed using a promoter optimization template (SEQ ID NO:51) to produce RNA SEQ ID NO:52. Each bar represents the RNA yield when the reference nucleotide at that position is replaced by the nucleotide indicated in color. Yields are presented relative to the yield of the reference promoter, indicated by a dashed line. Error bars represent the standard error of three technical replicates.

Example 11: Impact of Promoter Selection on RNA Yield Using Cold-Active RNA Polymerase Selection of the bacteriophage promoter in the IVT template influences the transcriptional RNA yield. The T7 φ10 promoter is commonly used with T7 RNA polymerase owing to its high promoter strength. Initial transcription reactions with cold-active RNA polymerase used a promoter located upstream of the structural genes in analogy to T7 φ10. To identify the optimal Njord promoter and gain insight into promoter sequence specificity, every position in the Njord promoter was systematically replaced with each other nucleotide. For the 19 positions considered, which include the first two initiating nucleotides (+1 and +2), this corresponds to 58 promoter sequences for which transcriptional yields were measured (FIG. 2). A preference for guanosine at the +1 position is observed although adenosine may also be used as the initiating nucleotide with lower yield. Most nucleotide replacements reduce the transcriptional yield. Mutation of nucleotides at positions −8 and −10 strongly attenuates transcription, indicating a polymerase-promoter binding mode in common with T7 RNA polymerase. Two replacements, T to G at position −17 and G to A at position +2, marginally increase RNA yield relative to the reference promoter. The resulting sequence corresponds to one of the identified Njord promoters (SEQ ID NO:17), located downstream of putative metabolic genes and directly upstream of three predicted open reading frames encoding proteins lacking known function but which are conserved among the Colwellvirinae. In this light, using a promoter sequence comprising GTTTAAGTTGCATTATAGA (SEQ ID NO: 32) with a cold-active RNA polymerase may maximize RNA yield under like circumstances.

Example 12: Transcriptional Fidelity and Co-Transcriptional Capping with Cold-Active RNA Polymerase Robust RNA synthesis at low temperature is a compelling feature of cold-active RNA polymerase and prompted a more detailed investigation into the enzyme, with attention to properties relevant for therapeutic mRNA synthesis. Transcriptional fidelity describes the selectivity of the RNA polymerase for the correctly base-paired nucleotide during transcription. A low-fidelity polymerase will produce transcripts encoding mutated proteins, with potentially dangerous consequences. We used an established Pacific Biosciences Single Molecule Real-Time (SMRT) sequencing-based assay to measure the error rates of first-strand cDNA synthesis (Sci. Rep. 12, 13017 (2022); Nucleic Acids Res. 46, 5753-5763 (2018)). This apparent error rate represents the combined errors of RNA polymerase and reverse transcriptase (RT) but allows for comparison between polymerases when the same RT is used.

Figure 3A:
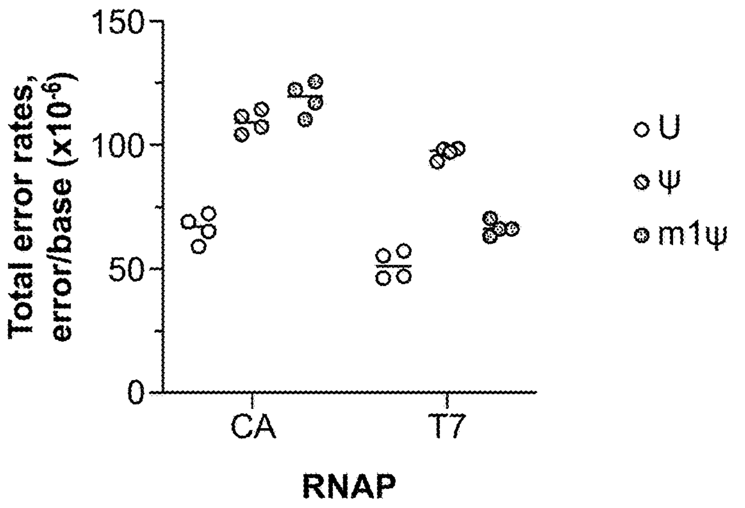
FIG. 3A and FIG. 3B show results of example error profiles in nucleotide incorporation of IVT reactions with uridine analogs. Cold-active RNA polymerase and T7 RNA polymerase incorporate uridine analogs with varying error rates during in vitro transcription. RNA transcripts produced by each enzyme were converted into cDNA with ProtoScript II reverse transcriptase and the cDNAs produced were subjected to library preparation and Pacific Biosciences SMRT sequencing.
Figure 3B:
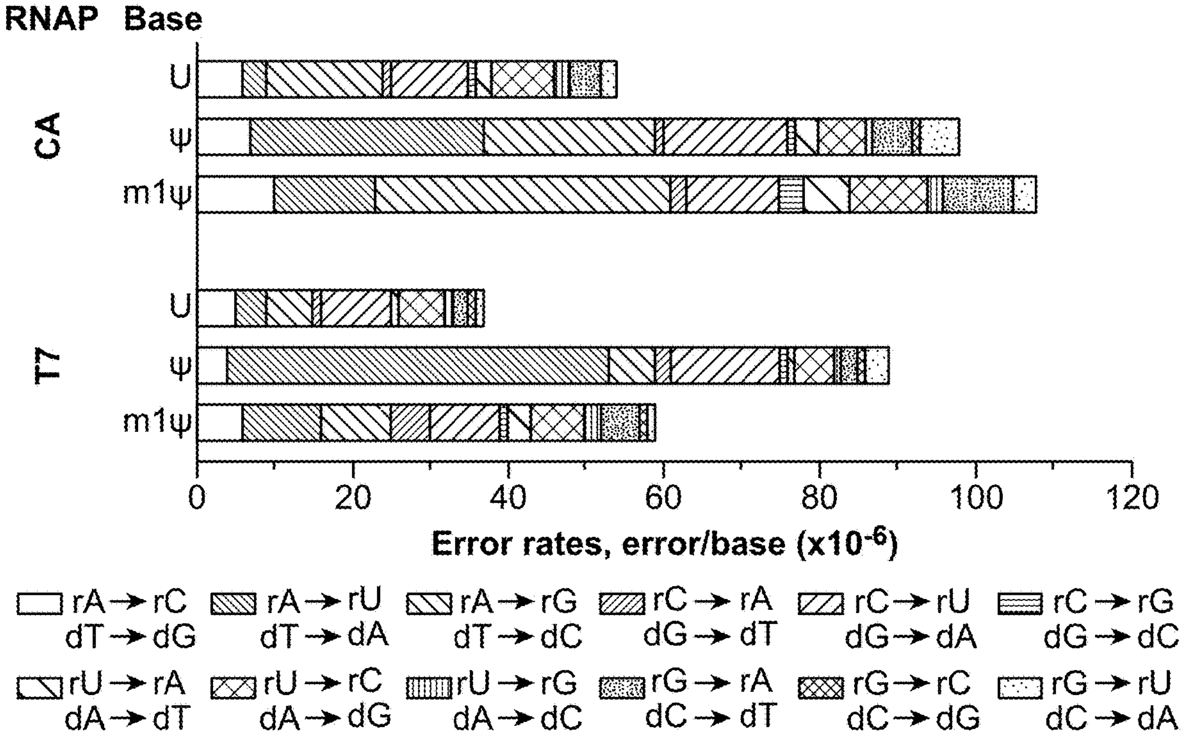

Cold-active RNA polymerase in vitro transcribed unmodified RNAs with a combined error rate of $67 \pm 8 \times 10^{-6}$ errors/base (FIG. 3A). For the ψ and m1ψ incorporation, the combined error rates were $105 \pm 6 \times 10^{-6}$ and $118 \pm 6 \times 10^{-6}$ errors/base, respectively, about 1.6-fold and 1.8-fold compared to unmodified uridine incorporation. The combined error rates of T7 RNA polymerase for unmodified and w-incorporated RNA were $51 \pm 6 \times 10^{-6}$ and $97 \pm 3 \times 10^{-6}$ errors/base, respectively, 0.8-fold compared to those of cold-active RNA polymerase. Noticeably, the combined error rate of T7 RNA polymerase for m1ψ-incorporated IVT was $66 \pm 3 \times 10^{-6}$ errors/base, about 0.6-fold compared to that of cold-active RNA polymerase. To further understand the errors when modified uridines was incorporated by cold-active RNA polymerase, we characterized the combined errors for transcripts made with all the three uridine analogs. The predominant error type was single base substitution ranging from 80% to 92%, which is comparable to T7 RNA polymerase ranging from 74% to 91%. The highest base substitution in unmodified RNA transcribed with cold-active RNA polymerase was rA-to-rG/dT-to-dC ($15 \times 10^{-6}$ errors/base) (FIG. 3B). For the modified RNA, the highest substitute error in w-incorporated RNA became rA-to-rU/dT-to-dA ($30 \times 10^{-6}$ errors/base), while the highest in mlw-incorporated transcript remained to be rA-to-rC/dT-to-dG ($38 \times 10^{-6}$ errors/base). In contrast, the highest base substitution in unmodified RNA transcribed with T7 RNA polymerase was rC-to-rU/dG-to-dT ($9\times10^{-6}$ errors/base). In both ψ- and m1ψ-incorporated RNA, the highest substitution error was rA-to-rU/dT-to-dA ($49\times10^{-6}$ and $10\times10^{-6}$ errors/base, respectively). SP6 RNA polymerase discriminates uridine and m1ψ more effectively than T7 RNA polymerase (Nucleic Acids Res. 51, 1914-1926 (2023)), a result that may be related to the reduced fidelity of incorporation of m1ψ by cold-active RNA polymerase.

Having confirmed that the fidelity of cold-active RNA polymerase is comparable to T7 RNA polymerase, the ability of the RNA polymerase to produced capped mRNA was assessed. A typical capped mRNA contains an N7-methylguanosine ($m^7G$) residue attached to the first nucleotide of the transcript with a 5'-5' triphosphate linkage. Installation of this covalent modification in therapeutic mRNAs can be accomplished by supplying the IVT reaction with short oligonucleotides which T7 RNA polymerase can use to initiate transcription. When the dinucleotide anti-reverse cap analog (ARCA, ($m_2^{7,3'\text{-}O}$G)ppp(G)) is used in molar excess of GTP in IVT reactions, the resulting mRNA may be over 70% capped. This approach was extended using trinucleotide cap analogs, including ($m^7G$)ppp(2'-OMeA)pG (Cap AG), which produce mRNA in high yield that is >90% capped.

Figure 4B:
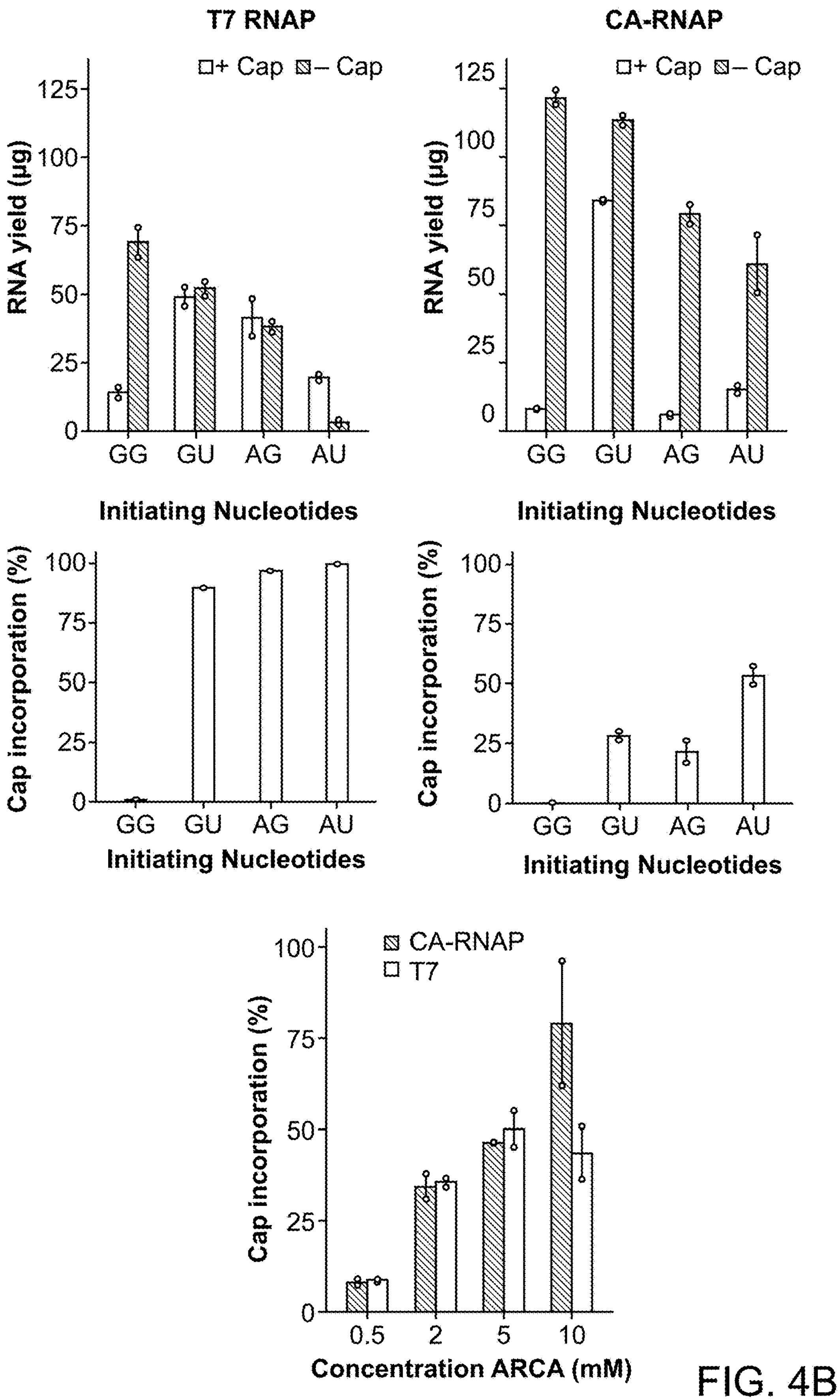

Cold-active RNA polymerase and T7 RNA polymerase were tested for their abilities to incorporate ARCA and a panel of commercially available trinucleotide cap analogs. Trinucleotide caps all contained a $m^7G$ linked by a 5'-5' triphosphate to a 2'OMe modified dinucleotide. The nucleobases of the dinucleotide portion were varied to match the +1 and +2 positions of an appropriate IVT template (FIG. 4A). Transcriptional yields were measured using these templates with and without addition of cap analogs (FIG. 4B). Inclusion of trinucleotide caps at equimolar concentration with all four NTPs tended to reduce RNA yield, except for Cap-AU which rescued the activity of T7 RNA polymerase on the T7-AU template. Strikingly and in contrast to T7 RNA polymerase, Cap-AG appeared to be a competitive transcriptional inhibitor of cold-active RNA polymerase when the AG promoter (SEQ ID NO: 45) was used.

Mass spectrometry was used to assess the 5' mRNA structure of these IVT products (FIG. 4B). An assay was employed which uses a biotinylated DNA oligo to protect the 5' mRNA end from digestion by human RNase 4 (ACS Pharmacol. Transl. Sci. 6, 1692-1702 (2023)). When only NTPs are included in IVT, the mass of the 5' mRNA fragment corresponds to the expected sequence with a 5'ppp or 5'pp group. Neither polymerase produces significant amounts of transcripts with inhomogeneous 5' ends using these promoters and initiating sequences. T7 RNA polymerase efficiently incorporates all of the cap analogs except Cap-GG and in the case of Cap-AU the proportion of capped oligo approaches 100%. This polymerase prefers to initiate from these trinucleotides when NTPs are available, whereas cold-active RNA polymerase displays the opposite behavior. Regardless of the dinucleotide combination used in this example, cold-active RNA polymerase did not incorporate the trinucleotide cap analog with the high efficiency of T7 RNA polymerase under the conditions tested. This is not the case for ARCA, which both polymerases discriminate against GTP to similar degrees (FIG. 4B). When ARCA is used in 5-fold molar excess over GTP, cold-active RNA polymerase is capable of co-transcriptional capping to ~80% efficiency, demonstrating that the polymerase is not specifically discriminating against the pre-installed $m^7G$ 5' cap. Advances made in co-transcriptional capping with T7 RNA polymerase evidently do not transfer to cold-active RNA polymerase, though there may be other cap analog oligonucleotides which function well with cold-active polymerases. These include trinucleotide cap analogs with tetraphosphate linkages, disrupted ribose rings, additional covalent modifications, longer oligonucleotides with more capping analogs, and pairing of existing trinucleotide analogs with DNA templates of different sequences.

Example 13: Analysis of Cold-Active RNA Polymerase Reaction Products

T7 RNA polymerase produces varied RNA species in addition to the desired run-off transcript, including short 'abortive' transcripts, transcripts with heterogenous 5' ends, transcripts with extended 3' ends, and even full-length antisense transcripts. Overextension of the 3' end may occur in a template-independent manner, or in a templated mechanism wherein the 3' RNA end folds on itself and primes T7 RNA polymerase for RNA-dependent RNA polymerase (RdRp) activity. This self-templated mechanism can lead to the production of immunostimulatory dsRNA species. dsRNA species are also formed via DNA-terminus initiated transcription, in which T7 RNA polymerase synthesizes an RNA fully complementary to the desired transcript and produces a long dsRNA molecule. Not all T7 homologs display these aberrant behaviors.

Figure 5A:
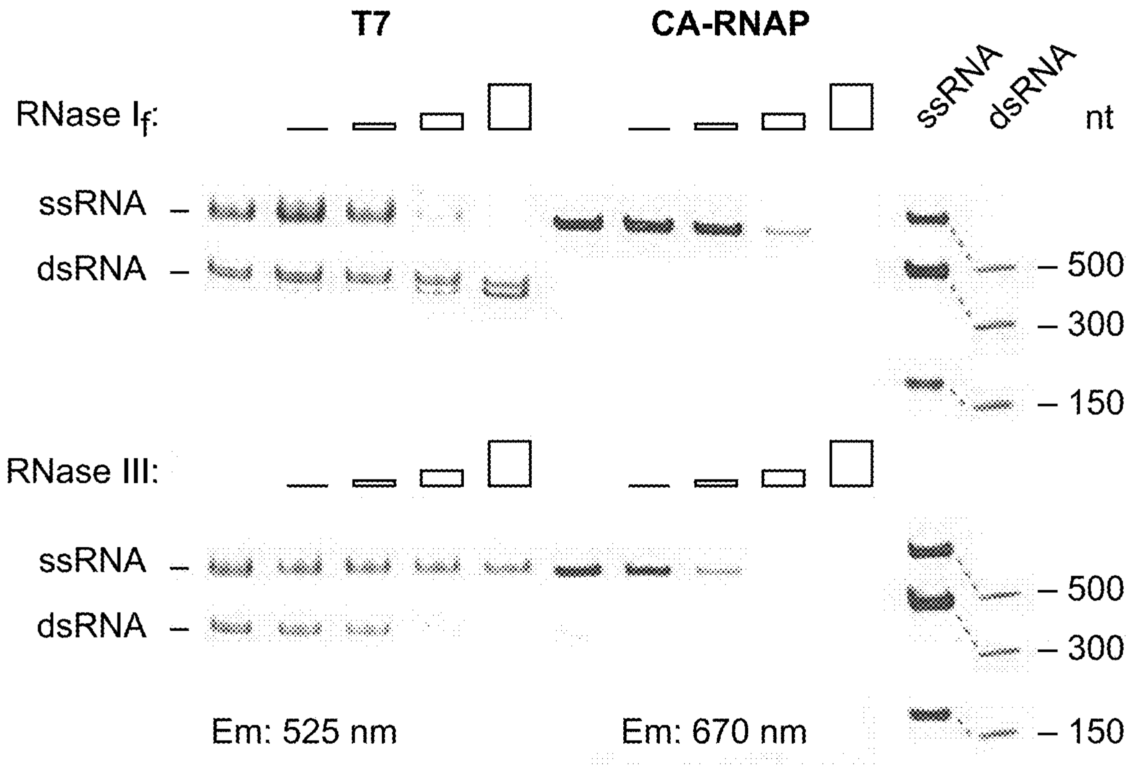
FIG. 5A and FIG. 5B show example production of double-stranded RNA by T7 and cold-active RNA polymerases.

One experiment using a model substrate was used to observe DNA-terminus initiated transcription activity and compare them between Njord and T7 promoters. DNA-terminus initiated transcription was assayed by generating IVT templates which contained either the T7 or Njord promoter at one end, and a sequence ending in a tetraguanosine tract at the other end. The terminal sequence was selected because it is known to be a substrate for promoter-independent transcription by T7 RNA polymerase. Indeed, T7 produces additional species that migrate faster in a native polyacrylamide gel electrophoresis (PAGE) than the expected 300 nt run-off transcript (FIG. 5A). The multiple fast-migrating bands can together be assigned as dsRNA of size ~300 bp by their sensitivity to RNAse III digestion, resistance to RNAse $I_f$ digestion, and ability to intercalate acridine orange dye. Cold-active RNA polymerase produces nearly undetectable levels of these dsRNA species.

Figure 5B:
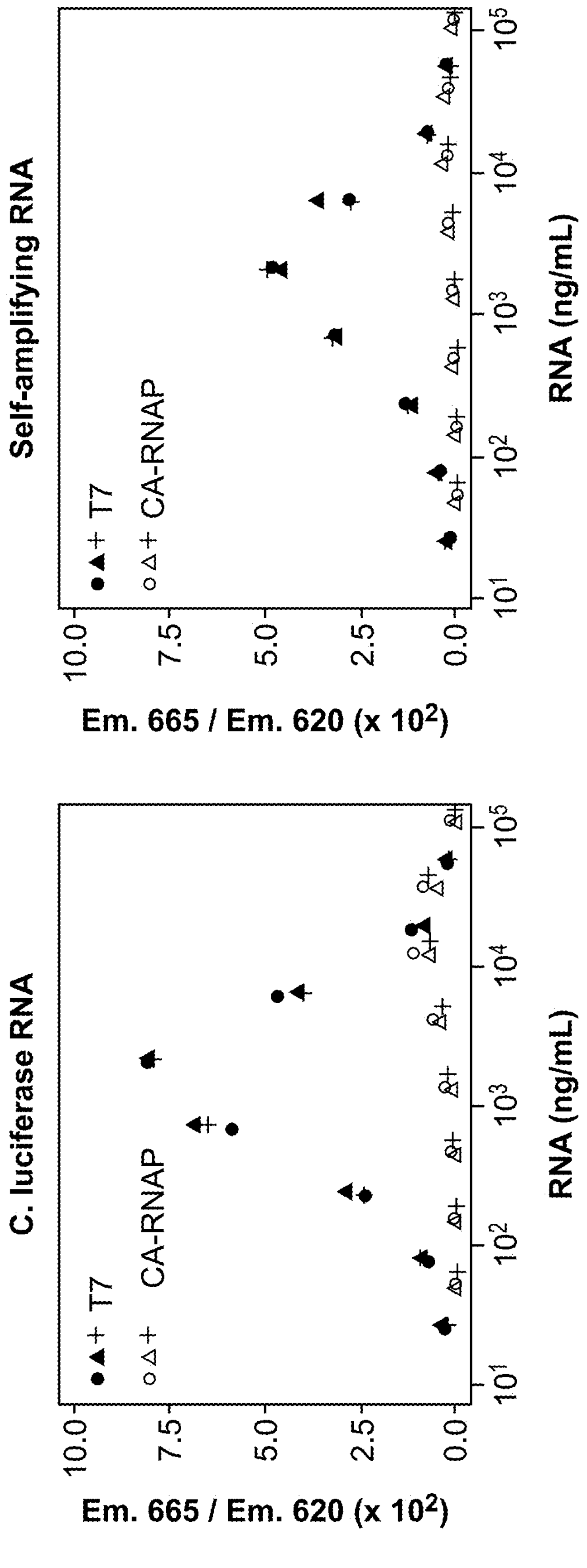

Absolute dsRNA content in IVT mRNA is typically measured using monoclonal antibodies, either in a dot-blot assay or an enzyme-linked immunosorbent assay (ELISA). Here we adapted a homogeneous time resolved fluorescence (HTRF) kit designed for quantification of dsRNA content in virus-infected cells (Anal. Biochem. 566, 46-49 (2019)). This assay uses two dsRNA-specific antibodies tagged with either a donor or acceptor fluorophore and measures fluorescence resonance energy transfer when both bind the analyte. The assay was employed for qualitative assessment of dsRNA content in IVT RNA produced by the two RNA polymerases using multiple templates. RNA produced with cold-active RNA polymerase clearly has a lower proportion of dsRNA compared to RNA produced with T7 RNA polymerase (FIG. 5B). At the maximum input of cold-active RNA polymerase the HTRF signal is low, and its response to dilution is suggestive of dsRNA species shorter than ~100 bp. These results are consistent with the absence of DNA-terminus initiated transcription activity in cold-active RNA polymerase and indicate that long dsRNA molecules may be the principle immunostimulatory species in IVT RNA, as previously suggested.

Figure 6A:
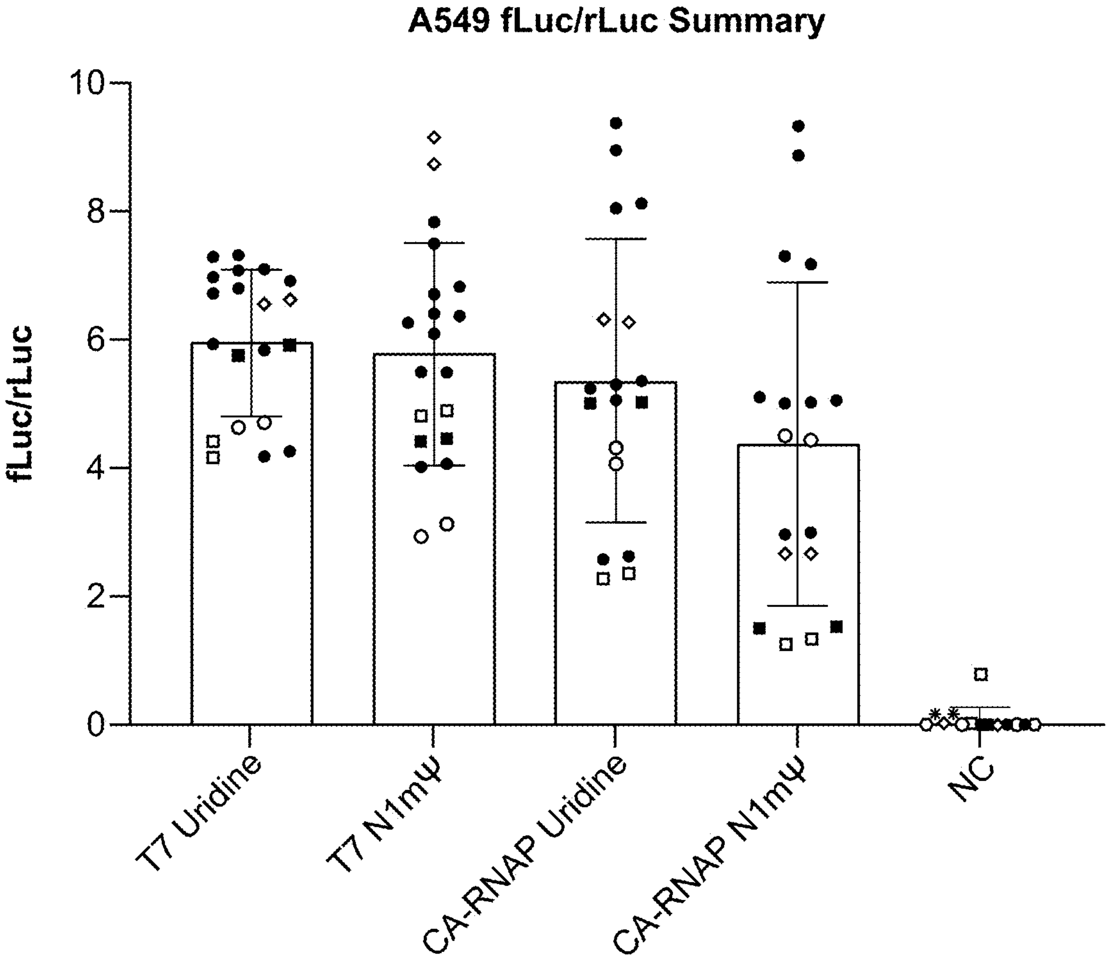
FIG. 6A and FIG. 6B shows the effect of transfection of example luciferase mRNA preparations into A549 human lung cancer cell culture. The mRNA species (SEQ ID NO: 50) were prepared by reaction of appropriate templates (T7 SEQ ID NO:92; CA-RNAP SEQ ID NO:91) with either T7 RNAP or cold-active RNAP polymerase in the presence of either unmodified uridine (U) or N1-methylpseudouridine (N1mΨ). "CA-RNAP" refers to cold-active RNA polymerase.
Figure 6B:
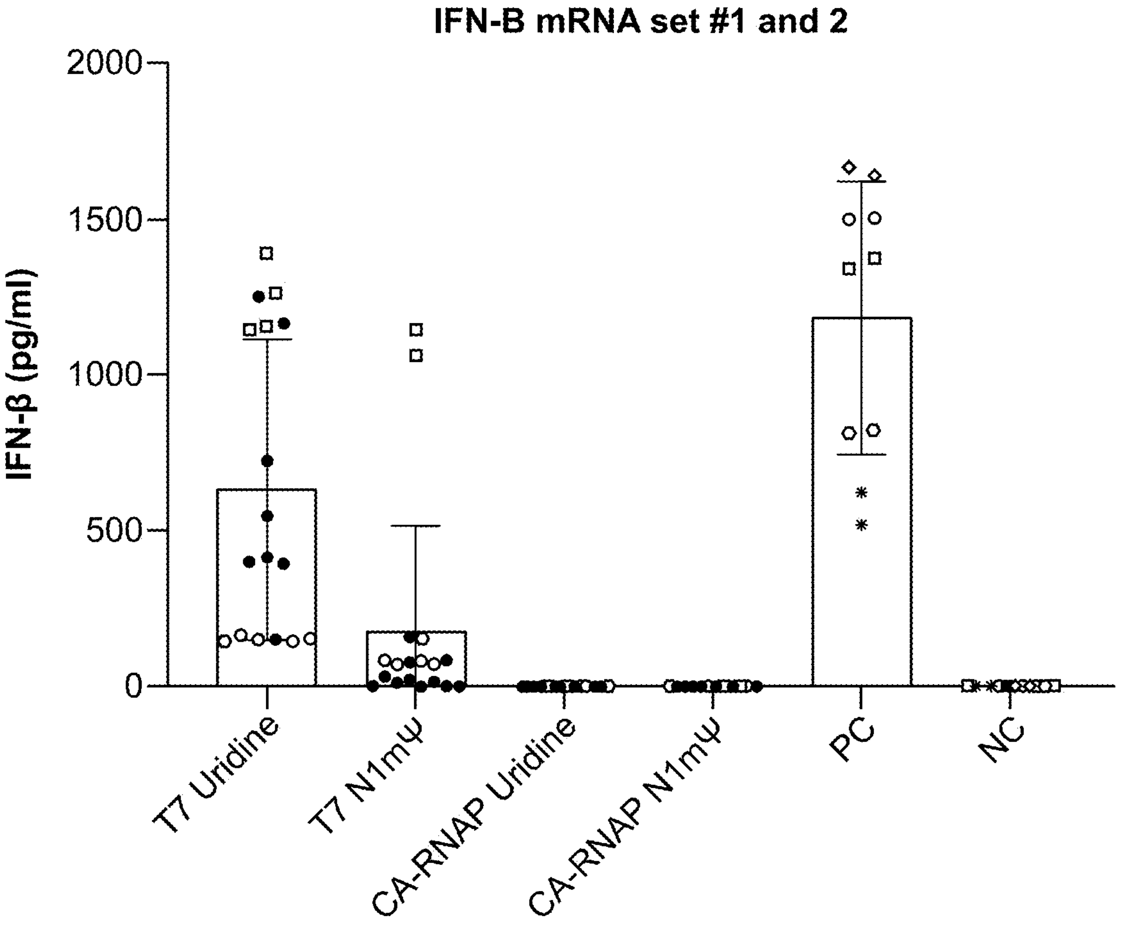

Example 14: Expression and Immunogenicity of mRNA Made by a Cold-Active RNA Polymerase in Cell Culture In mammalian cells, the innate immune system can sense dsRNA species and mount an immune response. The immune response can take different forms, including the inhibition of ribosomal translation and the production of pro-inflammatory cytokines. The low dsRNA content observed in IVT reactions suggests that cold-active RNA polymerase may be specifically well-suited for synthesizing mRNA. To test this hypothesis, mRNA encoding the firefly luciferase gene (SEQ ID NO:50) was synthesized using either T7 or cold-active RNA polymerase with unmodified uridine or N1mΨ. The mRNA was enzymatically capped using the Faustovirus capping enzyme and purified. These mRNAs were introduced into A549 cell culture by transfection with a lipid reagent, and expression of the encoded luciferase was measured alongside the degree of cytokine induction. Regardless of the polymerase or nucleotide modifications used, the expression of the luciferase mRNA relative to a standard control mRNA was comparable (FIG. 6A). This indicates that both RNA polymerases produce similar levels of translatable, in-tact mRNA. In contrast, both nucleotide modification and polymerase strongly affected the degree of cytokine induction (FIG. 6B). When N1mΨ is fully incorporated into the mRNA, the amount of interferon beta (IFN-B) excreted by the lung cancer cells is reduced, and when cold-active polymerase is used in place of T7 RNA polymerase, the IFN-β levels are below the detection limit of the assay. These results clearly demonstrate cold active RNA polymerase produces less immunostimulatory byproducts than the current state-of-the-art polymerase.

Figure 7A:
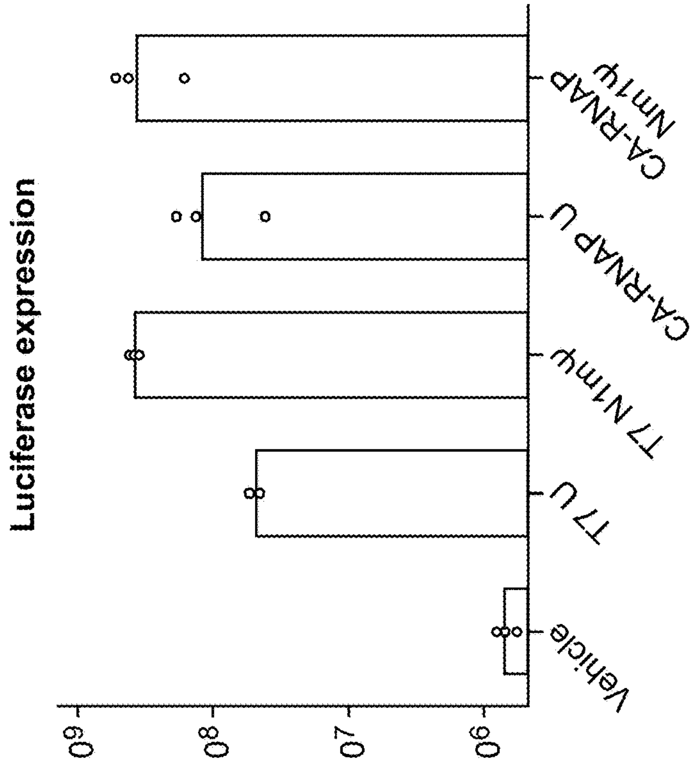
FIG. 7A and FIG. 7B illustrate the results from complexing firefly luciferase mRNA with a commercial lipid reagent and introducing the mRNA nanoparticles into mice. The mRNA species (SEQ ID NO:50) were prepared by reaction of appropriate templates (T7 SEQ ID NO:92; CA-RNAP SEQ ID NO:91) with either T7 RNAP or cold-active RNAP polymerase in the presence of either unmodified uridine (U) or N1-methylpseudouridine (N1mΨ). "CA-RNAP" refers to cold-active RNA polymerase and "Vehicle" refers to the lipid reagent without mRNA. Mice that received a lower dose of the mRNA nanoparticles were also injected with luciferin. In vivo images revealed expression in the liver.
Figure 7B:
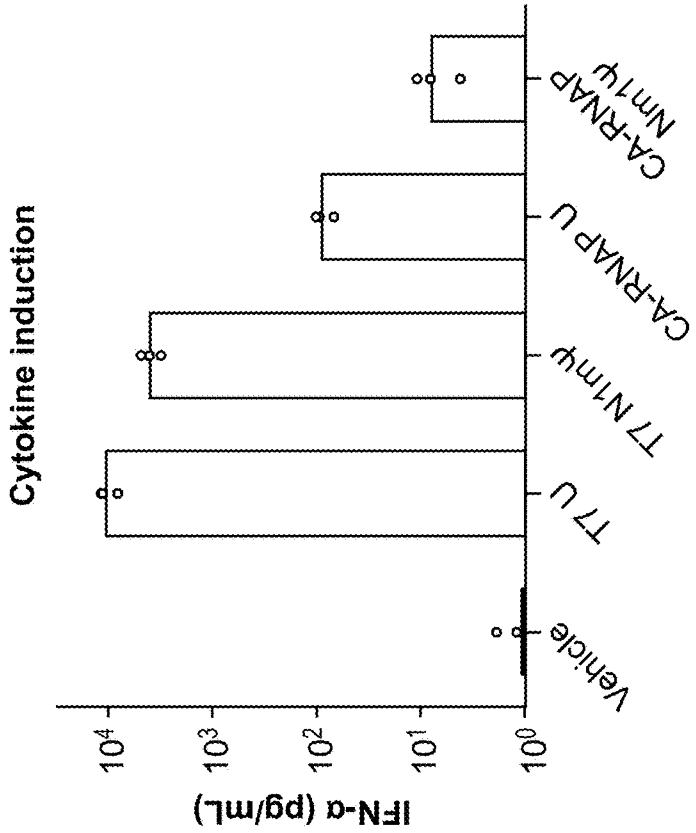

Example 15: Expression and Immunogenicity of Luciferase mRNA Made by Cold-Active RNA Polymerase in Live Mice Immunostimulatory properties of mRNA produced by the cold active RNA polymerase in cell culture motivated additional experiments in living animals. Cell culture cannot fully recapitulate the complexities of the innate immune system. Mouse models were employed to confirm the trends in cytokine induction by mRNA produced using different polymerases, with or without the modified nucleotide N1mΨ. Firefly luciferase mRNA (SEQ ID NO:49) synthesized by T7 or cold active RNA polymerases was complexed with a commercial reagent to form lipid nanoparticles containing the mRNA. These test articles were delivered to mice by injection to the dorsal tail vein at two different dosages. Six hours later, mice in the low-dose arm of the study were injected with luciferin. Localization of luciferase and the degree of its expression were quantified by in vivo imaging (FIG. 7A). All test articles localized to the liver as expected. Inclusion of N1mΨ was critical for high levels of expression regardless of the polymerase used. In the high-dose arm of the study, mice were sacrificed six hours after injection of the mRNA lipid nanoparticles, serum was collected, and levels of circulating interferon alpha (IFN-A) were measured (FIG. 7B). As in cell culture, both nucleotide modification and RNA polymerase had a significant effect on cytokine induction, with N1mΨ and the cold active RNA polymerase each independently reducing the degree of immune system stimulation. Whether or not modified nucleotides were used, replacement of T7 RNA polymerase with the cold active polymerase described here reduced IFN-A stimulation by multiple orders of magnitude. When cold active polymerase is used together with N1mΨ, IFN-A is only barely detected. These data are consistent with results from cell culture and clearly demonstrate the superiority of cold active polymerase to current methods in mRNA synthesis.

Example 16: Co-Transcriptional Capping with Cold-Active RNA Polymerase, a Capping Enzyme, and a Fusion Enzyme A cold-active RNA polymerase may be combined with a capping enzyme in an appropriate buffer containing S-adenosyl methionine (SAM) for installation and methylation of the 5' guanosine cap. To promote co-transcriptional capping, a capping enzyme may be fused to the cold-active RNA polymerase. A fusion enzyme of Faustovirus capping enzyme linked to a cold-active RNA polymerase was designed with an example linker peptide (SEQ ID NO: 20).

The fusion enzyme was overexpressed in *E. coli* cells and purified according to a miniaturized version of the method described for the cold-active RNA polymerase (Example 3). Co-transcriptional capping RNA synthesis reactions were carried out by combining the fusion enzyme in reaction buffer with an appropriate DNA template, NTPs and SAM at 25° C. RNA reactions products were purified and subjected to RNase 4 digestion. Following digestion, 5' RNA fragments were further affinity purified using a specific biotinylated oligo and analyzed by gel electrophoresis for the incorporation of the 5' guanosine cap. The protocol for measurement of 5' cap incorporation is described in greater detail in Example 7, except that here denaturing polyacrylamide gel electrophoresis is used in place of mass spectrometry to resolve the uncapped and capped 5' RNA fragments.

Figure 8:
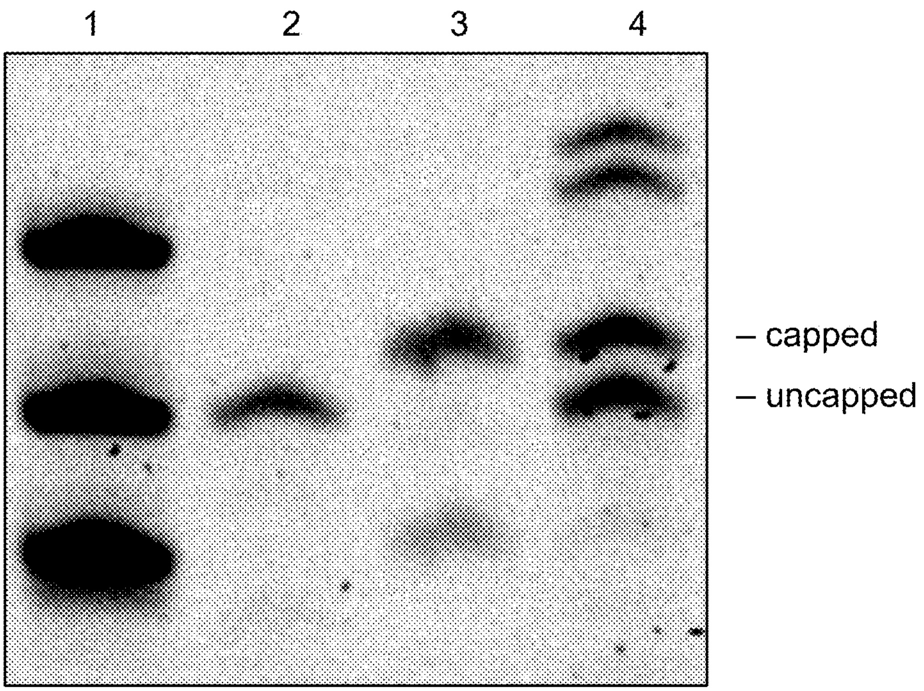
FIG. 8 shows results of an example co-transcriptional capping reaction in which either a cold-active RNA polymerase plus Faustovirus capping enzyme (FCE) or a cold-active RNA polymerase::FCE fusion was used to prepare capped RNA. Reaction products were treated with RNase 4 and loaded on a denaturing polyacrylamide gel for short RNA species. Lane 1 was loaded with a microRNA ladder (sizes 17, 21, and 25 nt). Lane 2 is the 5' fragment of an RNA species synthesized by a cold-active RNA polymerase alone; the prominent band represents the results uncapped transcript. Lane 3 is the 5' fragment of an RNA species synthesized by a cold-active RNA polymerase and subsequently reacted with a Faustovirus capping enzyme; the prominent band represents 5' N7-methylguanosine capped transcript. Lane 4 is the 5' fragment of an RNA species synthesized and co-transcriptionally capped by a cold-active RNA polymerase::FCE fusion. Bands corresponding to the uncapped product of lane 2 and the capped product of lane 3 demonstrate the fusion has capping activity, although under the specific conditions tested did not cap 100% of the available RNA.

Co-transcriptional capping by a Faustovirus capping enzyme and cold-active RNA polymerase fusion is demonstrated in FIG. 8. Lane 1 contains a set of RNA standards of size 17, 21 and 25 nucleotides. In lane 2, the 5' fragment of an RNA produce by cold-active RNA polymerase is shown. This corresponds to the region of RNA that is protected from RNase 4 by annealing with a biotinylated DNA oligo and serves as a standard for the uncapped RNA product. Similarly, the single RNA species in lane 3 was prepared by sequentially transcribing the RNA and then capping it with Faustovirus capping enzyme in separate reactions. Slower migration in the acrylamide gel reflects the addition of the 5' guanosine cap nucleotide. Co-transcriptional capping by the fusion enzyme is represented in lane 4, where both 5' uncapped and capped RNA fragments are visible. Slower-migrating bands present in lane 4 likely correspond to incomplete digestion of both capped and uncapped RNA species by RNase 4. Additional bands corresponding to larger RNA species have been omitted from FIG. 8 and these are also assigned to partially digested RNA fragments. The results shown demonstrate the ability of the fusion enzyme to perform co-transcriptional capping and to generate mRNA suitable for transfection in a mammalian cell in a single reaction.

What is claimed is:

1. A composition comprising:

a cold-active RNA polymerase having an amino acid sequence at least 95% identical to any of SEQ ID NOS: 1, 5, 6, 8-10, 12, 13, 18, and 19; and a capping enzyme, wherein the cold-active RNA polymerase is a non-naturally occurring cold-active RNA polymerase or a cold-active RNA polymerase of *Pseudomonas* phage Njord, *Pseudomonas* phage uligo, *Vibrio* phage φA318, *Vibrio* phage Vp670, *Vibrio* phage Vc1, *Vibrio* phage VEN, and the capping enzyme is a non-naturally occurring capping enzyme or a capping enzyme of Faustovirus, mimivirus, or moumouvirus.

2. A composition according to claim 1, wherein the polymerase comprises at least one conservative substitution relative to SEQ ID NO:1.

3. A composition according to claim 1, wherein the amino acid sequence of the polymerase is less than 100% identical to SEQ ID NOS: 1, 5, 6, 8-10, 12, and 13 and/or wherein the amino acid sequence of the polymerase is 100% identical to SEQ ID NO:17.

4. A composition according to claim 1, wherein the polymerase is immobilized to a support or the capping enzyme is immobilized to a support or the polymerase and the capping enzyme are each immobilized to a separate support or the polymerase and the capping enzyme are each immobilized to a common support.

5. A composition according to claim 1, wherein the polymerase and the capping enzyme are included in a fusion comprising, in an N-terminal to C-terminal direction, (a) the polymerase and the capping enzyme or (b) the capping enzyme and the polymerase.

6. A composition according to claim 5, wherein the fusion further comprises a linker between the polymerase and the capping enzyme.

7. A composition according to claim 1 further comprising one or more of:

guanosine triphosphate (GTP) or modified GTP;

a methyl group donor;

a 2' O-methyltransferase; and a buffering agent.

8. A composition according to claim 1 further comprising a polynucleotide template comprising, in a 5' to 3' direction, a promoter corresponding to the polymerase and a sequence of interest.

9. A composition according to claim 8, wherein the promoter has a nucleotide sequence according to one of SEQ ID NOS: 31-34, 35-37, and 39-41 and/or wherein the sequence of interest comprises a coding sequence.

10. A composition according to claim 1 further comprising a polyribonucleotide product of the polymerase, wherein the product has fewer double-stranded RNA molecules than a polyribonucleotide product of T7 RNA polymerase having the same nucleotide sequence.

11. A composition according to claim 1 further comprising at least one of a buffering agent and/or a polyamine.

12. A composition according to claim 11, wherein the buffering agent comprises HEPES, MES, MOPS, TAPS, tricine, Tris, ACES, ADA, BES, Bicine, CAPS, carbonic acid/bicarbonic acid, CHES, citric acid, DIPSO, EPPS, histidine, MOPSO, phosphoric acid, PIPES, POPSO, TAPS, TAPSO, or triethanolamine.

13. A composition according to claim 11, wherein the polyamine comprises spermidine, spermine, putrescine, polyethylenimine, 1,4,7-triazacyclononane, cyclen, ethylenediamine, or 1, 3, 5,-triazinane.

14. A method comprising:

(a) contacting:

(i) a composition according to claim 1;

(ii) a polynucleotide template comprising an expression control sequence of the RNA polymerase and a coding sequence encoding an artificial transcript, the coding sequence operably linked to the expression control sequence; and (iii) ribonucleotide triphosphates, to produce the artificial transcript.

15. A method according to claim 14 further comprising:

(b) contacting the artificial transcript with the capping enzyme and one or more of (i) guanosine triphosphate (GTP) or modified GTP, (ii) a methyl group donor, (iii) a 2' O-methyltransferase, and (iv) a buffering agent, to produce a capped artificial transcript.

16. A method comprising contacting:

(a) a composition according to claim 1;

(b) a polynucleotide template comprising an expression control sequence of the RNA polymerase and a coding sequence encoding an artificial transcript, the coding sequence operably linked to the expression control sequence;

(c) ribonucleotide triphosphates;

(d) guanosine triphosphate (GTP) or modified GTP;

(e) a methyl group donor;

(f) a 2' O-methyltransferase; and (g) a buffering agent, to produce the artificial transcript, wherein the artificial transcript is capped.

* * * * *

SEQUENCE LISTING

Sequence total quantity: 92
SEQ ID NO: 1 moltype = AA length = 886
FEATURE Location/Qualifiers
source 1..886
mol_type = protein
note = Pseudomonas phage Njord
organism = Uliginvirus njord
SEQUENCE: 1
MPNIETQEAL EAKMHGAGLD RFIRNNDRAI TGGSASDTDW YRRLTRQFVK PMADGIQAYL 60
DYYEGRRGKP SASLVHLRCL PTETASYIAI KTIFDGLTNP NQTAQNLSEQ IGKRIEDEVR 120
FMKLDNAAPK FIKAIKESLK RSSSQKYSHG HDVMVHAEKL LAEDKERQDK YGVMIDRHLS 180
WPDNDIFNLG SKLIELFANN MLLDGEVLIQ KRLIVRSQID RVTVIEATPA MEKWIEEYKV 240
VVGEMAPAFA PCVIKPLDWT GPRFGGWHTE KMRRQMPLAK CKQQSVLSRL TKKQMPRVYS 300
AVNALQAVEW RVNHRILSVA NEARLRGLPL ALPDREKLAT PPCPVPHMYA ELRGAELMSV 360
LSESQKEAFR TWKADAAKTY NDEAERKAKY REVCATIDQG IQYKDFDKIH FVYTLDFRGR 420
VYCQSSLISP QGGDLQKSLC QFANGMPLGE SGVHWFKVQG ANVWGWDKKQ FEERDELVMA 480
DDFVELCLDI AADPLTFTDW TQADKPWQFL AWCFEYADFV SHCETNPPET FVSRIAVAMD 540
GSCSGIQHYS AMLRDEIGGK EVNLVPGDRP QDIYGAVAKI VGRWMEDISE LQVPCESFTR 600
MLSKGAVEGQ FKLCPLEAQM LSRAWVEIGV TRSMTKKPVM TLPYGSSQMT CRESMAQYLN 660
DLQKKENEQS RAQNRKPVAV HPFNDSKGSM SRMQAELFAS GLTWEAIGHV VVAARAAMRF 720
IKKVTHETSS RNVALEWIAP TGFIVNQCIF DSTPRRVKTQ MMGETFFTIR EENPTISVNK 780
MKSSAAPNFV HSMDASHLCI AVDEFALAGI TSIAVIHDSF GTHAGNTERM RKLLINSFVD 840
MYQNHDVIRD FYEAQCERVK CDLELDLPAV GTLDLETVRH SKYIFA 886

SEQ ID NO: 2 moltype = AA length = 884
FEATURE Location/Qualifiers
source 1..884
mol_type = protein
note = Pseudomonas phage Nerthus
organism = Uliginvirus nerthus
SEQUENCE: 2
MHGAGMERFV RNNERAISAG SASDTDWFRR LTRNFVKPMA DGIQAYLDYY EGRRGRPSAS 60
LVHLRCMPTE VSSYIAIKTI FDGLMNPNQT AQNLAEQIGR RIEDEVRFTK LENAAPKYIK 120
AIKESLKRQA SQKYSHGHDV LVHAEKLLSE DQTRKDKYGV ELERFTGWSD NDIFNLGSKL 180
IELFANNMLL NGVPVIRKRN IHRSLRDEVV VIEATDAMEQ WIEEYKVVVG EMSPAYAPCV 240
VRPLDWTGPR MGGWHTEKMR RGMPLVKCRD HKVLSRLTRK QMPSVYAAVN ALQGVEWRVN 300
QRILQVANEA RLRGLPLGLP ERERLAMPPC PVPSHFAELR GKELMDVLEP EQQEAFRSWK 360
MEAAKTYNDE AERKAKYREV CATIDQGIQY QEFERIHFVY TCDFRGRVYA QSSLISPQGG 420
DLQKALCQFA NAMALGDEGE YWFKVHGANV WGWDKLPFDE RVANVSSAEF IDDCLDIAAD 480
PLTFTNWTQA DSPWQFLAWC FEYADFVSHC ETEAPETFLS RVAVAMDGSC SGIQHYSAML 540
RDEIGGKEVN LVPGDRPQDI YGAVAKIVAS WMEQIVAGTV PCESFERMLA KGDRIRTAGD 600
WESAHQAPFI LNAFEAQMIA AEWLRIGVTR SLCKKPVMTL PYGSSQMTCR ESMSQHLDQL 660
QKDENERARG QFRKAVAVHN FNDGKGSMSR QQGELFASGL TWEGIGHVVV AARAAMKFIK 720
KVTHEVGSRN TPLEWVTPTG FIVHQAIYDS TCRRVKTQMM GDTFFTLREE EPVISVNKMK 780
SSAAPNFVHS MDASHLVLAT EGFHNNAITS IAVIHDSFGT HAGNTAKLRR ILTNSFVDMY 840
QQHDVIKDFY DAQCDRVMTD LELDLPATGS LDLEAVRESK YIFA 884

SEQ ID NO: 3 moltype = AA length = 900
FEATURE Location/Qualifiers
source 1..900
mol_type = protein
note = Pseudomonas phage Alpheus
organism = Uliginvirus alpheus
SEQUENCE: 3
MLDTQLALEA KMHGAGMERF IRNNDRAIAA GAASDTDWFR RLTRNFVKPM ADGIQAYLDY 60
YEGRRGRPSA SLVHLRCMPT EVSSYIAIKC IFDGLMNPNQ TAQNLAETIG RRIEDEVRFT 120
KLENAAPKYI QAIKESLKRQ SSQKYGHGHD VMVHAEKLLS EDQTRKDKFG VDLERFVGWS 180
DNDIFNLGSK LIELFANNML LNGVPVIQKR NIHRGVRDEV VVIEATEAME QWIEEYKAVV 240
GEMSPAYAPC VVRPLDWTGP RSGGWHTPKM QRGMPLVKCR DHKVLSRLTR KQMPSVYAAV 300
NALQGVEWRV NKRILQVANE ARLRGLPLAL PAREKLATPP CPVPSMFSEL RGKELMDVLE 360
PEQQEAFKAW KMEAAKTYND EAERKAKYRE ASATIDQGLQ YQDFERMHFV YTCDFRGRVY 420
AQSSLISPQG GDLQKALCQF ANAMALGDEG EYWFKVHGAN VWGWDKKEFD ERVALVSEDS 480
FIDLCLDIAA DPLTFTDWTQ ADKPWQFLAW CLEYADFVSH CETEAPEKFL SRVAVAMDGS 540
CSGIQHYSAM LRDEVGGKEV NLVPGTTPQD IYGAVAKIVR RWMEDIVDGH VPCESFERML 600
SKAAARHKAI VEDGGVWDSA MAPPFTLNAL ESQMIATEWL RIGVTRSLCK KPVMTLPYGS 660
SQMTCRESMA QHLDSLQKDE NDKARAQFRK PTAVHNFNDG KGSMSRMQAE LFASGLTWEG 720
IGHVVVAARA AMKFIKKVTH EVSIRNVPLE HVTPTGFIVH QAIYDSTARR VKTQMMGDTF 780
FTIREENPQL SARAMKSSAA PNFVHSMDAS HLVLATEGFS NNGIHSIAVI HDSFGTHAGN 840
TAKLRKILVD SFVDMYQKHD VVKDFYEAQC DRVMADLELD LPATGTLDLE TVRESKYIFA 900

SEQ ID NO: 4 moltype = AA length = 900
FEATURE Location/Qualifiers
source 1..900
mol_type = protein
note = Pseudomonas phage Achelous
organism = Uliginvirus achelous
SEQUENCE: 4
MQDIQLALEA KMHGAGMDRF IRNNDRAIAG GSGSDTDWFR RLTRNFVKPM ADGIQAYLDY 60

-continued

```
YEGRRGRPSA SLVHLRCMPT EVSSYIAIKT IFDGLMNPNQ TAQGIAEQIG RRIEDEVRFT  120
KLENAAPKYI KAIKESLKRQ ASQKYSHGHD VLVHAEKLLS EDQARKDKFG VDLERFTGWS  180
DNDIFNLGGK LVELFANNML LNGVPVIRKR NIHRSLRDEV VVLEATEVME AWIEEYKVVV  240
GEMSPAYAPC VVRPLDWTGP RAGGWHTEKM RRGMPLVKCR DHSVLSRLTK RQMPSVYAAV  300
NALQGVQWRV NKRILQVANE ARLRALPLGI PARERLETPP CPVPSHFAEL RGQELMAVLD  360
AQQQEDFKAW KMEAAKTYND EAERKAKYRE AAATIDQGIQ YQDFEHMHFV YTCDFRGRVY  420
AQSSLISPQG GDLQKALCQF ANAMPFGASG EYWFKVHGAN VWGWDKLPFD ERVAKVNSDE  480
FLDTCLDIAA DPLTFTDWTQ ADKPWQFLAW CVEYADFVSH CETEAPETFP SRIAVAMDGS  540
CSGIQHYSAM LRDEVGGKEV NLVPGDSPRD IYGAVAKIVQ RWMEDIVEGL VPCESFERML  600
AKAEARMKIQ QSEGGSWDSI SSPPFTLNQM ESRLIAAEWL TIGVTRSLCK KPVMTLPYGS  660
SQMTCRESMS QHLSDLQKAE NEKARGQFRQ PVQMHNFNDG KGSMSRQQGE LFASGLTWEA  720
IGKVVVAARA AMQFIKKVTH EVSIRNHGLE WVTPTGFIVN QCVYDSTARR VKTQMMGETF  780
FTIREENPTV SVHKMKSSSA PNFVHSMDAS HLVLATEDFA ENGITSIAVI HDSFGTHAGN  840
TELLRKLLTD SFVDMYLEHD VIKEFYDAQC DRVLCDLELD LPATGTLDLE DVRNSKYIFA  900

SEQ ID NO: 5           moltype = AA  length = 887
FEATURE                Location/Qualifiers
source                 1..887
                       mol_type = protein
                       note = Pseudomonas phage uligo
                       organism = Uliginvirus uligo
SEQUENCE: 5
MNDMQQIQLD LEAKMHGAGL DRFVRNNDRA VNGGMGSDTD WYRRLTRQFV KPMADGIQAY  60
LDYYEGRRGK PSASLVHLRC LPTEVSSYIA IKTIFDGLTN PNQTAQNLAE QIGKRIEDEV  120
RFMKLEGAAP RFIKAIKESL KRSSSQKYSH GHDVLVHAEK LLSEDKTRQD KYGVAVDRHL  180
SWSDNDVFNL GGKLIELFAN NMLMDGEPLI QKRLIIRSAT DKVNVIESTP AMDLWVEKYK  240
VVVGEMSPAF APCVVKPLDW TGPRFGGWHT EKMRRQMPLA KCKSQAVLSR LTQKQMPTVY  300
RAVNALQAVE WRVHQQILSV ANEARLRGLP VAMPAREKLE TPPCPVPSMF NELRGAELMA  360
VLDDDQKEAF RQWKADAAKT YNDEAERKAK YREVVATIDQ GIQYKDFDRI HFVYTLDFRG  420
RVYCQSSLIS PQGGDLQKAL CQFANGMALG TEGVKWFKIQ GANVWGWDKK TFPERVRLVS  480
EGDFVELCLD IAADPLTFTD WTQADKPWQF LAWCFEYAAF VSHCETEPAE TFISRIAVAM  540
DGSCSGIQHY SAMLRDEVGG REVNLVPGDA PQDIYGAVAK IVGRWMEDIS ELQEPCESYT  600
RMLSKGALEG QFKLDPLEAQ MLARAWLNIG VTRSMTKKPV MTLPYGSSQM TCRESIAQYL  660
NDLQKKENDQ ARGQFRKPVP VHPFNETKGS MSRMQGELLA SGLTWEAIGH VVVAARAAMR  720
FIKKVTHECG IRNQHLEWVT PTGFIVNQCI FDSTARRVKT QMMGETFFTI REETKTISVN  780
KMKSSSAPNF VHSMDASHLC IAVDDLAAHG ITSIAVIHDS FGTHAGNTEL LRKLLINSFV  840
DMYLSHDVIK DFYEAQCDRM MVDLELDLPA VGTLDLETVR SSQYIFA                887

SEQ ID NO: 6           moltype = AA  length = 928
FEATURE                Location/Qualifiers
source                 1..928
                       mol_type = protein
                       note = Vibrio phage phi-A318
                       organism = Kaohsiungvirus A318
SEQUENCE: 6
MNKDLMQIQL ELEAEMHGAG ILRFEKNNQR ALESGNGSDA DWYRRLTREF VRPMADAIQA  60
YIDYYTGRRG KPSACLMHLK CLSPEAAAYI AIKTIFDGLS NHEITAQNLA NNIGRRIEDE  120
VRFTKLNNAA PKYIQAIKES LKKRNSNSYK FDHDVMVHAE KELKLLADFQ ALLGAGEEKL  180
EIMRLLSIDN DKYQHLLDKA EFAIDIDRWI PWSDNDVIQL GAKLIEIFGK NMLMDGQPLI  240
AKQVNGQGRG KTTAKIVATD ALETWIQGYK EVVGNMSPAY EPCVVPPKEW KSPFNGGYHS  300
KEVSSNLPIA KVRDKKHLRR LTRKQMPKVY QALNALQNVK WQINPSIYAI ANEIRLRELP  360
LGMPEFKKYN KPACPVPAIY SDLRGEDLMQ VLDDDQKAAF KNWKRQIASI YAKENKRKSD  420
VREVVATLDQ ANKFKDFENL HFVYTLDFRG RVYCHSSLVS PQGGDLQKAL IRFADSMPLG  480
STGAYWFKVH GANVWGWDKE TFAERVSRCE TEEFKEMCLD IAADPITFTD WTKADKPWQF  540
LAWCYEYAAL LEWIDEGNNE QDFPSHIAVA MDGSCSGIQH YSAMLRDSVG GKEVNLLPSE  600
KPQDIYGAVS KVVVEWMEAI TNNDERDCPI YDKLIDSLVA KFEKAKLTGD LESKARIMAY  660
KFCEEWLRIG VTRSMTKKPV MTLPYGSSQL TCRDSIADYL KDLQEKADNK ARARGMKAGS  720
IHAFTDSDGD LPLRDAISFA SMLTWAAIGE VVVAARAGMK YIKEVCSAIA KDNKPLEWMT  780
PTGFIVKQAV YEVKEDKRIK TQMLGETFFR TSVRTDKIDP RRMASSAAPN FVHSMDASHL  840
VLAVCAFEDN GITSIAVIHD SFGTHAGNTE LLRLHLSGSF VQMYEENDVI KDFIEYNEAL  900
ILTEIEATVP EKGELDLQEV LKSLYCFA                                     928

SEQ ID NO: 7           moltype = AA  length = 930
FEATURE                Location/Qualifiers
source                 1..930
                       mol_type = protein
                       note = Vibrio phage AS51
                       organism = Kaohsiungvirus AS51
SEQUENCE: 7
MNKDLMQIQL ELEAEMHGAG ILRFEKNNQR ALESGNGSDA DWYRRLTREF VRPMADAIQA  60
YIDYYTGRRG KPSACLMHLK CLSPEAAAYI AIKTIFDGLS NHEITAQNLA NNIGRRIEDE  120
VRFTKLNNAA PKYIQAIKES LKKRNSNSYK FDHDVMVHAE KELKLLADFQ ALLGAGEEKL  180
EIMRLLSIDN DKYQHLLDKA EFAIDIDRWI PWSDNDVIQL GAKLIEIFGK NMLMDGQPLI  240
AKQVNGQGRG KTTAKIVATD ALETWIQGYK EVVGNMSPAY EPCVVPPKEW KSPFNGGYHS  300
KEVSSNLPIA KVRDKKHLRR LTRKQMPKVY QALNALQNVK WQINPSIYAI ANEIRLRELP  360
LGMPEFKKYN KPACPVPAIY SDLRGEDLMQ VLDDDQKAAF KNWKRQIASI YAKENKRKSD  420
VREVVATLDQ ANKFKDFENL HFVYTLDFRG RVYCHSSLVS PQGGDLQKAL IRFADSMPLG  480
STGAYWFKVH GANVWGWDKE TFAERVSRCE TEEFKGVPVC LDIAADPITF TDWTKADKPW  540
QFLAWCYEYA ALLEWIDEGN NEQDFPSHIA VAMDGSCSGI QHYSAMLRDS VGGKEVNLLP  600
```

```
SEKPQDIYGA VSKVVVEWME AITNNDERDC PIYDKLIDSL VAKFEKAKLT GDLESKARIM  660
AYKFCEEWLR IGVTRSMTKK PVMTLPYGSS QLTCRDSIAD YLKDLQEKAD NKARARGMKA  720
GSIHAFTDSD GDLPLRDAIS FASMLTWAAI GEVVVAARAG MKYIKEVCSA IAKDNKPLEW  780
MTPTGFIVKQ AVYEVKEDKR IKTQMLGETF FRTSVRTDKI DPRRMASSAA PNFVHSMDAS  840
HLVLAVCAFE DNGITSIAVI HDSFGTHAGN TELLRLHLSG SFVQMYEEND VIKDFIEYNE  900
ALILTEIEAT VPEKGELDLQ EVLKSLYCFA                                   930

SEQ ID NO: 8            moltype = AA  length = 928
FEATURE                 Location/Qualifiers
source                  1..928
                        mol_type = protein
                        note = Vibrio phage Vp670
                        organism = Kaohsiungvirus Vp670
SEQUENCE: 8
MNKDLMQIQL ELEAEMHGAG ILRFEKNNQR ALESGNGSDA DWYRRLTREF VRPMADAIQA  60
YIDYYTGRRG KPSACLMHLK CLSPEAAAYI AIKTIFDGLS NHEITAQNLA NNIGRRIEDE  120
VRFTKLNNAA PKYIQAIKDS LKKRNSNSYK FDHDVMVHAE KELKLLADFQ ALLGAGEEKL  180
EIMRLLSIDN DKYQHLLDKA EFAIDIDRWI PWSDNDVIQL GAKLIEIFGK NMLMDGQPLI  240
AKQVNGQGRG KTTAKIVATD ALETWIQGYK EVVGNMSPAY EPCVVPPKEW KSPFNGGYHS  300
KEVSSNLPIA KVRDKKHLRR LTRKQMPKVY QALNALQNVK WQINPSIYAI ANEIRLRELP  360
LGMPEFKKYN KPACPVPAIY SDLRGEDLMQ VLDDDQKAAF KNWKRQIASV YAKENKRKSD  420
VREVVATLDQ ANKFKDFENL HFVYTLDFRG RVYCHSSLVS PQGGDLQKAL IRFAESMPLG  480
STGAYWFKVH GANVWGWDKE TFAERVSRCE TEEFKEMCLD IAADPITFTD WTKADKPWQF  540
LAWCYEYAAL LEWIDEGNNE QDFPSHIAVA MDGSCSGIQH YSAMLRDSVG GKEVNLLPSD  600
KPQDIYGAVS KVVVEWMEAI TNNDERDCPI YDKLIDSLVS KFEKAKLTGD LESKARIMAY  660
KFCEEWLRIG VTRSMTKKPV MTLPYGSSQL TCRDSIADYL KDLQEKADNK ARARGMKAGS  720
IHAFTDSDGD LPLRDAISFA SMLTWSAIGE VVVAARAGMK YIKEVCTAIA KDNKPLEWMT  780
PTGFIVKQAV YEVKEDKRIK TQMLGETFFR TSVRTDKIDP RRMASSAAPN FVHSMDASHL  840
VLAVCAFEDN GITSIAVIHD SFGTHAGNTE LLRLHLSGSF VQMYEENDVI KDFIEYNEAL  900
ILTEIEATVP EKGELDLQEV LKSLYCFA                                     928

SEQ ID NO: 9            moltype = AA  length = 914
FEATURE                 Location/Qualifiers
source                  1..914
                        mol_type = protein
                        note = Vibrio phage Vc1
                        organism = Jhansiroadvirus gwaliVC1
SEQUENCE: 9
MKDLHAVQIE LEEEMHGAGI LRFTKNNQRS IDSGQAGETD WFRRLTREFV RPMADAIDAY  60
KDYYAGRRGK PSATIGHLKC ISSEAAGYIA IKTIFDSMAG HTTSAQALAN HIGRRIEDEI  120
RFTKLSEAAP EYIGAIKESL KKRSNQSYKF EHDSLVHAEK ELKMLSDFQA LHNGGVDKQE  180
IMRLLGADEE KYKALLEKVE YAIDFDRWIP WAQNDVLQLG AKMIDIFANN MLLNGKPVVE  240
RVTISTGTAS NRQTPAAIVP TESLEAWVEE YKQVMGSIAP AYEPCVVPPR PWKSPFNGGY  300
HSKKVSSRLN MVKCPDKKHL KRLSRSQMPK VYEAVNALQE VKWQIHPSVL AVANEIRLRG  360
LPLGMPRMDK ADKPICPVPA IYSELRGAEL MACLDEDQKE AFLKWKRDTV AYYASEQKRR  420
SDVRETIATI DQGLKFKDYE ALHYVYTLDF RGRVYAQGSL ISPQGGDLQK GLIRFAEAYP  480
LGEKGAYWFK VQGANVWGWD KEIFDERVSR CETEEFKDMC LDIAADPISF TDWTKADKPW  540
QFLAWCFEYA ALLEWIDEGN DESDFLSHVA VAMDGSCSGI QHYSAMLRDS VGGKEVNLLP  600
SDKPQDIYGA VANIVRGWME SVIDDYTQDV PMWDKIEEKF GAVKGYKFAE EWLRVCVTRS  660
MTKKPVMTLP YGSSQLTCRD SMDDYLSDLQ SKADKKALAT GMATGNIHNF TDKDGDLPRN  720
EAVSYASMMT WKAIGEVVIA ARAAMKYIKE VTKVVAELGE SLEWTTPLGF IVKQSVFEVR  780
EDKQVFTNML GGCKFRVKEI TDKIDARRMG SSCAPNFVHS MDASHLLLAT TYFSRAGIKA  840
IAVIHDSFGT HAGKTEELRS LLINSFVDMY LEHDVITNFK EENEERLMIE IDVEIPEQGD  900
LDLEEVRLSP YCFA                                                    914

SEQ ID NO: 10           moltype = AA  length = 921
FEATURE                 Location/Qualifiers
source                  1..921
                        mol_type = protein
                        note = Vibrio phage Ven
                        organism = Trungvirus VEN
SEQUENCE: 10
MKDLLQVQLE HEAEMHGAGI LRFEKNNQRN LDSGNASDAD WYRRLTREFV RPMADAIDAY  60
KSYYEGRRGK PSACLSHLRC LSSEKAAYIA MKVIFNSLHG DKIPAQVLAN NIGRSIEDEV  120
RFTKLEDVAP AYISAIKDSL KKRSSKSQKF EHDSMVHAEK EVVLFSHFCK LLDNGYTSEK  180
VKELLGINKE KFEHLSQKRE RAKEASTNDE YVVDFDRWVA WPVNDVLQLG AKMIDIFANN  240
ILLEGQPIIE KVNISSGKGR AKNTPAAIVP TEATEKWIDG YKEVMGNMAP AFEPCVVKPR  300
DWTSPFNGGY HSKEVSSKLH IAKVKNKQHL KRLTQKQMPK VYKALNALQS VRWQIHPSVL  360
DAANQILLRG LPLGMPSTHK PKKPVCPVPA IYADLRGEEL MAMLDEEQKE AFFQWKRDTV  420
AYYTNEQKRK ADVREAKATL DQANKFSKFE ELFFVYTLDF RGRVYAQGSL VSPQGGDLQK  480
ALIRFAEAKP LGATGEYWFK VQGANVWGWD KETFAERVSR CETEEFTEMC LDIAADPITF  540
TDWTKADKPW QFLAWCYEYA AYLEWLEDGK DGKDFPSHVA VAMDGSCSGI QHYSAMLRDS  600
VGGKEVNLLP SDKPQDIYGA VSNLVVEWME AIIDSKESDC PIWDKLEEKY GPVSCYKFAE  660
EWLRLGVNRS MTKRSVMTLP YGSSQLTCRD SIDDYLKDLQ SKADKKALAS GQAVGTIHRF  720
DKDLPMKDAI SFASMLVWRA IGEVVVAARE GMAYIKAMSN AVSSLNKPME WVTPTGFIVL  780
QEVFTVTDDK QVFTSMMGNC KFRIKEETTT IDKTRMASSS APNFVHSMDA SHLLLSVLAF  840
ADNGIDSIAV IHDSFGTHAC DTEKLRGLLS GAFVKMYEEN DVILQFKEHN EDVLLTVFEV  900
DLPTKGNLDL QEVLVSSYCF A                                            921
```

-continued

```
SEQ ID NO: 11          moltype = AA  length = 912
FEATURE                Location/Qualifiers
source                 1..912
                       mol_type = protein
                       note = Marinomonas phage CPP1m
                       organism = Murciavirus CPP1m
SEQUENCE: 11
MTELYSKQLG IEMEMHGAGI ARFEKANQRN LEAGQASETE WNRRILRELV KPMSDALEAY  60
IDYYENNAGR MSHSIHYMKC LPPQAASYIT IKSVMDNLSG GFIKTRELVM DIAKRIEDEV  120
RFTRLEDTQP KYIKAIKEGL KKRASKSYKF EHDSMVHAER ELALLGHFSK LDAAGVDKEE  180
IKRILSLDED KYKALYSKRE YAVDFDRWVA WPDNHLLLLG ANMLEIFTEN MTLNGNSLIV  240
KENVRDNSKA GVQVLSLIRA SDYLNEWVEE YKEAMADMYP TFAPCVIPPR DWESATDGGY  300
HTREVGSKVN LVKIRDKKHL AKLTKEQMPA IYKAVNGLQS VKWAINSEIL EIAKEIRSRS  360
LPLGMPSMKK TDPPVCPVPE VLSDLRGEEL KRALSTGQWE EFKKWKHSMA AYHTAEVKRS  420
STIREITSTL DIATKYVEFD SLHFVYTLDF RSRFNAQSTY LTPQGGDLQK SLIRFRKKEK  480
LGKDDGEFWF LVQGANVWGW DKEEFKERVR LAEAEEFQAM CLDIAADPTT FVEWTAAEKP  540
WQFLSWCLEY AKLIEWKEEG NDACEFKSFS IVAMDGSCSG IQHYSGMLRD EVGGKEVNLV  600
PSNKPQDIYR AVSDVALGHM EAIMDFRERD VPNWPAIKDK YGYVKAVELS KGWIETGVTR  660
SLSKKPVMTM PYGSSPRTCY QAVQDYLHDI DAKERKKVLA QGLEYKKMTK FSENLDQKEI  720
TSFASSLVWS SIGEVVVAAR AGMKFIKQVT GKVSASNKPL VWTTPTGFIV KQAIYVVDSN  780
NRVNTKLMGG TSFRDYRETK QINATKMASS AAPNFIHSMD ASHLCFAVNG FIDAGIADIA  840
VIHDSFGTHA CHTKKARSIL NNTFVDMYQE NDVIAGFKEA AEGQIKDKID VELPEYGTLD  900
LEVVRDSEYL FG                                                    912

SEQ ID NO: 12          moltype = AA  length = 912
FEATURE                Location/Qualifiers
source                 1..912
                       mol_type = protein
                       note = Marinomonas phage CB5A
                       organism = Murciavirus CB5A
SEQUENCE: 12
MTELYSKQLE IEMEMHGAGI ARFEKANQRN LEAGQASETE WNRRILRELV KPMSDALEAY  60
IDYYENNAGR MSHSIHYMKC LPPQAASYIT IKSVMDHLSG GFIKTRELVM DIAKRIEDEV  120
RFTRLEDTQP KYIKAIKEGL KKRASRSYKF EHDSMVHAER ELALLGHFSK LDAAGVDKEE  180
IKRILSLDED KYKVLYSKRE YAVDFDRWVA WPDNHLLLLG ANMLEIFTEN MTLNGNPLIV  240
KENVRDNSKA GVQVLSLIRA SDYLNEWVEE YKEAMADMYP TFAPCVIPPR DWESATDGGY  300
HTREVGSKVN LVKIRDKKHL AKLTKEQMPA IYKAVNGLQS VKWAINSEIL EIAKEIRSRS  360
LPLGMPSMKK TDPPVCPVPE VLSDLRGEEL KRALSTGQWE EFKKWKHSMA AYHTAEVKRS  420
STIREITSTL DIATKYVEFD SLHFVYTLDF RSRFNAQSTY LTPQGGDLQK SLIRFRKKEK  480
LGKDDGEFWF LVQGANVWGW DKEEFKERVR LAEAEEFQAM CLDIAADPTT FVEWTAAEKP  540
WQFLSWCLEY AKLIEWKEEG NDACEFESFS IVAMDGSCSG IQHYSGMLRD EVGGKEVNLV  600
PSNKPQDIYR AVSDVALGHM EAILDFRERD VPNWPAIKDK YGYVKAVELS KGWIETGVTR  660
SLSKTPVMTM PYGSSPRTCY QAVQDYLHDI DAKERKKVLA QGLEYKKMTK FSENLDQKEI  720
TSFASGLVWS SIGEVVVAAR AGMKFIKQVT GKVSASNKPL VWTTPTGFIV KQAIYVVDSD  780
NRVNTKLMGG TSFRDYRETK QINATKMASS AAPNFIHSMD ASHLCFAVNG FIDAGIADIA  840
VIHDSFGTHA CHTKKARSIL NNTFVDMYQE NDVIAGFKEA AEGQIKDKID VELPEYGTLD  900
LEVVRDSEYL FG                                                    912

SEQ ID NO: 13          moltype = AA  length = 895
FEATURE                Location/Qualifiers
source                 1..895
                       mol_type = protein
                       organism = synthetic construct
SEQUENCE: 13
MLETQLILES KMHGAGMERF VRNNDRAINA GAASETDWFR RLTRNWVKPM ADGIQAYLDY  60
YEGRRGRPSA SLVHLRCLPT EVASYIAIKT IFDGLRDPSM TAQNLAERIG RRIEDEVRFT  120
KLETAAPKYI KAIKESLKRK ASQKYSHGHD VLVHAEKLLS EDQSRKDKFG VEMTRFEGWA  180
ENDIFNLGSK LIELFANNML LNGVPVIRKR NIHRSLRDEI VIIEATEAME AWIEEYKVVI  240
GEMSPSYAPC VVRPLDWTGP RMGGWHTEKM RRGMPLVKCN DHKVLSRLTK AQMPSVYAAV  300
NALQGVEWRV NKRILQVANE ARLRGLPLAI PARERFEMPP CPVPSHFSAL RGAELMDALE  360
PVQQEAFRAW KMEAAKTHND EAERKAKYRS VSATIDQGIQ YQDFERLHFV YTCDFRGRVY  420
AQSSLISPQG GDLQKALCQF ANGMELGDSG EYWFKVHGAN VWGWDKKEFD ERVSLVSEQS  480
FIDDCLDIAA DPLTFTDWTQ ADSPWQFLAW CFEYADFVSH CETSPAEKFI SRVAVAMDGS  540
CSGIQHYSAM LRDEIGGKEV NLVPSDRPQD IYGAVAKIVA RWMEDIVEGK VPCESFERML  600
TKGEKLLSNS EWSAAQQAPF VLNAFESQMI AAEWLRIGVT RSLCKKPVMT LPYGSSQMTC  660
REAMSQHLEQ LQKDENEKAR GQFRKPAMMH GFNDGKGSMS RQQAELFASG LTWEAIGDVV  720
VAARAAMTFI KKVTHEVSQR NTALEWATPT GFIVHQSIFD TTCRRVKTQM MGDTFFTLRE  780
ETPVISVNKM KSSAAPNFVH SMDASHLVLA VEGFSNNAIH SIAVVHDSFG THAGNTAKLR  840
SILSNSFVDM YQKHDVVKDF YDQQCDRVMC DLELDLPATG SLDLEAVRTS KYMFA      895

SEQ ID NO: 14          moltype = AA  length = 895
FEATURE                Location/Qualifiers
source                 1..895
                       mol_type = protein
                       organism = synthetic construct
SEQUENCE: 14
MLDTQLTLEA KMHGAGMERF VRNNERAISG GAASDTDWFR RLTRNFVKPM AEGIQAYLDY  60
YEGRRGRPSA SLVHLRCMPT EVSSYIAIKT IFDGLMNPNQ TAQNLAEQIG RRIEDEVRFT  120
KLENAAPKYI KAIKESLKRN ASQKYSHGHD VLVHAEKLLS EDQARKDKYG VDLERFTGWS  180
```

```
DNDIFNLGGK LIELFASNML LNGVPVIRKR NIHRSLRDEV VVIEATEAME QWIEEYKVVI  240
GEMSPAYAPC VVRPLDWTGP RMGGWHTEKM RRGMPLVKSR DHKVLSRLTK AQMPAVYAAV  300
NALQGVEWRV NQRILQVANE ARLRGLPLAM AAREKVETPP CPVPSHFADL RGSELMEVLE  360
PEQQEAFKKW KMEAAKAYNA EAERKAKYRE DSATIDQGIQ YQEFERMHFV YTCDFRGRVY  420
AQSSLISPQG GDLQKALCQF ANGMALGDTG EYWFKVHGAN VWGWDKKEFD ERVQLVSEAD  480
FIDRCLDIAA DPLTFTEWTQ ADSPWQFLAW CFEYADFVSH CETSPAEKFI SRVAVAMDGS  540
CSGIQHYSAM LRDEIGGKEV NLVPSDRPQD IYGAVAKIVA RWMEDIVEGK VPCESFERML  600
AKGERILTTG DWTAAHQAPF VLNAFESQMI AAEWLRIGVT RSLCKKPVMT LPYGSSQMTC  660
RESMGQHLDA MQKEENEKAR GQFRKPVAMH NFTDGKGSMS RQQAELFASG LTWEGIGHVV  720
VAARAAMTFI KKVTHEVGSR NHALEWVTPT GFIVRQSIFD STCRRVKTQM MGETFFTIRE  780
ETPVIAVAKM KASAPPNFVH SMDASHLVLA TEESSNNAIH SLAVVHDSFG THAGNTAKLR  840
SILANTFVDM YLQHDVIKDF YDAQCDAVMV DLELDLPATG TLDLEAVRTS KYLFA       895

SEQ ID NO: 15          moltype = AA  length = 895
FEATURE                Location/Qualifiers
source                 1..895
                       mol_type = protein
                       organism = synthetic construct
SEQUENCE: 15
MLDTQLTLEA KMHGAGMERF VRNNERAISG GAASDTDWFR RLTRNFVKPM AEGIQAYLDY  60
YEGRRGRPSA SLVHLRCMPT EVSSYIAIKT IFDGLMNPNQ TAQNLAEQIG RRIEDEVRFT  120
KLENAAPKYI KAIKESLKRN ASQKYSHGHD VLVHAEKLLS EDQARKDKYG VDLERFTGWS  180
DNDIFNLGGK LIELFASNML LNGVPVIRKR NIHRSLRDEV VVIEATEAME QWIEEYKVVI  240
GEMSPAYAPC VVRPLDWTGP RMGGWHTEKM RRGMPLVKSR DHKVLSRLTK AQMPAVYAAV  300
NALQGVEWRV NKRILQVANE ARLRGLPLAM AAREKVETPP CPVPSHFADL RGSELMEVLE  360
PEQQEAFKKW KMEAAKAYNA EAERKAKYRE DAATIDQGIQ YQEFERMHFV YTCDFRGRVY  420
AQSSLISPQG GDLQKALCQF ANGMALGDTG EYWFKVHGAN VWGWDKKEFD ERVQLVSEAD  480
FIDRCLDIAA DPLTFTEWTQ ADSPWQFLAW CFEYADFVSH CETSPAEKFI SRVAVAMDGS  540
CSGIQHYSAM LRDEIGGKEV NLVPSDRPQD IYGAVAKIVA RWMEDIVEGK VPCESFERML  600
AKGERILTTG DWTAAHQAPF VLNAFESQMI AAEWLRIGVT RSLCKKPVMT LPYGSSQMTC  660
RESMGQHLDA MQKEENEKAR GQFRKPVAMH NFTDGKGSMS RQQAELFASG LTWEGIGHVV  720
VAARAAMTFI KKVTHEVGSR NHALEWVTPT GFIVRQSIFD STCRRVKTQM MGETFFTIRE  780
ETPVIAVAKM KASAPPNFVH SMDASHLVLA TEESSNNAIH SLAVVHDSFG THAGNTAKLR  840
SILANTFVDM YLQHDVIKDF YDAQCDAVMV DLELDLPATG TLDLEAVRTS KYLFA       895

SEQ ID NO: 16          moltype = AA  length = 895
FEATURE                Location/Qualifiers
source                 1..895
                       mol_type = protein
                       organism = synthetic construct
SEQUENCE: 16
MGSSHHHHHH PNIETQEALE AKMHGAGLDR FIRNNDRAIT GGSASDTDWY RRLTRQFVKP  60
MADGIQAYLD YYEGRRGKPS ASLVHLRCLP TETASYIAIK TIFDGLTNPN QTAQNLSEQI  120
GKRIEDEVRF MKLDNAAPKF IKAIKESLKR SSSQKYSHGH DVMVHAEKLL AEDKERQDKY  180
GVMIDRHLSW PDNDIFNLGS KLIELFANNM LLDGEVLIQK RLIVRSQIDR VTVIEATPAM  240
EKWIEEYKVV VGEMAPAFAP CVIKPLDWTG PRFGGWHTEK MRRQMPLAKC KQQSVLSRLT  300
KKQMPRVYSA VNALQAVEWR VNHRILSVAN EARLRGLPLA LPDREKLATP PCPVPHMYAE  360
LRGAELMSVL SESQKEAFRT WKADAAKTYN DEAERKAKYR EVCATIDQGI QYKDFDKIHF  420
VYTLDFRGRV YCQSSLISPQ GGDLQKSLCQ FANGMPLGES GVHWFKVQGA NVWGWDKKQF  480
EERDELVMAD DFVELCLDIA ADPLTFTDWT QADKPWQFLA WCFEYADFVS HCETNPPETF  540
VSRIAVAMDG SCSGIQHYSA MLRDEIGGKE VNLVPGDRPQ DIYGAVAKIV GRWMEDISEL  600
QVPCESFTRM LSKGAVEGQF KLCPLEAQML SRAWVEIGVT RSMTKKPVMT LPYGSSQMTC  660
RESMAQYLND LQKKENEQSR AQNRKPVAVH PFNDSKGSMS RMQAELFASG LTWEAIGHVV  720
VAARAAMRFI KKVTHETSSR NVALEWIAPT GFIVNQCIFD STPRRVKTQM MGETFFTIRE  780
ENPTISVNKM KSSAAPNFVH SMDASHLCIA VDEFALAGIT SIAVIHDSFG THAGNTERMR  840
KLLINSFVDM YQNHDVIRDF YEAQCERVKC DLELDLPAVG TLDLETVRHS KYIFA       895

SEQ ID NO: 17          moltype = AA  length = 952
FEATURE                Location/Qualifiers
source                 1..952
                       mol_type = protein
                       note = B=D or N, J =I or L, Z = Q or X= any residue
                       organism = synthetic construct
SEQUENCE: 17
MXXXXXXXQX XXEXXMHGAG XXRFXXXNXR XXXXGXXXXX XWXRRJXRXX VXPMXXXJXA  60
YXXYYXXXXG XXSXXJXXXX CXXXZXXXYI XXKXXXBXXX XXXXXXXXJX XXIXXXIEDE  120
XRFXXLXXXX PXXIXAIKXX LKXXXXXXXX XXHDXXVHAE XXXXXXXXXX XXXXXXXXXX  180
XXXXJLXXBX XXXXXXXXXX XXXXXXXXXX XXXXXXXRXX XWXXNXXXXL GXXXXXJFXX  240
NXXXXGXXXX XXXXXXXXXX XXXXXXXXJX XXXXXXXWXX XYKXXXXXXX PXXXPCVXXP  300
XXWXXXXXGG XHXXXXXXXX XXXKXXXXXX LXXLXXXQMP XXYXAXNXLQ XVXWXXXXXX  360
XXXAXZXXXR XLPXXXXXXX XXXXPXCPVP XXXXXLRGXX LXXXLXXXQX XXFXXWKXXX  420
XXXXXXEXXR XXXXRXXXXT JDXXXXXXXX XXXXXVYTXD FRXRXXXXXX XXXPQGGDLQ  480
KXLXXFXXXX XXGXXXGXXW FXXXGANVWG WDKXXFXERX XXXXXXXFXX XXXCLDIAAD  540
PXXFXXWTXA XXPWQFLXWC XEYAXXXXXX XXXXXXXXFX SXXXVAMDGS CSGIQHYSXM  600
LRDXXGGXEV NLXPXXXPXD IYXAVXXXXX XXMEXXXXXX XXXXXXXXXX XXXXXXXXXX  660
XXXXXXXXXX XXXXXXXXXX XXXXXXXXXW XXXXVXRSXX KXXVMTXPYG SSXXTCXXXX  720
XXXLXXXXXX XXXXXXXXXX XXXXXXXFXX XXXXXXXXXX XXXASXXXWX XIGXVVXAAR  780
XXMXXIKXXX XXXXXXXXXX XXXXPXGFIV XQXXXXXXXX XXXXTXXXGX XXFXXXXXXX  840
XXXXXXMXXS XXPNFXHSMD ASHLXXXXXX XXXXXIXXJA VXHDSFGTHA XXTXXXRXXL  900
```

```
XXXFVXMYXX XDVXXXFXXX XXXXXXXXXX XXXPXXGXLD LZXVXXSXYX FX         952

SEQ ID NO: 18          moltype = AA  length = 880
FEATURE                Location/Qualifiers
source                 1..880
                       mol_type = protein
                       organism = synthetic construct
SEQUENCE: 18
MEDLMEVQLE LEAEMHGAGI ERFEKNNQRA IDSGSASDTD WYRRLTREFV KPMADGIQAY  60
LDYYEGRRGR PSASLTHLKC LPPEAAAYIA IKTIFDSLSN HNITAQNLAN NIGRRIEDEV  120
RFTKLEDAAP KYIKAIKESL KRRSSQSYKH EHDVMVHAEK KLAEDKERKD EYAVDIDRWV  180
SWPDNDVLHL GSKLIEIFAN NMLLDGEPVI QKQNISTGGR KTVAVIAPTE ALEEWIEEYK  240
EVMGEMSPAY APCVVPPRDW TSPTNGGYHT EEVSSKLPLV KCRDKKHLRR LTRKQMPKVY  300
KAVNALQAVK WQINERILAV ANEVRLRGLP LGMPSREKLD KPPCPVPEMF SDLRGEELMA  360
ALDPDQWEAF KEWKREAAKT YNDEQERKSK FREVVATLDQ ANKYKDFDSI HFVYTLDFRG  420
RVYCQSSLVS PQGGDLQKAL IRFADGMPLG EEGEYWFKVH GANVWGWDKK PFDERVSLVS  480
EEEFTEMCLD IAADPITFTD WTKADKPWQF LAWCFEYADL LEWIEEGNNP EDFVSHIAVA  540
MDGSCSGIQH YSAMLRDSVG GKEVNLVPSD KPQDIYGAVA KVVVKWMEAI VDGNERDANF  600
EKLEEKLNPV KAQKLAKEWL RIGVTRSLTK KPVMTLPYGS SQLTCRESVS DYLKDLQKKE  660
NKKARAQGRE PKKVHPFNDK DGSMPLKEAE SFASGLTWES IGEVVVAARA GMKFIKEVTN  720
EVAKANKPLE WTTPTGFIVK QAIYETESRR VKTQMMGGTF FTIREETDKI DVRKMKSSAA  780
PNFVHSMDAS HLVLAVNGFA DNGITSIAVI HDSFGTHAGN TEKLRSLLSN SFVDMYQEND  840
VITDFKEHNE DRLMTEIEVE VPEKGDLDLE EVRESEYCFA                        880

SEQ ID NO: 19          moltype = AA  length = 884
FEATURE                Location/Qualifiers
source                 1..884
                       mol_type = protein
                       organism = synthetic construct
SEQUENCE: 19
MKDLMQLELE AKMHGAGIER FERNNQRAIE GGAASDTDWF RRLTREFVKP MADGIQAYLD  60
YYEGRRGRPS ASLVHLRCLP TEVASYIAIK TIFDGLMNPN QTAQNLAEQI GRRIEDEVRF  120
TKLENAAPKY IKAIKESLKR RASQKYSHGH DVMVHAEKLL SEDQDRKDKY GVDLDRWIGW  180
SDNDIFNLGA KLIELFANNM LLNGVPVIRK RNIHRSLRDE VVVIEATEAM EQWIEEYKVV  240
VGEMSPAYAP CVVRPLDWTG PRNGGWHTEK MRRGMPLVKC RDKKVLSRLT KKQMPKVYAA  300
VNALQGVEWR VNPRILQVAN EARLRGLPLG MPAREKLETP PCPVPSHFSD LRGEELMAVL  360
DPEQKEAFKK WKMEAAKTYN DEAERKAKYR EVVATIDQGI QYKDFERLHF VYTLDFRGRV  420
YAQSSLISPQ GGDLQKALCQ FANGMPLGDT GEYWFKVHGA NVWGWDKEEF DERVSLVETE  480
EFIDMCLDIA ADPLTFTDWT QADKPWQFLA WCFEYADFVS HCETNPAEDF PSRVAVAMDG  540
SCSGIQHYSA MLRDEVGGKE VNLVPSDKPQ DIYGAVAKIV ARWMEDIVEG EVPCESFERM  600
LAKGLTAPFK LNAVEAQMIA AEWLRIGVTR SLTKKPVMTL PYGSSQMTCR ESMAQYLDDL  660
QKKENEKARA QFRKPVAMHN FTDGKGSMSR QQAELFASGL TWEAIGEVVV AARAAMKFIK  720
KVTHEVSSRN KPLEWVTPTG FIVKQAIYDS TDRRVKTQMM GETFFTIREE TPVISVRKMK  780
SSAAPNFVHS MDASHLVLAV EGFSDNGITS IAVIHDSFGT HAGNTEKLRS ILSNSFVDMY  840
QEHDVIKDFY EAQCDRVMTD LELDLPATGT LDLEEVRTSK YIFA                   884

SEQ ID NO: 20          moltype = AA  length = 1765
FEATURE                Location/Qualifiers
source                 1..1765
                       mol_type = protein
                       organism = synthetic construct
SEQUENCE: 20
MAKRLQRCQD VNQVCEIYNS KGGIGELELR FDKLPQNLFA GVFDKLKPDG EIQTTMRVSN  60
RDGVAREITF GGGVKTNEIF VKKQNICVFD VVDIFSYKVA VSTEETVVEK PTMETTAGVR  120
FKIRLSVEDV VKDWRIDLTA VKTAELGKIA QHTASIVQRT FPDNLLKLTG AEVAKLAADS  180
YELELEYTGK SPATNEKVNV AAKYAVELLS SVRNANSTAA ASFGESVSDL CRVAKIIHTH  240
EYANVVCRTP SFKMLLPQVV SLTKSSYYGG LYPPENLWLA GKTDGVRALV VCEDGVAKVI  300
TAESVDITHG VCSATTILDC ELNVDAKILY VFDVIISNNT QVYTQPFSTR ITTDISDIKI  360
DGYKIEMKPF VKVVKADEAT FKSAYKAPHN EGLIMIEDGA AYAATKTYKW KPLSHNTIDF  420
LIKACPKQLI NVDPYKPRAG YKLWLLFTTI SLDQQRELGI EFIPAWKILF TDINMFGSRV  480
PIQFQPAINP LAYVCYLPED VNVNDGDIVE MRAVDGYDTI PKWELVRSRN DRKNEPGFYG  540
NNYKIASDIY LNYIDVFHFE DLYKYNPGYF EKNKSDIYVA PNKYRRYLIK SLFGRYLRDA  600
KWVIDAAAGR GADLHLYKAE CVEHLLAIDI DPTAISELVR RRNEITGYNK SHRGGRNMHS  660
HRGQSHCAKS TSLHALVADL RENPDVLIPK IIQSRPHERC YDAIVINFAI HYLCDTDEHI  720
RDFLITVSRL LAPNGVFIFT TMDGESIVKL LADHKVRPGE AWTIHTGDVN SPDSTVPKYS  780
IRRLYDSDKL TKTGGQIEVL LPMSGEMKAE PLCNIKNIIS MARKMGLDLV ESANFSVLYE  840
AYARDYPDIY ARMTPDDKLY NDLHTYAVFK RKKGAATAGT PNIETQEALE AKMHGAGLDR  900
FIRNNDRAIT GGSASDTDWY RRLTRQFVKP MADGIQAYLD YYEGRRGKPS ASLVHLRCLP  960
TETASYIAIK TIFDGLTNPN QTAQNLSEQI GKRIEDEVRF MKLDNAAPKF IKAIKESLKR  1020
SSSQKYSHGH DVMVHAEKLL AEDKERQDKY GVMIDRHLSW PDNDIFNLGS KLIELFANNM  1080
LLDGEVLIQK RLIVRSQIDR VTVIEATPAM EKWIEEYKVV VGEMAPAFAP CVIKPLDWTG  1140
PRFGGWHTEK MRRQMPLAKC KQQSVLSRLT KKQMPRVYSA VNALQAVEWR VNHRILSVAN  1200
EARLRGLPLA LPDREKLATP PCPVPHMYAE LRGAELMSVL SESQKEAFRT WKADAAKTYN  1260
DEAERKAKYR EVCATIDQGI QYKDFDKIHF VYTLDFRGRV YCQSSLISPQ GGDLQKSLCQ  1320
FANGMPLGES GVHWFKVQGA NVWGWDKKQF EERDELVMAD DFVELCLDIA ADPLTFTDWT  1380
QADKPWQFLA WCFEYADFVS HCETNPPETF VSRIAVAMDG SCSGIQHYSA MLRDEIGGKE  1440
VNLVPGDRPQ DIYGAVAKIV GRWMEDISEL QVPCESFTRM LSKGAVEGQF KLCPLEAQML  1500
SRAWVEIGVT RSMTKKPVMT LPYGSSQMTC RESMAQYLND LQKKENEQSR AQNRKPVAVH  1560
PFNDSKGSMS RMQAELFASG LTWEAIGHVV VAARAAMRFI KKVTHETSSR NVALEWIAPT  1620
```

```
GFIVNQCIFD STPRRVKTQM MGETFFTIRE ENPTISVNKM KSSAAPNFVH SMDASHLCIA  1680
VDEFALAGIT SIAVIHDSFG THAGNTERMR KLLINSFVDM YQNHDVIRDF YEAQCERVKC  1740
DLELDLPAVG TLDLETVRHS KYIFA                                        1765

SEQ ID NO: 21           moltype = AA  length = 1764
FEATURE                 Location/Qualifiers
source                  1..1764
                        mol_type = protein
                        organism = synthetic construct
SEQUENCE: 21
MAKRLQRCQD VNQVCEIYNS KGGIGELELR FDKLPQNLFA GVFDKLKPDG EIQTTMRVSN  60
RDGVAREITF GGGVKTNEIF VKKQNICVFD VVDIFSYKVA VSTEETVVEK PTMETTAGVR  120
FKIRLSVEDV VKDWRIDLTA VKTAELGKIA QHTASIVQRT FPDNLLKLTG AEVAKLAADS  180
YELELEYTGK SPATNEKVNV AAKYAVELLS SVRNANSTAA ASFGESVSDL CRVAKIIHTH  240
EYANVVCRTP SFKMLLPQVV SLTKSSYYGG LYPPENLWLA GKTDGVRALV VCEDGVAKVI  300
TAESVDITHG VCSATTILDC ELNVDAKILY VFDVIISNNT QVYTQPFSTR ITTDISDIKI  360
DGYKIEMKPF VKVVKADEAT FKSAYKAPHN EGLIMIEDGA AYAATKTYKW KPLSHNTIDF  420
LIKACPKQLI NVDPYKPRAG YKLWLLFTTI SLDQQRELGI EFIPAWKILF TDINMFGSRV  480
PIQFQPAINP LAYVCYLPED VNVNDGDIVE MRAVDGYDTI PKWELVRSRN DRKNEPGFYG  540
NNYKIASDIY LNYIDVFHFE DLYKYNPGYF EKNKSDIYVA PNKYRRYLIK SLFGRYLRDA  600
KWVIDAAAGR GADLHLYKAE CVEHLLAIDI DPTAISELVR RRNEITGYNK SHRGGRNMHS  660
HRGQSHCAKS TSLHALVADL RENPDVLIPK IIQSRPHERC YDAIVINFAI HYLCDTDEHI  720
RDFLITVSRL LAPNGVFIFT TMDGESIVKL LADHKVRPGE AWTIHTGDVN SPDSTVPKYS  780
IRRLYDSDKL TKTGGQIEVL LPMSGEMKAE PLCNIKNIIS MARKMGLDLV ESANFSVLYE  840
AYARDYPDIY ARMTPDDKLY NDLHTYAVFK RKKGAATAGP NIETQEALEA KMHGAGLDRF  900
IRNNDRAITG GSASDTDWYR RLTRQFVKPM ADGIQAYLDY YEGRRGKPSA SLVHLRCLPT  960
ETASYIAIKT IFDGLTNPNQ TAQNLSEQIG KRIEDEVRFM KLDNAAPKFI KAIKESLKRS  1020
SSQKYSHGHD VMVHAEKLLA EDKERQDKYG VMIDRHLSWP DNDIFNLGSK LIELFANNML  1080
LDGEVLIQKR LIVRSQIDRV TVIEATPAME KWIEEYKVVV GEMAPAFAPC VIKPLDWTGP  1140
RFGGWHTEKM RRQMPLAKCK QQSVLSRLTK KQMPRVYSAV NALQAVEWRV NHRILSVANE  1200
ARLRGLPLAL PDREKLATPP CPVPHMYAEL RGAELMSVLS ESQKEAFRTW KADAAKTYND  1260
EAERKAKYRE VCATIDQGIQ YKDFDKIHFV YTLDFRGRVY CQSSLISPQG GDLQKSLCQF  1320
ANGMPLGESG VHWFKVQGAN VWGWDKKQFE ERDELVMADD FVELCLDIAA DPLTFTDWTQ  1380
ADKPWQFLAW CFEYADFVSH CETNPPETFV SRIAVAMDGS CSGIQHYSAM LRDEIGGKEV  1440
NLVPGDRPQD IYGAVAKIVG RWMEDISELQ VPCESFTRML SKGAVEGQFK LCPLEAQMLS  1500
RAWVEIGVTR SMTKKPVMTL PYGSSQMTCR ESMAQYLNDL QKKENEQSRA QNRKPVAVHP  1560
FNDSKGSMSR MQAELFASGL TWEAIGHVVV AARAAMRFIK KVTHETSSRN VALEWIAPTG  1620
FIVNQCIFDS TPRRVKTQMM GETFFTIREE NPTISVNKMK SSAAPNFVHS MDASHLCIAV  1680
DEFALAGITS IAVIHDSFGT HAGNTERMRK LLINSFVDMY QNHDVIRDFY EAQCERVKCD  1740
LELDLPAVGT LDLETVRHSK YIFA                                         1764

SEQ ID NO: 22           moltype = AA  length = 1772
FEATURE                 Location/Qualifiers
source                  1..1772
                        mol_type = protein
                        organism = synthetic construct
SEQUENCE: 22
MAKRLQRCQD VNQVCEIYNS KGGIGELELR FDKLPQNLFA GVFDKLKPDG EIQTTMRVSN  60
RDGVAREITF GGGVKTNEIF VKKQNICVFD VVDIFSYKVA VSTEETVVEK PTMETTAGVR  120
FKIRLSVEDV VKDWRIDLTA VKTAELGKIA QHTASIVQRT FPDNLLKLTG AEVAKLAADS  180
YELELEYTGK SPATNEKVNV AAKYAVELLS SVRNANSTAA ASFGESVSDL CRVAKIIHTH  240
EYANVVCRTP SFKMLLPQVV SLTKSSYYGG LYPPENLWLA GKTDGVRALV VCEDGVAKVI  300
TAESVDITHG VCSATTILDC ELNVDAKILY VFDVIISNNT QVYTQPFSTR ITTDISDIKI  360
DGYKIEMKPF VKVVKADEAT FKSAYKAPHN EGLIMIEDGA AYAATKTYKW KPLSHNTIDF  420
LIKACPKQLI NVDPYKPRAG YKLWLLFTTI SLDQQRELGI EFIPAWKILF TDINMFGSRV  480
PIQFQPAINP LAYVCYLPED VNVNDGDIVE MRAVDGYDTI PKWELVRSRN DRKNEPGFYG  540
NNYKIASDIY LNYIDVFHFE DLYKYNPGYF EKNKSDIYVA PNKYRRYLIK SLFGRYLRDA  600
KWVIDAAAGR GADLHLYKAE CVEHLLAIDI DPTAISELVR RRNEITGYNK SHRGGRNMHS  660
HRGQSHCAKS TSLHALVADL RENPDVLIPK IIQSRPHERC YDAIVINFAI HYLCDTDEHI  720
RDFLITVSRL LAPNGVFIFT TMDGESIVKL LADHKVRPGE AWTIHTGDVN SPDSTVPKYS  780
IRRLYDSDKL TKTGGQIEVL LPMSGEMKAE PLCNIKNIIS MARKMGLDLV ESANFSVLYE  840
AYARDYPDIY ARMTPDDKLY NDLHTYAVFK RKKGAATAGT GAATAGTPNI ETQEALEAKM  900
HGAGLDRFIR NNDRAITGGS ASDTDWYRRL TRQFVKPMAD GIQAYLDYYE GRRGKPSASL  960
VHLRCLPTET ASYIAIKTIF DGLTNPNQTA QNLSEQIGKR IEDEVRFMKL DNAAPKFIKA  1020
IKESLKRSSS QKYSHGHDVM VHAEKLLAED KERQDKYGVM IDRHLSWPDN DIFNLGSKLI  1080
ELFANNMLLD GEVLIQKRLI VRSQIDRVTV IEATPAMEKW IEEYKVVVGE MAPAFAPCVI  1140
KPLDWTGPRF GGWHTEKMRR QMPLAKCKQQ SVLSRLTKKQ MPRVYSAVNA LQAVEWRVNH  1200
RILSVANEAR LRGLPLALPD REKLATPPCP VPHMYAELRG AELMSVLSES QKEAFRTWKA  1260
DAAKTYNDEA ERKAKYREVC ATIDQGIQYK DFDKIHFVYT LDFRGRVYCQ SSLISPQGGD  1320
LQKSLCQFAN GMPLGESGVH WFKVQGANVW GWDKKQFEER DELVMADDFV ELCLDIAADP  1380
LTFTDWTQAD KPWQFLAWCF EYADFVSHCE TNPPETFVSR IAVAMDGSCS GIQHYSAMLR  1440
DEIGGKEVNL VPGDRPQDIY GAVAKIVGRW MEDISELQVP CESFTRMLSK GAVEGQFKLC  1500
PLEAQMLSRA WVEIGVTRSM TKKPVMTLPY GSSQMTCRES MAQYLNDLQK KENEQSRAQN  1560
RKPVAVHPFN DSKGSMSRMQ AELFASGLTW EAIGHVVVAA RAAMRFIKKV THETSSRNVA  1620
LEWIAPTGFI VNQCIFDSTP RRVKTQMMGE TFFTIREENP TISVNKMKSS AAPNFVHSMD  1680
ASHLCIAVDE FALAGITSIA VIHDSFGTHA GNTERMRKLL INSFVDMYQN HDVIRDFYEA  1740
QCERVKCDLE LDLPAVGTLD LETVRHSKYI FA                                1772

SEQ ID NO: 23           moltype = AA  length = 1770
```

```
FEATURE                Location/Qualifiers
source                 1..1770
                       mol_type = protein
                       organism = synthetic construct
SEQUENCE: 23
MAKRLQRCQD VNQVCEIYNS KGGIGELELR FDKLPQNLFA GVFDKLKPDG EIQTTMRVSN  60
RDGVAREITF GGGVKTNEIF VKKQNICVFD VVDIFSYKVA VSTEETVVEK PTMETTAGVR  120
FKIRLSVEDV VKDWRIDLTA VKTAELGKIA QHTASIVQRT FPDNLLKLTG AEVAKLAADS  180
YELELEYTGK SPATNEKVNV AAKYAVELLS SVRNANSTAA ASFGESVSDL CRVAKIIHTH  240
EYANVVCRTP SFKMLLPQVV SLTKSSYYGG LYPPENLWLA GKTDGVRALV VCEDGVAKVI  300
TAESVDITHG VCSATTILDC ELNVDAKILY VFDVIISNNT QVYTQPFSTR ITTDISDIKI  360
DGYKIEMKPF VKVVKADEAT FKSAYKAPHN EGLIMIEDGA AYAATKTYKW KPLSHNTIDF  420
LIKACPKQLI NVDPYKPRAG YKLWLLFTTI SLDQQRELGI EFIPAWKILF TDINMFGSRV  480
PIQFQPAINP LAYVCYLPED VNVNDGDIVE MRAVDGYDTI PKWELVRSRN DRKNEPGFYG  540
NNYKIASDIY LNYIDVFHFE DLYKYNPGYF EKNKSDIYVA PNKYRRYLIK SLFGRYLRDA  600
KWVIDAAAGR GADLHLYKAE CVEHLLAIDI DPTAISELVR RRNEITGYNK SHRGGRNMHS  660
HRGQSHCAKS TSLHALVADL RENPDVLIPK IIQSRPHERC YDAIVINFAI HYLCDTDEHI  720
RDFLITVSRL LAPNGVFIFT TMDGESIVKL LADHKVRPGE AWTIHTGDVN SPDSTVPKYS  780
IRRLYDSDKL TKTGGQIEVL LPMSGEMKAE PLCNIKNIIS MARKMGLDLV ESANFSVLYE  840
AYARDYPDIY ARMTPDDKLY NDLHTYAVFK RKKGAATAGT GAATAPNIET QEALEAKMHG  900
AGLDRFIRNN DRAITGGSAS DTDWYRRLTR QFVKPMADGI QAYLDYYEGR RGKPSASLVH  960
LRCLPTETAS YIAIKTIFDG LTNPNQTAQN LSEQIGKRIE DEVRFMKLDN AAPKFIKAIK  1020
ESLKRSSSQK YSHGHDVMVH AEKLLAEDKE RQDKYGVMID RHLSWPDNDI FNLGSKLIEL  1080
FANNMLLDGE VLIQKRLIVR SQIDRVTVIE ATPAMEKWIE EYKVVVGEMA PAFAPCVIKP  1140
LDWTGPRFGG WHTEKMRRQM PLAKCKQQSV LSRLTKKQMP RVYSAVNALQ AVEWRVNHRI  1200
LSVANEARLR GLPLALPDRE KLATPPCPVP HMYAELRGAE LMSVLSESQK EAFRTWKADA  1260
AKTYNDEAER KAKYREVCAT IDQGIQYKDF DKIHFVYTLD FRGRVYCQSS LISPQGGDLQ  1320
KSLCQFANGM PLGESGVHWF KVQGANVWGW DKKQFEERDE LVMADDFVEL CLDIAADPLT  1380
FTDWTQADKP WQFLAWCFEY ADFVSHCETN PPETFVSRIA VAMDGSCSGI QHYSAMLRDE  1440
IGGKEVNLVP GDRPQDIYGA VAKIVGRWME DISELQVPCE SFTRMLSKGA VEGQFKLCPL  1500
EAQMLSRAWV EIGVTRSMTK KPVMTLPYGS SQMTCRESMA QYLNDLQKKE NEQSRAQNRK  1560
PVAVHPFNDS KGSMSRMQAE LFASGLTWEA IGHVVVAARA AMRFIKKVTH ETSSRNVALE  1620
WIAPTGFIVN QCIFDSTPRR VKTQMMGETF FTIREENPTI SVNKMKSSAA PNFVHSMDAS  1680
HLCIAVDEFA LAGITSIAVI HDSFGTHAGN TERMRKLLIN SFVDMYQNHD VIRDFYEAQC  1740
ERVKCDLELD LPAVGTLDLE TVRHSKYIFA                                   1770

SEQ ID NO: 24          moltype = AA  length = 1768
FEATURE                Location/Qualifiers
source                 1..1768
                       mol_type = protein
                       organism = synthetic construct
SEQUENCE: 24
MAKRLQRCQD VNQVCEIYNS KGGIGELELR FDKLPQNLFA GVFDKLKPDG EIQTTMRVSN  60
RDGVAREITF GGGVKTNEIF VKKQNICVFD VVDIFSYKVA VSTEETVVEK PTMETTAGVR  120
FKIRLSVEDV VKDWRIDLTA VKTAELGKIA QHTASIVQRT FPDNLLKLTG AEVAKLAADS  180
YELELEYTGK SPATNEKVNV AAKYAVELLS SVRNANSTAA ASFGESVSDL CRVAKIIHTH  240
EYANVVCRTP SFKMLLPQVV SLTKSSYYGG LYPPENLWLA GKTDGVRALV VCEDGVAKVI  300
TAESVDITHG VCSATTILDC ELNVDAKILY VFDVIISNNT QVYTQPFSTR ITTDISDIKI  360
DGYKIEMKPF VKVVKADEAT FKSAYKAPHN EGLIMIEDGA AYAATKTYKW KPLSHNTIDF  420
LIKACPKQLI NVDPYKPRAG YKLWLLFTTI SLDQQRELGI EFIPAWKILF TDINMFGSRV  480
PIQFQPAINP LAYVCYLPED VNVNDGDIVE MRAVDGYDTI PKWELVRSRN DRKNEPGFYG  540
NNYKIASDIY LNYIDVFHFE DLYKYNPGYF EKNKSDIYVA PNKYRRYLIK SLFGRYLRDA  600
KWVIDAAAGR GADLHLYKAE CVEHLLAIDI DPTAISELVR RRNEITGYNK SHRGGRNMHS  660
HRGQSHCAKS TSLHALVADL RENPDVLIPK IIQSRPHERC YDAIVINFAI HYLCDTDEHI  720
RDFLITVSRL LAPNGVFIFT TMDGESIVKL LADHKVRPGE AWTIHTGDVN SPDSTVPKYS  780
IRRLYDSDKL TKTGGQIEVL LPMSGEMKAE PLCNIKNIIS MARKMGLDLV ESANFSVLYE  840
AYARDYPDIY ARMTPDDKLY NDLHTYAVFK RKKGAATAGT GAAPNIETQE ALEAKMHGAG  900
LDRFIRNNDR AITGGSASDT DWYRRLTRQF VKPMADGIQA YLDYYEGRRG KPSASLVHLR  960
CLPTETASYI AIKTIFDGLT NPNQTAQNLS EQIGKRIEDE VRFMKLDNAA PKFIKAIKES  1020
LKRSSSQKYS HGHDVMVHAE KLLAEDKERQ DKYGVMIDRH LSWPDNDIFN LGSKLIELFA  1080
NNMLLDGEVL IQKRLIVRSQ IDRVTVIEAT PAMEKWIEEY KVVVGEMAPA FAPCVIKPLD  1140
WTGPRFGGWH TEKMRRQMPL AKCKQQSVLS RLTKKQMPRV YSAVNALQAV EWRVNHRILS  1200
VANEARLRGL PLALPDREKL ATPPCPVPHM YAELRGAELM SVLSESQKEA FRTWKADAAK  1260
TYNDEAERKA KYREVCATID QGIQYKDFDK IHFVYTLDFR GRVYCQSSLI SPQGGDLQKS  1320
LCQFANGMPL GESGVHWFKV QGANVWGWDK KQFEERDELV MADDFVELCL DIAADPLTFT  1380
DWTQADKPWQ FLAWCFEYAD FVSHCETNPP ETFVSRIAVA MDGSCSGIQH YSAMLRDEIG  1440
GKEVNLVPGD RPQDIYGAVA KIVGRWMEDI SELQVPCESF TRMLSKGAVE GQFKLCPLEA  1500
QMLSRAWVEI GVTRSMTKKP VMTLPYGSSQ MTCRESMAQY LNDLQKKENE QSRAQNRKPV  1560
AVHPFNDSKG SMSRMQAELF ASGLTWEAIG HVVVAARAAM RFIKKVTHET SSRNVALEWI  1620
APTGFIVNQC IFDSTPRRVK TQMMGETFFT IREENPTISV NKMKSSAAPN FVHSMDASHL  1680
CIAVDEFALA GITSIAVIHD SFGTHAGNTE RMRKLLINSF VDMYQNHDVI RDFYEAQCER  1740
VKCDLELDLP AVGTLDLETV RHSKYIFA                                     1768

SEQ ID NO: 25          moltype = AA  length = 1779
FEATURE                Location/Qualifiers
source                 1..1779
                       mol_type = protein
                       organism = synthetic construct
SEQUENCE: 25
```

-continued

```
MAKRLQRCQD VNQVCEIYNS KGGIGELELR FDKLPQNLFA GVFDKLKPDG EIQTTMRVSN  60
RDGVAREITF GGGVKTNEIF VKKQNICVFD VVDIFSYKVA VSTEETVVEK PTMETTAGVR  120
FKIRLSVEDV VKDWRIDLTA VKTAELGKIA QHTASIVQRT FPDNLLKLTG AEVAKLAADS  180
YELELEYTGK SPATNEKVNV AAKYAVELLS SVRNANSTAA ASFGESVSDL CRVAKIIHTH  240
EYANVVCRTP SFKMLLPQVV SLTKSSYYGG LYPPENLWLA GKTDGVRALV VCEDGVAKVI  300
TAESVDITHG VCSATTILDC ELNVDAKILY VFDVIISNNT QVYTQPFSTR ITTDISDIKI  360
DGYKIEMKPF VKVVKADEAT FKSAYKAPHN EGLIMIEDGA AYAATKTYKW KPLSHNTIDF  420
LIKACPKQLI NVDPYKPRAG YKLWLLFTTI SLDQQRELGI EFIPAWKILF TDINMFGSRV  480
PIQFQPAINP LAYVCYLPED VNVNDGDIVE MRAVDGYDTI PKWELVRSRN DRKNEPGFYG  540
NNYKIASDIY LNYIDVFHFE DLYKYNPGYF EKNKSDIYVA PNKYRRYLIK SLFGRYLRDA  600
KWVIDAAAGR GADLHLYKAE CVEHLLAIDI DPTAISELVR RRNEITGYNK SHRGGRNMHS  660
HRGQSHCAKS TSLHALVADL RENPDVLIPK IIQSRPHERC YDAIVINFAI HYLCDTDEHI  720
RDFLITVSRL LAPNGVFIFT TMDGESIVKL LADHKVRPGE AWTIHTGDVN SPDSTVPKYS  780
IRRLYDSDKL TKTGGQIEVL LPMSGEMKAE PLCNIKNIIS MARKMGLDLV ESANFSVLYE  840
AYARDYPDIY ARMTPDDKLY NDLHTYAVFK RKKGAATAGT GAATAGTGAA TAGTPNIETQ  900
EALEAKMHGA GLDRFIRNND RAITGGSASD TDWYRRLTRQ FVKPMADGIQ AYLDYYEGRR  960
GKPSASLVHL RCLPTETASY IAIKTIFDGL TNPNQTAQNL SEQIGKRIED EVRFMKLDNA  1020
APKFIKAIKE SLKRSSSQKY SHGHDVMVHA EKLLAEDKER QDKYGVMIDR HLSWPDNDIF  1080
NLGSKLIELF ANNMLLDGEV LIQKRLIVRS QIDRVTVIEA TPAMEKWIEE YKVVVGEMAP  1140
AFAPCVIKPL DWTGPRFGGW HTEKMRRQMP LAKCKQQSVL SRLTKKQMPR VYSAVNALQA  1200
VEWRVNHRIL SVANEARLRG LPLALPDREK LATPPCPVPH MYAELRGAEL MSVLSESQKE  1260
AFRTWKADAA KTYNDEAERK AKYREVCATI DQGIQYKDFD KIHFVYTLDF RGRVYCQSSL  1320
ISPQGGDLQK SLCQFANGMP LGESGVHWFK VQGANVWGWD KKQFEERDEL VMADDFVELC  1380
LDIAADPLTF TDWTQADKPW QFLAWCFEYA DFVSHCETNP PETFVSRIAV AMDGSCSGIQ  1440
HYSAMLRDEI GGKEVNLVPG DRPQDIYGAV AKIVGRWMED ISELQVPCES FTRMLSKGAV  1500
EGQFKLCPLE AQMLSRAWVE IGVTRSMTKK PVMTLPYGSS QMTCRESMAQ YLNDLQKKEN  1560
EQSRAQNRKP VAVHPFNDSK GSMSRMQAEL FASGLTWEAI GHVVVAARAA MRFIKKVTHE  1620
TSSRNVALEW IAPTGFIVNQ CIFDSTPRRV KTQMMGETFF TIREENPTIS VNKMKSSAAP  1680
NFVHSMDASH LCIAVDEFAL AGITSIAVIH DSFGTHAGNT ERMRKLLINS FVDMYQNHDV  1740
IRDFYEAQCE RVKCDLELDL PAVGTLDLET VRHSKYIFA                        1779

SEQ ID NO: 26           moltype = AA  length = 1781
FEATURE                 Location/Qualifiers
source                  1..1781
                        mol_type = protein
                        organism = synthetic construct
SEQUENCE: 26
MAKRLQRCQD VNQVCEIYNS KGGIGELELR FDKLPQNLFA GVFDKLKPDG EIQTTMRVSN  60
RDGVAREITF GGGVKTNEIF VKKQNICVFD VVDIFSYKVA VSTEETVVEK PTMETTAGVR  120
FKIRLSVEDV VKDWRIDLTA VKTAELGKIA QHTASIVQRT FPDNLLKLTG AEVAKLAADS  180
YELELEYTGK SPATNEKVNV AAKYAVELLS SVRNANSTAA ASFGESVSDL CRVAKIIHTH  240
EYANVVCRTP SFKMLLPQVV SLTKSSYYGG LYPPENLWLA GKTDGVRALV VCEDGVAKVI  300
TAESVDITHG VCSATTILDC ELNVDAKILY VFDVIISNNT QVYTQPFSTR ITTDISDIKI  360
DGYKIEMKPF VKVVKADEAT FKSAYKAPHN EGLIMIEDGA AYAATKTYKW KPLSHNTIDF  420
LIKACPKQLI NVDPYKPRAG YKLWLLFTTI SLDQQRELGI EFIPAWKILF TDINMFGSRV  480
PIQFQPAINP LAYVCYLPED VNVNDGDIVE MRAVDGYDTI PKWELVRSRN DRKNEPGFYG  540
NNYKIASDIY LNYIDVFHFE DLYKYNPGYF EKNKSDIYVA PNKYRRYLIK SLFGRYLRDA  600
KWVIDAAAGR GADLHLYKAE CVEHLLAIDI DPTAISELVR RRNEITGYNK SHRGGRNMHS  660
HRGQSHCAKS TSLHALVADL RENPDVLIPK IIQSRPHERC YDAIVINFAI HYLCDTDEHI  720
RDFLITVSRL LAPNGVFIFT TMDGESIVKL LADHKVRPGE AWTIHTGDVN SPDSTVPKYS  780
IRRLYDSDKL TKTGGQIEVL LPMSGEMKAE PLCNIKNIIS MARKMGLDLV ESANFSVLYE  840
AYARDYPDIY ARMTPDDKLY NDLHTYAVFK RKKGAATAGT PGAATAGTPG AATAGTPNIE  900
TQEALEAKMH GAGLDRFIRN NDRAITGGSA SDTDWYRRLT RQFVKPMADG IQAYLDYYEG  960
RRGKPSASLV HLRCLPTETA SYIAIKTIFD GLTNPNQTAQ NLSEQIGKRI EDEVRFMKLD  1020
NAAPKFIKAI KESLKRSSSQ KYSHGHDVMV HAEKLLAEDK ERQDKYGVMI DRHLSWPDND  1080
IFNLGSKLIE LFANNMLLDG EVLIQKRLIV RSQIDRVTVI EATPAMEKWI EEYKVVVGEM  1140
APAFAPCVIK PLDWTGPRFG GWHTEKMRRQ MPLAKCKQQS VLSRLTKKQM PRVYSAVNAL  1200
QAVEWRVNHR ILSVANEARL RGLPLALPDR EKLATPPCPV PHMYAELRGA ELMSVLSESQ  1260
KEAFRTWKAD AAKTYNDEAE RKAKYREVCA TIDQGIQYKD FDKIHFVYTL DFRGRVYCQS  1320
SLISPQGGDL QKSLCQFANG MPLGESGVHW FKVQGANVWG WDKKQFEERD ELVMADDFVE  1380
LCLDIAADPL TFTDWTQADK PWQFLAWCFE YADFVSHCET NPPETFVSRI AVAMDGSCSG  1440
IQHYSAMLRD EIGGKEVNLV PGDRPQDIYG AVAKIVGRWM EDISELQVPC ESFTRMLSKG  1500
AVEGQFKLCP LEAQMLSRAW VEIGVTRSMT KKPVMTLPYG SSQMTCRESM AQYLNDLQKK  1560
ENEQSRAQNR KPVAVHPFND SKGSMSRMQA ELFASGLTWE AIGHVVVAAR AAMRFIKKVT  1620
HETSSRNVAL EWIAPTGFIV NQCIFDSTPR RVKTQMMGET FFTIREENPT ISVNKMKSSA  1680
APNFVHSMDA SHLCIAVDEF ALAGITSIAV IHDSFGTHAG NTERMRKLLI NSFVDMYQNH  1740
DVIRDFYEAQ CERVKCDLEL DLPAVGTLDL ETVRHSKYIF A                     1781

SEQ ID NO: 27           moltype = AA  length = 1763
FEATURE                 Location/Qualifiers
source                  1..1763
                        mol_type = protein
                        organism = synthetic construct
SEQUENCE: 27
MAKRLQRCQD VNQVCEIYNS KGGIGELELR FDKLPQNLFA GVFDKLKPDG EIQTTMRVSN  60
RDGVAREITF GGGVKTNEIF VKKQNICVFD VVDIFSYKVA VSTEETVVEK PTMETTAGVR  120
FKIRLSVEDV VKDWRIDLTA VKTAELGKIA QHTASIVQRT FPDNLLKLTG AEVAKLAADS  180
YELELEYTGK SPATNEKVNV AAKYAVELLS SVRNANSTAA ASFGESVSDL CRVAKIIHTH  240
EYANVVCRTP SFKMLLPQVV SLTKSSYYGG LYPPENLWLA GKTDGVRALV VCEDGVAKVI  300
```

```
TAESVDITHG VCSATTILDC ELNVDAKILY VFDVIISNNT QVYTQPFSTR ITTDISDIKI  360
DGYKIEMKPF VKVVKADEAT FKSAYKAPHN EGLIMIEDGA AYAATKTYKW KPLSHNTIDF  420
LIKACPKQLI NVDPYKPRAG YKLWLLFTTI SLDQQRELGI EFIPAWKILF TDINMFGSRV  480
PIQFQPAINP LAYVCYLPED VNVNDGDIVE MRAVDGYDTI PKWELVRSRN DRKNEPGFYG  540
NNYKIASDIY LNYIDVFHFE DLYKYNPGYF EKNKSDIYVA PNKYRRYLIK SLFGRYLRDA  600
KWVIDAAAGR GADLHLYKAE CVEHLLAIDI DPTAISELVR RRNEITGYNK SHRGGRNMHS  660
HRGQSHCAKS TSLHALVADL RENPDVLIPK IIQSRPHERC YDAIVINFAI HYLCDTDEHI  720
RDFLITVSRL LAPNGVFIFT TMDGESIVKL LADHKVRPGE AWTIHTGDVN SPDSTVPKYS  780
IRRLYDSDKL TKTGQQIEVL LPMSGEMKAE PLCNIKNIIS MARKMGLDLV ESANFSVLYE  840
AYARDYPDIY ARMTPDDKLY NDLHTYAVFK RKKGGGGSPN IETQEALEAK MHGAGLDRFI  900
RNNDRAITGG SASDTDWYRR LTRQFVKPMA DGIQAYLDYY EGRRGKPSAS LVHLRCLPTE  960
TASYIAIKTI FDGLTNPNQT AQNLSEQIGK RIEDEVRFMK LDNAAPKFIK AIKESLKRSS  1020
SQKYSHGHDV MVHAEKLLAE DKERQDKYGV MIDRHLSWPD NDIFNLGSKL IELFANNMLL  1080
DGEVLIQKRL IVRSQIDRVT VIEATPAMEK WIEEYKVVVG EMAPAFAPCV IKPLDWTGPR  1140
FGGWHTEKMR RQMPLAKCKQ QSVLSRLTKK QMPRVYSAVN ALQAVEWRVN HRILSVANEA  1200
RLRGLPLALP DREKLATPPC PVPHMYAELR GAELMSVLSE SQKEAFRTWK ADAAKTYNDE  1260
AERKAKYREV CATIDQGIQY KDFDKIHFVY TLDFRGRVYC QSSLISPQGG DLQKSLCQFA  1320
NGMPLGESGV HWFKVQGANV WGWDKKQFEE RDELVMADDF VELCLDIAAD PLTFTDWTQA  1380
DKPWQFLAWC FEYADFVSHC ETNPPETFVS RIAVAMDGSC SGIQHYSAML RDEIGGKEVN  1440
LVPGDRPQDI YGAVAKIVGR WMEDISELQV PCESFTRMLS KGAVEGQFKL CPLEAQMLSR  1500
AWVEIGVTRS MTKKPVMTLP YGSSQMTCRE SMAQYLNDLQ KKENEQSRAQ NRKPVAVHPF  1560
NDSKGSMSRM QAELFASGLT WEAIGHVVVA ARAAMRFIKK VTHETSSRNV ALEWIAPTGF  1620
IVNQCIFDST PRRVKTQMMG ETFFTIREEN PTISVNKMKS SAAPNFVHSM DASHLCIAVD  1680
EFALAGITSI AVIHDSFGTH AGNTERMRKL LINSFVDMYQ NHDVIRDFYE AQCERVKCDL  1740
ELDLPAVGTL DLETVRHSKY IFA                                         1763

SEQ ID NO: 28          moltype = AA  length = 1770
FEATURE                Location/Qualifiers
source                 1..1770
                       mol_type = protein
                       organism = synthetic construct
SEQUENCE: 28
MAKRLQRCQD VNQVCEIYNS KGGIGELELR FDKLPQNLFA GVFDKLKPDG EIQTTMRVSN  60
RDGVAREITF GGGVKTNEIF VKKQNICVFD VVDIFSYKVA VSTEETVVEK PTMETTAGVR  120
FKIRLSVEDV VKDWRIDLTA VKTAELGKIA QHTASIVQRT FPDNLLKLTG AEVAKLAADS  180
YELELEYTGK SPATNEKVNV AAKYAVELLS SVRNANSTAA ASFGESVSDL CRVAKIIHTH  240
EYANVVCRTP SFKMLLPQVV SLTKSSYYGG LYPPENLWLA GKTDGVRALV VCEDGVAKVI  300
TAESVDITHG VCSATTILDC ELNVDAKILY VFDVIISNNT QVYTQPFSTR ITTDISDIKI  360
DGYKIEMKPF VKVVKADEAT FKSAYKAPHN EGLIMIEDGA AYAATKTYKW KPLSHNTIDF  420
LIKACPKQLI NVDPYKPRAG YKLWLLFTTI SLDQQRELGI EFIPAWKILF TDINMFGSRV  480
PIQFQPAINP LAYVCYLPED VNVNDGDIVE MRAVDGYDTI PKWELVRSRN DRKNEPGFYG  540
NNYKIASDIY LNYIDVFHFE DLYKYNPGYF EKNKSDIYVA PNKYRRYLIK SLFGRYLRDA  600
KWVIDAAAGR GADLHLYKAE CVEHLLAIDI DPTAISELVR RRNEITGYNK SHRGGRNMHS  660
HRGQSHCAKS TSLHALVADL RENPDVLIPK IIQSRPHERC YDAIVINFAI HYLCDTDEHI  720
RDFLITVSRL LAPNGVFIFT TMDGESIVKL LADHKVRPGE AWTIHTGDVN SPDSTVPKYS  780
IRRLYDSDKL TKTGQQIEVL LPMSGEMKAE PLCNIKNIIS MARKMGLDLV ESANFSVLYE  840
AYARDYPDIY ARMTPDDKLY NDLHTYAVFK RKKGGGGSSG GGGSSPNIET QEALEAKMHG  900
AGLDRFIRNN DRAITGGSAS DTDWYRRLTR QFVKPMADGI QAYLDYYEGR RGKPSASLVH  960
LRCLPTETAS YIAIKTIFDG LTNPNQTAQN LSEQIGKRIE DEVRFMKLDN AAPKFIKAIK  1020
ESLKRSSSQK YSHGHDVMVH AEKLLAEDKE RQDKYGVMID RHLSWPDNDI FNLGSKLIEL  1080
FANNMLLDGE VLIQKRLIVR SQIDRVTVIE ATPAMEKWIE EYKVVVGEMA PAFAPCVIKP  1140
LDWTGPRFGG WHTEKMRRQM PLAKCKQQSV LSRLTKKQMP RVYSAVNALQ AVEWRVNHRI  1200
LSVANEARLR GLPLALPDRE KLATPPCPVP HMYAELRGAE LMSVLSESQK EAFRTWKADA  1260
AKTYNDEAER KAKYREVCAT IDQGIQYKDF DKIHFVYTLD FRGRVYCQSS LISPQGGDLQ  1320
KSLCQFANGM PLGESGVHWF KVQGANVWGW DKKQFEERDE LVMADDFVEL CLDIAADPLT  1380
FTDWTQADKP WQFLAWCFEY ADFVSHCETN PPETFVSRIA VAMDGSCSGI QHYSAMLRDE  1440
IGGKEVNLVP GDRPQDIYGA VAKIVGRWME DISELQVPCE SFTRMLSKGA VEGQFKLCPL  1500
EAQMLSRAWV EIGVTRSMTK KPVMTLPYGS SQMTCRESMA QYLNDLQKKE NEQSRAQNRK  1560
PVAVHPFNDS KGSMSRMQAE LFASGLTWEA IGHVVVAARA AMRFIKKVTH ETSSRNVALE  1620
WIAPTGFIVN QCIFDSTPRR VKTQMMGETF FTIREENPTI SVNKMKSSAA PNFVHSMDAS  1680
HLCIAVDEFA LAGITSIAVI HDSFGTHAGN TERMRKLLIN SFVDMYQNHD VIRDFYEAQC  1740
ERVKCDLELD LPAVGTLDLE TVRHSKYIFA                                  1770

SEQ ID NO: 29          moltype = AA  length = 1779
FEATURE                Location/Qualifiers
source                 1..1779
                       mol_type = protein
                       organism = synthetic construct
SEQUENCE: 29
MAKRLQRCQD VNQVCEIYNS KGGIGELELR FDKLPQNLFA GVFDKLKPDG EIQTTMRVSN  60
RDGVAREITF GGGVKTNEIF VKKQNICVFD VVDIFSYKVA VSTEETVVEK PTMETTAGVR  120
FKIRLSVEDV VKDWRIDLTA VKTAELGKIA QHTASIVQRT FPDNLLKLTG AEVAKLAADS  180
YELELEYTGK SPATNEKVNV AAKYAVELLS SVRNANSTAA ASFGESVSDL CRVAKIIHTH  240
EYANVVCRTP SFKMLLPQVV SLTKSSYYGG LYPPENLWLA GKTDGVRALV VCEDGVAKVI  300
TAESVDITHG VCSATTILDC ELNVDAKILY VFDVIISNNT QVYTQPFSTR ITTDISDIKI  360
DGYKIEMKPF VKVVKADEAT FKSAYKAPHN EGLIMIEDGA AYAATKTYKW KPLSHNTIDF  420
LIKACPKQLI NVDPYKPRAG YKLWLLFTTI SLDQQRELGI EFIPAWKILF TDINMFGSRV  480
PIQFQPAINP LAYVCYLPED VNVNDGDIVE MRAVDGYDTI PKWELVRSRN DRKNEPGFYG  540
NNYKIASDIY LNYIDVFHFE DLYKYNPGYF EKNKSDIYVA PNKYRRYLIK SLFGRYLRDA  600
```

```
KWVIDAAAGR GADLHLYKAE CVEHLLAIDI DPTAISELVR RRNEITGYNK SHRGGRNMHS  660
HRGQSHCAKS TSLHALVADL RENPDVLIPK IIQSRPHERC YDAIVINFAI HYLCDTDEHI  720
RDFLITVSRL LAPNGVFIFT TMDGESIVKL LADHKVRPGE AWTIHTGDVN SPDSTVPKYS  780
IRRLYDSDKL TKTGQQIEVL LPMSGEMKAE PLCNIKNIIS MARKMGLDLV ESANFSVLYE  840
AYARDYPDIY ARMTPDDKLY NDLHTYAVFK RKKGSSAGSA ALINKERATE THERPNIETQ  900
EALEAKMHGA GLDRFIRNND RAITGGSASD TDWYRRLTRQ FVKPMADGIQ AYLDYYEGRR  960
GKPSASLVHL RCLPTETASY IAIKTIFDGL TNPNQTAQNL SEQIGKRIED EVRFMKLDNA  1020
APKFIKAIKE SLKRSSSQKY SHGHDVMVHA EKLLAEDKER QDKYGVMIDR HLSWPDNDIF  1080
NLGSKLIELF ANNMLLDGEV LIQKRLIVRS QIDRVTVIEA TPAMEKWIEE YKVVVGEMAP  1140
AFAPCVIKPL DWTGPRFGGW HTEKMRRQMP LAKCKQQSVL SRLTKKQMPR VYSAVNALQA  1200
VEWRVNHRIL SVANEARLRG LPLALPDREK LATPPCPVPH MYAELRGAEL MSVLSESQKE  1260
AFRTWKADAA KTYNDEAERK AKYREVCATI DQGIQYKDFD KIHFVYTLDF RGRVYCQSSL  1320
ISPQGGDLQK SLCQFANGMP LGESGVHWFK VQGANVWGWD KKQFEERDEL VMADDFVELC  1380
LDIAADPLTF TDWTQADKPW QFLAWCFEYA DFVSHCETNP PETFVSRIAV AMDGSCSGIQ  1440
HYSAMLRDEI GGKEVNLVPG DRPQDIYGAV AKIVGRWMED ISELQVPCES FTRMLSKGAV  1500
EGQFKLCPLE AQMLSRAWVE IGVTRSMTKK PVMTLPYGSS QMTCRESMAQ YLNDLQKKEN  1560
EQSRAQNRKP VAVHPFNDSK GSMSRMQAEL FASGLTWEAI GHVVVAARAA MRFIKKVTHE  1620
TSSRNVALEW IAPTGFIVNQ CIFDSTPRRV KTQMMGETFF TIREENPTIS VNKMKSSAAP  1680
NFVHSMDASH LCIAVDEFAL AGITSIAVIH DSFGTHAGNT ERMRKLLINS FVDMYQNHDV  1740
IRDFYEAQCE RVKCDLELDL PAVGTLDLET VRHSKYIFA                        1779

SEQ ID NO: 30          moltype = DNA  length = 7921
FEATURE                Location/Qualifiers
source                 1..7921
                       mol_type = other DNA
                       organism = synthetic construct
SEQUENCE: 30
tggcgaatgg gacgcgccct gtagcggcgc attaagcgcg gcgggtgtgg tggttacgcg  60
cagcgtgacc gctacacttg ccagcgccct agcgcccgct cctttcgctt tcttcccttc  120
ctttctcgcc acgttcgccg gctttccccg tcaagctcta aatcgggggc tccctttagg  180
gttccgattt agtgctttac ggcacctcga ccccaaaaaa cttgattagg gtgatggttc  240
acgtagtggg ccatcgccct gatagacggt ttttcgccct ttgacgttgg agtccacgtt  300
ctttaatagt ggactcttgt tccaaactgg aacaacactc aaccctatct cggtctattc  360
ttttgattta taagggattt tgccgatttc ggcctattgg ttaaaaaatg agctgattta  420
acaaaaattt aacgcgaatt ttaacaaaat attaacgttt acaatttcag gtggcacttt  480
tcggggaaat gtgcgcggaa cccctatttg tttatttttc taaatacatt caaatatgta  540
tccgctcatg aattaattct tagaaaaact catcgagcat caaatgaaac tgcaatttat  600
tcatatcagg attatcaata ccatattttt gaaaaagccg tttctgtaat gaaggagaaa  660
actcaccgag gcagttccat aggatggcaa gatcctggta tcggtctgcg attccgactc  720
gtccaacatc aatacaacct attaatttcc cctcgtcaaa aataaggtta tcaagtgaga  780
aatcaccatg agtgacgact gaatccggtg agaatggcaa aagtttatgc atttctttcc  840
agacttgttc aacaggccag ccattacgct cgtcatcaaa atcactcgca tcaaccaaac  900
cgttattcat tcgtgattgc gcctgagcga gacgaaatac gcgatcgctg ttaaaaggac  960
aattacaaac aggaatcgaa tgcaaccggc gcaggaacac tgccagcgca tcaacaatat  1020
tttcacctga atcaggatat tcttctaata cctggaatgc tgttttcccg gggatcgcag  1080
tggtgagtaa ccatgcatca tcaggagtac ggataaaatg cttgatggtc ggaagaggca  1140
taaattccgt cagccagttt agtctgacca tctcatctgt aacatcattg gcaacgctac  1200
ctttgccatg tttcagaaac aactctggcg catcgggctt cccatacaat cgatagattg  1260
tcgcacctga ttgcccgaca ttatcgcgag cccatttata cccatataaa tcagcatcca  1320
tgttggaatt taatcgcggc ctagagcaag acgtttcccg ttgaatatgg ctcataacac  1380
cccttgtatt actgtttatg taagcagaca gttttattgt tcatgaccaa aatcccttaa  1440
cgtgagtttt cgttccactg agcgtcagac cccgtagaaa agatcaaagg atcttcttga  1500
gatccttttt ttctgcgcgt aatctgctgc ttgcaaacaa aaaaaccacc gctaccagcg  1560
gtggtttgtt tgccggatca agagctacca actctttttc cgaaggtaac tggcttcagc  1620
agagcgcaga taccaaatac tgtccttcta gtgtagccgt agttaggcca ccacttcaag  1680
aactctgtag caccgcctac atacctcgct ctgctaatcc tgttaccagt ggctgctgcc  1740
agtggcgata agtcgtgtct taccgggttg gactcaagac gatagttacc ggataaggcg  1800
cagcggtcgg gctgaacggg gggttcgtgc acacagccca gcttggagcg aacgacctac  1860
accgaactga gatacctaca gcgtgagcta tgagaaagcg ccacgcttcc cgaagggaga  1920
aaggcggaca ggtatccggt aagcggcagg gtcggaacag gagagcgcac gagggagctt  1980
ccagggggaa acgcctggta tctttatagt cctgtcgggt ttcgccacct ctgacttgag  2040
cgtcgatttt tgtgatgctc gtcagggggg cggagcctat ggaaaaacgc cagcaacgcg  2100
gcctttttac ggttcctggc cttttgctgg ccttttgctc acatgttctt tcctgcgtta  2160
tcccctgatt ctgtggataa ccgtattacc gcctttgagt gagctgatac cgctcgccgc  2220
agccgaacga ccgagcgcag cgagtcagtg agcgaggaag cggaagagcg cctgatgcgg  2280
tattttctcc ttacgcatct gtgcggtatt tcacaccgca tatatggtgc actctcagta  2340
caatctgctc tgatgccgca tagttaagcc agtatacact ccgctatcgc tacgtgactg  2400
ggtcatggct gcgccccgac acccgccaac acccgctgac gcgccctgac gggcttgtct  2460
gctcccggca tccgcttaca gacaagctgt gaccgtctcc gggagctgca tgtgtcagag  2520
gttttcaccg tcatcaccga aacgcgcgag gcagctgcgg taaagctcat cagcgtggtc  2580
gtgaagcgat tcacagatgt ctgcctgttc atccgcgtcc agctcgttga gtttctccag  2640
aagcgttaat gtctggcttc tgataaagcg ggccatgtta agggcggttt tttcctgttt  2700
ggtcactgat gcctccgtgt aagggggatt tctgttcatg ggggtaatga taccgatgaa  2760
acgagagagg atgctcacga tacgggttac tgatgatgaa catgcccggt tactggaacg  2820
ttgtgagggt aaacaactgg cggtatggat gcggcgggac cagagaaaaa tcactcaggg  2880
tcaatgccag cgcttcgtta atacagatgt aggtgttcca cagggtagcc agcagcatcc  2940
tgcgatgcag atccggaaca taatggtgca gggcgctgac ttccgcgttt ccagacttta  3000
cgaaacacgg aaaccgaaga ccattcatgt tgttgctcag gtcgcagacg ttttgcagca  3060
gcagtcgctt cacgttcgct cgcgtatcgg tgattcattc tgctaaccag taaggcaacc  3120
```

-continued

```
ccgccagcct agccgggtcc tcaacgacag gagcacgatc atgcgcaccc gtggggccgc  3180
catgccggcg ataatggcct gcttctcgcc gaaacgtttg gtggcgggac cagtgacgaa  3240
ggcttgagcg agggcgtgca agattccgaa taccgcaagc gacaggccga tcatcgtcgc  3300
gctccagcga aagcggtcct cgccgaaaat gacccagagc gctgccggca cctgtcctac  3360
gagttgcatg ataaagaaga cagtcataag tgcggcgacg atagtcatgc cccgcgccca  3420
ccggaaggag ctgactgggt tgaaggctct caagggcatc ggtcgagatc ccggtgccta  3480
atgagtgagc taacttacat taattgcgtt gcgctcactg cccgctttcc agtcgggaaa  3540
cctgtcgtgc cagctgcatt aatgaatcgg ccaacgcgcg gggagaggcg gtttgcgtat  3600
tgggcgccag ggtggttttt cttttcacca gtgagacggg caacagctga ttgcccttca  3660
ccgcctggcc ctgagagagt tgcagcaagc ggtccacgct ggtttgcccc agcaggcgaa  3720
aatcctgttt gatggtggtt aacggcggga tataacatga gctgtcttcg gtatcgtcgt  3780
atcccactac cgagatatcc gcaccaacgc gcagcccgga ctcggtaatg gcgcgcattg  3840
cgcccagcgc catctgatcg ttggcaacca gcatcgcagt gggaacgatg ccctcattca  3900
gcatttgcat ggtttgttga aaaccggaca tggcactcca gtcgccttcc cgttccgcta  3960
tcggctgaat ttgattgcga gtgagatatt tatgccagcc agccagacgc agacgcgccg  4020
agacagaact taatgggccc gctaacagcg cgatttgctg gtgacccaat gcgaccagat  4080
gctccacgcc cagtcgcgta ccgtcttcat gggagaaaat aatactgttg atgggtgtct  4140
ggtcagagac atcaagaaat aacgccggaa cattagtgca ggcagcttcc acagcaatgg  4200
catcctggtc atccagcgga tagttaatga tcagcccact gacgcgttgc gcgagaagat  4260
tgtgcaccgc cgctttacag gcttcgacgc cgcttcgttc taccatcgac accaccacgc  4320
tggcacccag ttgatcggcg cgagatttaa tcgccgcgac aatttgcgac ggcgcgtgca  4380
gggccagact ggaggtggca acgccaatca gcaacgactg tttgcccgcc agttgttgtg  4440
ccacgcggtt gggaatgtaa ttcagctccg ccatcgccgc ttccactttt tcccgcgttt  4500
tcgcagaaac gtggctggcc tggttcacca cgcgggaaac ggtctgataa gagacaccgg  4560
catactctgc gacatcgtat aacgttactg gtttcacatt caccaccctg aattgactct  4620
cttccgggcg ctatcatgcc ataccgcgaa aggttttgcg ccattcgatg gtgtccggga  4680
tctcgacgct ctcccttatg cgactcctgc attaggaagc agcccagtag taggttgagg  4740
ccgttgagca ccgccgccgc aaggaatggt gcatgcaagg agatggcgcc caacagtccc  4800
ccggccacgg ggcctgccac catacccacg ccgaaacaag cgctcatgag cccgaagtgg  4860
cgagcccgat cttccccatc ggtgatgtcg gcgatatagg cgccagcaac cgcacctgtg  4920
gcgccggtga tgccggccac gatgcgtccg gcgtagagga tcgagatctc gatcccgcga  4980
aattaatacg actcactata ggggaattgt gagcggataa caattcccct ctagaaataa  5040
ttttgtttaa ctttaagaag gagatatacc atgggcagca gccatcatca tcatcatcac  5100
cctaatattg aaactcagga agcgctggag gccaaaatgc atggagctgg gttggaccgc  5160
ttcatccgta acaacgaccg tgctattacc gggggaagtg cttctgatac ggactggtat  5220
cgtcgcttaa cacgtcaatt cgttaagcca atggcagatg gaattcaagc ttacctggat  5280
tattatgagg gccgtcgtgg taagccttcg gccagcctgg tccatcttcg ctgtttgcct  5340
acagaaaccg catcttatat tgctatcaaa actatcttcg atggattgac gaaccccaat  5400
cagaccgcgc aaaacttaag tgagcagatt ggaaagcgca tcgaagatga agttcgcttc  5460
atgaagcttg ataatgcagc cccaaaattc attaaggcta tcaaggagtc gttaaaacgc  5520
tcatcatctc agaaatactc gcatggccat gatgtgatgg tgcatgctga aaagctgttg  5580
gcggaagaca aagagcgtca agacaagtat ggggtcatga ttgatcgcca cttatcctgg  5640
cctgataatg acatttttaa tcttggttcc aagttaattg agttatttgc aaacaacatg  5700
ctgttggatg gagaagtact gatccaaaaa cgccttatcg tccgctctca aatcgatcgt  5760
gtaacagtta tcgaggcaac gcctgctatg gagaagtgga ttgaggagta caaggttgtc  5820
gttggcgaaa tggctcccgc cttcgcacca tgtgtcatta agccactgga ttggacagga  5880
cctcgtttcg gaggatggca cactgagaaa atgcgtcgtc aaatgccact tgccaagtgc  5940
aaacaacaat cggttcttag tcgcttgact aagaaacaga tgccgcgtgt ttactcagcc  6000
gtaaatgctc tgcaagcggt ggaatggcgc gttaatcacc gtattttgtc tgtcgcgaat  6060
gaggctcgcc tgcgtggttt gccgttagcc ttaccggacc gtgaaaagct tgcaactccg  6120
ccatgcccgg ttcctcacat gtatgcggag cttcgtggtg cagaactgat gagtgtctta  6180
agtgaatccc agaaggaagc gtttcgtact tggaaagcgg atgcggcaaa gacttacaac  6240
gatgaagctg agcgcaaggc aaaatatcgc gaagtgtgcg cgacgatcga tcaaggaatt  6300
cagtacaagg atttcgacaa gattcatttc gtttatacat tagactttcg cgggcgcgtg  6360
tactgtcaga gttctttgat cagcccacag ggtggggact tgcaaaagtc cttgtgccag  6420
tttgccaatg gtatgccctt aggagaatcg ggagttcact ggttcaaggt ccaaggagcg  6480
aatgtctggg gctgggataa aaaacaattt gaagagcgtg acgaattagt gatggctgac  6540
gattttgtag agctttgctt agacattgcg gcggaccccc tgactttcac tgactggacg  6600
caagccgaca agccgtggca attcttagcg tggtgttttg agtatgcaga ctttgtttca  6660
cactgtgaga ctaatcctcc agagaccttt gtctcacgta ttgcggtcgc gatggacgga  6720
tcatgttcgg gcatccagca ctactccgct atgttgcgcg acgagattgg aggcaaggaa  6780
gttaatttgg tacctgggga ccgtccccaa gatatctatg gagctgttgc caagatcgtc  6840
ggacgttgga tggaggatat ctcagagctt caggtgccct gtgaatcatt cacgcgtatg  6900
ttgtcgaaag gtgcagtgga agggcaattt aagttgtgcc ctttggaggc gcagatgctg  6960
tcccgcgctt gggtcgaaat cggggtgact cgcagcatga ccaagaaacc agtcatgacg  7020
cttccgtacg gaagctcaca aatgacatgt cgcgaaagca tggctcagta tctgaatgat  7080
ttacagaaga aggagaatga acaatcacgc gctcaaaatc gcaaacccgt tgcggtacat  7140
ccttttaatg attcaaaagg ctccatgtct cgtatgcaag ccgagttatt tgcttccggt  7200
cttacatggg aggctatcgg gcacgtggta gtagccgcgc gtgcggcgat gcgcttcatc  7260
aagaaagtca cacatgaaac ttcgtcgcgt aacgtcgcgt tggaatggat tgcgccaact  7320
ggttttatcg tcaatcaatg catttttgac tccacccctc gccgtgtcaa aacgcagatg  7380
atgggtgaga cgttttttac cattcgcgag gaaaacccaa caattagtgt aaacaagatg  7440
aaatcatccg cagctcctaa cttcgtgcac agcatggacg cgtctcactt gtgcattgca  7500
gttgacgagt tcgcattggc cggaatcacc tctattgccg tcattcacga ctccttcggc  7560
acccatgcgg gaaataccga acgtatgcgt aagttactta ttaacagctt tgttgatatg  7620
taccaaaacc atgacgttat tcgcgacttt tatgaggcac aatgcgaacg tgtgaagtgc  7680
gatcttgaac tggatttacc tgcggtgggc accctggacc tggaaactgt gcgccacagt  7740
aagtatatct ttgcctaact cgagcaccac caccaccacc actgagatcc ggctgctaac  7800
aaagcccgaa aggaagctga gttggctgct gccaccgctg agcaataact agcataaccc  7860
```

```
cttggggcct ctaaacgggt cttgaggggt tttttgctga aaggaggaac tatatccgga  7920
t                                                                  7921

SEQ ID NO: 31           moltype = DNA  length = 19
FEATURE                 Location/Qualifiers
source                  1..19
                        mol_type = other DNA
                        organism = synthetic construct
SEQUENCE: 31
aattaagttg cattataga                                               19

SEQ ID NO: 32           moltype = DNA  length = 19
FEATURE                 Location/Qualifiers
source                  1..19
                        mol_type = other DNA
                        organism = synthetic construct
SEQUENCE: 32
gtttaagttg cattataga                                               19

SEQ ID NO: 33           moltype = DNA  length = 19
FEATURE                 Location/Qualifiers
source                  1..19
                        mol_type = other DNA
                        organism = synthetic construct
SEQUENCE: 33
ttttaagttg cattatagg                                               19

SEQ ID NO: 34           moltype = DNA  length = 19
FEATURE                 Location/Qualifiers
source                  1..19
                        mol_type = other DNA
                        organism = synthetic construct
SEQUENCE: 34
gattaggttg cattatagg                                               19

SEQ ID NO: 35           moltype = DNA  length = 19
FEATURE                 Location/Qualifiers
source                  1..19
                        mol_type = other DNA
                        organism = synthetic construct
SEQUENCE: 35
gattaagttg cattaaagg                                               19

SEQ ID NO: 36           moltype = DNA  length = 19
FEATURE                 Location/Qualifiers
source                  1..19
                        mol_type = other DNA
                        organism = synthetic construct
SEQUENCE: 36
atttaggttg cattagagg                                               19

SEQ ID NO: 37           moltype = DNA  length = 19
FEATURE                 Location/Qualifiers
source                  1..19
                        mol_type = other DNA
                        organism = synthetic construct
SEQUENCE: 37
atttaagttg cattataga                                               19

SEQ ID NO: 38           moltype = DNA  length = 19
FEATURE                 Location/Qualifiers
source                  1..19
                        mol_type = other DNA
                        organism = synthetic construct
SEQUENCE: 38
atttaagttg cattatagg                                               19

SEQ ID NO: 39           moltype = DNA  length = 16
FEATURE                 Location/Qualifiers
source                  1..16
                        mol_type = other DNA
                        organism = synthetic construct
SEQUENCE: 39
ttaagttgca ttatag                                                  16

SEQ ID NO: 40           moltype = DNA  length = 16
FEATURE                 Location/Qualifiers
source                  1..16
                        mol_type = other DNA
```

```
                       organism = synthetic construct
SEQUENCE: 40
ttaggttgca ttatag                                                 16

SEQ ID NO: 41          moltype = DNA  length = 16
FEATURE                Location/Qualifiers
source                 1..16
                       mol_type = other DNA
                       organism = synthetic construct
SEQUENCE: 41
ttaggttgca ttagag                                                 16

SEQ ID NO: 42          moltype = DNA  length = 19
FEATURE                Location/Qualifiers
source                 1..19
                       mol_type = other DNA
                       organism = synthetic construct
SEQUENCE: 42
ttttaagttg cattatagg                                              19

SEQ ID NO: 43          moltype = DNA  length = 19
FEATURE                Location/Qualifiers
source                 1..19
                       mol_type = other DNA
                       organism = synthetic construct
SEQUENCE: 43
ttttaagttg cattatagg                                              19

SEQ ID NO: 44          moltype = DNA  length = 19
FEATURE                Location/Qualifiers
source                 1..19
                       mol_type = other DNA
                       organism = synthetic construct
SEQUENCE: 44
ttttaagttg cattatagt                                              19

SEQ ID NO: 45          moltype = DNA  length = 19
FEATURE                Location/Qualifiers
source                 1..19
                       mol_type = other DNA
                       organism = synthetic construct
SEQUENCE: 45
ttttaagttg cattataag                                              19

SEQ ID NO: 46          moltype = DNA  length = 19
FEATURE                Location/Qualifiers
source                 1..19
                       mol_type = other DNA
                       organism = synthetic construct
SEQUENCE: 46
ttttaagttg cattataat                                              19

SEQ ID NO: 47          moltype = DNA  length = 4083
FEATURE                Location/Qualifiers
source                 1..4083
                       mol_type = other DNA
                       organism = synthetic construct
SEQUENCE: 47
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatggc tagccccgcg aaatgtttaa gttgcattat agggaaataa gagagaaaag  240
aagagtaaga agaaatataa gagccaccgc caccatggag gacgccaaga acatcaagaa  300
gggccccgcc cccttctacc ccctggagga cggcaccgcc ggcgagcagc tgcacaaggc  360
catgaagcgg tacgccctgg tgcccggcac catcgccttc accgacgccc acatcgaggt  420
ggacatcacc tacgccgagt acttcgagat gagcgtgcgg ctggccgagg ccatgaagcg  480
gtacggcctg aacaccaacc accggatcgt ggtgtgcagc gagaacagcc tgcagttctt  540
catgcccgtg ctgggcgccc tgttcatcgg cgtggccgtg gcccccgcca acgacatcta  600
caacgagcgg gagctgctga acagcatggg catcagccag cccaccgtgg tgttcgtgag  660
caagaagggc ctgcagaaga tcctgaacgt gcagaagaag ctgcccatca tccagaagat  720
catcatcatg gacagcaaga ccgactacca gggcttccag agcatgtaca ccttcgtgac  780
cagccacctg ccccccggct tcaacgagta cgacttcgtg cccgagagct tcgaccggga  840
caagaccatc gccctgatca tgaacagcag cggcagcacc ggcctgccca agggcgtggc  900
cctgccccac cggaccgcct gcgtgcggtt cagccacgcc cgggacccca tcttcggcaa  960
ccagatcatc cccgacaccg ccatcctgag cgtggtgccc ttccaccacg gcttcggcat  1020
gttcaccacc ctgggctacc tgatctgcgg cttccgggtg gtgctgatgt accggttcga  1080
ggaggagctg ttcctgcgga gcctgcagga ctacaagatc cagagcgccc tgctggtgcc  1140
caccctgttc agcttcttcg ccaagagcac cctgatcgac aagtacgacc tgagcaacct  1200
gcacgagatc gccagcggcg gcgccccccct gagcaaggag gtgggcgagg ccgtggccaa  1260
```

```
gcggttccac ctgcccggca tccggcaggg ctacggcctg accgagacca ccagcgccat  1320
cctgatcacc cccgagggcg acgacaagcc cggcgccgtg ggcaaggtgg tgcccttctt  1380
cgaggccaag gtggtggacc tggacaccgg caagaccctg ggcgtgaacc agcggggcga  1440
gctgtgcgtg cggggcccca tgatcatgag cggctacgtg aacaaccccg aggccaccaa  1500
cgccctgatc gacaaggacg gctggctgca cagcggcgac atcgcctact gggacgagga  1560
cgagcacttc ttcatcgtgg accggctgaa aagtctgatc aagtacaagg gctaccaggt  1620
ggcccccgcc gagctggaga gcatcctgct gcagcacccc aacatcttcg acgccggcgt  1680
ggccggcctg cccgacgacg acgccggcga gctgcccgcc gccgtggtgg tgctggagca  1740
cggcaagacc atgaccgaga aggagatcgt ggactacgtg gccagccagg tgaccaccgc  1800
caagaagctg cggggcggcg tggtgttcgt ggacgaggtg cccaagggcc tgaccggcaa  1860
gctggacgcc cggaagatcc gggagatcct gatcaaggcc aagaagggcg gcaagatcgc  1920
cgtgtgaggc gcgcctatgt tacgtgcaaa ggtgattgtc accccccgaa agaccatatt  1980
gtgacacacc ctcagtatca cgcccaaaca tttacagccg cggtgtcaaa aaccgcgtgg  2040
acgtggttaa catccctgct gggaggatca gccgtaatta ttataattgg cttggtgctg  2100
gctactattg tggccatgta cgtgctgacc aaccagaaac ataattgaat acagcagcaa  2160
ttggcaagct gcttacatag aactcgcggc gattggcatg ccgccttaaa atttttattt  2220
tatttttctt ttcttttccg aatcggattt tgtttttaat atttcaaaaa aaaaaaaaaa  2280
aaaaaaaaaa aaaaaaaaaa aaaaaaaaaa aaaaaaaaaa aaaaaagaag agcacatgtg  2340
agcaaaaggc cagcaaaagg ccaggaaccg taaaaaggcc gcgttgctgg cgtttttcca  2400
taggctccgc ccccctgacg agcatcacaa aaatcgacgc tcaagtcaga ggtggcgaaa  2460
cccgacagga ctataaagat accaggcgtt tccccctgga agctccctcg tgcgctctcc  2520
tgttccgacc ctgccgctta ccggatacct gtccgccttt ctcccttcgg gaagcgtggc  2580
gctttctcat agctcacgct gtaggtatct cagttcggtg taggtcgttc gctccaagct  2640
gggctgtgtg cacgaacccc ccgttcagcc cgaccgctgc gccttatccg gtaactatcg  2700
tcttgagtcc aacccggtaa gacacgactt atcgccactg gcagcagcca ctggtaacag  2760
gattagcaga gcgaggtatg taggcggtgc tacagagttc ttgaagtggt ggcctaacta  2820
cggctacact agaagaacag tatttggtat ctgcgctctg ctgaagccag ttaccttcgg  2880
aaaaagagtt ggtagctctt gatccggcaa acaaaccacc gctggtagcg gtggtttttt  2940
tgtttgcaag cagcagatta cgcgcagaaa aaaaggatct caagaagatc ctttgatctt  3000
ttctacgggg tctgacgctc agtggaacga aaactcacgt taagggattt tggtcatgag  3060
attatcaaaa aggatcttca cctagatcct tttaaattaa aaatgaagtt ttaaatcaag  3120
cccaatctga ataatgttac aaccaattaa ccaattctga ttagaaaaac tcatcgagca  3180
tcaaatgaaa ctgcaattta ttcatatcag gattatcaat accatatttt tgaaaaagcc  3240
gtttctgtaa tgaaggagaa aactcaccga ggcagttcca taggatggca agatcctggt  3300
atcggtctgc gattccgact cgtccaacat caatacaacc tattaatttc ccctcgtcaa  3360
aaataaggtt atcaagtgag aaatcaccat gagtgacgac tgaatccggt gagaatggca  3420
aaagtttatg catttctttc cagacttgtt caacaggcca gccattacgc tcgtcatcaa  3480
aatcactcgc atcaaccaaa ccgttattca ttcgtgattg cgcctgagcg agacgaaata  3540
cgcgatcgct gttaaaagga caattacaaa caggaatcga atgcaaccgg cgcaggaaca  3600
ctgccagcgc atcaacaata ttttcacctg aatcaggata ttcttctaat acctggaatg  3660
ctgtttttcc ggggatcgca gtggtgagta accatgcatc atcaggagta cggataaaat  3720
gcttgatggt cggaagaggc ataaattccg tcagccagtt tagtctgacc atctcatctg  3780
taacatcatt ggcaacgcta cctttgccat gtttcagaaa caactctggc gcatcgggct  3840
tcccatacaa gcgatagatt gtcgcacctg attgcccgac attatcgcga gcccatttat  3900
acccatataa atcagcatcc atgttggaat ttaatcgcgg cctcgacgtt tcccgttgaa  3960
tatggctcat aacacccctt gtattactgt ttatgtaagc agacagtttt attgttcatg  4020
atgatatatt tttatcttgt gcaatgtaac atcagagatt ttgagacacg ggccagagct  4080
gca                                                                4083

SEQ ID NO: 48           moltype = DNA  length = 4083
FEATURE                 Location/Qualifiers
source                  1..4083
                        mol_type = other DNA
                        organism = synthetic construct
SEQUENCE: 48
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatggc tagccccgcg aaattaatac gactcactat agggaaataa gagagaaaag  240
aagagtaaga agaaatataa gagccaccgc caccatggag gacgccaaga acatcaagaa  300
gggccccgcc cccttctacc ccctggagga cggcaccgcc ggcgagcagc tgcacaaggc  360
catgaagcgg tacgccctgg tgcccggcac catcgccttc accgacgccc acatcgaggt  420
ggacatcacc tacgccgagt acttcgagat gagcgtgcgg ctggccgagg ccatgaagcg  480
gtacggcctg aacaccaacc accggatcgt ggtgtgcagc gagaacagcc tgcagttctt  540
catgcccgtg ctgggcgccc tgttcatcgg cgtggccgtg gcccccgcca acgacatcta  600
caacgagcgg gagctgctga acagcatggg catcagccag cccaccgtgg tgttcgtgag  660
caagaagggc ctgcagaaga tcctgaacgt gcagaagaag ctgcccatca tccagaagat  720
catcatcatg gacagcaaga ccgactacca gggcttccag agcatgtaca ccttcgtgac  780
cagccacctg cccccggct tcaacgagta cgacttcgtg cccgagagct tcgaccggga  840
caagaccatc gccctgatca tgaacagcag cggcagcacc ggcctgccca agggcgtggc  900
cctgccccac cggaccgcct gcgtgcggtt cagccacgcc cgggacccca tcttcggcaa  960
ccagatcatc cccgacaccg ccatcctgag cgtggtgccc ttccaccacg gcttcggcat  1020
gttcaccacc ctgggctacc tgatctgcgg cttccgggtg gtgctgatgt accggttcga  1080
ggaggagctg ttcctgcgga gcctgcagga ctacaagatc cagagcgccc tgctggtgcc  1140
caccctgttc agcttcttcg ccaagagcac cctgatcgac aagtacgacc tgagcaacct  1200
gcacgagatc gccagcggcg gcgcccccct gagcaaggag gtgggcgagg ccgtggccaa  1260
gcggttccac ctgcccggca tccggcaggg ctacggcctg accgagacca ccagcgccat  1320
cctgatcacc cccgagggcg acgacaagcc cggcgccgtg ggcaaggtgg tgcccttctt  1380
cgaggccaag gtggtggacc tggacaccgg caagaccctg ggcgtgaacc agcggggcga  1440
```

-continued

```
gctgtgcgtg cggggcccca tgatcatgag cggctacgtg aacaaccccg aggccaccaa  1500
cgccctgatc gacaaggacg gctggctgca cagcggcgac atcgcctact gggacgagga  1560
cgagcacttc ttcatcgtgg accggctgaa aagtctgatc aagtacaagg gctaccaggt  1620
ggcccccgcc gagctggaga gcatcctgct gcagcacccc aacatcttcg acgccggcgt  1680
ggccggcctg cccgacgacg acgccggcga gctgcccgcc gccgtggtgg tgctggagca  1740
cggcaagacc atgaccgaga aggagatcgt ggactacgtg gccagccagg tgaccaccgc  1800
caagaagctg cggggcggcg tggtgttcgt ggacgaggtg cccaagggcc tgaccggcaa  1860
gctggacgcc cggaagatcc gggagatcct gatcaaggcc aagaagggcg gcaagatcgc  1920
cgtgtgaggc gcgcctatgt tacgtgcaaa ggtgattgtc acccccccgaa agaccatatt  1980
gtgacacacc ctcagtatca cgcccaaaca tttacagccg cggtgtcaaa aaccgcgtgg  2040
acgtggttaa catccctgct gggaggatca gccgtaatta ttataattgg cttggtgctg  2100
gctactattg tggccatgta cgtgctgacc aaccagaaac ataattgaat acagcagcaa  2160
ttggcaagct gcttacatag aactcgcggc gattggcatg ccgccttaaa atttttattt  2220
tatttttctt ttcttttccg aatcggattt tgttttttaat atttcaaaaa aaaaaaaaaa  2280
aaaaaaaaaa aaaaaaaaaa aaaaaaaaaa aaaaaaaaaa aaaaaagaag agcacatgtg  2340
agcaaaaggc cagcaaaagg ccaggaaccg taaaaaggcc gcgttgctgg cgtttttcca  2400
taggctccgc ccccctgacg agcatcacaa aaatcgacgc tcaagtcaga ggtggcgaaa  2460
cccgacagga ctataaagat accaggcgtt tccccctgga agctccctcg tgcgctctcc  2520
tgttccgacc ctgccgctta ccggatacct gtccgccttt ctcccttcgg gaagcgtggc  2580
gctttctcat agctcacgct gtaggtatct cagttcggtg taggtcgttc gctccaagct  2640
gggctgtgtg cacgaacccc ccgttcagcc cgaccgctgc gccttatccg gtaactatcg  2700
tcttgagtcc aacccggtaa gacacgactt atcgccactg gcagcagcca ctggtaacag  2760
gattagcaga gcgaggtatg taggcggtgc tacagagttc ttgaagtggt ggcctaacta  2820
cggctacact agaagaacag tatttggtat ctgcgctctg ctgaagccag ttaccttcgg  2880
aaaaagagtt ggtagctctt gatccggcaa acaaaccacc gctggtagcg gtggtttttt  2940
tgtttgcaag cagcagatta cgcgcagaaa aaaaggatct caagaagatc ctttgatctt  3000
ttctacgggg tctgacgctc agtggaacga aaactcacgt taagggattt tggtcatgag  3060
attatcaaaa aggatcttca cctagatcct tttaaattaa aaatgaagtt ttaaatcaag  3120
cccaatctga ataatgttac aaccaattaa ccaattctga ttagaaaaac tcatcgagca  3180
tcaaatgaaa ctgcaattta ttcatatcag gattatcaat accatatttt tgaaaaagcc  3240
gtttctgtaa tgaaggagaa aactcaccga ggcagttcca taggatggca agatcctggt  3300
atcggtctgc gattccgact cgtccaacat caatacaacc tattaatttc ccctcgtcaa  3360
aaataaggtt atcaagtgag aaatcaccat gagtgacgac tgaatccggt gagaatggca  3420
aaagtttatg catttctttc cagacttgtt caacaggcca gccattacgc tcgtcatcaa  3480
aatcactcgc atcaaccaaa ccgttattca ttcgtgattg cgcctgagcg agacgaaata  3540
cgcgatcgct gttaaaagga caattacaaa caggaatcga atgcaaccgg cgcaggaaca  3600
ctgccagcgc atcaacaata ttttcacctg aatcaggata ttcttctaat acctggaatg  3660
ctgtttttcc ggggatcgca gtggtgagta accatgcatc atcaggagta cggataaaat  3720
gcttgatggt cggaagaggc ataaattccg tcagccagtt tagtctgacc atctcatctg  3780
taacatcatt ggcaacgcta cctttgccat gtttcagaaa caactctggc gcatcgggct  3840
tcccatacaa gcgatagatt gtcgcacctg attgcccgac attatcgcga gcccatttat  3900
acccatataa atcagcatcc atgttggaat ttaatcgcgg cctcgacgtt tcccgttgaa  3960
tatggctcat aacacccctt gtattactgt ttatgtaagc agacagtttt attgttcatg  4020
atgatatatt tttatcttgt gcaatgtaac atcagagatt ttgagacacg ggccagagct  4080
gca                                                                4083

SEQ ID NO: 49          moltype = RNA  length = 2101
FEATURE                Location/Qualifiers
source                 1..2101
                       mol_type = other RNA
                       organism = synthetic construct
SEQUENCE: 49
gggaaataag agagaaaaga agagtaagaa gaaatataag agccaccgcc accatggagg  60
acgccaagaa catcaagaag ggccccgccc ccttctaccc cctggaggac ggcaccgccg  120
gcgagcagct gcacaaggcc atgaagcggt acgccctggt gcccggcacc atcgccttca  180
ccgacgccca catcgaggtg gacatcacct acgccgagta cttcgagatg agcgtgcggc  240
tggccgaggc catgaagcgg tacggcctga acaccaacca ccggatcgtg gtgtgcagcg  300
agaacagcct gcagttcttc atgcccgtgc tgggcgccct gttcatcggc gtggccgtgg  360
cccccgccaa cgacatctac aacgagcggg agctgctgaa cagcatgggc atcagccagc  420
ccaccgtggt gttcgtgagc aagaagggcc tgcagaagat cctgaacgtg cagaagaagc  480
tgcccatcat ccagaagatc atcatcatgg acagcaagac cgactaccag ggcttccaga  540
gcatgtacac cttcgtgacc agccacctgc cccccggctt caacgagtac gacttcgtgc  600
ccgagagctt cgaccgggac aagaccatcg ccctgatcat gaacagcagc ggcagcaccg  660
gcctgcccaa gggcgtggcc ctgccccacc ggaccgcctg cgtgcggttc agccacgccc  720
gggaccccat cttcggcaac cagatcatcc ccgacaccgc catcctgagc gtggtgccct  780
tccaccacgg cttcggcatg ttcaccaccc tgggctacct gatctgcggc ttccgggtgg  840
tgctgatgta ccggttcgag gaggagctgt tcctgcggag cctgcaggac tacaagatcc  900
agagcgccct gctggtgccc accctgttca gcttcttcgc caagagcacc ctgatcgaca  960
agtacgacct gagcaacctg cacgagatcg ccagcggcgg cgccccccctg agcaaggagg  1020
tgggcgaggc cgtggccaag cggttccacc tgcccggcat ccggcagggc tacggcctga  1080
ccgagaccac cagcgccatc ctgatcaccc ccgagggcga cgacaagccc ggcgccgtgg  1140
gcaaggtggt gcccttcttc gaggccaagg tggtggacct ggacaccggc aagaccctgg  1200
gcgtgaacca gcggggcgag ctgtgcgtgc ggggccccat gatcatgagc ggctacgtga  1260
acaaccccga ggccaccaac gccctgatcg acaaggacgg ctggctgcac agcggcgaca  1320
tcgcctactg ggacgaggac gagcacttct tcatcgtgga ccggctgaaa agtctgatca  1380
agtacaaggg ctaccaggtg gcccccgccg agctggagag catcctgctg cagcacccca  1440
acatcttcga cgccggcgtg gccggcctgc ccgacgacga cgccggcgag ctgcccgccg  1500
ccgtggtggt gctggagcac ggcaagacca tgaccgagaa ggagatcgtg gactacgtgg  1560
ccagccaggt gaccaccgcc aagaagctgc ggggcggcgt ggtgttcgtg gacgaggtgc  1620
```

```
ccaagggcct gaccggcaag ctggacgccc ggaagatccg ggagatcctg atcaaggcca  1680
agaagggcgg caagatcgcc gtgtgaggcg cgcctatgtt acgtgcaaag gtgattgtca  1740
ccccccgaaa gaccatattg tgacacaccc tcagtatcac gcccaaacat ttacagccgc  1800
ggtgtcaaaa accgcgtgga cgtggttaac atccctgctg ggaggatcag ccgtaattat  1860
tataattggc ttggtgctgg ctactattgt ggccatgtac gtgctgacca accagaaaca  1920
taattgaata cagcagcaat tggcaagctg cttacataga actcgcggcg attggcatgc  1980
cgccttaaaa tttttatttt atttttcttt tcttttccga atcggatttt gtttttaata  2040
tttcaaaaaa aaaaaaaaaa aaaaaaaaaa aaaaaaaaaa aaaaaaaaaa aaaaaaaaaa  2100
a                                                                  2101

SEQ ID NO: 50          moltype = RNA  length = 2062
FEATURE                Location/Qualifiers
source                 1..2062
                       mol_type = other RNA
                       organism = synthetic construct
SEQUENCE: 50
gggaaataag agagaaaaga agagtaagaa gaaatataag accccggcgc cgccaccatg  60
gaggacgcca agaacatcaa gaagggcccc gcccccttct accccctgga ggacggcacc  120
gccggcgagc agctgcacaa ggccatgaag cggtacgccc tggtgcccgg caccatcgcc  180
ttcaccgacg cccacatcga ggtggacatc acctacgccg agtacttcga gatgagcgtg  240
cggctggccg aggccatgaa gcggtacggc ctgaacacca accaccggat cgtggtgtgc  300
agcgagaaca gcctgcagtt cttcatgccc gtgctgggcg ccctgttcat cggcgtggcc  360
gtggcccccg ccaacgacat ctacaacgag cgggagctgc tgaacagcat gggcatcagc  420
cagcccaccg tggtgttcgt gagcaagaag ggcctgcaga agatcctgaa cgtgcagaag  480
aagctgccca tcatccagaa gatcatcatc atggacagca agaccgacta ccagggcttc  540
cagagcatgt acaccttcgt gaccagccac ctgcccccccg gcttcaacga gtacgacttc  600
gtgcccgaga gcttcgaccg ggacaagacc atcgccctga tcatgaacag cagcggcagc  660
accggcctgc ccaagggcgt ggccctgccc caccggaccg cctgcgtgcg gttcagccac  720
gcccgggacc ccatcttcgg caaccagatc atccccgaca ccgccatcct gagcgtggtg  780
cccttccacc acggcttcgg catgttcacc accctgggct acctgatctg cggcttccgg  840
gtggtgctga tgtaccggtt cgaggaggag ctgttcctgc ggagcctgca ggactacaag  900
atccagagcg ccctgctggt gcccaccctg ttcagcttct tcgccaagag caccctgatc  960
gacaagtacg acctgagcaa cctgcacgag atcgccagcg gcggcgcccc cctgagcaag  1020
gaggtgggcg aggccgtggc caagcggttc cacctgcccg gcatccggca gggctacggc  1080
ctgaccgaga ccaccagcgc catcctgatc acccccgagg gcgacgacaa gcccggcgcc  1140
gtgggcaagg tggtgccctt cttcgaggcc aaggtggtgg acctggacac cggcaagacc  1200
ctgggcgtga accagcgggg cgagctgtgc gtgcggggcc ccatgatcat gagcggctac  1260
gtgaacaacc ccgaggccac caacgccctg atcgacaagg acggctggct gcacagcggc  1320
gacatcgcct actgggacga ggacgagcac ttcttcatcg tggaccggct gaaaagtctg  1380
atcaagtaca agggctacca ggtggccccc gccgagctgg agagcatcct gctgcagcac  1440
cccaacatct tcgacgccgg cgtggccggc ctgcccgacg acgacgccgg cgagctgccc  1500
gccgccgtgg tggtgctgga gcacggcaag accatgaccg agaaggagat cgtggactac  1560
gtggccagcc aggtgaccac cgccaagaag ctgcgggggcg gcgtggtgtt cgtggacgag  1620
gtgcccaagg gcctgaccgg caagctggac gcccggaaga tccgggagat cctgatcaag  1680
gccaagaagg gcggcaagat cgccgtgtga ctcgagctgg tactgcatgc acgcaatgct  1740
agctgcccct ttcccgtcct gggtaccccg agtctccccc gacctcgggt cccaggtatg  1800
ctcccacctc cacctgcccc actcaccacc tctgctagtt ccagacacct cccaagcacg  1860
cagcaatgca gctcaaaacg cttagcctag ccacaccccc acgggaaaca gcagtgatta  1920
acctttagca ataaacgaaa gtttaactaa gctatactaa ccccagggtt ggtcaatttc  1980
gtgccagcca caccctggag ctagcaaaaa aaaaaaaaaa aaaaaaaaaa aaaaaaaaaa  2040
aaaaaaaaaa aaaaaaaaaa aa                                           2062

SEQ ID NO: 51          moltype = DNA  length = 1823
FEATURE                Location/Qualifiers
source                 1..1823
                       mol_type = other DNA
                       organism = synthetic construct
SEQUENCE: 51
ttttaagttg cattataggg agacccaagc ttggtaccga gctcggatcc gccaccatga  60
agaccttaat tcttgccgtt gcattagtct actgcgccac tgttcattgc caggactgtc  120
cttacgaacc tgatccacca aacacagttc caacttcctg tgaagctaaa gaaggagaat  180
gtattgatag cagctgtggc acctgcacga gagacatact atcagatgga ctgtgtgaaa  240
ataaaccagg aaaaacatgt tgccgaatgt gtcagtatgt aattgaatgc agagtagagg  300
ccgcaggatg gtttagaaca ttctatggaa agagattcca gttccaggaa cctggtacat  360
acgtgttggg tcaaggaacc aagggcggcg actggaaggt gtccatcacc ctggagaacc  420
tggatggaac caagggggct gtgctgacca agacaagact ggaagtggct ggagacatca  480
ttgacatcgc tcaagctact gagaatccca tcactgtaaa cggtggagct gaccctatca  540
tcgccaaccc gtacaccatc ggcgaggtca ccatcgctgt tgttgagatg ccaggcttca  600
acatcaccgt cattgagttc ttcaaactga tcgtgatcga catcctcgga ggaagatctg  660
taagaatcgc cccagacaca gcaaacaaag gaatgatctc tggcctctgt ggagatctta  720
aaatgatgga agatacagac ttcacttcag atccagaaca actcgctatt cagcctaaga  780
tcaaccagga gtttgacggt tgtccactct atggaaatcc tgatgacgtt gcatactgca  840
aaggtcttct ggagccgtac aaggacagct gccgcaaccc catcaacttc tactactaca  900
ccatctcctg cgccttcgcc cgctgtatgg gtggagacga gcgagcctca cacgtgctgc  960
ttgactacag ggagacgtgc gctgctcccg aaactagagg aacctgcgtt ttgtctggac  1020
atactttcta cgatacattt gacaaagcaa gataccaatt ccagggtccc tgcaaggaga  1080
ttcttatggc cgccgactgt ttctggaaca cttgggatgt gaaggtttca cacaggaatg  1140
ttgactctta cactgaagta gagaaagtac gaatcaggaa acaatcgact gtagtagaac  1200
tcattgttga tggaaaacag attctggttg gaggagaagc cgtgtccgtc ccgtacagct  1260
```

```
ctcagaacac ttccatctac tggcaagatg gtgacatact gactacagcc atcctacctg  1320
aagctctggt ggtcaagttc aacttcaagc aactgctcgt cgtacatatt agagatccat  1380
tcgatggtaa gacttgcggt atttgcggta actacaacca ggatttcagt gatgattctt  1440
ttgatgctga aggagcctgt gatctgaccc ccaacccacc gggatgcacc gaagaacaga  1500
aacctgaagc tgaacgactc tgcaatagtc tcttcgccgg tcaaagtgat cttgatcaga  1560
aatgtaacgt gtgccacaag cctgaccgtg tcgaacgatg catgtacgag tattgcctga  1620
ggggacaaca gggtttctgt gaccacgcat gggagttcaa gaaagaatgc tacataaagc  1680
atggagacac cctagaagta ccagatgaat gcaaataggc ggccgcaata aaatatcttt  1740
attttcatta catctgtgtg ttggtttttt gtgtgtctag aaataattct tactgtcatg  1800
ccaagtaaga tgcttttctg tgc                                           1823
```

```
SEQ ID NO: 52          moltype = RNA  length = 1806
FEATURE                Location/Qualifiers
source                 1..1806
                       mol_type = other RNA
                       organism = synthetic construct
SEQUENCE: 52
gggagaccca agcttggtac cgagctcgga tccgccacca tgaagacctt aattcttgcc  60
gttgcattag tctactgcgc cactgttcat tgccaggact gtccttacga acctgatcca  120
ccaaacacag ttccaacttc ctgtgaagct aaagaaggag aatgtattga tagcagctgt  180
ggcacctgca cgagagacat actatcagat ggactgtgtg aaaataaacc aggaaaaaca  240
tgttgccgaa tgtgtcagta tgtaattgaa tgcagagtag aggccgcagg atggtttaga  300
acattctatg gaaagagatt ccagttccag gaacctggta catacgtgtt gggtcaagga  360
accaagggcg gcgactggaa ggtgtccatc accctggaga acctggatgg aaccaagggg  420
gctgtgctga ccaagacaag actggaagtg gctggagaca tcattgacat cgctcaagct  480
actgagaatc ccatcactgt aaacggtgga gctgacccta tcatcgccaa cccgtacacc  540
atcggcgagg tcaccatcgc tgttgttgag atgccaggct tcaacatcac cgtcattgag  600
ttcttcaaac tgatcgtgat cgacatcctc ggaggaagat ctgtaagaat cgccccagac  660
acagcaaaca aaggaatgat ctctggcctc tgtggagatc ttaaaatgat ggaagataca  720
gacttcactt cagatccaga acaactcgct attcagccta agatcaacca ggagtttgac  780
ggttgtccac tctatggaaa tcctgatgac gttgcatact gcaaaggtct tctggagccg  840
tacaaggaca gctgccgcaa ccccatcaac ttctactact acaccatctc ctgcgccttc  900
gcccgctgta tgggtggaga cgagcgagcc tcacacgtgc tgcttgacta cagggagacg  960
tgcgctgctc ccgaaactag aggaacctgc gttttgtctg gacatacttt ctacgataca  1020
tttgacaaag caagatacca attccagggt ccctgcaagg agattcttat ggccgccgac  1080
tgtttctgga acacttggga tgtgaaggtt tcacacagga atgttgactc ttacactgaa  1140
gtagagaaag tacgaatcag gaaacaatcg actgtagtag aactcattgt tgatggaaaa  1200
cagattctgg ttggaggaga agccgtgtcc gtcccgtaca gctctcagaa cacttccatc  1260
tactggcaag atggtgacat actgactaca gccatcctac ctgaagctct ggtggtcaag  1320
ttcaacttca agcaactgct cgtcgtacat attagagatc cattcgatgg taagacttgc  1380
ggtatttgcg gtaactacaa ccaggatttc agtgatgatt cttttgatgc tgaaggagcc  1440
tgtgatctga cccccaaccc accgggatgc accgaagaac agaaacctga agctgaacga  1500
ctctgcaata gtctcttcgc cggtcaaagt gatcttgatc agaaatgtaa cgtgtgccac  1560
aagcctgacc gtgtcgaacg atgcatgtac gagtattgcc tgaggggaca acagggtttc  1620
tgtgaccacg catgggagtt caagaaagaa tgctacataa agcatggaga caccctagaa  1680
gtaccagatg aatgcaaata ggcggccgca ataaaatatc tttattttca ttacatctgt  1740
gtgttggttt tttgtgtgtc tagaaataat tcttactgtc atgccaagta agatgctttt  1800
ctgtgc                                                              1806
```

```
SEQ ID NO: 53          moltype = DNA  length = 3294
FEATURE                Location/Qualifiers
source                 1..3294
                       mol_type = other DNA
                       organism = synthetic construct
SEQUENCE: 53
gctagtggtg ctagccccgc gaaatgttta agttgcatta tagggtctag aaataatttt  60
gtttaacttt agagtacacg agtcaggcta cagcatcctc tggttcagac tacttgattc  120
atgtgtaccc tatatgcgag gatatgtgta tcgtagaaat tgtcaggcag taacgttccg  180
cgagttttaa tgggcgcgcc atgactctaa gagtgatata cctcctcggt ctcgggcccg  240
gggtgtaatt agcccagtta gacacgatcg cccgacgtat attgttgctt gggtatcgtc  300
gcatgcgaag tattgcccaa ggagacacaa caagcaactt atgttgactc ccttcgacca  360
ttaaaatttg ttagaacgga cagaaaggat gcgccttata aatgtcctgt gcagtgatga  420
agcgacctca aaacgcttca tgatctaacc gactcacctt gccgttccct ccgcgcctta  480
aaaccggccg gtcttgcgaa aagcgggaaa cgagtttacc cacggatagc agggaatgtt  540
gcggctggct agggagcatg aaggtagata ctccacggct tacctttccg gggctcaaca  600
tctagccaca gaccttttcg ttaagcccac ccccactgga tactgaatca tcagggaacc  660
ggacccaacc agtttgggct cgtccaagct tcggtctcgt ccctaagtgc aaagatatgg  720
aaagagcagc ataggtatat ggattattct tttaccactc gtttcttacc gtaacttacg  780
caatggatca cgtgccgagg cggcggtaca gctgttcgaa gggctctgtc gggaacgcta  840
acatccagcc ggtaaattcc aaactaggga aaggacacgc actgaattga atatagtcgt  900
gaagggtggt gtaagtcgtg cacagcccgc attaagtact aaacagcgtc caatcttgat  960
ctacttacgg cctgatgttc ttcagcacct cctagcactg gagtacttcg ctatcaatga  1020
gattagcact ttgtacatgt catccagccc gagtctgggg tccgacaatg cggtcgccga  1080
ttggtatctg catgtagtat taaacggagc tgccgcggct gcggattata gttcatgtct  1140
tgacggtcct cgtgaactgt ggttaacctg caggaggcct ttaattaagg tggtgcggcc  1200
gcgctagcgg tcccggggga tcgatccggc tgctaacaaa gcccgaaagg aagctgagtt  1260
ggctgctgcc accgctgagc aataactagc ataacccctt ggggcctcta aacgggtctt  1320
gaggggtttt ttgctgaaag gaggaactat atccggaagc ttggcactgg ccgaccgggg  1380
tcgagcactg actcgctgcg ctcggtcgtt cggctgcggc gagcggtatc agctcactca  1440
```

-continued aaggcggtaa tacggttatc cacagaatca ggggataacg caggaaagaa catgtgagca 1500
aaaggccagc aaaaggccag gaaccgtaaa aaggccgcgt tgctggcgtt tttccatagg 1560
ctccgccccc ctgacgagca tcacaaaaat cgacgctcaa gtcagaggtg gcgaaacccg 1620
acaggactat aaagatacca ggcgtttccc cctggaagct ccctcgtgcg ctctcctgtt 1680
ccgaccctgc cgcttaccgg atacctgtcc gcctttctcc cttcgggaag cgtggcgctt 1740
tctcatagct cacgctgtag gtatctcagt tcggtgtagg tcgttcgctc caagctgggc 1800
tgtgtgcacg aaccccccgt tcagcccgac cgctgcgcct tatccggtaa ctatcgtctt 1860
gagtccaacc cgctaagaca cgacttatcg ccactggcag cagccactgg taacaggatt 1920
agcagagcga ggtatgtagg cggtgctaca gagttcttga agtggtggcc taactacggc 1980
tacactagaa gaacagtatt tggtatctgc gctctgctga agccagttac cttcggaaaa 2040
agagttggta gctcttgatc cggcaaacaa accaccgctg gtagcggtgg tttttttgtt 2100
tgcaagcagc agattacgcg cagaaaaaaa ggatctcaag aagatccttt gatcttttct 2160
acggggtctg acgctcagtg gaacgaaaac tcacagatcc gggattttgg tcatgagatt 2220
atcaaaaagg atcttcacct agatcctttt aaattaaaaa tgaagtttta aatcaatcta 2280
aagtatatat gagtaaactt ggtctgacag ttaccaatgc ttaatcagtg aggcacctat 2340
ctcagcgatc tgtctatttc gttcatccat agttgcctga ctccccgtcg tgtagataac 2400
tacgatacgg gagggcttac catctggccc cagtgctgca atgataccgc gagacccacg 2460
ctcaccggct ccagatttat cagcaataaa ccagccagcc ggaagggccg agcgcagaag 2520
tggtcctgca actttatccg cctccatcca gtctattaat tgttgccggg aagctagagt 2580
aagtagttcg ccagttaata gtttgcgcaa cgttgttgcc attgctacag gcatcgtggt 2640
gtcacgctcg tcgtttggta tggcttcatt cagctccggt tcccaacgat caaggcgagt 2700
tacatgatcc cccatgttgt gcaaaaaagc ggttagctcc ttcggtcctc cgatcgttgt 2760
cagaagtaag ttggccgcag tgttatcact catggttatg gcagcactgc ataattctct 2820
tactgtcatg ccatccgtaa gatgcttttc tgtgactggt gagtactcaa ccaagtcatt 2880
ctgagaatag tgtatgcggc gaccgagttg ctcttgcccg gcgtcaatac gggataatac 2940
cgcgccacat agcagaactt taaaagtgct catcattgga aaacgttctt cggggcgaaa 3000
actctcaagg atcttaccgc tgttgagatc cagttcgatg taacccactc gtgcacccaa 3060
ctgatcttca gcatctttta ctttcaccag cgtttctggg tgagcaaaaa caggaaggca 3120
aaatgccgca aaaaagggaa taagggcgac acggaaatgt tgaatactca tactcttcct 3180
ttttcaatat tattgaagca tttatcaggg ttattgtctc atgagcggat acatatttga 3240
atgtatttag aaaaataaac aaataggggt tccgcgcaca tttccccgaa aagt 3294

SEQ ID NO: 54 moltype = DNA length = 3294
FEATURE Location/Qualifiers
source 1..3294
mol_type = other DNA
organism = synthetic construct
SEQUENCE: 54
gctagtggtg ctagccccgc gaaattaata cgactcacta tagggtctag aaataatttt 60
gtttaacttt agagtacacg agtcaggcta cagcatcctc tggttcagac tacttgattc 120
atgtgtaccc tatatgcgag gatatgtgta tcgtagaaat tgtcaggcag taacgttccg 180
cgagttttaa tgggcgcgcc atgactctaa gagtgatata cctcctcggt ctcgggcccg 240
gggtgtaatt agcccagtta gacacgatcg cccgacgtat attgttgctt gggtatcgtc 300
gcatgcgaag tattgcccaa ggagacacaa caagcaactt atgttgactc ccttcgacca 360
ttaaaatttg ttagaacgga cagaaaggat gcgccttata aatgtcctgt gcagtgatga 420
agcgacctca aaacgcttca tgatctaacc gactcacctt gccgttccct ccgcgcctta 480
aaaccggccg gtcttgcgaa aagcgggaaa cgagtttacc cacggatagc agggaatgtt 540
gcggctggct agggagcatg aaggtagata ctccacggct tacctttccg gggctcaaca 600
tctagccaca gaccttttcg ttaagcccac ccccactgga tactgaatca tcagggaacc 660
ggacccaacc agtttgggct cgtccaagct tcggtctcgt ccctaagtgc aaagatatgg 720
aaagagcagc ataggtatat ggattattct tttaccactc gtttcttacc gtaacttacg 780
caatggatca cgtgccgagg cggcggtaca gctgttcgaa gggctctgtc gggaacgcta 840
acatccagcc ggtaaattcc aaactaggga aaggacacgc actgaattga atatagtcgt 900
gaagggtggt gtaagtcgtg cacagcccgc attaagtact aaacagcgtc caatcttgat 960
ctacttacgg cctgatgttc ttcagcacct cctagcactg gagtacttcg ctatcaatga 1020
gattagcact ttgtacatgt catccagccc gagtctgggg tccgacaatg cggtcgccga 1080
ttggtatctg catgtagtat taaacggagc tgccgcggct gcggattata gttcatgtct 1140
tgacggtcct cgtgaactgt ggttaacctg caggaggcct ttaattaagg tggtgcggcc 1200
gcgctagcgg tcccggggga tcgatccggc tgctaacaaa gcccgaaagg aagctgagtt 1260
ggctgctgcc accgctgagc aataactagc ataacccctt ggggcctcta aacgggtctt 1320
gaggggtttt ttgctgaaag gaggaactat atccggaagc ttggcactgg ccgaccgggg 1380
tcgagcactg actcgctgcg ctcggtcgtt cggctgcggc gagcggtatc agctcactca 1440
aaggcggtaa tacggttatc cacagaatca ggggataacg caggaaagaa catgtgagca 1500
aaaggccagc aaaaggccag gaaccgtaaa aaggccgcgt tgctggcgtt tttccatagg 1560
ctccgccccc ctgacgagca tcacaaaaat cgacgctcaa gtcagaggtg gcgaaacccg 1620
acaggactat aaagatacca ggcgtttccc cctggaagct ccctcgtgcg ctctcctgtt 1680
ccgaccctgc cgcttaccgg atacctgtcc gcctttctcc cttcgggaag cgtggcgctt 1740
tctcatagct cacgctgtag gtatctcagt tcggtgtagg tcgttcgctc caagctgggc 1800
tgtgtgcacg aaccccccgt tcagcccgac cgctgcgcct tatccggtaa ctatcgtctt 1860
gagtccaacc cgctaagaca cgacttatcg ccactggcag cagccactgg taacaggatt 1920
agcagagcga ggtatgtagg cggtgctaca gagttcttga agtggtggcc taactacggc 1980
tacactagaa gaacagtatt tggtatctgc gctctgctga agccagttac cttcggaaaa 2040
agagttggta gctcttgatc cggcaaacaa accaccgctg gtagcggtgg tttttttgtt 2100
tgcaagcagc agattacgcg cagaaaaaaa ggatctcaag aagatccttt gatcttttct 2160
acggggtctg acgctcagtg gaacgaaaac tcacagatcc gggattttgg tcatgagatt 2220
atcaaaaagg atcttcacct agatcctttt aaattaaaaa tgaagtttta aatcaatcta 2280
aagtatatat gagtaaactt ggtctgacag ttaccaatgc ttaatcagtg aggcacctat 2340
ctcagcgatc tgtctatttc gttcatccat agttgcctga ctccccgtcg tgtagataac 2400
tacgatacgg gagggcttac catctggccc cagtgctgca atgataccgc gagacccacg 2460

```
ctcaccggct ccagatttat cagcaataaa ccagccagcc ggaagggccg agcgcagaag  2520
tggtcctgca actttatccg cctccatcca gtctattaat tgttgccggg aagctagagt  2580
aagtagttcg ccagttaata gtttgcgcaa cgttgttgcc attgctacag gcatcgtggt  2640
gtcacgctcg tcgtttggta tggcttcatt cagctccggt tcccaacgat caaggcgagt  2700
tacatgatcc cccatgttgt gcaaaaaagc ggttagctcc ttcggtcctc cgatcgttgt  2760
cagaagtaag ttggccgcag tgttatcact catggttatg gcagcactgc ataattctct  2820
tactgtcatg ccatccgtaa gatgcttttc tgtgactggt gagtactcaa ccaagtcatt  2880
ctgagaatag tgtatgcggc gaccgagttg ctcttgcccg gcgtcaatac gggataatac  2940
cgcgccacat agcagaactt taaaagtgct catcattgga aaacgttctt cggggcgaaa  3000
actctcaagg atcttaccgc tgttgagatc cagttcgatg taacccactc gtgcacccaa  3060
ctgatcttca gcatctttta ctttcaccag cgtttctggg tgagcaaaaa caggaaggca  3120
aaatgccgca aaaaagggaa taagggcgac acggaaatgt tgaatactca tactcttcct  3180
ttttcaatat tattgaagca tttatcaggg ttattgtctc atgagcggat acatatttga  3240
atgtatttag aaaaataaac aaataggggt tccgcgcaca tttccccgaa aagt        3294

SEQ ID NO: 55          moltype = RNA  length = 1118
FEATURE                Location/Qualifiers
source                 1..1118
                       mol_type = other RNA
                       organism = synthetic construct
SEQUENCE: 55
gggtctagaa ataattttgt ttaactttag agtacacgag tcaggctaca gcatcctctg  60
gttcagacta cttgattcat gtgtacccta tatgcgagga tatgtgtatc gtagaaattg  120
tcaggcagta acgttccgcg agttttaatg ggcgcgccat gactctaaga gtgatatacc  180
tcctcggtct cgggcccggg gtgtaattag cccagttaga cacgatcgcc cgacgtatat  240
tgttgcttgg gtatcgtcgc atgcgaagta ttgcccaagg agacacaaca agcaacttat  300
gttgactccc ttcgaccatt aaaatttgtt agaacggaca gaaaggatgc gccttataaa  360
tgtcctgtgc agtgatgaag cgacctcaaa acgcttcatg atctaaccga ctcaccttgc  420
cgttccctcc gcgccttaaa accggccggt cttgcgaaaa gcgggaaacg agtttaccca  480
cggatagcag ggaatgttgc ggctggctag ggagcatgaa ggtagatact ccacggctta  540
cctttccggg gctcaacatc tagccacaga ccttttcgtt aagcccaccc ccactggata  600
ctgaatcatc agggaaccgg acccaaccag tttgggctcg tccaagcttc ggtctcgtcc  660
ctaagtgcaa agatatggaa agagcagcat aggtatatgg attattcttt taccactcgt  720
ttcttaccgt aacttacgca atggatcacg tgccgaggcg gcggtacagc tgttcgaagg  780
gctctgtcgg gaacgctaac atccagccgg taaattccaa actagggaaa ggacacgcac  840
tgaattgaat atagtcgtga agggtggtgt aagtcgtgca cagcccgcat taagtactaa  900
acagcgtcca atcttgatct acttacggcc tgatgttctt cagcacctcc tagcactgga  960
gtacttcgct atcaatgaga ttagcacttt gtacatgtca tccagcccga gtctggggtc  1020
cgacaatgcg gtcgccgatt ggtatctgca tgtagtatta aacggagctg ccgcggctgc  1080
ggattatagt tcatgtcttg acggtcctcg tgaactgt                         1118

SEQ ID NO: 56          moltype = DNA  length = 3296
FEATURE                Location/Qualifiers
source                 1..3296
                       mol_type = other DNA
                       organism = synthetic construct
SEQUENCE: 56
gctagtggtg ctagccccgc gaaatgttta agttgcatta tagggtctag aaataatttt  60
gtttaacttt agagtacacg agtcaggcta cagcatcttg acaccagaat attatggatt  120
ggacgcttcc cactaaatgg aagactgttc ggtcataaac actactagga attcctctcc  180
agtcatcatg ttcgatcgtc tagcagcaat ctcttccgat cgatatttgc gcgtgactca  240
ggcgagccca tgacagcttc tccccgtgag aaccacgact agaagttatc tgttgagctg  300
ctagcttcgt ggcccggcca tggtagtagc ggctcactcg cgctaacttt gcctgctcga  360
gaaaacggcc gaaacaccca gcaacacaag ccacttaatt tgttgataga taataagatc  420
aggttattag tcgctctgca cttactttaa gtgccaacta tgctgtatcg gccagggtga  480
aaacgggtgc cgccacttca gtgtgtcgga gtctgctgac ggattagggc acagacgtat  540
ggttatatcc taaggtagtg tgtcaatgta ctggggacaa agtcagtggg caccgcatca  600
ggagtgcaac ctccgctagt accgactcgt caatgctttg agcgatggct tgcgctccca  660
aatccttaag cttttatgca ttcggctctg gccctcaggc ctgacctgga atttcatcgg  720
aaacgcctta accgacatta catcgacacc aagatcccga cgcttcatgc ggagacgata  780
gagactctaa ccaagaataa aaggagtagt ccctaatcta ctgaaacggg gatacctcaa  840
atcacgggaa tgcgttactg acccgctatg tgaggctcgg atcaccctcg ttctattgcc  900
ttgtaatcat ggtggggcgg cggagcggga ttagagggtg tccctaatgt gagtagatct  960
gtagtaatga tacgtctcct caatatgagg cgtattgcag gtcacagcac agggagattt  1020
cggcgcaccc agccgagttg cctccgtcgt tgtttaggta tatgcataac tgctcacgac  1080
aaatacagca gagcctacgt tggttatcg  aatccttgtg gacaagaagc ttcttcatgt  1140
cttgacggtc ctcgtgaact gtggttaacc tgcaggaggc ctttaattaa ggtggtgcgg  1200
ccgcgctagc ggtcccgggg gatcgatccg gctgctaaca aagcccgaaa ggaagctgag  1260
ttggctgctg ccaccgctga gcaataacta gcataacccc ttggggcctc taaacgggtc  1320
ttgaggggtt ttttgctgaa aggaggaact atatccggaa gcttggcact ggccgaccgg  1380
ggtcgagcac tgactcgctg cgctcggtcg ttcggctgcg gcgagcggta tcagctcact  1440
caaaggcggt aatacggtta tccacagaat caggggataa cgcaggaaag aacatgtgag  1500
caaaaggcca gcaaaaggcc aggaaccgta aaaaggccgc gttgctggcg tttttccata  1560
ggctccgccc ccctgacgag catcacaaaa atcgacgctc aagtcagagg tggcgaaacc  1620
cgacaggact ataaagatac caggcgtttc cccctggaag ctccctcgtg cgctctcctg  1680
ttccgaccct gccgcttacc ggatacctgt ccgcctttct cccttcggga agcgtggcgc  1740
tttctcatag ctcacgctgt aggtatctca gttcggtgta ggtcgttcgc tccaagctgg  1800
gctgtgtgca cgaacccccc gttcagcccg accgctgcgc cttatccggt aactatcgtc  1860
ttgagtccaa cccgctaaga cacgacttat cgccactggc agcagccact ggtaacagga  1920
```

```
ttagcagagc gaggtatgta ggcggtgcta cagagttctt gaagtggtgg cctaactacg  1980
gctacactag aagaacagta tttggtatct gcgctctgct gaagccagtt accttcggaa  2040
aaagagttgg tagctcttga tccggcaaac aaaccaccgc tggtagcggt ggtttttttg  2100
tttgcaagca gcagattacg cgcagaaaaa aaggatctca agaagatcct ttgatctttt  2160
ctacggggtc tgacgctcag tggaacgaaa actcacagat ccgggatttt ggtcatgaga  2220
ttatcaaaaa ggatcttcac ctagatcctt ttaaattaaa aatgaagttt taaatcaatc  2280
taaagtatat atgagtaaac ttggtctgac agttaccaat gcttaatcag tgaggcacct  2340
atctcagcga tctgtctatt tcgttcatcc atagttgcct gactccccgt cgtgtagata  2400
actacgatac gggagggctt accatctggc cccagtgctg caatgatacc gcgagaccca  2460
cgctcaccgg ctccagattt atcagcaata aaccagccag ccggaagggc cgagcgcaga  2520
agtggtcctg caactttatc cgcctccatc cagtctatta attgttgccg ggaagctaga  2580
gtaagtagtt cgccagttaa tagtttgcgc aacgttgttg ccattgctac aggcatcgtg  2640
gtgtcacgct cgtcgtttgg tatggcttca ttcagctccg gttcccaacg atcaaggcga  2700
gttacatgat cccccatgtt gtgcaaaaaa gcggttagct ccttcggtcc tccgatcgtt  2760
gtcagaagta agttggccgc agtgttatca ctcatggtta tggcagcact gcataattct  2820
cttactgtca tgccatccgt aagatgcttt tctgtgactg gtgagtactc aaccaagtca  2880
ttctgagaat agtgtatgcg gcgaccgagt tgctcttgcc cggcgtcaat acgggataat  2940
accgcgccac atagcagaac tttaaaagtg ctcatcattg gaaaacgttc ttcggggcga  3000
aaactctcaa ggatcttacc gctgttgaga tccagttcga tgtaacccac tcgtgcaccc  3060
aactgatctt cagcatcttt tactttcacc agcgtttctg ggtgagcaaa aacaggaagg  3120
caaaatgccg caaaaaaggg aataagggcg acacggaaat gttgaatact catactcttc  3180
ctttttcaat attattgaag catttatcag ggttattgtc tcatgagcgg atacatattt  3240
gaatgtattt agaaaaataa acaaataggg gttccgcgca catttccccg aaaagt      3296

SEQ ID NO: 57           moltype = DNA  length = 3296
FEATURE                 Location/Qualifiers
source                  1..3296
                        mol_type = other DNA
                        organism = synthetic construct
SEQUENCE: 57
gctagtggtg ctagccccgc gaaattaata cgactcacta tagggtctag aaataatttt  60
gtttaacttt agagtacacg agtcaggcta cagcatcttg acaccagaat attatggatt  120
ggacgcttcc cactaaatgg aagactgttc ggtcataaac actactagga attcctctcc  180
agtcatcatg ttcgatcgtc tagcagcaat ctcttccgat cgatatttgc gcgtgactca  240
ggcgagccca tgacagcttc tccccgtgag aaccacgact agaagttatc tgttgagctg  300
ctagcttcgt ggcccggcca tggtagtagc ggctcactcg cgctaacttt gcctgctcga  360
gaaaacgggc gaaacaccca gcaacacaag ccacttaatt tgttgataga taataagatc  420
aggttattag tcgctctgca cttactttaa gtgccaacta tgctgtatcg gccagggtga  480
aaacgggtgc cgccacttca gtgtgtcgga gtctgctgac ggattagggc acagacgtat  540
ggttatatcc taaggtagtg tgtcaatgta ctggggacaa agtcagtggg caccgcatca  600
ggagtgcaac ctccgctagt accgactcgt caatgctttg agcgatggct tgcgctccca  660
aatccttaag cttttatgca ttcggctctg gccctcaggc ctgacctgga atttcatcgg  720
aaacgcctta accgacatta catcgacacc aagatcccga cgcttcatgc ggagacgata  780
gagactctaa ccaagaataa aaggagtagt ccctaatcta ctgaaacggg gatacctcaa  840
atcacgggaa tgcgttactg acccgctatg tgaggctcgg atcaccctcg ttctattgcc  900
ttgtaatcat ggtggggcgg cggagcggga ttagagggtg tccctaatgt gagtagatct  960
gtagtaatga tacgtctcct caatatgagg cgtattgcag gtcacagcac agggagattt  1020
cggcgcaccc agccgagttg cctccgtcgt tgtttaggta tatgcataac tgctcacgac  1080
aaatacagca gagcctacgt tgggttatcg aatccttgtg gacaagaagc ttcttcatgt  1140
cttgacggtc ctcgtgaact gtggttaacc tgcaggaggc ctttaattaa ggtggtgcgg  1200
ccgcgctagc ggtcccgggg gatcgatccg gctgctaaca aagcccgaaa ggaagctgag  1260
ttggctgctg ccaccgctga gcaataacta gcataacccc ttggggcctc taaacgggtc  1320
ttgaggggtt ttttgctgaa aggaggaact atatccggaa gcttggcact ggccgaccgg  1380
ggtcgagcac tgactcgctg cgctcggtcg ttcggctgcg gcgagcggta tcagctcact  1440
caaaggcggt aatacggtta tccacagaat caggggataa cgcaggaaag aacatgtgag  1500
caaaaggcca gcaaaaggcc aggaaccgta aaaaggccgc gttgctggcg tttttccata  1560
ggctccgccc ccctgacgag catcacaaaa atcgacgctc aagtcagagg tggcgaaacc  1620
cgacaggact ataaagatac caggcgtttc cccctggaag ctccctcgtg cgctctcctg  1680
ttccgaccct gccgcttacc ggatacctgt ccgcctttct cccttcggga agcgtggcgc  1740
tttctcatag ctcacgctgt aggtatctca gttcggtgta ggtcgttcgc tccaagctgg  1800
gctgtgtgca cgaacccccc gttcagcccg accgctgcgc cttatccggt aactatcgtc  1860
ttgagtccaa cccgctaaga cacgacttat cgccactggc agcagccact ggtaacagga  1920
ttagcagagc gaggtatgta ggcggtgcta cagagttctt gaagtggtgg cctaactacg  1980
gctacactag aagaacagta tttggtatct gcgctctgct gaagccagtt accttcggaa  2040
aaagagttgg tagctcttga tccggcaaac aaaccaccgc tggtagcggt ggtttttttg  2100
tttgcaagca gcagattacg cgcagaaaaa aaggatctca agaagatcct ttgatctttt  2160
ctacggggtc tgacgctcag tggaacgaaa actcacagat ccgggatttt ggtcatgaga  2220
ttatcaaaaa ggatcttcac ctagatcctt ttaaattaaa aatgaagttt taaatcaatc  2280
taaagtatat atgagtaaac ttggtctgac agttaccaat gcttaatcag tgaggcacct  2340
atctcagcga tctgtctatt tcgttcatcc atagttgcct gactccccgt cgtgtagata  2400
actacgatac gggagggctt accatctggc cccagtgctg caatgatacc gcgagaccca  2460
cgctcaccgg ctccagattt atcagcaata aaccagccag ccggaagggc cgagcgcaga  2520
agtggtcctg caactttatc cgcctccatc cagtctatta attgttgccg ggaagctaga  2580
gtaagtagtt cgccagttaa tagtttgcgc aacgttgttg ccattgctac aggcatcgtg  2640
gtgtcacgct cgtcgtttgg tatggcttca ttcagctccg gttcccaacg atcaaggcga  2700
gttacatgat cccccatgtt gtgcaaaaaa gcggttagct ccttcggtcc tccgatcgtt  2760
gtcagaagta agttggccgc agtgttatca ctcatggtta tggcagcact gcataattct  2820
cttactgtca tgccatccgt aagatgcttt tctgtgactg gtgagtactc aaccaagtca  2880
ttctgagaat agtgtatgcg gcgaccgagt tgctcttgcc cggcgtcaat acgggataat  2940
```

```
accgcgccac atagcagaac tttaaaagtg ctcatcattg gaaaacgttc ttcggggcga  3000
aaactctcaa ggatcttacc gctgttgaga tccagttcga tgtaacccac tcgtgcaccc  3060
aactgatctt cagcatcttt tactttcacc agcgtttctg ggtgagcaaa aacaggaagg  3120
caaaatgccg caaaaaaggg aataagggcg acacggaaat gttgaatact catactcttc  3180
ctttttcaat attattgaag catttatcag ggttattgtc tcatgagcgg atacatattt  3240
gaatgtattt agaaaaataa acaaataggg gttccgcgca catttccccg aaaagt      3296

SEQ ID NO: 58          moltype = RNA  length = 1120
FEATURE                Location/Qualifiers
source                 1..1120
                       mol_type = other RNA
                       organism = synthetic construct
SEQUENCE: 58
gggtctagaa ataattttgt ttaactttag agtacacgag tcaggctaca gcatcttgac  60
accagaatat tatggattgg acgcttccca ctaaatggaa gactgttcgg tcataaacac  120
tactaggaat tcctctccag tcatcatgtt cgatcgtcta gcagcaatct cttccgatcg  180
atatttgcgc gtgactcagg cgagcccatg acagcttctc cccgtgagaa ccacgactag  240
aagttatctg ttgagctgct agcttcgtgg cccggccatg gtagtagcgg ctcactcgcg  300
ctaactttgc ctgctcgaga aaacgggcga aacacccagc aacacaagcc acttaatttg  360
ttgatagata ataagatcag gttattagtc gctctgcact tactttaagt gccaactatg  420
ctgtatcggc cagggtgaaa acgggtgccg ccacttcagt gtgtcggagt ctgctgacgg  480
attagggcac agacgtatgg ttatatccta aggtagtgtg tcaatgtact ggggacaaag  540
tcagtgggca ccgcatcagg agtgcaacct ccgctagtac cgactcgtca atgctttgag  600
cgatggcttg cgctcccaaa tccttaagct tttatgcatt cggctctggc cctcaggcct  660
gacctggaat ttcatcggaa acgccttaac cgacattaca tcgacaccaa gatcccgacg  720
cttcatgcgg agacgataga gactctaacc aagaataaaa ggagtagtcc ctaatctact  780
gaaacgggga tacctcaaat cacgggaatg cgttactgac ccgctatgtg aggctcggat  840
caccctcgtt ctattgcctt gtaatcatgg tggggcggcg gagcgggatt agagggtgtc  900
cctaatgtga gtagatctgt agtaatgata cgtctcctca atatgaggcg tattgcaggt  960
cacagcacag ggagatttcg gcgcacccag ccgagttgcc tccgtcgttg tttaggtata  1020
tgcataactg ctcacgacaa atacagcaga gcctacgttg ggttatcgaa tccttgtgga  1080
caagaagctt cttcatgtct tgacggtcct cgtgaactgt                        1120

SEQ ID NO: 59          moltype = DNA  length = 11580
FEATURE                Location/Qualifiers
source                 1..11580
                       mol_type = other DNA
                       organism = synthetic construct
SEQUENCE: 59
ttttaagttg cattatagga ttgacggcgt agtacacact attgaatcaa acagccgacc  60
aattgcacta ccatcacaat ggagaagcca gtagtaaacg tagacgtaga cccccagagt  120
ccgtttgtcg tgcaactgca aaaaagcttc ccgcaatttg aggtagtagc acagcaggtc  180
actccaaatg accatgctaa tgccagagca ttttcgcatc tggccagtaa actaatcgag  240
ctggaggttc ctaccacagc gacgatcttg gacataggca gcgcaccggc tcgtagaatg  300
ttttccgagc accagtatca ttgtgtctgc cccatgcgta gtccagaaga cccggaccgc  360
atgatgaaat acgccagtaa actggcggaa aaagcgtgca agattacaaa caagaacttg  420
catgagaaga ttaaggatct ccggaccgta cttgatacgc cggatgctga aacaccatcg  480
ctctgctttc acaacgatgt tacctgcaac atgcgtgccg aatattccgt catgcaggac  540
gtgtatatca acgctcccgg aactatctat catcaggcta tgaaaggcgt gcggaccctg  600
tactggattg gcttcgacac cacccagttc atgttctcgg ctatggcagg ttcgtaccct  660
gcgtacaaca ccaactgggc cgacgagaaa gtccttgaag cgcgtaacat cggactttgc  720
agcacaaagc tgagtgaagg taggacagga aaattgtcga taatgaggaa gaaggagttg  780
aagcccgggt cgcgggttta tttctccgta ggatcgacac tttatccaga acacagagcc  840
agcttgcaga gctggcatct tccatcggtg ttccacttga atggaaagca gtcgtacact  900
tgccgctgtg atacagtggt gagttgcgaa ggctacgtag tgaagaaaat caccatcagt  960
cccgggatca cgggagaaac cgtgggatac gcggttacac acaatagcga gggcttcttg  1020
ctatgcaaag ttactgacac agtaaaagga gaacgggtat cgttccctgt gtgcacgtac  1080
atcccggcca ccatatgcga tcagatgact ggtataatgg ccacggatat atcacctgac  1140
gatgcacaaa aacttctggt tgggctcaac cagcgaattg tcattaacgg taggactaac  1200
aggaacacca acaccatgca aaattacctt ctgccgatca tagcacaagg gttcagcaaa  1260
tgggctaagg agcgcaagga tgatcttgat aacgagaaaa tgctgggtac tagagaacgc  1320
aagcttacgt atggctgctt gtgggcgttt cgcactaaga aagtacattc gttttatcgc  1380
ccacctggaa cgcagacctg cgtaaaagtc ccagcctctt ttagcgcttt tcccatgtcg  1440
tccgtatgga cgacctcttt gcccatgtcg ctgaggcaga aattgaaact ggcattgcaa  1500
ccaaagaagg aggaaaaact gctgcaggtc tcggaggaat tagtcatgga ggccaaggct  1560
gcttttgagg atgctcagga ggaagccaga gcggagaagc tccgagaagc acttccacca  1620
ttagtggcag acaaaggcat cgaggcagcc gcagaagttg tctgcgaagt ggaggggctc  1680
caggcggaca tcggagcagc attagttgaa accccgcgcg gtcacgtaag gataatacct  1740
caagcaaatg accgtatgat cggacagtat atcgttgtct cgccaaactc tgtgctgaag  1800
aatgccaaac tcgcaccagc gcacccgcta gcagatcagg ttaagatcat aacacactcc  1860
ggaagatcag gaaggtacgc ggtcgaacca tacgacgcta aagtactgat gccagcagga  1920
ggtgccgtac catggccaga attcctagca ctgagtgaga gcgccacgtt agtgtacaac  1980
gaaagagagt ttgtgaaccg caaactatac cacattgcca tgcatggccc cgccaagaat  2040
acagaagagg agcagtacaa ggttacaaag gcagagcttg cagaaacaga gtacgtgttt  2100
gacgtggaca agaagcgttg cgttaagaag gaagaagcct caggtctggt cctctcggga  2160
gaactgacca accctcccta tcatgagcta gctctggagg gactgaagac ccgacctgcg  2220
gtcccgtaca aggtcgaaac aataggagtg ataggcacac cggggtcggg caagtcagct  2280
attatcaagt caactgtcac ggcacgagat cttgttacca gcggaaagaa agaaaattgt  2340
cgcgaaattg aggccgacgt gctaagactg aggggtatgc agattacgtc gaagacagta  2400
```

```
gattcggtta tgctcaacgg atgccacaaa gccgtagaag tgctgtacgt tgacgaagcg  2460
ttcgcgtgcc acgcaggagc actacttgcc ttgattgcta tcgtcaggcc ccgcaagaag  2520
gtagtactat gcggagaccc catgcaatgc ggattcttca acatgatgca actaaaggta  2580
catttcaatc accctgaaaa agacatatgc accaagacat tctacaagta tatctcccgg  2640
cgttgcacac agccagttac agctattgta tcgacactgc attacgatgg aaagatgaaa  2700
accacgaacc cgtgcaagaa gaacattgaa atcgatatta caggggccac aaagccgaag  2760
ccaggggata tcatcctgac atgtttccgc gggtgggtta agcaattgca aatcgactat  2820
cccggacatg aagtaatgac agccgcggcc tcacaagggc taaccagaaa aggagtgtat  2880
gccgtccggc aaaaagtcaa tgaaaaccca ctgtacgcga tcacatcaga gcatgtgaac  2940
gtgttgctca cccgcactga ggacaggcta gtgtggaaaa ccttgcaggg cgacccatgg  3000
attaagcagc ccactaacat acctaaagga aactttcagg ctactataga ggactgggaa  3060
gctgaacaca agggaataat tgctgcaata aacagcccca ctccccgtgc caatccgttc  3120
agctgcaaga ccaacgtttg ctgggcgaaa gcattggaac cgatactagc cacggccggt  3180
atcgtactta ccggttgcca gtggagcgaa ctgttcccac agtttgcgga tgacaaacca  3240
cattcggcca tttacgcctt agacgtaatt tgcattaagt tttcggcat ggacttgaca   3300
agcggactgt tttctaaaca gagcatccca ctaacgtacc atcccgccga ttcagcgagg  3360
ccggtagctc attgggacaa cagcccagga acccgcaagt atgggtacga tcacgccatt  3420
gccgccgaac tctcccgtag atttccggtg ttccagctag ctgggaaggg cacacaactt  3480
gatttgcaga cggggagaac cagagttatc tctgcacagc ataacctggt cccggtgaac  3540
cgcaatcttc ctcacgcctt agtccccgag tacaaggaga agcaacccgg cccggtcaaa  3600
aaattcttga accagttcaa acaccactca gtacttgtgg tatcagagga aaaaattgaa  3660
gctccccgta agagaatcga atggatcgcc ccgattggca tagccggtgc agataagaac  3720
tacaacctgg ctttcgggtt tccgccgcag gcacggtacg acctggtgtt catcaacatt  3780
ggaactaaat acagaaacca ccactttcag cagtgcgaag accatgcggc gaccttaaaa  3840
accctttcgc gttcggccct gaattgcctt aacccaggag gcaccctcgt ggtgaagtcc  3900
tatggctacg ccgaccgcaa cagtgaggac gtagtcaccg ctcttgccag aaagtttgtc  3960
agggtgtctg cagcgagacc agattgtgtc tcaagcaata cagaaatgta cctgattttc  4020
cgacaactag acaacagccg tacacggcaa ttcacccgc accatctgaa ttgcgtgatt   4080
tcgtccgtgt atgagggtac aagagatgga gttggagccg cgccgtcata ccgcaccaaa  4140
agggagaata ttgctgactg tcaagaggaa gcagttgtca acgcagccaa tccgctgggt  4200
agaccaggcg aaggagtctg ccgtgccatc tataaacgtt ggccgaccag ttttaccgat  4260
tcagccacgg agacaggcac cgcaagaatg actgtgtgcc taggaaagaa agtgatccac  4320
gcggtcggcc ccgatttccg gaagcaccca gaagcagaag ccttgaaatt gctacaaaac  4380
gcctaccatg cagtggcaga cttagtaaat gaacataaca tcaagtctgt cgccattcca  4440
ctgctatcta caggcattta cgcagccgga aaagaccgcc ttgaagtatc acttaactgc  4500
ttgacaaccg cgctagacag aactgacgcg gacgtaacca tctattgcct ggataagaag  4560
tggaaggaaa gaatcgacgc ggcactccaa cttaaggagt ctgtaacaga gctgaaggat  4620
gaagatatgg agatcgacga tgagttagta tggatccatc cagacagttg cttgaaggga  4680
agaaagggat tcagtactac aaaaggaaaa ttgtattcgt acttcgaagg caccaaattc  4740
catcaagcag caaaagacat ggcggagata aaggtcctgt tccctaatga ccaggaaagt  4800
aatgaacaac tgtgtgccta catattgggt gagaccatgg aagcaatccg cgaaaagtgc  4860
ccggtcgacc ataacccgtc gtctagcccg cccaaaacgt tgccgtgcct ttgcatgtat  4920
gccatgacgc cagaaagggt ccacagactt agaagcaata acgtcaaaga agttacagta  4980
tgctcctcca cccccccttcc taagcacaaa attaagaatg ttcagaaggt tcagtgcacg  5040
aaagtagtcc tgtttaatcc gcacactccc gcattcgttc ccgcccgtaa gtacatagaa  5100
gtgccagaac agcctaccgc tcctcctgca caggccgagg aggcccccga agttgtagcg  5160
acaccgtcac catctacagc tgataacacc tcgcttgatg tcacagacat ctcactggat  5220
atggatgaca gtagcgaagg ctcacttttt tcgagcttta gcggatcgga caactctatt  5280
actagtatgg acagttggtc gtcaggacct agttcactag agatagtaga ccgaaggcag  5340
gtggtggtgg ctgacgttca tgccgtccaa gagcctgccc ctattccacc gccaaggcta  5400
aagaagatgg cccgcctggc agcggcaaga aaagagccca ctccaccggc aagcaatagc  5460
tctgagtccc tccacctctc ttttggtggg gtatccatgt ccctcggatc aattttcgac  5520
ggagagacgg cccgccaggc agcggtacaa cccctggcaa caggccccac ggatgtgcct  5580
atgtctttcg gatcgtttc cgacggagag attgatgagc tgagccgcag agtaactgag   5640
tccgaacccg tcctgtttgg atcatttgaa ccgggcgaag tgaactcaat tatatcgtcc  5700
cgatcagccg tatcttttcc actacgcaag cagagacgta gacgcaggag caggaggact  5760
gaatactgac taaccggggt aggtgggtac atattttcga cggacacagg ccctgggcac  5820
ttgcaaaaga agtccgttct gcagaaccag cttacagaac cgaccttgga gcgcaatgtc  5880
ctggaaagaa ttcatgcccc ggtgctcgac acgtcgaaag aggaacaact caaactcagg  5940
taccagatga tgcccaccga agccaacaaa agtaggtacc agtctcgtaa agtagaaaat  6000
cagaaagcca taaccactga gcgactactg tcaggactac gactgtataa ctctgccaca  6060
gatcagccag aatgctataa gatcacctat ccgaaaccat tgtactccag tagcgtaccg  6120
gcgaactact ccgatccaca gttcgctgta gctgtctgta acaactatct gcatgagaac  6180
tatccgacag tagcatctta tcagattact gacgagtacg atgcttactt ggatatggta  6240
gacgggacag tcgcctgcct ggatactgca accttctgcc ccgctaagct tagaagttac  6300
ccgaaaaaac atgagtatag agccccgaat atccgcagtg cggttccatc agcgatgcag  6360
aacacgctac aaaatgtgct cattgccgca actaaaagaa attgcaacgt cacgcagatg  6420
cgtgaactgc caacactgga ctcagcgaca ttcaatgtcg aatgctttcg aaaatatgca  6480
tgtaatgacg agtattggga ggagttcgct cggaagccaa ttaggattac cactgagttt  6540
gtcaccgcat atgtagctag actgaaaggc cctaaggccg ccgcactatt tgcaaagacg  6600
tataatttgg tcccattgca agaagtgcct atggatagat tcgtcatgga catgaaaaga  6660
gacgtgaaag ttacaccagg cacgaaacac acagaagaaa gaccgaaagt acaagtgata  6720
caagccgcag aacccctggc gactgcttac ttatgcggga ttcaccggga attagtgcgt  6780
aggcttacgg ccgtcttgct tccaaacatt cacacgcttt ttgacatgtc ggcggaggat  6840
tttgatgcaa tcatagcaga acacttcaag caaggcgacc cggtactgga gacggatatc  6900
gcatcattcg acaaaagcca agacgacgct atggcgttaa ccggtctgat gatcttggag  6960
gacctgggtg tggatcaacc actactcgac ttgatcgagt gcgcctttgg agaaatatca  7020
tccacccatc tacctacggg tactcgtttt aaattcgggg cgatgatgaa atccggaatg  7080
ttcctcacac tttttgtcaa cacagttttg aatgtcgtta tcgccagcag agtactagag  7140
```

```
gaacggctta aaacgtccag atgtgcagcg ttcattggcg acgacaacat catacatgga  7200
gtagtatctg acaaagaaat ggctgagagg tgcgccacct ggctcaacat ggaggttaag  7260
atcatcgacg cagtcatcgg tgagagacca ccttacttct gcggcggatt tatcttgcaa  7320
gattcggtta cttccacagc gtgccgcgtg gcggatcccc tgaaaaggct gtttaagttg  7380
ggtaaaccgc tcccagccga cgacgagcaa gacgaagaca gaagacgcgc tctgctagat  7440
gaaacaaagg cgtggtttag agtaggtata acaggcactt tagcagtggc cgtgacgacc  7500
cggtatgagg tagacaatat tacacctgtc ctactggcat tgagaacttt tgcccagagc  7560
aaaagagcat tccaagccat cagaggggaa ataaagcatc tctacggtgg tcctaaatag  7620
tcagcatagt acatttcatc tgactaatac tacaacacca ccaccatgaa gaccttaatt  7680
cttgccgttg cattagtcta ctgcgccact gttcattgcc aggactgtcc ttacgaacct  7740
gatccaccaa acacagttcc aacttcctgt gaagctaaag aaggagaatg tattgatagc  7800
agctgtggca cctgcacgag agacatacta tcagatggac tgtgtgaaaa taaaccagga  7860
aaaacatgtt gccgaatgtg tcagtatgta attgaatgca gagtagaggc cgcaggatgg  7920
tttagaacat tctatggaaa gagattccag ttccaggaac ctggtacata cgtgttgggt  7980
caaggaacca agggcggcga ctggaaggtg tccatcaccc tggagaacct ggatggaacc  8040
aagggggctg tgctgaccaa gacaagactg gaagtggctg gagacatcat tgacatcgct  8100
caagctactg agaatcccat cactgtaaac ggtggagctg accctatcat cgccaacccg  8160
tacaccatcg gcgaggtcac catcgctgtt gttgagatgc caggcttcaa catcaccgtc  8220
attgagttct tcaaactgat cgtgatcgac atcctcggag gaagatctgt aagaatcgcc  8280
ccagacacag caaacaaagg aatgatctct ggcctctgtg gagatcttaa aatgatggaa  8340
gatacagact tcacttcaga tccagaacaa ctcgctattc agcctaagat caaccaggag  8400
tttgacggtt gtccactcta tggaaatcct gatgacgttg catactgcaa aggtcttctg  8460
gagccgtaca aggacagctg ccgcaacccc atcaacttct actactacac catctcctgc  8520
gccttcgccc gctgtatggg tggagacgag cgagcctcac acgtgctgct tgactacagg  8580
gagacgtgcg ctgctcccga aactagagga acctgcgttt tgtctggaca tactttctac  8640
gatacatttg acaaagcaag ataccaattc cagggtccct gcaaggagat tcttatggcc  8700
gccgactgtt tctggaacac ttgggatgtg aaggtttcac acaggaatgt tgactcttac  8760
actgaagtag agaaagtacg aatcaggaaa caatcgactg tagtagaact cattgttgat  8820
ggaaaacaga ttctggttgg aggagaagcc gtgtccgtcc cgtacagctc tcagaacact  8880
tccatctact ggcaagatgg tgacatactg actacagcca tcctacctga agctctggtg  8940
gtcaagttca acttcaagca actgctcgtc gtacatatta gagatccatt cgatggtaag  9000
acttgcggta tttgcggtaa ctacaaccag gatttcagtg atgattcttt tgatgctgaa  9060
ggagcctgtg atctgacccc caacccaccg ggatgcaccg aagaacagaa acctgaagct  9120
gaacgactct gcaatagtct cttcgccggt caaagtgatc ttgatcagaa atgtaacgtg  9180
tgccacaagc ctgaccgtgt cgaacgatgc atgtacgagt attgcctgag ggacaacag  9240
ggtttctgtg accacgcatg ggagttcaag aaagaatgct acataaagca tggagacacc  9300
ctagaagtac cagatgaatg caaatagggc gcgcctatgt tacgtgcaaa ggtgattgtc  9360
accccccgaa agaccatatt gtgacacacc ctcagtatca cgcccaaaca tttacagccg  9420
cggtgtcaaa aaccgcgtgg acgtggttaa catccctgct gggagaatca gccgtaatta  9480
ttataattgg cttggtgctg gctactattg tggccatgta cgtgctgacc aaccagaaac  9540
ataattgaat acagcagcaa ttggcaagct gcttacatag aactcgcggc gattggcatg  9600
cgccttaaaa tttttatttt atttttcttt tcttttccga atcggatttt gtttttaata  9660
tttcaaaaaa aaaaaaaaaa aaaaaaaaaa aagcatatga ctaaaaaaaa aaaaaaaaaa  9720
aaaaaaaaaa aaaaaaaaaa aaaaaaaaaa aaaaaaaaaa gaagagctag ggataacagg  9780
gtaattgagc aaaaggccag caaaaggcca ggaaccgtaa aaaggccgcg ttgctggcgt  9840
ttttccatag gctccgcccc cctgacgagc atcacaaaaa tcgacgctca agtcagaggt  9900
ggcgaaaccc gacaggacta taaagatacc aggcgtttcc ccctggaagc tccctcgtgc  9960
gctctcctgt tccgaccctg ccgcttaccg gatacctgtc cgcctttctc ccttcgggaa  10020
gcgtggcgct ttctcatagc tcacgctgta ggtatctcag ttcggtgtag gtcgttcgct  10080
ccaagctggg ctgtgtgcac gaaccccccg ttcagcccga ccgctgcgcc ttatccggta  10140
actatcgtct tgagtccaac ccggtaagac acgacttatc gccactggca gcagccactg  10200
gtaacaggat tagcagagcg aggtatgtag gcggtgctac agagttcttg aagtggtggc  10260
ctaactacgg ctacactaga agaacagtat ttggtatctg cgctctgctg aagccagtta  10320
ccttcggaaa aagagttggt agctcttgat ccggcaaaca aaccaccgct ggtagcggtg  10380
gtttttttgt ttgcaagcag cagattacgc gcagaaaaaa aggatctcaa gaagatcctt  10440
tgatcttttc tacggggtct gacgctcagt ggaacgaaaa ctcacgttaa gggattttgg  10500
tcatgagatt atcaaaaagg atcttcacct agatcctttt aaattaaaaa tgaagtttta  10560
aatcaatcta aagtatatat gagtaaactt ggtctgacag tacaaccaat taaccaattc  10620
tgattagaaa aactcatcga gcatcaaatg aaactgcaat ttattcatat caggattatc  10680
aataccatat ttttgaaaaa gccgtttctg taatgaagga gaaaactcac cgaggcagtt  10740
ccataggatg gcaagatcct ggtatcggtc tgcgattccg actcgtccaa catcaataca  10800
acctattaat ttcccctcgt caaaaataag gttatcaagt gagaaatcac catgagtgac  10860
gactgaatcc ggtgagaatg gcaaaagttt atgcatttct ttccagactt gttcaacagg  10920
ccagccatta cgctcgtcat caaaatcact cgcatcaacc aaaccgttat tcattcgtga  10980
ttgcgcctga gcgagacgaa atacgcgatc gctgttaaaa ggacaattac aaacaggaat  11040
cgaatgcaac cggcgcagga acactgccag cgcatcaaca atattttcac ctgaatcagg  11100
atattcttct aatacctgga atgctgtttt tccggggatc gcagtggtga gtaaccatgc  11160
atcatcagga gtacggataa aatgcttgat ggtcggaaga ggcataaatt ccgtcagcca  11220
gtttagtctg accatctcat ctgtaacatc attggcaacg ctacctttgc catgtttcag  11280
aaacaactct ggcgcatcgg gcttcccata caagcgatag attgtcgcac ctgattgccc  11340
gacattatcg cgagcccatt tatacccata taaatcagca tccatgttgg aatttaatcg  11400
cggcctcgac gtttcccgtt gaatatggct cataacaccc cttgtattac tgtttatgta  11460
agcagacagt tttattgttc atgatgatat atttttatct tgtgcaatgt aacatcagag  11520
attttgagac accacatttc cccgaaaagt gccacctgac gttagggata acagggtaat  11580
```

```
SEQ ID NO: 60          moltype = DNA  length = 11526
FEATURE                Location/Qualifiers
source                 1..11526
                       mol_type = other DNA
```

organism = synthetic construct
SEQUENCE: 60

```
taatacgact cactatagga ttgacggcgt agtacacact attgaatcaa acagccgacc  60
aattgcacta ccatcacaat ggagaagcca gtagtaaacg tagacgtaga cccccagagt  120
ccgtttgtcg tgcaactgca aaaaagcttc ccgcaatttg aggtagtagc acagcaggtc  180
actccaaatg accatgctaa tgccagagca ttttcgcatc tggccagtaa actaatcgag  240
ctggaggttc ctaccacagc gacgatcttg gacataggca gcgcaccggc tcgtagaatg  300
ttttccgagc accagtatca ttgtgtctgc cccatgcgta gtccagaaga cccggaccgc  360
atgatgaaat acgccagtaa actggcggaa aaagcgtgca agattacaaa caagaacttg  420
catgagaaga ttaaggatct ccggaccgta cttgatacgc cggatgctga aacaccatcg  480
ctctgctttc acaacgatgt tacctgcaac atgcgtgccg aatattccgt catgcaggac  540
gtgtatatca acgctcccgg aactatctat catcaggcta tgaaaggcgt gcggaccctg  600
tactggattg gcttcgacac cacccagttc atgttctcgg ctatggcagg ttcgtaccct  660
gcgtacaaca ccaactgggc cgacgagaaa gtccttgaag cgcgtaacat cggactttgc  720
agcacaaagc tgagtgaagg taggacagga aaattgtcga taatgaggaa gaaggagttg  780
aagcccgggt cgcgggttta tttctccgta ggatcgacac tttatccaga acacagagcc  840
agcttgcaga gctggcatct tccatcggtg ttccacttga atggaaagca gtcgtacact  900
tgccgctgtg atacagtggt gagttgcgaa ggctacgtag tgaagaaaat caccatcagt  960
cccgggatca cgggagaaac cgtgggatac gcggttacac acaatagcga gggcttcttg  1020
ctatgcaaag ttactgacac agtaaaagga gaacgggtat cgttccctgt gtgcacgtac  1080
atcccggcca ccatatgcga tcagatgact ggtataatgg ccacggatat atcacctgac  1140
gatgcacaaa aacttctggt tgggctcaac cagcgaattg tcattaacgg taggactaac  1200
aggaacacca acaccatgca aaattacctt ctgccgatca tagcacaagg gttcagcaaa  1260
tgggctaagg agcgcaagga tgatcttgat aacgagaaaa tgctgggtac tagagaacgc  1320
aagcttacgt atggctgctt gtgggcgttt cgcactaaga aagtacattc gttttatcgc  1380
ccacctggaa cgcagacctg cgtaaaagtc ccagcctctt ttagcgcttt tcccatgtcg  1440
tccgtatgga cgacctcttt gcccatgtcg ctgaggcaga aattgaaact ggcattgcaa  1500
ccaaagaagg aggaaaaact gctgcaggtc tcggaggaat tagtcatgga ggccaaggct  1560
gcttttgagg atgctcagga ggaagccaga gcggagaagc tccgagaagc acttccacca  1620
ttagtggcag acaaaggcat cgaggcagcc gcagaagttg tctgcgaagt ggaggggctc  1680
caggcggaca tcggagcagc attagttgaa accccgcgcg gtcacgtaag gataatacct  1740
caagcaaatg accgtatgat cggacagtat atcgttgtct cgccaaactc tgtgctgaag  1800
aatgccaaac tcgcaccagc gcacccgcta gcagatcagg ttaagatcat aacacactcc  1860
ggaagatcag gaaggtacgc ggtcgaacca tacgacgcta aagtactgat gccagcagga  1920
ggtgccgtac catggccaga attcctagca ctgagtgaga gcgccacgtt agtgtacaac  1980
gaaagagagt ttgtgaaccg caaactatac cacattgcca tgcatggccc cgccaagaat  2040
acagaagagg agcagtacaa ggttacaaag gcagagcttg cagaaacaga gtacgtgttt  2100
gacgtggaca agaagcgttg cgttaagaag gaagaagcct caggtctggt cctctcggga  2160
gaactgacca accctcccta tcatgagcta gctctggagg gactgaagac ccgacctgcg  2220
gtcccgtaca aggtcgaaac aataggagtg ataggcacac cggggtcggg caagtcagct  2280
attatcaagt caactgtcac ggcacgagat cttgttacca gcggaaagaa agaaaattgt  2340
cgcgaaattg aggccgacgt gctaagactg aggggtatgc agattacgtc gaagacagta  2400
gattcggtta tgctcaacgg atgccacaaa gccgtagaag tgctgtacgt tgacgaagcg  2460
ttcgcgtgcc acgcaggagc actacttgcc ttgattgcta tcgtcaggcc ccgcaagaag  2520
gtagtactat gcggagaccc catgcaatgc ggattcttca acatgatgca actaaaggta  2580
catttcaatc accctgaaaa agacatatgc accaagacat tctacaagta tatctcccgg  2640
cgttgcacac agccagttac agctattgta tcgacactgc attacgatgg aaagatgaaa  2700
accacgaacc cgtgcaagaa gaacattgaa atcgatatta caggggccac aaagccgaag  2760
ccaggggata tcatcctgac atgtttccgc gggtgggtta agcaattgca aatcgactat  2820
cccggacatg aagtaatgac agccgcggcc tcacaagggc taaccagaaa aggagtgtat  2880
gccgtccggc aaaaagtcaa tgaaaaccca ctgtacgcga tcacatcaga gcatgtgaac  2940
gtgttgctca cccgcactga ggacaggcta gtgtggaaaa ccttgcaggg cgacccatgg  3000
attaagcagc ccactaacat acctaaagga aactttcagg ctactataga ggactgggaa  3060
gctgaacaca agggaataat tgctgcaata aacagcccca ctccccgtgc caatccgttc  3120
agctgcaaga ccaacgtttg ctgggcgaaa gcattggaac cgatactagc cacggccggt  3180
atcgtactta ccggttgcca gtggagcgaa ctgttcccac agtttgcgga tgacaaacca  3240
cattcggcca tttacgcctt agacgtaatt tgcattaagt ttttcggcat ggacttgaca  3300
agcggactgt tttctaaaca gagcatccca ctaacgtacc atcccgccga ttcagcgagg  3360
ccggtagctc attgggacaa cagcccagga acccgcaagt atgggtacga tcacgccatt  3420
gccgccgaac tctcccgtag atttccggtg ttccagctag ctgggaaggg cacacaactt  3480
gatttgcaga cggggagaac cagagttatc tctgcacagc ataacctggt cccggtgaac  3540
cgcaatcttc ctcacgcctt agtccccgag tacaaggaga agcaacccgg cccggtcaaa  3600
aaattcttga accagttcaa acaccactca gtacttgtgg tatcagagga aaaaattgaa  3660
gctccccgta agagaatcga atggatcgcc ccgattggca tagccggtgc agataagaac  3720
tacaacctgg ctttcgggtt tccgccgcag gcacggtacg acctggtgtt catcaacatt  3780
ggaactaaat acagaaacca ccactttcag cagtgcgaag accatgcggc gaccttaaaa  3840
acccttttcgc gttcggccct gaattgcctt aacccaggag gcaccctcgt ggtgaagtcc  3900
tatggctacg ccgaccgcaa cagtgaggac gtagtcaccg ctcttgccag aaagtttgtc  3960
agggtgtctg cagcgagacc agattgtgtc tcaagcaata cagaaatgta cctgattttc  4020
cgacaactag acaacagccg tacacggcaa ttcacccccgc accatctgaa ttgcgtgatt  4080
tcgtccgtgt atgagggtac aagagatgga gttggagccg cgccgtcata ccgcaccaaa  4140
agggagaata ttgctgactg tcaagaggaa gcagttgtca acgcagccaa tccgctgggt  4200
agaccaggcg aaggagtctg ccgtgccatc tataaacgtt ggccgaccag ttttaccgat  4260
tcagccacgg agacaggcac cgcaagaatg actgtgtgcc taggaaagaa agtgatccac  4320
gcggtcggcc ccgatttccg gaagcaccca gaagcagaag ccttgaaatt gctacaaaac  4380
gcctaccatg cagtggcaga cttagtaaat gaacataaca tcaagtctgt cgccattcca  4440
ctgctatcta caggcattta cgcagccgga aaagaccgcc ttgaagtatc acttaactgc  4500
ttgacaaccg cgctagacag aactgacgcg gacgtaacca tctattgcct ggataagaag  4560
tggaaggaaa gaatcgacgc ggcactccaa cttaaggagt ctgtaacaga gctgaaggat  4620
```

```
gaagatatgg agatcgacga tgagttagta tggatccatc cagacagttg cttgaaggga  4680
agaaagggat tcagtactac aaaaggaaaa ttgtattcgt acttcgaagg caccaaattc  4740
catcaagcag caaaagacat ggcggagata aaggtcctgt tccctaatga ccaggaaagt  4800
aatgaacaac tgtgtgccta catattgggt gagaccatgg aagcaatccg cgaaaagtgc  4860
ccggtcgacc ataacccgtc gtctagcccg cccaaaacgt tgccgtgcct ttgcatgtat  4920
gccatgacgc cagaaagggt ccacagactt agaagcaata acgtcaaaga agttacagta  4980
tgctcctcca cccccttcc taagcacaaa attaagaatg ttcagaaggt tcagtgcacg  5040
aaagtagtcc tgtttaatcc gcacactccc gcattcgttc ccgcccgtaa gtacatagaa  5100
gtgccagaac agcctaccgc tcctcctgca caggccgagg aggcccccga agttgtagcg  5160
acaccgtcac catctacagc tgataacacc tcgcttgatg tcacagacat ctcactggat  5220
atggatgaca gtagcgaagg ctcacttttt tcgagcttta gcggatcgga caactctatt  5280
actagtatgg acagttggtc gtcaggacct agttcactag agatagtaga ccgaaggcag  5340
gtggtggtgg ctgacgttca tgccgtccaa gagcctgccc ctattccacc gccaaggcta  5400
aagaagatgg cccgcctggc agcggcaaga aaagagccca ctccaccggc aagcaatagc  5460
tctgagtccc tccacctctc ttttggtggg gtatccatgt ccctcggatc aatttcgac  5520
ggagagacgg cccgccaggc agcggtacaa cccctggcaa caggccccac ggatgtgcct  5580
atgtctttcg gatcgtttc cgacggagag attgatgagc tgagccgcag agtaactgag  5640
tccgaacccg tcctgtttgg atcatttgaa ccgggcgaag tgaactcaat tatatcgtcc  5700
cgatcagccg tatcttttcc actacgcaag cagagacgta gacgcaggag caggaggact  5760
gaatactgac taaccggggt aggtgggtac atattttcga cggacacagg ccctgggcac  5820
ttgcaaaaga agtccgttct gcagaaccag cttacagaac cgaccttgga gcgcaatgtc  5880
ctggaaagaa ttcatgcccc ggtgctcgac acgtcgaaag aggaacaact caaactcagg  5940
taccagatga tgcccaccga agccaacaaa agtaggtacc agtctcgtaa agtagaaaat  6000
cagaaagcca taaccactga gcgactactg tcaggactac gactgtataa ctctgccaca  6060
gatcagccag aatgctataa gatcacctat ccgaaaccat tgtactccag tagcgtaccg  6120
gcgaactact ccgatccaca gttcgctgta gctgtctgta acaactatct gcatgagaac  6180
tatccgacag tagcatctta tcagattact gacgagtacg atgcttactt ggatatggta  6240
gacgggacag tcgcctgcct ggatactgca accttctgcc ccgctaagct tagaagttac  6300
ccgaaaaaac atgagtatag agccccgaat atccgcagtg cggttccatc agcgatgcag  6360
aacacgctac aaaatgtgct cattgccgca actaaaagaa attgcaacgt cacgcagatg  6420
cgtgaactgc caacactgga ctcagcgaca ttcaatgtcg aatgctttcg aaaatatgca  6480
tgtaatgacg agtattggga ggagttcgct cggaagccaa ttaggattac cactgagttt  6540
gtcaccgcat atgtagctag actgaaaggc cctaaggccg ccgcactatt tgcaaagacg  6600
tataatttgg tcccattgca agaagtgcct atggatagat tcgtcatgga catgaaaaga  6660
gacgtgaaag ttacaccagg cacgaaacac acagaagaaa gaccgaaagt acaagtgata  6720
caagccgcag aacccctggc gactgcttac ttatgcggga ttcaccggga attagtgcgt  6780
aggcttacgg ccgtcttgct tccaaacatt cacacgcttt ttgacatgtc ggcggaggat  6840
tttgatgcaa tcatagcaga acacttcaag caaggcgacc cggtactgga gacggatatc  6900
gcatcattcg acaaaagcca agacgacgct atggcgttaa ccggtctgat gatcttggag  6960
gacctgggtg tggatcaacc actactcgac ttgatcgagt gcgcctttgg agaaatatca  7020
tccacccatc tacctacggg tactcgtttt aaattcgggg cgatgatgaa atccggaatg  7080
ttcctcacac tttttgtcaa cacagttttg aatgtcgtta tcgccagcag agtactagag  7140
gaacggctta aaacgtccag atgtgcagcg ttcattggcg acgacaacat catacatgga  7200
gtagtatctg acaaagaaat ggctgagagg tgcgccacct ggctcaacat ggaggttaag  7260
atcatcgacg cagtcatcgg tgagagacca ccttacttct gcggcggatt tatcttgcaa  7320
gattcggtta cttccacagc gtgccgcgtg gcggatcccc tgaaaaggct gtttaagttg  7380
ggtaaaccgc tcccagccga cgacgagcaa gacgaagaca gaagacgcgc tctgctagat  7440
gaaacaaagg cgtggtttag agtaggtata acaggcactt tagcagtggc cgtgacgacc  7500
cggtatgagg tagacaatat tacacctgtc ctactggcat tgagaacttt tgcccagagc  7560
aaaagagcat tccaagccat cagaggggaa ataaagcatc tctacggtgg tcctaaatag  7620
tcagcatagt acatttcatc tgactaatac tacaacacca ccaccatgaa gaccttaatt  7680
cttgccgttg cattagtcta ctgcgccact gttcattgcc aggactgtcc ttacgaacct  7740
gatccaccaa acacagttcc aacttcctgt gaagctaaag aaggagaatg tattgatagc  7800
agctgtggca cctgcacgag agacatacta tcagatggac tgtgtgaaaa taaaccagga  7860
aaaacatgtt gccgaatgtg tcagtatgta attgaatgca gagtagaggc cgcaggatgg  7920
tttagaacat tctatggaaa gagattccag ttccaggaac ctggtacata cgtgttgggt  7980
caaggaacca agggcggcga ctggaaggtg tccatcaccc tggagaacct ggatggaacc  8040
aagggggctg tgctgaccaa gacaagactg gaagtggctg gagacatcat tgacatcgct  8100
caagctactg agaatcccat cactgtaaac ggtggagctg accctatcat cgccaacccg  8160
tacaccatcg gcgaggtcac catcgctgtt gttgagatgc caggcttcaa catcaccgtc  8220
attgagttct tcaaactgat cgtgatcgac atcctcggag gaagatctgt aagaatcgcc  8280
ccagacacag caaacaaagg aatgatctct ggcctctgtg gagatcttaa aatgatggaa  8340
gatacagact tcacttcaga tccagaacaa ctcgctattc agcctaagat caaccaggag  8400
tttgacggtt gtccactcta tggaaatcct gatgacgttg catactgcaa aggtcttctg  8460
gagccgtaca aggacagctg ccgcaacccc atcaacttct actactacac catctcctgc  8520
gccttcgccc gctgtatggg tggagacgag cgagcctcac acgtgctgct tgactacagg  8580
gagacgtgcg ctgctcccga aactagagga acctgcgttt tgtctggaca tactttctac  8640
gatacatttg acaaagcaag ataccaattc cagggtccct gcaaggagat tcttatggcc  8700
gccgactgtt tctggaacac ttgggatgtg aaggtttcac acaggaatgt tgactcttac  8760
actgaagtag agaaagtacg aatcaggaaa caatcgactg tagtagaact cattgttgat  8820
ggaaaacaga ttctggttgg aggagaagcc gtgtccgtcc cgtacagctc tcagaacact  8880
tccatctact ggcaagatgg tgacatactg actacagcca tcctacctga agctctggtg  8940
gtcaagttca acttcaagca actgctcgtc gtacatatta gagatccatt cgatggtaag  9000
acttgcggta tttgcggtaa ctacaaccag gatttcagtg atgattcttt tgatgctgaa  9060
ggagcctgtg atctgacccc caacccaccg ggatgcaccg aagaacagaa acctgaagct  9120
gaacgactct gcaatagtct cttcgccggt caaagtgatc ttgatcagaa atgtaacgtg  9180
tgccacaagc ctgaccgtgt cgaacgatgc atgtacgagt attgcctgag ggacaacag  9240
ggtttctgtg accacgcatg ggagttcaag aaagaatgct acataaagca tggagacacc  9300
ctagaagtac cagatgaatg caaatagggc gcgcctatgt tacgtgcaaa ggtgattgtc  9360
```

```
acccccccgaa agaccatatt gtgacacacc ctcagtatca cgcccaaaca tttacagccg  9420
cggtgtcaaa aaccgcgtgg acgtggttaa catccctgct gggagaatca gccgtaatta  9480
ttataattgg cttggtgctg gctactattg tggccatgta cgtgctgacc aaccagaaac  9540
ataattgaat acagcagcaa ttggcaagct gcttacatag aactcgcggc gattggcatg  9600
cgccttaaaa tttttatttt atttttcttt tcttttccga atcggatttt gtttttaata  9660
tttcaaaaaa aaaaaaaaaa aaaaaaaaaa aaaaaaaaaa aaaaaagaag agctagggat  9720
aacagggtaa ttgagcaaaa ggccagcaaa aggccaggaa ccgtaaaaag gccgcgttgc  9780
tggcgttttt ccataggctc cgcccccctg acgagcatca caaaaatcga cgctcaagtc  9840
agaggtggcg aaacccgaca ggactataaa gataccaggc gtttccccct ggaagctccc  9900
tcgtgcgctc tcctgttccg accctgccgc ttaccggata cctgtccgcc tttctccctt  9960
cgggaagcgt ggcgctttct catagctcac gctgtaggta tctcagttcg gtgtaggtcg  10020
ttcgctccaa gctgggctgt gtgcacgaac cccccgttca gcccgaccgc tgcgccttat  10080
ccggtaacta tcgtcttgag tccaacccgg taagacacga cttatcgcca ctggcagcag  10140
ccactggtaa caggattagc agagcgaggt atgtaggcgg tgctacagag ttcttgaagt  10200
ggtggcctaa ctacggctac actagaagaa cagtatttgg tatctgcgct ctgctgaagc  10260
cagttacctt cggaaaaaga gttggtagct cttgatccgg caaacaaacc accgctggta  10320
gcggtggttt ttttgtttgc aagcagcaga ttacgcgcag aaaaaaagga tctcaagaag  10380
atcctttgat cttttctacg gggtctgacg ctcagtggaa cgaaaactca cgttaaggga  10440
ttttggtcat gagattatca aaaaggatct tcacctagat ccttttaaat taaaaatgaa  10500
gttttaaatc aatctaaatt atatatgagt aaacttggtc tgacagtaca accaattaac  10560
caattctgat tagaaaaact catcgagcat caaatgaaac tgcaatttat tcatatcagg  10620
attatcaata ccatattttt gaaaaagccg tttctgtaat gaaggagaaa actcaccgag  10680
gcagttccat aggatggcaa gatcctggta tcggtctgcg attccgactc gtccaacatc  10740
aatacaacct attaatttcc cctcgtcaaa aataaggtta tcaagtgaga aatcaccatg  10800
agtgacgact gaatccggtg agaatggcaa aagtttatgc atttctttcc agacttgttc  10860
aacaggccag ccattacgct cgtcatcaaa atcactcgca tcaaccaaac cgttattcat  10920
tcgtgattgc gcctgagcga gacgaaatac gcgatcgctg ttaaaaggac aattacaaac  10980
aggaatcgaa tgcaaccggc gcaggaacac tgccagcgca tcaacaatat tttcacctga  11040
atcaggatat tcttctaata cctggaatgc tgtttttccg gggatcgcag tggtgagtaa  11100
ccatgcatca tcaggagtac ggataaaatg cttgatggtc ggaagaggca taaattccgt  11160
cagccagttt agtctgacca tctcatctgt aacatcattg gcaacgctac ctttgccatg  11220
tttcagaaac aactctggcg catcgggctt cccatacaag cgatagattg tcgcacctga  11280
ttgcccgaca ttatcgcgag cccatttata cccatataaa tcagcatcca tgttggaatt  11340
taatcgcggc ctcgacgttt cccgttgaat atggctcata acaccccttg tattactgtt  11400
tatgtaagca gacagtttta ttgttcatga tgatatattt ttatcttgtg caatgtaaca  11460
tcagagattt tgagacacca catttccccg aaaagtgcca cctgacgtta gggataacag  11520
ggtaat                                                            11526

SEQ ID NO: 61           moltype = RNA  length = 9742
FEATURE                 Location/Qualifiers
source                  1..9742
                        mol_type = other RNA
                        organism = synthetic construct
SEQUENCE: 61
ggattgacgg cgtagtacac actattgaat caaacagccg accaattgca ctaccatcac  60
aatggagaag ccagtagtaa acgtagacgt agacccccag agtccgtttg tcgtgcaact  120
gcaaaaaagc ttcccgcaat ttgaggtagt agcacagcag gtcactccaa atgaccatgc  180
taatgccaga gcattttcgc atctggccag taaactaatc gagctggagg ttcctaccac  240
agcgacgatc ttggacatag gcagcgcacc ggctcgtaga atgttttccg agcaccagta  300
tcattgtgtc tgccccatgc gtagtccaga agacccggac cgcatgatga aatacgccag  360
taaactggcg gaaaaagcgt gcaagattac aaacaagaac ttgcatgaga agattaagga  420
tctccggacc gtacttgata cgccggatgc tgaaacacca tcgctctgct ttcacaacga  480
tgttacctgc aacatgcgtg ccgaatattc cgtcatgcag gacgtgtata tcaacgctcc  540
cggaactatc tatcatcagg ctatgaaagg cgtgcggacc ctgtactgga ttggcttcga  600
caccacccag ttcatgttct cggctatggc aggttcgtac cctgcgtaca acaccaactg  660
ggccgacgag aaagtccttg aagcgcgtaa catcggactt tgcagcacaa agctgagtga  720
aggtaggaca ggaaaattgt cgataatgag gaagaaggag ttgaagcccg ggtcgcgggt  780
ttatttctcc gtaggatcga cactttatcc agaacacaga gccagcttgc agagctggca  840
tcttccatcg gtgttccact tgaatggaaa gcagtcgtac acttgccgct gtgatacagt  900
ggtgagttgc gaaggctacg tagtgaagaa aatcaccatc agtcccggga tcacgggaga  960
aaccgtggga tacgcggtta cacacaatag cgagggcttc ttgctatgca aagttactga  1020
cacagtaaaa ggagaacggg tatcgttccc tgtgtgcacg tacatcccgg ccaccatatg  1080
cgatcagatg actggtataa tggccacgga tatatcacct gacgatgcac aaaaacttct  1140
ggttgggctc aaccagcgaa ttgtcattaa cggtaggact aacaggaaca ccaacaccat  1200
gcaaaattac cttctgccga tcatagcaca agggttcagc aaatgggcta aggagcgcaa  1260
ggatgatctt gataacgaga aaatgctggg tactagagaa cgcaagctta cgtatggctg  1320
cttgtgggcg tttcgcacta agaaagtaca ttcgttttat cgcccacctg gaacgcagac  1380
ctgcgtaaaa gtcccagcct cttttagcgc ttttcccatg tcgtccgtat ggacgacctc  1440
tttgcccatg tcgctgaggc agaaattgaa actggcattg caaccaaaga aggaggaaaa  1500
actgctgcag gtctcggagg aattagtcat ggaggccaag gctgcttttg aggatgctca  1560
ggaggaagcc agagcggaga agctccgaga agcacttcca ccattagtgg cagacaaagg  1620
catcgaggca gccgcagaag ttgtctgcga agtggagggg ctccaggcgg acatcggagc  1680
agcattagtt gaaaccccgc gcggtcacgt aaggataata cctcaagcaa atgaccgtat  1740
gatcggacag tatatcgttg tctcgccaaa ctctgtgctg aagaatgcca aactcgcacc  1800
agcgcacccg ctagcagatc aggttaagat cataacacac tccggaagat caggaaggta  1860
cgcggtcgaa ccatacgacg ctaaagtact gatgccagca ggaggtgccg taccatggcc  1920
agaattccta gcactgagtg agagcgccac gttagtgtac aacgaaagag agtttgtgaa  1980
ccgcaaacta taccacattg ccatgcatgg ccccgccaag aatacagaag aggagcagta  2040
caaggttaca aaggcagagc ttgcagaaac agagtacgtg tttgacgtgg acaagaagcg  2100
```

```
ttgcgttaag aaggaagaag cctcaggtct ggtcctctcg ggagaactga ccaaccctcc  2160
ctatcatgag ctagctctgg agggactgaa gacccgacct gcggtcccgt acaaggtcga  2220
aacaatagga gtgataggca caccggggtc gggcaagtca gctattatca agtcaactgt  2280
cacggcacga gatcttgtta ccagcggaaa gaaagaaaat tgtcgcgaaa ttgaggccga  2340
cgtgctaaga ctgaggggta tgcagattac gtcgaagaca gtagattcgg ttatgctcaa  2400
cggatgccac aaagccgtag aagtgctgta cgttgacgaa gcgttcgcgt gccacgcagg  2460
agcactactt gccttgattg ctatcgtcag gccccgcaag aaggtagtac tatgcggaga  2520
ccccatgcaa tgcggattct tcaacatgat gcaactaaag gtacatttca atcaccctga  2580
aaaagacata tgcaccaaga cattctacaa gtatatctcc cggcgttgca cacagccagt  2640
tacagctatt gtatcgacac tgcattacga tggaaagatg aaaaccacga acccgtgcaa  2700
gaagaacatt gaaatcgata ttacaggggc cacaaagccg aagccagggg atatcatcct  2760
gacatgtttc cgcgggtggg ttaagcaatt gcaaatcgac tatcccggac atgaagtaat  2820
gacagccgcg gcctcacaag ggctaaccag aaaaggagtg tatgccgtcc ggcaaaaagt  2880
caatgaaaac ccactgtacg cgatcacatc agagcatgtg aacgtgttgc tcacccgcac  2940
tgaggacagg ctagtgtgga aaaccttgca gggcgaccca tggattaagc agcccactaa  3000
catacctaaa ggaaactttc aggctactat agaggactgg gaagctgaac acaagggaat  3060
aattgctgca ataaacagcc ccactccccg tgccaatccg ttcagctgca agaccaacgt  3120
ttgctgggcg aaagcattgg aaccgatact agccacggcc ggtatcgtac ttaccggttg  3180
ccagtggagc gaactgttcc cacagtttgc ggatgacaaa ccacattcgg ccatttacgc  3240
cttagacgta atttgcatta agtttttcgg catggacttg acaagcggac tgttttctaa  3300
acagagcatc ccactaacgt accatcccgc cgattcagcg aggccggtag ctcattggga  3360
caacagccca ggaacccgca agtatgggta cgatcacgcc attgccgccg aactctcccg  3420
tagatttccg gtgttccagc tagctgggaa gggcacacaa cttgatttgc agacggggag  3480
aaccagagtt atctctgcac agcataacct ggtcccggtg aaccgcaatc ttcctcacgc  3540
cttagtcccc gagtacaagg agaagcaacc cggcccggtc aaaaaattct tgaaccagtt  3600
caaacaccac tcagtacttg tggtatcaga ggaaaaaatt gaagctcccc gtaagagaat  3660
cgaatggatc gccccgattg gcatagccgg tgcagataag aactacaacc tggctttcgg  3720
gtttccgccg caggcacggt acgacctggt gttcatcaac attggaacta aatacagaaa  3780
ccaccacttt cagcagtgcg aagaccatgc ggcgacctta aaaccctttt cgcgttcggc  3840
cctgaattgc cttaacccag gaggcaccct cgtggtgaag tcctatggct acgccgaccg  3900
caacagtgag gacgtagtca ccgctcttgc cagaaagttt gtcagggtgt ctgcagcgag  3960
accagattgt gtctcaagca atacagaaat gtacctgatt ttccgacaac tagacaacag  4020
ccgtacacgg caattcaccc cgcaccatct gaattgcgtg atttcgtccg tgtatgaggg  4080
tacaagagat ggagttggag ccgcgccgtc ataccgcacc aaaagggaga atattgctga  4140
ctgtcaagag gaagcagttg tcaacgcagc caatccgctg ggtagaccag gcgaaggagt  4200
ctgccgtgcc atctataaac gttggccgac cagttttacc gattcagcca cggagacagg  4260
caccgcaaga atgactgtgt gcctaggaaa gaaagtgatc cacgcggtcg gccccgattt  4320
ccggaagcac ccagaagcag aagccttgaa attgctacaa aacgcctacc atgcagtggc  4380
agacttagta aatgaacata acatcaagtc tgtcgccatt ccactgctat ctacaggcat  4440
ttacgcagcc ggaaaagacc gccttgaagt atcacttaac tgcttgacaa ccgcgctaga  4500
cagaactgac gcggacgtaa ccatctattg cctggataag aagtggaagg aaagaatcga  4560
cgcggcactc caacttaagg agtctgtaac agagctgaag gatgaagata tggagatcga  4620
cgatgagtta gtatggatcc atccagacag ttgcttgaag ggaagaaagg gattcagtac  4680
tacaaaagga aaattgtatt cgtacttcga aggcaccaaa ttccatcaag cagcaaaaga  4740
catggcggag ataaaggtcc tgttccctaa tgaccaggaa agtaatgaac aactgtgtgc  4800
ctacatattg ggtgagacca tggaagcaat ccgcgaaaag tgcccggtcg accataaccc  4860
gtcgtctagc ccgcccaaaa cgttgccgtg cctttgcatg tatgccatga cgccagaaag  4920
ggtccacaga cttagaagca ataacgtcaa agaagttaca gtatgctcct ccacccccct  4980
tcctaagcac aaaattaaga atgttcagaa ggttcagtgc acgaaagtag tcctgtttaa  5040
tccgcacact cccgcattcg ttcccgcccg taagtacata gaagtgccag aacagcctac  5100
cgctcctcct gcacaggccg aggaggcccc cgaagttgta gcgacaccgt caccatctac  5160
agctgataac acctcgcttg atgtcacaga catctcactg gatatggatg acagtagcga  5220
aggctcactt ttttcgagct ttagcggatc ggacaactct attactagta tggacagttg  5280
gtcgtcagga cctagttcac tagagatagt agaccgaagg caggtggtgg tggctgacgt  5340
tcatgccgtc caagagcctg cccctattcc accgccaagg ctaaagaaga tggcccgcct  5400
ggcagcggca agaaaagagc ccactccacc ggcaagcaat agctctgagt ccctccacct  5460
ctcttttggt ggggtatcca tgtccctcgg atcaattttc gacggagaga cggcccgcca  5520
ggcagcggta caacccctgg caacaggccc cacggatgtg cctatgtctt tcggatcgtt  5580
ttccgacgga gagattgatg agctgagccg cagagtaact gagtccgaac ccgtcctgtt  5640
tggatcattt gaaccgggcg aagtgaactc aattatatcg tcccgatcag ccgtatcttt  5700
tccactacgc aagcagagac gtagacgcag gagcaggagg actgaatact gactaaccgg  5760
ggtaggtggg tacatatttt cgacggacac aggccctggg cacttgcaaa agaagtccgt  5820
tctgcagaac cagcttacag aaccgacctt ggagcgcaat gtcctggaaa gaattcatgc  5880
cccggtgctc gacacgtcga aagaggaaca actcaaactc aggtaccaga tgatgcccac  5940
cgaagccaac aaaagtaggt accagtctcg taaagtagaa aatcagaaag ccataaccac  6000
tgagcgacta ctgtcaggac tacgactgta taactctgcc acagatcagc cagaatgcta  6060
taagatcacc tatccgaaac cattgtactc cagtagcgta ccggcgaact actccgatcc  6120
acagttcgct gtagctgtct gtaacaacta tctgcatgag aactatccga cagtagcatc  6180
ttatcagatt actgacgagt acgatgctta cttggatatg gtagacggga cagtcgcctg  6240
cctggatact gcaaccttct gccccgctaa gcttagaagt taccccgaaaa aacatgagta  6300
tagagccccg aatatccgca gtgcggttcc atcagcgatg cagaacacgc tacaaaatgt  6360
gctcattgcc gcaactaaaa gaaattgcaa cgtcacgcag atgcgtgaac tgccaacact  6420
ggactcagcg acattcaatg tcgaatgctt tcgaaaatat gcatgtaatg acgagtattg  6480
ggaggagttc gctcggaagc caattaggat taccactgag tttgtcaccg catatgtagc  6540
tagactgaaa ggccctaagg ccgccgcact atttgcaaag acgtataatt tggtcccatt  6600
gcaagaagtg cctatggata gattcgtcat ggacatgaaa agagacgtga aagttacacc  6660
aggcacgaaa cacacagaag aaagaccgaa agtacaagtg atacaagccg cagaacccct  6720
ggcgactgct tacttatgcg ggattcaccg ggaattagtg cgtaggctta cggccgtctt  6780
gcttccaaac attcacacgc tttttgacat gtcggcggag gattttgatg caatcatagc  6840
```

```
agaacacttc aagcaaggcg acccggtact ggagacggat atcgcatcat tcgacaaaag  6900
ccaagacgac gctatggcgt taaccggtct gatgatcttg gaggacctgg gtgtggatca  6960
accactactc gacttgatcg agtgcgcctt tggagaaata tcatccaccc atctacctac  7020
gggtactcgt tttaaattcg gggcgatgat gaaatccgga atgttcctca cactttttgt  7080
caacacagtt ttgaatgtcg ttatcgccag cagagtacta gaggaacggc ttaaaacgtc  7140
cagatgtgca gcgttcattg gcgacgacaa catcatacat ggagtagtat ctgacaaaga  7200
aatggctgag aggtgcgcca cctggctcaa catggaggtt aagatcatcg acgcagtcat  7260
cggtgagaga ccaccttact tctgcggcgg atttatcttg caagattcgg ttacttccac  7320
agcgtgccgc gtggcggatc ccctgaaaag gctgtttaag ttgggtaaac cgctcccagc  7380
cgacgacgag caagacgaag acagaagacg cgctctgcta gatgaaacaa aggcgtggtt  7440
tagagtaggt ataacaggca ctttagcagt ggccgtgacg acccggtatg aggtagacaa  7500
tattacacct gtcctactgg cattgagaac ttttgcccag agcaaaagag cattccaagc  7560
catcagaggg gaaataaagc atctctacgg tggtcctaaa tagtcagcat agtacatttc  7620
atctgactaa tactacaaca ccaccaccat gaagacctta attcttgccg ttgcattagt  7680
ctactgcgcc actgttcatt gccaggactg tccttacgaa cctgatccac caaacacagt  7740
tccaacttcc tgtgaagcta aagaaggaga atgtattgat agcagctgtg gcacctgcac  7800
gagagacata ctatcagatg gactgtgtga aaataaacca ggaaaaacat gttgccgaat  7860
gtgtcagtat gtaattgaat gcagagtaga ggccgcagga tggtttagaa cattctatgg  7920
aaagagattc cagttccagg aacctggtac atacgtgttg ggtcaaggaa ccaagggcgg  7980
cgactggaag gtgtccatca ccctggagaa cctggatgga accaaggggg ctgtgctgac  8040
caagacaaga ctggaagtgg ctggagacat cattgacatc gctcaagcta ctgagaatcc  8100
catcactgta aacggtggag ctgaccctat catcgccaac ccgtacacca tcggcgaggt  8160
caccatcgct gttgttgaga tgccaggctt caacatcacc gtcattgagt tcttcaaact  8220
gatcgtgatc gacatcctcg gaggaagatc tgtaagaatc gccccagaca cagcaaacaa  8280
aggaatgatc tctggcctct gtggagatct taaaatgatg gaagatacag acttcacttc  8340
agatccagaa caactcgcta ttcagcctaa gatcaaccag gagtttgacg gttgtccact  8400
ctatggaaat cctgatgacg ttgcatactg caaaggtctt ctggagccgt acaaggacag  8460
ctgccgcaac cccatcaact tctactacta caccatctcc tgcgccttcg cccgctgtat  8520
gggtggagac gagcgagcct cacacgtgct gcttgactac agggagacgt gcgctgctcc  8580
cgaaactaga ggaacctgcg ttttgtctgg acatactttc tacgatacat ttgacaaagc  8640
aagataccaa ttccagggtc cctgcaagga gattcttatg gccgccgact gtttctggaa  8700
cacttgggat gtgaaggttt cacacaggaa tgttgactct tacactgaag tagagaaagt  8760
acgaatcagg aaacaatcga ctgtagtaga actcattgtt gatggaaaac agattctggt  8820
tggaggagaa gccgtgtccg tcccgtacag ctctcagaac acttccatct actggcaaga  8880
tggtgacata ctgactacag ccatcctacc tgaagctctg gtggtcaagt tcaacttcaa  8940
gcaactgctc gtcgtacata ttagagatcc attcgatggt aagacttgcg gtatttgcgg  9000
taactacaac caggatttca gtgatgattc ttttgatgct gaaggagcct gtgatctgac  9060
ccccaaccca ccgggatgca ccgaagaaca gaaacctgaa gctgaacgac tctgcaatag  9120
tctcttcgcc ggtcaaagtg atcttgatca gaaatgtaac gtgtgccaca agcctgaccg  9180
tgtcgaacga tgcatgtacg agtattgcct gaggggacaa cagggtttct gtgaccacgc  9240
atgggagttc aagaaagaat gctacataaa gcatggagac accctagaag taccagatga  9300
atgcaaatag ggcgcgccta tgttacgtgc aaaggtgatt gtcacccccc gaaagaccat  9360
attgtgacac accctcagta tcacgcccaa acatttacag ccgcggtgtc aaaaaccgcg  9420
tggacgtggt taacatccct gctgggagaa tcagccgtaa ttattataat tggcttggtg  9480
ctggctacta ttgtggccat gtacgtgctg accaaccaga aacataattg aatacagcag  9540
caattggcaa gctgcttaca tagaactcgc ggcgattggc atgcgcctta aaatttttat  9600
tttatttttc ttttctttc cgaatcggat tttgttttta atatttcaaa aaaaaaaaaa  9660
aaaaaaaaaa aaaaagcata tgactaaaaa aaaaaaaaaa aaaaaaaaaa aaaaaaaaaa  9720
aaaaaaaaaa aaaaaaaaaa aa                                          9742

SEQ ID NO: 62          moltype = DNA  length = 6904
FEATURE                Location/Qualifiers
source                 1..6904
                       mol_type = other DNA
                       organism = synthetic construct
SEQUENCE: 62
gacggatcgg gagatctccc gatcccctat ggtcgactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggac tatttacggt aaactgccca cttggcagta catcaagtgt  480
atcatatgcc aagtacgccc cctattgacg tcaatgacgg taaatggccc gcctggcatt  540
atgcccagta catgacctta tggggacttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attttaagtt gcattatagg agaacccaag cttggtaccg  900
agctcggatc cgccaccatg aagaccttaa ttcttgccgt tgcattagtc tactgcgcca  960
ctgttcattg ccaggactgt ccttacgaac ctgatccacc aaacacagtt ccaacttcct  1020
gtgaagctaa agaaggagaa tgtattgata gcagctgtgg cacctgcacg agagacatac  1080
tatcagatgg actgtgtgaa aataaaccag gaaaaacatg ttgccgaatg tgtcagtatg  1140
taattgaatg cagagtagag gccgcaggat ggtttagaac attctatgga aagagattcc  1200
agttccagga acctggtaca tacgtgttgg gtcaaggaac caagggcggc gactggaagg  1260
tgtccatcac cctggagaac ctggatggaa ccaaggggc tgtgctgacc aagacaagac  1320
tggaagtggc tggagacatc attgacatcg ctcaagctac tgagaatccc atcactgtaa  1380
```

-continued

```
acggtggagc tgaccctatc atcgccaacc cgtacaccat cggcgaggtc accatcgctg  1440
ttgttgagat gccaggcttc aacatcaccg tcattgagtt cttcaaactg atcgtgatcg  1500
acatcctcgg aggaagatct gtaagaatcg ccccagacac agcaaacaaa ggaatgatct  1560
ctggcctctg tggagatctt aaaatgatgg aagatacaga cttcacttca gatccagaac  1620
aactcgctat tcagcctaag atcaaccagg agtttgacgg ttgtccactc tatggaaatc  1680
ctgatgacgt tgcatactgc aaaggtcttc tggagccgta caaggacagc tgccgcaacc  1740
ccatcaactt ctactactac accatctcct gcgccttcgc ccgctgtatg ggtggagacg  1800
agcgagcctc acacgtgctg cttgactaca gggagacgtg cgctgctccc gaaactagag  1860
gaacctgcgt tttgtctgga catactttct acgatacatt tgacaaagca agataccaat  1920
tccagggtcc ctgcaaggag attcttatgg ccgccgactg tttctggaac acttgggatg  1980
tgaaggtttc acacaggaat gttgactctt acactgaagt agagaaagta cgaatcagga  2040
aacaatcgac tgtagtagaa ctcattgttg atggaaaaca gattctggtt ggaggagaag  2100
ccgtgtccgt cccgtacagc tctcagaaca cttccatcta ctggcaagat ggtgacatac  2160
tgactacagc catcctacct gaagctctgg tggtcaagtt caacttcaag caactgctcg  2220
tcgtacatat tagagatcca ttcgatggta agacttgcgg tatttgcggt aactacaacc  2280
aggatttcag tgatgattct tttgatgctg aaggagcctg tgatctgacc cccaacccac  2340
cgggatgcac cgaagaacag aaacctgaag ctgaacgact ctgcaatagt ctcttcgccg  2400
gtcaaagtga tcttgatcag aaatgtaacg tgtgccacaa gcctgaccgt gtcgaacgat  2460
gcatgtacga gtattgcctg aggggacaac agggtttctg tgaccacgca tgggagttca  2520
agaaagaatg ctacataaag catggagaca ccctagaagt accagatgaa tgcaaatagg  2580
cggccgcaat aaaatatctt tattttcatt acatctgtgt gttggttttt tgtgtgtcta  2640
gaaataattc ttactgtcat gccaagtaag atgcttttct gtgctgcaat agcaggcatg  2700
ctggggatgc ggtgggctct atggcttctg aggcggaaag aaccagctgg ggctctaggg  2760
ggtatcccca cgcgccctgt agcggcgcat taagcgcggc gggtgtggtg gttacgcgca  2820
gcgtgaccgc tacacttgcc agcgccctag cgcccgctcc tttcgctttc ttcccttcct  2880
ttctcgccac gttcgccggc tttccccgtc aagctctaaa tcggggcatc cctttagggt  2940
tccgatttag tgctttacgg cacctcgacc ccaaaaaact tgattagggt gatggttcac  3000
gtagtgggcc atcgccctga tagacggttt ttcgcccttt gacgttggag tccacgttct  3060
ttaatagtgg actcttgttc caaactggaa caacactcaa ccctatctcg gtctattctt  3120
ttgatttata agggattttg gggatttcgg cctattggtt aaaaaatgag ctgatttaac  3180
aaaaatttaa cgcgaattaa ttctgtggaa tgtgtgtcag ttagggtgtg gaaagtcccc  3240
aggctcccca ggcaggcaga agtatgcaaa gcatgcatct caattagtca gcaaccaggt  3300
gtggaaagtc cccaggctcc ccagcaggca gaagtatgca aagcatgcat ctcaattagt  3360
cagcaaccat agtcccgccc ctaactccgc ccatcccgcc cctaactccg cccagttccg  3420
cccattctcc gccccatggc tgactaattt tttttattta tgcagaggcc gaggccgcct  3480
ctgcctctga gctattccag aagtagtgag gaggcttttt tggaggccta ggcttttgca  3540
aaaagctccc gggagcttgt atatccattt tcggatctga tcaagagaca ggatgaggat  3600
cgtttcgcat gattgaacaa gatggattgc acgcaggttc tccggccgct tgggtggaga  3660
ggctattcgg ctatgactgg gcacaacaga caatcggctg ctctgatgcc gccgtgttcc  3720
ggctgtcagc gcaggggcgc ccggttcttt ttgtcaagac cgacctgtcc ggtgccctga  3780
atgaactgca ggacgaggca gcgcggctat cgtggctggc cacgacgggc gttccttgcg  3840
cagctgtgct cgacgttgtc actgaagcgg gaagggactg gctgctattg ggcgaagtgc  3900
cggggcagga tctcctgtca tctcaccttg ctcctgccga gaaagtatcc atcatggctg  3960
atgcaatgcg gcggctgcat acgcttgatc cggctacctg cccattcgac caccaagcga  4020
aacatcgcat cgagcgagca cgtactcgga tggaagccgg tcttgtcgat caggatgatc  4080
tggacgaaga gcatcagggg ctcgcgccag ccgaactgtt cgccaggctc aaggcgcgca  4140
tgcccgacgg cgaggatctc gtcgtgaccc atggcgatgc ctgcttgccg aatatcatgg  4200
tggaaaatgg ccgcttttct ggattcatcg actgtggccg gctgggtgtg gcggaccgct  4260
atcaggacat agcgttggct acccgtgata ttgctgaaga gcttggcggc gaatgggctg  4320
accgcttcct cgtgctttac ggtatcgccg ctcccgattc gcagcgcatc gccttctatc  4380
gccttcttga cgagttcttc tgagcgggac tctggggttc gaaatgaccg accaagcgac  4440
gcccaacctg ccatcacgag atttcgattc caccgccgcc ttctatgaaa ggttgggctt  4500
cggaatcgtt ttccgggacg ccggctggat gatcctccag cgcggggatc tcatgctgga  4560
gttcttcgcc caccccaact tgtttattgc agcttataat ggttacaaat aaagcaatag  4620
catcacaaat ttcacaaata aagcattttt ttcactgcat tctagttgtg gtttgtccaa  4680
actcatcaat gtatcttatc atgtctgtat accgtcgacc tctagctaga gcttggcgta  4740
atcatggtca tagctgtttc ctgtgtgaaa ttgttatccg ctcacaattc cacacaacat  4800
acgagccgga agcataaagt gtaaagcctg gggtgcctaa tgagtgagct aactcacatt  4860
aattgcgttg cgctcactgc ccgctttcca gtcgggaaac ctgtcgtgcc agctgcatta  4920
atgaatcggc caacgcgcgg ggagaggcgg tttgcgtatt gggcgctctt ccgcttcctc  4980
gctcactgac tcgctgcgct cggtcgttcg gctgcggcga gcggtatcag ctcactcaaa  5040
ggcggtaata cggttatcca cagaatcagg ggataacgca ggaaagaaca tgtgagcaaa  5100
aggccagcaa aaggccagga accgtaaaaa ggccgcgttg ctggcgtttt tccataggct  5160
ccgcccccct gacgagcatc acaaaaatcg acgctcaagt cagaggtggc gaaacccgac  5220
aggactataa agataccagg cgtttccccc tggaagctcc ctcgtgcgct ctcctgttcc  5280
gaccctgccg cttaccggat acctgtccgc ctttctccct tcgggaagcg tggcgctttc  5340
tcaatgctca cgctgtaggt atctcagttc ggtgtaggtc gttcgctcca agctgggctg  5400
tgtgcacgaa ccccccgttc agcccgaccg ctgcgcctta tccggtaact atcgtcttga  5460
gtccaacccg gtaagacacg acttatcgcc actggcagca gccactggta acaggattag  5520
cagagcgagg tatgtaggcg gtgctacaga gttcttgaag tggtggccta actacggcta  5580
cactagaagg acagtatttg gtatctgcgc tctgctgaag ccagttacct tcggaaaaag  5640
agttggtagc tcttgatccg gcaaacaaac caccgctggt agcggtggtt tttttgtttg  5700
caagcagcag attacgcgca gaaaaaaagg atctcaagaa gatcctttga tcttttctac  5760
ggggtctgac gctcagtgga acgaaaactc acgttaaggg attttggtca tgagattatc  5820
aaaaaggatc ttcacctaga tccttttaaa ttaaaaatga agttttaaat caatctaaag  5880
tatatatgag taaacttggt ctgacagtta ccaatgctta atcagtgagg cacctatctc  5940
agcgatctgt ctatttcgtt catccatagt tgcctgactc cccgtcgtgt agataactac  6000
gatacgggag ggcttaccat ctggccccag tgctgcaatg ataccgcgag acccacgctc  6060
accggctcca gatttatcag caataaacca gccagccgga agggccgagc gcagaagtgg  6120
```

```
tcctgcaact ttatccgcct ccatccagtc tattaattgt tgccgggaag ctagagtaag  6180
tagttcgcca gttaatagtt tgcgcaacgt tgttgccatt gctacaggca tcgtggtgtc  6240
acgctcgtcg tttggtatgg cttcattcag ctccggttcc caacgatcaa ggcgagttac  6300
atgatccccc atgttgtgca aaaaagcggt tagctccttc ggtcctccga tcgttgtcag  6360
aagtaagttg gccgcagtgt tatcactcat ggttatggca gcactgcata attctcttac  6420
tgtcatgcca tccgtaagat gcttttctgt gactggtgag tactcaacca agtcattctg  6480
agaatagtgt atgcggcgac cgagttgctc ttgcccggcg tcaatacggg ataataccgc  6540
gccacatagc agaactttaa aagtgctcat cattggaaaa cgttcttcgg ggcgaaaact  6600
ctcaaggatc ttaccgctgt tgagatccag ttcgatgtaa cccactcgtg cacccaactg  6660
atcttcagca tcttttactt tcaccagcgt ttctgggtga gcaaaaacag gaaggcaaaa  6720
tgccgcaaaa aagggaataa gggcgacacg gaaatgttga atactcatac tcttcctttt  6780
tcaatattat tgaagcattt atcagggtta ttgtctcatg agcggataca tatttgaatg  6840
tatttagaaa aataaacaaa taggggttcc gcgcacattt ccccgaaaag tgccacctga  6900
cgtc                                                               6904

SEQ ID NO: 63          moltype = DNA  length = 6906
FEATURE                Location/Qualifiers
source                 1..6906
                       mol_type = other DNA
                       organism = synthetic construct
SEQUENCE: 63
gacggatcgg gagatctccc gatcccctat ggtcgactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggac tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gcttggtacc  900
gagctcggat ccgccaccat gaagacctta attcttgccg ttgcattagt ctactgcgcc  960
actgttcatt gccaggactg tccttacgaa cctgatccac caaacacagt tccaacttcc  1020
tgtgaagcta aagaaggaga atgtattgat agcagctgtg gcacctgcac gagagacata  1080
ctatcagatg gactgtgtga aaataaacca ggaaaaacat gttgccgaat gtgtcagtat  1140
gtaattgaat gcagagtaga ggccgcagga tggtttagaa cattctatgg aaagagattc  1200
cagttccagg aacctggtac atacgtgttg ggtcaaggaa ccaagggcgg cgactggaag  1260
gtgtccatca ccctggagaa cctggatgga accaaggggg ctgtgctgac caagacaaga  1320
ctggaagtgg ctggagacat cattgacatc gctcaagcta ctgagaatcc catcactgta  1380
aacggtggag ctgaccctat catcgccaac ccgtacacca tcggcgaggt caccatcgct  1440
gttgttgaga tgccaggctt caacatcacc gtcattgagt tcttcaaact gatcgtgatc  1500
gacatcctcg gaggaagatc tgtaagaatc gccccagaca cagcaaacaa aggaatgatc  1560
tctggcctct gtggagatct taaaatgatg gaagatacag acttcacttc agatccagaa  1620
caactcgcta ttcagcctaa gatcaaccag gagtttgacg gttgtccact ctatggaaat  1680
cctgatgacg ttgcatactg caaaggtctt ctggagccgt acaaggacag ctgccgcaac  1740
cccatcaact tctactacta caccatctcc tgcgccttcg cccgctgtat gggtggagac  1800
gagcgagcct cacacgtgct gcttgactac agggagacgt gcgctgctcc cgaaactaga  1860
ggaacctgcg ttttgtctgg acatactttc tacgatacat ttgacaaagc aagataccaa  1920
ttccagggtc cctgcaagga gattcttatg gccgccgact gtttctggaa cacttgggat  1980
gtgaaggttt cacacaggaa tgttgactct tacactgaag tagagaaagt acgaatcagg  2040
aaacaatcga ctgtagtaga actcattgtt gatggaaaac agattctggt tggaggagaa  2100
gccgtgtccg tcccgtacag ctctcagaac acttccatct actggcaaga tggtgacata  2160
ctgactacag ccatcctacc tgaagctctg gtggtcaagt tcaacttcaa gcaactgctc  2220
gtcgtacata ttagagatcc attcgatggt aagacttgcg gtatttgcgg taactacaac  2280
caggatttca gtgatgattc ttttgatgct gaaggagcct gtgatctgac ccccaaccca  2340
ccgggatgca ccgaagaaca gaaacctgaa gctgaacgac tctgcaatag tctcttcgcc  2400
ggtcaaagtg atcttgatca gaaatgtaac gtgtgccaca agcctgaccg tgtcgaacga  2460
tgcatgtacg agtattgcct gaggggacaa cagggtttct gtgaccacgc atgggagttc  2520
aagaaagaat gctacataaa gcatggagac accctagaag taccagatga atgcaaatag  2580
gcggccgcaa taaaatatct ttattttcat tacatctgtg tgttggtttt ttgtgtgtct  2640
agaaataatt cttactgtca tgccaagtaa gatgcttttc tgtgctgcaa tagcaggcat  2700
gctggggatg cggtgggctc tatggcttct gaggcggaaa gaaccagctg gggctctagg  2760
gggtatcccc acgcgccctg tagcggcgca ttaagcgcgg cgggtgtggt ggttacgcgc  2820
agcgtgaccg ctacacttgc cagcgcccta gcgcccgctc ctttcgcttt cttcccttcc  2880
tttctcgcca cgttcgccgg ctttccccgt caagctctaa atcggggcat ccctttaggg  2940
ttccgattta gtgctttacg gcacctcgac cccaaaaaac ttgattaggg tgatggttca  3000
cgtagtgggc catcgccctg atagacggtt tttcgccctt tgacgttgga gtccacgttc  3060
tttaatagtg gactcttgtt ccaaactgga acaacactca accctatctc ggtctattct  3120
tttgatttat aagggatttt ggggatttcg gcctattggt taaaaaatga gctgatttaa  3180
caaaaattta acgcgaatta attctgtgga atgtgtgtca gttagggtgt ggaaagtccc  3240
caggctcccc aggcaggcag aagtatgcaa agcatgcatc tcaattagtc agcaaccagg  3300
tgtggaaagt ccccaggctc cccagcaggc agaagtatgc aaagcatgca tctcaattag  3360
tcagcaacca tagtcccgcc cctaactccg cccatcccgc ccctaactcc gcccagttcc  3420
gcccattctc cgccccatgg ctgactaatt ttttttattt atgcagaggc cgaggccgcc  3480
```

```
tctgcctctg agctattcca gaagtagtga ggaggctttt ttggaggcct aggcttttgc  3540
aaaaagctcc cgggagcttg tatatccatt ttcggatctg atcaagagac aggatgagga  3600
tcgtttcgca tgattgaaca agatggattg cacgcaggtt ctccggccgc ttgggtggag  3660
aggctattcg gctatgactg ggcacaacag acaatcggct gctctgatgc cgccgtgttc  3720
cggctgtcag cgcaggggcg cccggttctt tttgtcaaga ccgacctgtc cggtgccctg  3780
aatgaactgc aggacgaggc agcgcggcta tcgtggctgg ccacgacggg cgttccttgc  3840
gcagctgtgc tcgacgttgt cactgaagcg ggaagggact ggctgctatt gggcgaagtg  3900
ccggggcagg atctcctgtc atctcacctt gctcctgccg agaaagtatc catcatggct  3960
gatgcaatgc ggcggctgca tacgcttgat ccggctacct gcccattcga ccaccaagcg  4020
aaacatcgca tcgagcgagc acgtactcgg atggaagccg gtcttgtcga tcaggatgat  4080
ctggacgaag agcatcaggg gctcgcgcca gccgaactgt tcgccaggct caaggcgcgc  4140
atgcccgacg gcgaggatct cgtcgtgacc catggcgatg cctgcttgcc gaatatcatg  4200
gtggaaaatg gccgcttttc tggattcatc gactgtggcc ggctgggtgt ggcggaccgc  4260
tatcaggaca tagcgttggc tacccgtgat attgctgaag agcttggcgg cgaatgggct  4320
gaccgcttcc tcgtgcttta cggtatcgcc gctcccgatt cgcagcgcat cgccttctat  4380
cgccttcttg acgagttctt ctgagcggga ctctggggtt cgaaatgacc gaccaagcga  4440
cgcccaacct gccatcacga gatttcgatt ccaccgccgc cttctatgaa aggttgggct  4500
tcggaatcgt tttccgggac gccggctgga tgatcctcca gcgcggggat ctcatgctgg  4560
agttcttcgc ccaccccaac ttgtttattg cagcttataa tggttacaaa taaagcaata  4620
gcatcacaaa tttcacaaat aaagcatttt tttcactgca ttctagttgt ggtttgtcca  4680
aactcatcaa tgtatcttat catgtctgta taccgtcgac ctctagctag agcttggcgt  4740
aatcatggtc atagctgttt cctgtgtgaa attgttatcc gctcacaatt ccacacaaca  4800
tacgagccgg aagcataaag tgtaaagcct ggggtgccta atgagtgagc taactcacat  4860
taattgcgtt gcgctcactg cccgctttcc agtcgggaaa cctgtcgtgc cagctgcatt  4920
aatgaatcgg ccaacgcgcg gggagaggcg gtttgcgtat tgggcgctct tccgcttcct  4980
cgctcactga ctcgctgcgc tcggtcgttc ggctgcggcg agcggtatca gctcactcaa  5040
aggcggtaat acggttatcc acagaatcag gggataacgc aggaaagaac atgtgagcaa  5100
aaggccagca aaaggccagg aaccgtaaaa aggccgcgtt gctggcgttt ttccataggc  5160
tccgcccccc tgacgagcat cacaaaaatc gacgctcaag tcagaggtgg cgaaacccga  5220
caggactata aagataccag gcgtttcccc ctggaagctc cctcgtgcgc tctcctgttc  5280
cgaccctgcc gcttaccgga tacctgtccg cctttctccc ttcgggaagc gtggcgcttt  5340
ctcaatgctc acgctgtagg tatctcagtt cggtgtaggt cgttcgctcc aagctgggct  5400
gtgtgcacga accccccgtt cagcccgacc gctgcgcctt atccggtaac tatcgtcttg  5460
agtccaaccc ggtaagacac gacttatcgc cactggcagc agccactggt aacaggatta  5520
gcagagcgag gtatgtaggc ggtgctacag agttcttgaa gtggtggcct aactacggct  5580
acactagaag gacagtattt ggtatctgcg ctctgctgaa gccagttacc ttcggaaaaa  5640
gagttggtag ctcttgatcc ggcaaacaaa ccaccgctgg tagcggtggt ttttttgttt  5700
gcaagcagca gattacgcgc agaaaaaaag gatctcaaga agatcctttg atcttttcta  5760
cggggtctga cgctcagtgg aacgaaaact cacgttaagg gattttggtc atgagattat  5820
caaaaaggat cttcacctag atccttttaa attaaaaatg aagttttaaa tcaatctaaa  5880
gtatatatga gtaaacttgg tctgacagtt accaatgctt aatcagtgag gcacctatct  5940
cagcgatctg tctatttcgt tcatccatag ttgcctgact ccccgtcgtg tagataacta  6000
cgatacggga gggcttacca tctggcccca gtgctgcaat gataccgcga gacccacgct  6060
caccggctcc agatttatca gcaataaacc agccagccgg aagggccgag cgcagaagtg  6120
gtcctgcaac tttatccgcc tccatccagt ctattaattg ttgccgggaa gctagagtaa  6180
gtagttcgcc agttaatagt ttgcgcaacg ttgttgccat tgctacaggc atcgtggtgt  6240
cacgctcgtc gtttggtatg gcttcattca gctccggttc ccaacgatca aggcgagtta  6300
catgatcccc catgttgtgc aaaaaagcgg ttagctcctt cggtcctccg atcgttgtca  6360
gaagtaagtt ggccgcagtg ttatcactca tggttatggc agcactgcat aattctctta  6420
ctgtcatgcc atccgtaaga tgcttttctg tgactggtga gtactcaacc aagtcattct  6480
gagaatagtg tatgcggcga ccgagttgct cttgcccggc gtcaatacgg gataataccg  6540
cgccacatag cagaacttta aaagtgctca tcattggaaa acgttcttcg gggcgaaaac  6600
tctcaaggat cttaccgctg ttgagatcca gttcgatgta acccactcgt gcacccaact  6660
gatcttcagc atcttttact ttcaccagcg tttctgggtg agcaaaaaca ggaaggcaaa  6720
atgccgcaaa aaagggaata agggcgacac ggaaatgttg aatactcata ctcttccttt  6780
ttcaatatta ttgaagcatt tatcagggtt attgtctcat gagcggatac atatttgaat  6840
gtatttagaa aaataaacaa ataggggttc cgcgcacatt tccccgaaaa gtgccacctg  6900
acgtca                                                             6906
```

```
SEQ ID NO: 64          moltype = RNA  length = 1703
FEATURE                Location/Qualifiers
source                 1..1703
                       mol_type = other RNA
                       organism = synthetic construct
SEQUENCE: 64
ggagaaccca agcttggtac cgagctcgga tccgccacca tgaagacctt aattcttgcc  60
gttgcattag tctactgcgc cactgttcat tgccaggact gtccttacga acctgatcca  120
ccaaacacag ttccaacttc ctgtgaagct aaagaaggag aatgtattga tagcagctgt  180
ggcacctgca cgagagacat actatcagat ggactgtgtg aaaataaacc aggaaaaaca  240
tgttgccgaa tgtgtcagta tgtaattgaa tgcagagtag aggccgcagg atggtttaga  300
acattctatg gaaagagatt ccagttccag gaacctggta catacgtgtt gggtcaagga  360
accaagggcg gcgactggaa ggtgtccatc accctggaga acctggatgg aaccaagggg  420
gctgtgctga ccaagacaag actggaagtg gctggagaca tcattgacat cgctcaagct  480
actgagaatc ccatcactgt aaacggtgga gctgacccta tcatcgccaa cccgtacacc  540
atcggcgagg tcaccatcgc tgttgttgag atgccaggct tcaacatcac cgtcattgag  600
ttcttcaaac tgatcgtgat cgacatcctc ggaggaagat ctgtaagaat cgccccagac  660
acagcaaaca aaggaatgat ctctggcctc tgtggagatc ttaaaatgat ggaagataca  720
gacttcactt cagatccaga acaactcgct attcagccta agatcaacca ggagtttgac  780
ggttgtccac tctatggaaa tcctgatgac gttgcatact gcaaaggtct tctggagccg  840
```

-continued

```
tacaaggaca gctgccgcaa ccccatcaac ttctactact acaccatctc ctgcgccttc  900
gcccgctgta tgggtggaga cgagcgagcc tcacacgtgc tgcttgacta cagggagacg  960
tgcgctgctc ccgaaactag aggaacctgc gttttgtctg gacatacttt ctacgataca  1020
tttgacaaag caagatacca attccagggt ccctgcaagg agattcttat ggccgccgac  1080
tgtttctgga acacttggga tgtgaaggtt tcacacagga atgttgactc ttacactgaa  1140
gtagagaaag tacgaatcag gaaacaatcg actgtagtag aactcattgt tgatggaaaa  1200
cagattctgg ttggaggaga agccgtgtcc gtcccgtaca gctctcagaa cacttccatc  1260
tactggcaag atggtgacat actgactaca gccatcctac ctgaagctct ggtggtcaag  1320
ttcaacttca agcaactgct cgtcgtacat attagagatc cattcgatgg taagacttgc  1380
ggtatttgcg gtaactacaa ccaggatttc agtgatgatt cttttgatgc tgaaggagcc  1440
tgtgatctga cccccaaccc accgggatgc accgaagaac agaaacctga agctgaacga  1500
ctctgcaata gtctcttcgc cggtcaaagt gatcttgatc agaaatgtaa cgtgtgccac  1560
aagcctgacc gtgtcgaacg atgcatgtac gagtattgcc tgaggggaca acagggtttc  1620
tgtgaccacg catgggagtt caagaaagaa tgctacataa agcatggaga caccctagaa  1680
gtaccagatg aatgcaaata ggc                                          1703

SEQ ID NO: 65          moltype = DNA  length = 404
FEATURE                Location/Qualifiers
source                 1..404
                       mol_type = other DNA
                       organism = synthetic construct
SEQUENCE: 65
aaatttaaat ttaaataata cgactcacta taggctcgtt atagccaaca taactgcgca  60
gctgaaccgt cacgaatgcc acctatagcc caatacaaca caatcgtgca atgctgcaaa  120
tggtcctcgt tgcggtcaga cgtatgggaa ctctttgcta cagacccatt cggttcctac  180
tgcacgatga ttccgacaaa gaatcggtag actaacttta cgatacacgt acccggcgta  240
atattgtcgc gaactccata ggcttacgcc agtcatctta cgtagttgtg ggagcactag  300
tccgtgttat ccgctaccgt catacgaccc tctaattcgc tacataaggt gcatgcgtac  360
atggtaatcc tgggatggca tggatgaact gtacaactga gggg                   404

SEQ ID NO: 66          moltype = DNA  length = 404
FEATURE                Location/Qualifiers
source                 1..404
                       mol_type = other DNA
                       organism = synthetic construct
SEQUENCE: 66
aaatttaaat ttaaagttta agttgcatta taggctcgtt atagccaaca taactgcgca  60
gctgaaccgt cacgaatgcc acctatagcc caatacaaca caatcgtgca atgctgcaaa  120
tggtcctcgt tgcggtcaga cgtatgggaa ctctttgcta cagacccatt cggttcctac  180
tgcacgatga ttccgacaaa gaatcggtag actaacttta cgatacacgt acccggcgta  240
atattgtcgc gaactccata ggcttacgcc agtcatctta cgtagttgtg ggagcactag  300
tccgtgttat ccgctaccgt catacgaccc tctaattcgc tacataaggt gcatgcgtac  360
atggtaatcc tgggatggca tggatgaact gtacaactga gggg                   404

SEQ ID NO: 67          moltype = RNA  length = 372
FEATURE                Location/Qualifiers
source                 1..372
                       mol_type = other RNA
                       organism = synthetic construct
SEQUENCE: 67
ggctcgttat agccaacata actgcgcagc tgaaccgtca cgaatgccac ctatagccca  60
atacaacaca atcgtgcaat gctgcaaatg gtcctcgttg cggtcagacg tatgggaact  120
ctttgctaca gacccattcg gttcctactg cacgatgatt ccgacaaaga atcggtagac  180
taactttacg atacacgtac ccggcgtaat attgtcgcga actccatagg cttacgccag  240
tcatcttacg tagttgtggg agcactagtc cgtgttatcc gctaccgtca tacgaccctc  300
taattcgcta cataaggtgc atgcgtacat ggtaatcctg ggatggcatg gatgaactgt  360
acaactgagg gg                                                      372

SEQ ID NO: 68          moltype = DNA  length = 23
FEATURE                Location/Qualifiers
source                 1..23
                       mol_type = other DNA
                       organism = synthetic construct
misc_feature           1
                       note = 5Bios
SEQUENCE: 68
ggtgtgtact acgccgtcaa tcc                                          23

SEQ ID NO: 69          moltype = DNA  length = 19
FEATURE                Location/Qualifiers
source                 1..19
                       mol_type = other DNA
                       organism = synthetic construct
SEQUENCE: 69
taatacgact cactatagg                                               19

SEQ ID NO: 70          moltype = DNA  length = 19
FEATURE                Location/Qualifiers
source                 1..19
```

```
                          mol_type = other DNA
                          organism = synthetic construct
SEQUENCE: 70
atttaggtga cactataga                                                  19

SEQ ID NO: 71             moltype = DNA  length = 19
FEATURE                   Location/Qualifiers
source                    1..19
                          mol_type = other DNA
                          organism = synthetic construct
SEQUENCE: 71
taatacgact cactatagg                                                  19

SEQ ID NO: 72             moltype = DNA  length = 19
FEATURE                   Location/Qualifiers
source                    1..19
                          mol_type = other DNA
                          organism = synthetic construct
SEQUENCE: 72
taatacgact cactatagt                                                  19

SEQ ID NO: 73             moltype = DNA  length = 19
FEATURE                   Location/Qualifiers
source                    1..19
                          mol_type = other DNA
                          organism = synthetic construct
SEQUENCE: 73
taatacgact cactataag                                                  19

SEQ ID NO: 74             moltype = DNA  length = 19
FEATURE                   Location/Qualifiers
source                    1..19
                          mol_type = other DNA
                          organism = synthetic construct
SEQUENCE: 74
taatacgact cactataat                                                  19

SEQ ID NO: 75             moltype = AA  length = 873
FEATURE                   Location/Qualifiers
source                    1..873
                          mol_type = protein
                          organism = synthetic construct
SEQUENCE: 75
MAKRLQRCQD VNQVCEIYNS KGGIGELELR FDKLPQNLFA GVFDKLKPDG EIQTTMRVSN  60
RDGVAREITF GGGVKTNEIF VKKQNICVFD VVDIFSYKVA VSTEETVVEK PTMETTAGVR  120
FKIRLSVEDV VKDWRIDLTA VKTAELGKIA QHTASIVQRT FPDNLLKLTG AEVAKLAADS  180
YELELEYTGK SPATNEKVNV AAKYAVELLS SVRNANSTAA ASFGESVSDL CRVAKIIHTH  240
EYANVVCRTP SFKMLLPQVV SLTKSSYYGG LYPPENLWLA GKTDGVRALV VCEDGVAKVI  300
TAESVDITHG VCSATTILDC ELNVDAKILY VFDVIISNNT QVYTQPFSTR ITTDISDIKI  360
DGYKIEMKPF VKVVKADEAT FKSAYKAPHN EGLIMIEDGA AYAATKTYKW KPLSHNTIDF  420
LIKACPKQLI NVDPYKPRAG YKLWLLFTTI SLDQQRELGI EFIPAWKILF TDINMFGSRV  480
PIQFQPAINP LAYVCYLPED VNVNDGDIVE MRAVDGYDTI PKWELVRSRN DRKNEPGFYG  540
NNYKIASDIY LNYIDVFHFE DLYKYNPGYF EKNKSDIYVA PNKYRRYLIK SLFGRYLRDA  600
KWVIDAAAGR GADLHLYKAE CVEHLLAIDI DPTAISELVR RRNEITGYNK SHRGGRNMHS  660
HRGQSHCAKS TSLHALVADL RENPDVLIPK IIQSRPHERC YDAIVINFAI HYLCDTDEHI  720
RDFLITVSRL LAPNGVFIFT TMDGESIVKL LADHKVRPGE AWTIHTGDVN SPDSTVPKYS  780
IRRLYDSDKL TKTGQQIEVL LPMSGEMKAE PLCNIKNIIS MARKMGLDLV ESANFSVLYE  840
AYARDYPDIY ARMTPDDKLY NDLHTYAVFK RKK                                 873

SEQ ID NO: 76             moltype = AA  length = 890
FEATURE                   Location/Qualifiers
source                    1..890
                          mol_type = protein
                          organism = synthetic construct
SEQUENCE: 76
MRRVFNSAKK QQRCDSVEQV CEFYNADNKT NELELRFDKL NRELFVVLFD KLKPDGEITT  60
TMRVSNADGM AREITFGGGV KTGEMFVKKQ NICVFDVVDV FSYKVAVSSE DEIKDKPKMD  120
TNASVRFKIR LSCDTLIPDW RIDLTAVKVA DLGKIAQHTS TVVLQTFPEN LLRMKGAEVA  180
ALATNSYELE LEYIGKSAAS KEKVLAAAEY AMELLTNSRN AISPAAATLG ESVSDICRIA  240
KLIHPAEYAN VICRTPSFKN LLPQVISLTK SSYYGGIYPP VDMYIAGKTD GVRALVLCEN  300
GVAKIITATT VDTTTVGNTP ITILDCELST SGHNGATDNK HLYIFDVIMN RGVHSHREGF  360
NKRIDIDLSD LTPAGYTLEL KPFTKLVDAA SVNETTFKSV FKPPHNEGLV LVESGPPYAL  420
TKTYKWKPIT HNTIDFLIKA CPKQLINVDP FKPRNGHDLW LLFTTISLDQ QRELGIDLIP  480
AWKLLFTDVN LFGNKIPIQF MPAINPLAYI CYLPSSTGVN DGDIVEMRAV DGFDGIPTWE  540
LVRTRPDRKD ERGFYGNNYK IASDIYLNYI DVFNFDDLWK YNPGYFEKNK SDIYIAPNKY  600
RRYLIKSLFN KYIKNAKWVI DAAAGRGADL HLYKQECVEN LLAIDIDPTA ISELIRRRNE  660
ITGWQQRGRG GNTRHNARHN THCASSTSLH ALVADLRTEP NMLIPKIIQS RPPERGYDAI  720
VINFAIHYLC ETDDYIRNFL ITVSRLLAPD GVFIFTTMDG EAIVNLLAEH KVAPGASWVV  780
HTDGNANATD ANVVKYSIKR LYDSDKLTKT GQKIAVLLPM SGEMREEPLC NIKNIVSMAR  840
```

```
KMGLDLVESA NFSVLYGAYA KDYPEIYAKL TPDDKLYNDL HAFAVFKRKK          890

SEQ ID NO: 77          moltype = AA  length = 894
FEATURE                Location/Qualifiers
source                 1..894
                       mol_type = protein
                       organism = synthetic construct
SEQUENCE: 77
MRRVSNSAKK QQRCDSVEQV CEFYNADNKT NELELRFDKL NRELFVALFD KLKPDGEITT  60
TMRVSNADGM AREITFGGGV KTGEMFVKKQ NICVFDVVDV FSYKVAVSSE DEVKDKPKMD  120
TNASVRFKIR LSCDTLIPDW RIDLTAVKVA DLGKIAQHTS TVVLQTFPEN LLRMKGAEVA  180
ALATNSYELE LEYIGKSTAG KEKVLKAAEY AIELLTNLRN AVSPVAATLG ESVSDICRIA  240
KLIHPAEYAN VICRTPSFKN LLPQVISLTK SSYYGGIYPP VDMYITGKTD GVRALVLCEN  300
GVAKIITATT VDTTTVGDTP ITILDCELST SGHNGATDNK HLYVFDVIMN RGAHSHRDGF  360
NKRIDIDLSD LTPAGYTLEL KPFTKVADAA SVNETTFKSV FKPPHNEGLV LVESGPPYAL  420
TKTYKWKPIT HNTIDFLIKA CPKQLINVDP FKPRNGHDLW LLFTTISLDQ QRELGIDLIP  480
AWKLLFTDVN LFGNKIPIQF MPAINPLAYI CYLPSSTGVN DGDIVEMRAV DGFDGIPTWE  540
LVRTRPDRKD ERGFYGNNYK IASDIYLNYI DVFNFDDLWK YNPGYFEKNK SDIYIAPNKY  600
RRYLIKSLFN KYIKNAKWVI DAAAGRGADL HLYKQECVEN LLAIDIDPTA ISELIRRRNE  660
ITGWQQRGRG GNMHHNSRHN TRHNTHCASS TSLHALVADL RTEPNMLIPK IIQSRPPERG  720
YDALVINFAI HYLCETDDYI RNFLITVSRL LAHDGVFIFT TMDGEAIVNL LTEHKVAPGA  780
SWVVHTDGNT NATDANVVKY SIKRLYDSDK LTKTGQKIAV LLPMSGEMRE EPLCNIKNIV  840
SMARKMGLDL VESANFSVLY GAYAKDYPEI YAKLTPDDKL YNDLHAFAVF KRKK        894

SEQ ID NO: 78          moltype = AA  length = 901
FEATURE                Location/Qualifiers
source                 1..901
                       mol_type = protein
                       organism = synthetic construct
SEQUENCE: 78
LEYQYYKYIL VNIMSRRLQR CRDVDQVCEY YNAKGAIGEL ELRFDKLTPD LFAHVFDKLK  60
PDGEISTTMR VSNSDGTARE ITFGGGVKTG ETFVRKQNIC VFDVVDIFSY KVAVSTEETL  120
VDKPAMEKDA SVRFKIRMSV EGAVPNWRID LTAVKTAELG KIAQHTASLV LQTFPPNLLK  180
MSGAEVAKLA NNSYELELEY IGKTPATKER VDAAAKYAVD LLAGIKNANS AVGAVLGESI  240
SDICRVAKVI HTPDYATVVC RNPSFKMLLP QVISLTKSSY YGGIYPPEGM YVAGKTDGVR  300
ALVLCEDGVA KVITAESVDI TTGTCTGTTI LDCELSTGKS GATLHVFDII MHNSKPIHSQ  360
PFSTRIATDI SDVKIPEYKI AIKPFVKIQA TALEAAFKEV YKAPHNEGLI LIMDGNDYAM  420
TKTYKWKPLS HNTIDFLIKA CPKQLLNIDP YKPRPGHKLW LLFTTISLDQ QRELGIEFIP  480
AWKMLFTDIN LFGSRVPIQF MPAINPLAYI CYLPEAATCA NGDAINDGDI VEMRAVDGFD  540
TVPKWEPIRV RSDRKDEPGF YGNNYKIASD IYLNYIDIFQ FEDLYKYNPG YFEKNKSDIY  600
VAPNKYRRFL IKNIFSKYLK NAKWVIDAAA GRGADLHLYK AECVENLLAI DIDPTAISEL  660
VRRRNEITGY NRGHRGHRGG SMRAHMGASH HGAQNCAKST TLHALVADLR TDPDVLIPKI  720
IQSRPPERGY DAIVINFAIH YLCDTDEHIR DFLITVSRLL APNGIFMFTT MDGESIVKLL  780
ETHKVKSGES WTVHTGADDP EAGVIKYSIR RLYDSDKLTK TGQQIAVLLP MSGEMKTEPL  840
CNIKNIISIA RKMGLDLVES ADFSVMYDAF ARAYPEISAR LTPDDKLYND LHSYAVFKRK  900
K                                                                901

SEQ ID NO: 79          moltype = AA  length = 1217
FEATURE                Location/Qualifiers
source                 1..1217
                       mol_type = protein
                       organism = synthetic construct
SEQUENCE: 79
MQKSNIQSKI GNDNVKQIED LFKKINKDSE FEFIFFSKKD KHLTFEKYRT LVKFISKRAS  60
SDSKIKLVKN EQTLDISFSP EIEKVYRCTL IGKDAINTYM KKLSIANNHV IFRNLIKLSK  120
KDDKIEILKK EKKSDQTIDI DDLYMRARLS SETKISDEEY KKLIAIDETQ MDNIIFRYKE  180
RTSLYVYQND KDYIRIDLTI TKMDKKYNKL NNAISNYELE LETMCEKPKN EILEKMYNEI  240
EVIFKVVQQS NFIITKSEAN SVIENYKNLL AVPKQNERSL YGRQPISLEI QYVESLANKY  300
AVTDKADGER HFLVIFNNHV YLMNKNLDVK NTGIILKKEQ ERYNNSVIDG ELIFLKNRHV  360
FLTFDCLFNG GNDIRKEAKL EERLKNADII INDCFVFNGQ KGCKYLETEH HKEFNLNKTV  420
EFHRKQIKMT LDNLNHDIEI EKQFLLVRRK YFIHSIGAKP WEIARYTALI WESYTGDPEI  480
KCPYTLDGLI FQPNEQKYAV NKKDSRYDDY KWKPREKNSI DFYVEFLKDD DGNILTVYDN  540
SYSKISDDPN AVDNAQERNA NQTYRICRLH VGQIVGQLQA PVLFRENDNL YEAYIPLQNG  600
EIRDIEGNIL ADKTVVEFYY NSMSNLPNKF KWIPMRTRYD KTEMVMKYKQ NYGNFVSVAD  660
KVWQSIVNPV LMTDFEDLAK GNNPDKNQYF YDKKLDELRK RIGHDMIVSA AKEDKYFQLI  720
TKLGIPMRNF HNFIKSNIIF TFCHSMYQDN KQKSVLDLGC GRGGDQNRFY YAKVAFYVGV  780
DYDRDALFNP LDSSTSRYNQ QKRKPGFTKM FFIHGDQSNE LDYESQFASL GGMDFQNKQL  840
IERFFSKDPA KRTTFDVINC QFAIHYSFKN DDSLSNFKKN INNYLRNDGY VLITTFDGNA  900
IRKLLKNKER FTQEYVNEEG EVKILFDIVK KYDDVNDDVI MGTGNAIDVH MAWLFNEGVY  960
QTEYLVDEKF IIEEFKRDCN LELVTMDSFE NQFNILKEYL TEYVQYEADD RTREGILKRA  1020
GEFYKSNSVN DGCKKYTDLE KYYVFRKNIP KAKKQKGGNN DLTNTHKYSI SPLPGYDNNY  1080
SFINSIHHIL KNHEIIPKTL SPKTFCSDMG IDYENDINID SNFKKIAKNI VIYHANNDGK  1140
HEKILNGLNI LLAERNKDDE YTFKIIEKGK KITQNDNVIM LAKEGVMYAP IYQIDSDLRN  1200
GIFHMDDENI KQLLELQ                                               1217

SEQ ID NO: 80          moltype = AA  length = 1161
FEATURE                Location/Qualifiers
source                 1..1161
                       mol_type = protein
```

```
                        organism = synthetic construct
SEQUENCE: 80
MATKNKSDNI RNIIGLDNVS RVEEMINNFK KNRDMEFEIS VRKINYSNYI RISEYFVNTT  60
TDIQQITSLD ISIILEDGNT YRISFLDEAM INDFLSKYSN MKYGDIIRYI LSLNPSENIE  120
IIYKNRGSAD RLSIDDLNLV IKLTEELSLS NTTKPKLSGR EKIFYRYKNR YSFTIDNTTR  180
VDITDVKETP NIWELSRKPS NYEIELEFTN NKINSNQVFD KIFDLLKVVQ NTEIPIGIRE  240
SKQVINDYQN LLNLRSSNHL DSRNVVSIES QHIIKFIPNR YAITDKADGE RYFLFSTSSG  300
IYLLSTNMTV KKVNIPVLQK DFQNMLLDGE LIEIDGKELF MVFDVVYHNN IDYRYDNNYS  360
LTHRIIVIND IIDKAFNNLI PFTDYTDKYD NLELDKIKEF YSGGIKTYWK NFNKKLKNYP  420
GLFISRKLYF VPYGIDSSEV FMYADLVWKL CVYDQLTPYK LDGIIYTPIS SPYMIKTSAN  480
ELDSVPMEYK WKPPSQNSID FFIKFDKNAK GDEAIYYDNT VVAGEGRPYK ICSLYVGLNK  540
GGEEKPIPFK VAGVEQRAFI YLTNDEALDL SGNVINDNTV VEFIFDNFKT DMDDPYKWIA  600
VRTRYDKTES VQKYKKKYGN NLHIATRIWR TITNPVTEEI IAALGNTLTY EKEMSKLIKM  660
HESYNKQSFA YYQKNTSNAI GMRAFNNFIK SNMIITYCKE KLSVLDIGCG RGGDLIKFIH  720
ANIREYVGLD IDNNGLYVIN DSAFNRYKNL KKTNKNVPPM TFINADARGL FNVEAQEKIL  780
PNMPESNKKL INNYLSSNKR YDAINCQFTL HYYLSDDISW NNFCQNINNH IKDNGYLLIT  840
CFDGQLIYDK LKGKQKYSSS YTDNFGKKNI FFEINKIYSD EEIKPIGMPI DIYNSLISNP  900
GTYQREYLVF PDFLQKSLKD LCGLELVETD MFYNIFNLYR NYFRINDGTF SIGEISGKRY  960
NEIKDFYLAL EGKSSSTSES DIAFASFKLA MLNRYYVFKK KTVTNLTEPS HIVSGVNKKT  1020
DLGKVLMPYF ITNNMIIDHS LANNDVNKIY HIIRKKYNPV KPSVYLVRHN IIDNPMDGIT  1080
FSRNKLEFIK IKNGIDPKIL LIYKSPEKIF YPLYYQRFEN YDSSEDYSKG DIYLKDKGTY  1140
LLDSDKIVND LNMLVNISGK V                                           1161

SEQ ID NO: 81           moltype =   length =
SEQUENCE: 81
000

SEQ ID NO: 82           moltype =   length =
SEQUENCE: 82
000

SEQ ID NO: 83           moltype = AA  length = 14
FEATURE                 Location/Qualifiers
source                  1..14
                        mol_type = protein
                        organism = synthetic construct
SEQUENCE: 83
GAATAGTGAA TAGT                                                   14

SEQ ID NO: 84           moltype = AA  length = 12
FEATURE                 Location/Qualifiers
source                  1..12
                        mol_type = protein
                        organism = synthetic construct
SEQUENCE: 84
GAATAGTGAA TA                                                     12

SEQ ID NO: 85           moltype = AA  length = 10
FEATURE                 Location/Qualifiers
source                  1..10
                        mol_type = protein
                        organism = synthetic construct
SEQUENCE: 85
TAATAGTGAA                                                        10

SEQ ID NO: 86           moltype = AA  length = 21
FEATURE                 Location/Qualifiers
source                  1..21
                        mol_type = protein
                        organism = synthetic construct
SEQUENCE: 86
GAATAGTGAA TAGTGAATAG T                                           21

SEQ ID NO: 87           moltype = AA  length = 23
FEATURE                 Location/Qualifiers
source                  1..23
                        mol_type = protein
                        organism = synthetic construct
SEQUENCE: 87
GAATAGTPGA ATAGTPGAAT AGT                                         23

SEQ ID NO: 88           moltype = AA  length = 5
FEATURE                 Location/Qualifiers
source                  1..5
                        mol_type = protein
                        organism = synthetic construct
SEQUENCE: 88
GGGGS                                                             5
```

```
SEQ ID NO: 89          moltype = AA  length = 12
FEATURE                Location/Qualifiers
source                 1..12
                       mol_type = protein
                       organism = synthetic construct
SEQUENCE: 89
GGGGSSGGGG SS                                                    12

SEQ ID NO: 90          moltype = AA  length = 21
FEATURE                Location/Qualifiers
source                 1..21
                       mol_type = protein
                       organism = synthetic construct
SEQUENCE: 90
GSSAGSAALI NKERATETHE R                                          21

SEQ ID NO: 91          moltype = AA  length = 4044
FEATURE                Location/Qualifiers
source                 1..4044
                       mol_type = protein
                       organism = synthetic construct
SEQUENCE: 91
TCGCGCGTTT CGGTGATGAC GGTGAAAACC TCTGACACAT GCAGCTCCCG GAGACGGTCA  60
CAGCTTGTCT GTAAGCGGAT GCCGGGAGCA GACAAGCCCG TCAGGGCGCG TCAGCGGGTG  120
TTGGCGGGTG TCGGGGCTGG CTTAACTATG CGGCATCAGA GCAGATTGTA CTGAGAGTGC  180
ACCATATGGC TAGCCCCGCG AAATGTTTAA GTTGCATTAT AGGGAAATAA GAGAGAAAAG  240
AAGAGTAAGA AGAAATATAA GACCCCGGCG CCGCCACCAT GGAGGACGCC AAGAACATCA  300
AGAAGGGCCC CGCCCCCTTC TACCCCCTGG AGGACGGCAC CGCCGGCGAG CAGCTGCACA  360
AGGCCATGAA GCGGTACGCC CTGGTGCCCG GCACCATCGC CTTCACCGAC GCCCACATCG  420
AGGTGGACAT CACCTACGCC GAGTACTTCG AGATGAGCGT GCGGCTGGCC GAGGCCATGA  480
AGCGGTACGG CCTGAACACC AACCACCGGA TCGTGGTGTG CAGCGAGAAC AGCCTGCAGT  540
TCTTCATGCC CGTGCTGGGC GCCCTGTTCA TCGGCGTGGC CGTGGCCCCC GCCAACGACA  600
TCTACAACGA GCGGGAGCTG CTGAACAGCA TGGGCATCAG CCAGCCCACC GTGGTGTTCG  660
TGAGCAAGAA GGGCCTGCAG AAGATCCTGA ACGTGCAGAA GAAGCTGCCC ATCATCCAGA  720
AGATCATCAT CATGGACAGC AAGACCGACT ACCAGGGCTT CCAGAGCATG TACACCTTCG  780
TGACCAGCCA CCTGCCCCCC GGCTTCAACG AGTACGACTT CGTGCCCGAG AGCTTCGACC  840
GGGACAAGAC CATCGCCCTG ATCATGAACA GCAGCGGCAG CACCGGCCTG CCCAAGGGCG  900
TGGCCCTGCC CCACCGGACC GCCTGCGTGC GGTTCAGCCA CGCCCGGGAC CCCATCTTCG  960
GCAACCAGAT CATCCCCGAC ACCGCCATCC TGAGCGTGGT GCCCTTCCAC CACGGCTTCG  1020
GCATGTTCAC CACCCTGGGC TACCTGATCT GCGGCTTCCG GGTGGTGCTG ATGTACCGGT  1080
TCGAGGAGGA GCTGTTCCTG CGGAGCCTGC AGGACTACAA GATCCAGAGC GCCCTGCTGG  1140
TGCCCACCCT GTTCAGCTTC TTCGCCAAGA GCACCCTGAT CGACAAGTAC GACCTGAGCA  1200
ACCTGCACGA GATCGCCAGC GGCGGCGCCC CCCTGAGCAA GGAGGTGGGC GAGGCCGTGG  1260
CCAAGCGGTT CCACCTGCCC GGCATCCGGC AGGGCTACGG CCTGACCGAG ACCACCAGCG  1320
CCATCCTGAT CACCCCCGAG GGCGACGACA AGCCCGGCGC CGTGGGCAAG GTGGTGCCCT  1380
TCTTCGAGGC CAAGGTGGTG GACCTGGACA CCGGCAAGAC CCTGGGCGTG AACCAGCGGG  1440
GCGAGCTGTG CGTGCGGGGC CCCATGATCA TGAGCGGCTA CGTGAACAAC CCCGAGGCCA  1500
CCAACGCCCT GATCGACAAG GACGGCTGGC TGCACAGCGG CGACATCGCC TACTGGGACG  1560
AGGACGAGCA CTTCTTCATC GTGGACCGGC TGAAAAGTCT GATCAAGTAC AAGGGCTACC  1620
AGGTGGCCCC CGCCGAGCTG GAGAGCATCC TGCTGCAGCA CCCCAACATC TTCGACGCCG  1680
GCGTGGCCGG CCTGCCCGAC GACGACGCCG GCGAGCTGCC CGCCGCCGTG GTGGTGCTGG  1740
AGCACGGCAA GACCATGACC GAGAAGGAGA TCGTGGACTA CGTGGCCAGC CAGGTGACCA  1800
CCGCCAAGAA GCTGCGGGGC GGCGTGGTGT TCGTGGACGA GGTGCCCAAG GGCCTGACCG  1860
GCAAGCTGGA CGCCCGGAAG ATCCGGGAGA TCCTGATCAA GGCCAAGAAG GGCGGCAAGA  1920
TCGCCGTGTG ACTCGAGCTG GTACTGCATG CACGCAATGC TAGCTGCCCC TTTCCCGTCC  1980
TGGGTACCCC GAGTCTCCCC CGACCTCGGG TCCCAGGTAT GCTCCCACCT CCACCTGCCC  2040
CACTCACCAC CTCTGCTAGT TCCAGACACC TCCCAAGCAC GCAGCAATGC AGCTCAAAAC  2100
GCTTAGCCTA GCCACACCCC CACGGGAAAC AGCAGTGATT AACCTTTAGC AATAAACGAA  2160
AGTTTAACTA AGCTATACTA ACCCCAGGGT TGGTCAATTT CGTGCCAGCC ACACCCTGGA  2220
GCTAGCAAAA AAAAAAAAAA AAAAAAAAAA AAAAAAAAAA AAAAAAAAAA AAAAAAAAAA  2280
AAAAAAAGAA GAGCACATGT GAGCAAAAGG CCAGCAAAAG GCCAGGAACC GTAAAAAGGC  2340
CGCGTTGCTG GCGTTTTTCC ATAGGCTCCG CCCCCCTGAC GAGCATCACA AAAATCGACG  2400
CTCAAGTCAG AGGTGGCGAA ACCCGACAGG ACTATAAAGA TACCAGGCGT TTCCCCCTGG  2460
AAGCTCCCTC GTGCGCTCTC CTGTTCCGAC CCTGCCGCTT ACCGGATACC TGTCCGCCTT  2520
TCTCCCTTCG GGAAGCGTGG CGCTTTCTCA TAGCTCACGC TGTAGGTATC TCAGTTCGGT  2580
GTAGGTCGTT CGCTCCAAGC TGGGCTGTGT GCACGAACCC CCCGTTCAGC CCGACCGCTG  2640
CGCCTTATCC GGTAACTATC GTCTTGAGTC CAACCCGGTA AGACACGACT TATCGCCACT  2700
GGCAGCAGCC ACTGGTAACA GGATTAGCAG AGCGAGGTAT GTAGGCGGTG CTACAGAGTT  2760
CTTGAAGTGG TGGCCTAACT ACGGCTACAC TAGAAGAACA GTATTTGGTA TCTGCGCTCT  2820
GCTGAAGCCA GTTACCTTCG GAAAAAGAGT TGGTAGCTCT TGATCCGGCA AACAAACCAC  2880
CGCTGGTAGC GGTGGTTTTT TTGTTTGCAA GCAGCAGATT ACGCGCAGAA AAAAAGGATC  2940
TCAAGAAGAT CCTTTGATCT TTTCTACGGG GTCTGACGCT CAGTGGAACG AAAACTCACG  3000
TTAAGGGATT TTGGTCATGA GATTATCAAA AAGGATCTTC ACCTAGATCC TTTTAAATTA  3060
AAAATGAAGT TTTAAATCAA GCCCAATCTG AATAATGTTA CAACCAATTA ACCAATTCTG  3120
ATTAGAAAAA CTCATCGAGC ATCAAATGAA ACTGCAATTT ATTCATATCA GGATTATCAA  3180
TACCATATTT TTGAAAAAGC CGTTTCTGTA ATGAAGGAGA AAACTCACCG AGGCAGTTCC  3240
ATAGGATGGC AAGATCCTGG TATCGGTCTG CGATTCCGAC TCGTCCAACA TCAATACAAC  3300
CTATTAATTT CCCCTCGTCA AAAATAAGGT TATCAAGTGA GAAATCACCA TGAGTGACGA  3360
CTGAATCCGG TGAGAATGGC AAAAGTTTAT GCATTTCTTT CCAGACTTGT TCAACAGGCC  3420
```

```
AGCCATTACG CTCGTCATCA AAATCACTCG CATCAACCAA ACCGTTATTC ATTCGTGATT  3480
GCGCCTGAGC GAGACGAAAT ACGCGATCGC TGTTAAAAGG ACAATTACAA ACAGGAATCG  3540
AATGCAACCG GCGCAGGAAC ACTGCCAGCG CATCAACAAT ATTTTCACCT GAATCAGGAT  3600
ATTCTTCTAA TACCTGGAAT GCTGTTTTTC CGGGGATCGC AGTGGTGAGT AACCATGCAT  3660
CATCAGGAGT ACGGATAAAA TGCTTGATGG TCGGAAGAGG CATAAATTCC GTCAGCCAGT  3720
TTAGTCTGAC CATCTCATCT GTAACATCAT TGGCAACGCT ACCTTTGCCA TGTTTCAGAA  3780
ACAACTCTGG CGCATCGGGC TTCCCATACA AGCGATAGAT TGTCGCACCT GATTGCCCGA  3840
CATTATCGCG AGCCCATTTA TACCCATATA AATCAGCATC CATGTTGGAA TTTAATCGCG  3900
GCCTCGACGT TTCCCGTTGA ATATGGCTCA TAACACCCCT TGTATTACTG TTTATGTAAG  3960
CAGACAGTTT TATTGTTCAT GATGATATAT TTTTATCTTG TGCAATGTAA CATCAGAGAT  4020
TTTGAGACAC GGGCCAGAGC TGCA                                        4044

SEQ ID NO: 92          moltype = AA  length = 4044
FEATURE                Location/Qualifiers
source                 1..4044
                       mol_type = protein
                       organism = synthetic construct
SEQUENCE: 92
TCGCGCGTTT CGGTGATGAC GGTGAAAACC TCTGACACAT GCAGCTCCCG GAGACGGTCA  60
CAGCTTGTCT GTAAGCGGAT GCCGGGAGCA GACAAGCCCG TCAGGGCGCG TCAGCGGGTG  120
TTGGCGGGTG TCGGGGCTGG CTTAACTATG CGGCATCAGA GCAGATTGTA CTGAGAGTGC  180
ACCATATGGC TAGCCCCGCG AAATTAATAC GACTCACTAT AGGGAAATAA GAGAGAAAAG  240
AAGAGTAAGA AGAAATATAA GACCCCGGCG CCGCCACCAT GGAGGACGCC AAGAACATCA  300
AGAAGGGCCC CGCCCCCTTC TACCCCCTGG AGGACGGCAC CGCCGGCGAG CAGCTGCACA  360
AGGCCATGAA GCGGTACGCC CTGGTGCCCG GCACCATCGC CTTCACCGAC GCCCACATCG  420
AGGTGGACAT CACCTACGCC GAGTACTTCG AGATGAGCGT GCGGCTGGCC GAGGCCATGA  480
AGCGGTACGG CCTGAACACC AACCACCGGA TCGTGGTGTG CAGCGAGAAC AGCCTGCAGT  540
TCTTCATGCC CGTGCTGGGC GCCCTGTTCA TCGGCGTGGC CGTGGCCCCC GCCAACGACA  600
TCTACAACGA GCGGGAGCTG CTGAACAGCA TGGGCATCAG CCAGCCCACC GTGGTGTTCG  660
TGAGCAAGAA GGGCCTGCAG AAGATCCTGA ACGTGCAGAA GAAGCTGCCC ATCATCCAGA  720
AGATCATCAT CATGGACAGC AAGACCGACT ACCAGGGCTT CCAGAGCATG TACACCTTCG  780
TGACCAGCCA CCTGCCCCCC GGCTTCAACG AGTACGACTT CGTGCCCGAG AGCTTCGACC  840
GGGACAAGAC CATCGCCCTG ATCATGAACA GCAGCGGCAG CACCGGCCTG CCCAAGGGCG  900
TGGCCCTGCC CCACCGGACC GCCTGCGTGC GGTTCAGCCA CGCCCGGGAC CCCATCTTCG  960
GCAACCAGAT CATCCCCGAC ACCGCCATCC TGAGCGTGGT GCCCTTCCAC CACGGCTTCG  1020
GCATGTTCAC CACCCTGGGC TACCTGATCT GCGGCTTCCG GGTGGTGCTG ATGTACCGGT  1080
TCGAGGAGGA GCTGTTCCTG CGGAGCCTGC AGGACTACAA GATCCAGAGC GCCCTGCTGG  1140
TGCCCACCCT GTTCAGCTTC TTCGCCAAGA GCACCCTGAT CGACAAGTAC GACCTGAGCA  1200
ACCTGCACGA GATCGCCAGC GGCGGCGCCC CCCTGAGCAA GGAGGTGGGC GAGGCCGTGG  1260
CCAAGCGGTT CCACCTGCCC GGCATCCGGC AGGGCTACGG CCTGACCGAG ACCACCAGCG  1320
CCATCCTGAT CACCCCCGAG GGCGACGACA AGCCCGGCGC CGTGGGCAAG GTGGTGCCCT  1380
TCTTCGAGGC CAAGGTGGTG GACCTGGACA CCGGCAAGAC CCTGGGCGTG AACCAGCGGG  1440
GCGAGCTGTG CGTGCGGGGC CCCATGATCA TGAGCGGCTA CGTGAACAAC CCCGAGGCCA  1500
CCAACGCCCT GATCGACAAG GACGGCTGGC TGCACAGCGG CGACATCGCC TACTGGGACG  1560
AGGACGAGCA CTTCTTCATC GTGGACCGGC TGAAAAGTCT GATCAAGTAC AAGGGCTACC  1620
AGGTGGCCCC CGCCGAGCTG GAGAGCATCC TGCTGCAGCA CCCCAACATC TTCGACGCCG  1680
GCGTGGCCGG CCTGCCCGAC GACGACGCCG GCGAGCTGCC CGCCGCCGTG GTGGTGCTGG  1740
AGCACGGCAA GACCATGACC GAGAAGGAGA TCGTGGACTA CGTGGCCAGC CAGGTGACCA  1800
CCGCCAAGAA GCTGCGGGGC GGCGTGGTGT TCGTGGACGA GGTGCCCAAG GGCCTGACCG  1860
GCAAGCTGGA CGCCCGGAAG ATCCGGGAGA TCCTGATCAA GGCCAAGAAG GGCGGCAAGA  1920
TCGCCGTGTG ACTCGAGCTG GTACTGCATG CACGCAATGC TAGCTGCCCC TTTCCCGTCC  1980
TGGGTACCCC GAGTCTCCCC CGACCTCGGG TCCCAGGTAT GCTCCCACCT CCACCTGCCC  2040
CACTCACCAC CTCTGCTAGT TCCAGACACC TCCCAAGCAC GCAGCAATGC AGCTCAAAAC  2100
GCTTAGCCTA GCCACACCCC CACGGGAAAC AGCAGTGATT AACCTTTAGC AATAAACGAA  2160
AGTTTAACTA AGCTATACTA ACCCCAGGGT TGGTCAATTT CGTGCCAGCC ACACCCTGGA  2220
GCTAGCAAAA AAAAAAAAAA AAAAAAAAAA AAAAAAAAAA AAAAAAAAAA AAAAAAAAAA  2280
AAAAAAAGAA GAGCACATGT GAGCAAAAGG CCAGCAAAAG GCCAGGAACC GTAAAAAGGC  2340
CGCGTTGCTG GCGTTTTTCC ATAGGCTCCG CCCCCCTGAC GAGCATCACA AAAATCGACG  2400
CTCAAGTCAG AGGTGGCGAA ACCCGACAGG ACTATAAAGA TACCAGGCGT TTCCCCCTGG  2460
AAGCTCCCTC GTGCGCTCTC CTGTTCCGAC CCTGCCGCTT ACCGGATACC TGTCCGCCTT  2520
TCTCCCTTCG GGAAGCGTGG CGCTTTCTCA TAGCTCACGC TGTAGGTATC TCAGTTCGGT  2580
GTAGGTCGTT CGCTCCAAGC TGGGCTGTGT GCACGAACCC CCCGTTCAGC CCGACCGCTG  2640
CGCCTTATCC GGTAACTATC GTCTTGAGTC CAACCCGGTA AGACACGACT TATCGCCACT  2700
GGCAGCAGCC ACTGGTAACA GGATTAGCAG AGCGAGGTAT GTAGGCGGTG CTACAGAGTT  2760
CTTGAAGTGG TGGCCTAACT ACGGCTACAC TAGAAGAACA GTATTTGGTA TCTGCGCTCT  2820
GCTGAAGCCA GTTACCTTCG GAAAAAGAGT TGGTAGCTCT TGATCCGGCA AACAAACCAC  2880
CGCTGGTAGC GGTGGTTTTT TTGTTTGCAA GCAGCAGATT ACGCGCAGAA AAAAAGGATC  2940
TCAAGAAGAT CCTTTGATCT TTTCTACGGG GTCTGACGCT CAGTGGAACG AAAACTCACG  3000
TTAAGGGATT TTGGTCATGA GATTATCAAA AAGGATCTTC ACCTAGATCC TTTTAAATTA  3060
AAAATGAAGT TTTAAATCAA GCCCAATCTG AATAATGTTA CAACCAATTA ACCAATTCTG  3120
ATTAGAAAAA CTCATCGAGC ATCAAATGAA ACTGCAATTT ATTCATATCA GGATTATCAA  3180
TACCATATTT TTGAAAAAGC CGTTTCTGTA ATGAAGGAGA AAACTCACCG AGGCAGTTCC  3240
ATAGGATGGC AAGATCCTGG TATCGGTCTG CGATTCCGAC TCGTCCAACA TCAATACAAC  3300
CTATTAATTT CCCCTCGTCA AAAATAAGGT TATCAAGTGA GAAATCACCA TGAGTGACGA  3360
CTGAATCCGG TGAGAATGGC AAAAGTTTAT GCATTTCTTT CCAGACTTGT TCAACAGGCC  3420
AGCCATTACG CTCGTCATCA AAATCACTCG CATCAACCAA ACCGTTATTC ATTCGTGATT  3480
GCGCCTGAGC GAGACGAAAT ACGCGATCGC TGTTAAAAGG ACAATTACAA ACAGGAATCG  3540
AATGCAACCG GCGCAGGAAC ACTGCCAGCG CATCAACAAT ATTTTCACCT GAATCAGGAT  3600
ATTCTTCTAA TACCTGGAAT GCTGTTTTTC CGGGGATCGC AGTGGTGAGT AACCATGCAT  3660
```

-continued

```
CATCAGGAGT ACGGATAAAA TGCTTGATGG TCGGAAGAGG CATAAATTCC GTCAGCCAGT  3720
TTAGTCTGAC CATCTCATCT GTAACATCAT TGGCAACGCT ACCTTTGCCA TGTTTCAGAA  3780
ACAACTCTGG CGCATCGGGC TTCCCATACA AGCGATAGAT TGTCGCACCT GATTGCCCGA  3840
CATTATCGCG AGCCCATTTA TACCCATATA AATCAGCATC CATGTTGGAA TTTAATCGCG  3900
GCCTCGACGT TTCCCGTTGA ATATGGCTCA TAACACCCCT TGTATTACTG TTTATGTAAG  3960
CAGACAGTTT TATTGTTCAT GATGATATAT TTTTATCTTG TGCAATGTAA CATCAGAGAT  4020
TTTGAGACAC GGGCCAGAGC TGCA                                         4044
```